US011273058B2

(12) United States Patent
Ouidja et al.

(10) Patent No.: US 11,273,058 B2
(45) Date of Patent: Mar. 15, 2022

(54) CERVICAL PLATE AND INSERTER

(71) Applicant: Spinal Elements, Inc., Carlsbad, CA (US)

(72) Inventors: Rachid Ouidja, Carlsbad, CA (US); David Hart, Oceanside, CA (US); Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 15 days.

(21) Appl. No.: 16/867,915

(22) Filed: May 6, 2020

(65) Prior Publication Data

US 2020/0352739 A1    Nov. 12, 2020

Related U.S. Application Data

(60) Provisional application No. 63/011,110, filed on Apr. 16, 2020, provisional application No. 62/903,365, filed on Sep. 20, 2019, provisional application No. 62/844,346, filed on May 7, 2019.

(51) Int. Cl.
    *A61F 2/44*   (2006.01)
    *A61F 2/46*   (2006.01)
    *A61B 17/80*  (2006.01)

(52) U.S. Cl.
    CPC ........ *A61F 2/4611* (2013.01); *A61B 17/8061* (2013.01); *A61F 2/447* (2013.01)

(58) Field of Classification Search
    CPC .......... A61F 2/44; A61F 2/442; A61F 2/4455; A61F 2/447; A61F 2/46; A61F 2/4603; A61F 2/4611
    See application file for complete search history.

(56) References Cited

U.S. PATENT DOCUMENTS

| 3,486,505 A | 12/1969 | Morrison |
| 3,726,440 A | 4/1973 | Deeb |
| 5,055,104 A | 8/1991 | Ray |
| 5,122,130 A | 6/1992 | Keller |
| 5,235,966 A | 8/1993 | Jamner |

(Continued)

FOREIGN PATENT DOCUMENTS

| WO | WO 2010/111802 | 10/2010 |
| WO | WO 2017/175024 | 10/2017 |

OTHER PUBLICATIONS

International Search Report and Written Opinion in International Application No. PCT/US2020/031581, dated Oct. 14, 2020.

(Continued)

*Primary Examiner* — Eric S Gibson
(74) *Attorney, Agent, or Firm* — Knobbe, Martens, Olson & Bear, LLP

(57) ABSTRACT

Various embodiments of cervical plates for treating the spine are provided. The cervical plates include an access surface and a bone facing surface. The cervical plate further includes at least one hole between the access surface and the bone facing surface. The hole includes a trajectory surface that guides an anchor into a corner or edge of a vertebral body, wherein a portion of the hole extends into the disc space region. In some embodiments, the cervical plate includes a ledge to support high angle screw insertion. In some embodiments, an interbody implant is provided. The cervical plate and the interbody spacer can have a corresponding curvature.

26 Claims, 94 Drawing Sheets

(56) References Cited

U.S. PATENT DOCUMENTS

| | | |
|---|---|---|
| 5,263,953 A | 11/1993 | Bagby |
| 5,431,658 A | 7/1995 | Moskovich |
| 5,489,307 A | 2/1996 | Kuslich et al. |
| 5,662,683 A | 9/1997 | Kay |
| 5,824,008 A | 10/1998 | Bolduc et al. |
| 5,885,299 A | 3/1999 | Winslow et al. |
| 6,004,326 A | 12/1999 | Castro et al. |
| 6,015,426 A | 1/2000 | Griffiths |
| 6,056,749 A | 5/2000 | Kuslich |
| 6,066,175 A | 5/2000 | Henderson et al. |
| 6,096,038 A | 8/2000 | Michelson |
| 6,113,637 A | 9/2000 | Gill et al. |
| 6,156,037 A | 12/2000 | Le Huec et al. |
| 6,179,873 B1 | 1/2001 | Zientek |
| 6,224,599 B1 | 5/2001 | Baynham et al. |
| 6,231,610 B1 | 5/2001 | Geisler |
| 6,276,883 B1 | 8/2001 | Unsworth et al. |
| 6,296,656 B1 | 10/2001 | Bolduc et al. |
| 6,332,887 B1 | 12/2001 | Knox |
| 6,432,106 B1 | 8/2002 | Fraser |
| 6,478,800 B1 | 11/2002 | Fraser et al. |
| 6,551,319 B2 | 4/2003 | Lieberman |
| 6,551,322 B1 | 4/2003 | Lieberman |
| 6,652,533 B2 | 11/2003 | O'Neil |
| 6,730,127 B2 | 5/2004 | Michelson |
| 6,752,832 B2 | 6/2004 | Neumann |
| 6,755,841 B2 | 6/2004 | Fraser et al. |
| 6,896,676 B2 | 5/2005 | Zubok et al. |
| 6,953,462 B2 | 10/2005 | Lieberman |
| 6,984,234 B2 | 1/2006 | Bray |
| 7,018,416 B2 | 3/2006 | Hanson et al. |
| D524,443 S | 6/2006 | Blain |
| 7,056,341 B2 | 6/2006 | Crozet |
| 7,077,864 B2 | 7/2006 | Byrd, III et al. |
| 7,094,239 B1 | 8/2006 | Michelson |
| 7,112,222 B2 | 9/2006 | Fraser et al. |
| D533,277 S | 12/2006 | Blain |
| 7,172,627 B2 | 2/2007 | Fiere et al. |
| D539,934 S | 4/2007 | Blain |
| D541,940 S | 5/2007 | Blain |
| 7,211,085 B2 | 5/2007 | Michelson |
| 7,273,498 B2 | 9/2007 | Bianchi et al. |
| 7,601,167 B2 | 10/2009 | Liberman |
| 7,611,517 B2 | 11/2009 | Lim |
| 7,722,613 B2 | 5/2010 | Sutterlin et al. |
| 7,722,622 B2 | 5/2010 | Evans et al. |
| 7,744,612 B2 | 6/2010 | Blain |
| 7,766,947 B2 | 8/2010 | Hawkes et al. |
| 7,846,183 B2 | 12/2010 | Blain |
| 7,850,731 B2 * | 12/2010 | Brittan .................. A61F 2/4465 623/17.11 |
| 7,896,884 B2 | 3/2011 | Wing et al. |
| 7,935,123 B2 | 5/2011 | Fanger et al. |
| 8,062,304 B2 | 11/2011 | Blain et al. |
| 8,066,714 B2 | 11/2011 | Shipp et al. |
| 8,100,955 B2 | 1/2012 | Blain et al. |
| 8,142,504 B2 | 3/2012 | Petit |
| 8,333,804 B1 | 12/2012 | Wensel |
| 8,394,107 B2 | 3/2013 | Fanger et al. |
| 8,454,622 B2 | 6/2013 | Blain et al. |
| 8,500,811 B2 * | 8/2013 | Blain .................. A61B 17/808 623/17.11 |
| 8,523,945 B1 | 9/2013 | Wensel |
| 8,551,105 B2 | 10/2013 | Blain et al. |
| 8,740,983 B1 | 6/2014 | Arnold et al. |
| 8,801,785 B2 | 8/2014 | Brittan et al. |
| 8,808,304 B2 | 8/2014 | Weiman et al. |
| 8,840,668 B1 | 9/2014 | Donahoe et al. |
| 8,864,770 B2 | 10/2014 | Blain et al. |
| 8,900,310 B2 | 12/2014 | Carlson et al. |
| 8,926,702 B2 | 1/2015 | Gorek et al. |
| 8,945,227 B2 * | 2/2015 | Kirschman ............ A61B 17/70 623/17.16 |
| 8,986,344 B2 | 3/2015 | Sandhu |
| 9,180,022 B2 * | 11/2015 | Georges ............ A61B 17/7059 |
| 9,375,237 B2 | 6/2016 | Keegan et al. |
| 9,414,831 B2 | 8/2016 | Sandhu |
| 9,427,330 B2 * | 8/2016 | Petersheim .......... A61B 17/809 |
| 9,750,616 B2 | 9/2017 | Blain et al. |
| 10,238,439 B2 | 3/2019 | Prybis et al. |
| 10,342,678 B2 | 7/2019 | Flores et al. |
| 10,675,156 B2 | 6/2020 | Blain et al. |
| 2002/0022845 A1 | 2/2002 | Zdeblick et al. |
| 2002/0082695 A1 | 6/2002 | Neumann |
| 2002/0116009 A1 | 8/2002 | Fraser et al. |
| 2003/0028197 A1 | 2/2003 | Hanson et al. |
| 2003/0083747 A1 | 5/2003 | Winterbottom et al. |
| 2003/0199874 A1 | 10/2003 | Michelson |
| 2004/0002758 A1 | 1/2004 | Landry et al. |
| 2004/0030387 A1 | 2/2004 | Landry et al. |
| 2004/0225295 A1 | 11/2004 | Zubok et al. |
| 2004/0254579 A1 | 12/2004 | Buhren et al. |
| 2004/0258502 A1 | 12/2004 | Unsworth et al. |
| 2005/0049593 A1 | 3/2005 | Duong et al. |
| 2005/0071013 A1 | 3/2005 | Zubok et al. |
| 2005/0102029 A1 | 5/2005 | Blain |
| 2005/0107877 A1 | 5/2005 | Blain |
| 2005/0159818 A1 | 7/2005 | Blain |
| 2005/0165408 A1 | 7/2005 | Puno et al. |
| 2005/0192574 A1 | 9/2005 | Blain |
| 2006/0074425 A1 | 4/2006 | Sutterlin et al. |
| 2006/0195097 A1 | 8/2006 | Evans et al. |
| 2006/0201289 A1 | 9/2006 | Davidson et al. |
| 2006/0241641 A1 | 10/2006 | Albans et al. |
| 2006/0276801 A1 | 12/2006 | Yerby et al. |
| 2007/0123903 A1 | 5/2007 | Raymond et al. |
| 2007/0123904 A1 | 5/2007 | Stad et al. |
| 2008/0140203 A1 | 6/2008 | Davis |
| 2008/0161817 A1 | 7/2008 | Parsons et al. |
| 2008/0161925 A1 * | 7/2008 | Brittan .................. A61F 2/4465 623/17.16 |
| 2008/0294262 A1 * | 11/2008 | Levieux ................ A61F 2/4611 623/17.16 |
| 2008/0300634 A1 | 12/2008 | Gray |
| 2009/0012529 A1 * | 1/2009 | Blain .................... A61F 2/4611 606/99 |
| 2009/0018592 A1 | 1/2009 | Pitbladdo |
| 2009/0030520 A1 | 1/2009 | Biedermann et al. |
| 2009/0275988 A1 | 11/2009 | Baynham |
| 2010/0228297 A1 | 9/2010 | Bray et al. |
| 2010/0256690 A1 | 10/2010 | Appenzeller et al. |
| 2010/0305704 A1 | 12/2010 | Messerli |
| 2011/0166660 A1 | 7/2011 | Laurence |
| 2011/0190892 A1 * | 8/2011 | Kirschman ............ A61F 2/447 623/17.16 |
| 2011/0230918 A1 | 9/2011 | Gorek et al. |
| 2012/0232597 A1 | 9/2012 | Saidha et al. |
| 2013/0060337 A1 * | 3/2013 | Petersheim ........ A61B 17/8042 623/17.16 |
| 2013/0079879 A1 | 3/2013 | Suh |
| 2013/0190874 A1 | 7/2013 | Glazer |
| 2013/0268008 A1 | 10/2013 | McDonough et al. |
| 2016/0296341 A1 | 10/2016 | Tatsumi |
| 2017/0224389 A1 | 8/2017 | Tatsumi |
| 2019/0083270 A1 * | 3/2019 | Milz ...................... A61F 2/447 |
| 2019/0307579 A1 | 10/2019 | Flores et al. |
| 2020/0352739 A1 * | 11/2020 | Ouidja ............... A61B 17/8061 |

OTHER PUBLICATIONS

Invitation to Pay Additional Search Fees in International Application No. PCT/US2020/031581, dated Aug. 4, 2020.
"Luminary™ ALIF. Disc Preparation and Implant Insertion Instruments," Synthes® Spine, Technique Guide, 2006, p. 23.

* cited by examiner

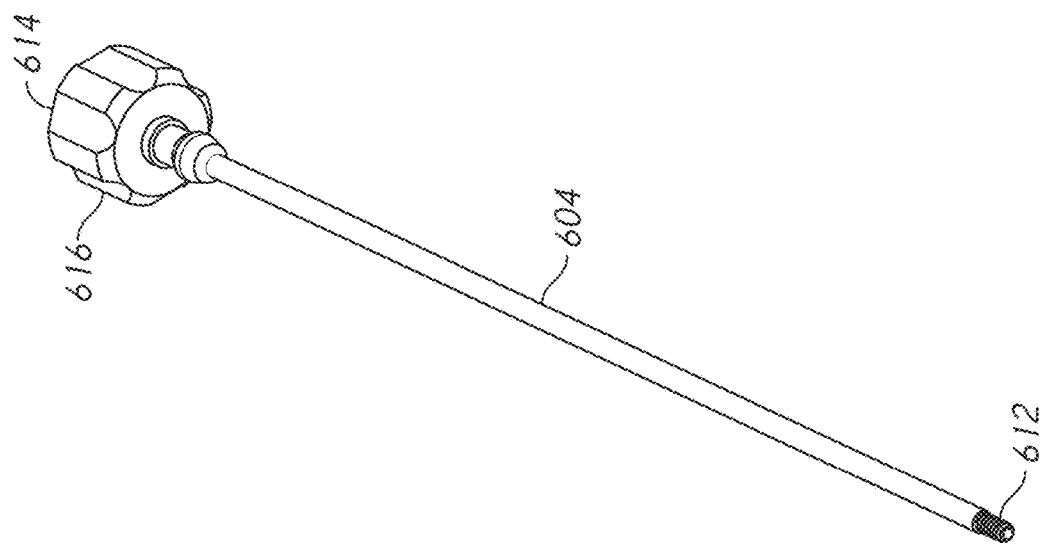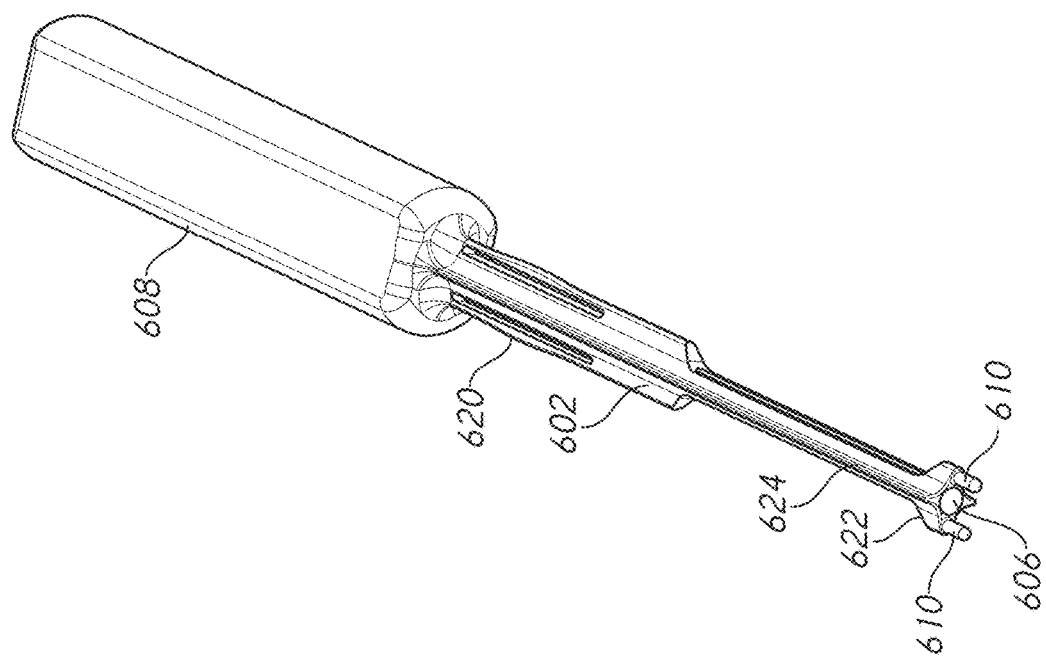
FIG. 34

CERVICAL PLATE AND INSERTER

CROSS-REFERENCE TO RELATED APPLICATIONS

This application claims priority benefit to U.S. Provisional Patent Application No. 62/844,346, filed May 7, 2019, U.S. Provisional Patent Application No. 62/903,365, filed Sep. 20, 2019, and U.S. Provisional Patent Application No. 63/011,110, filed Apr. 16, 2020, each of which is incorporated herein by reference in its entirety for all purposes.

BACKGROUND

Field

Some embodiments described herein relate generally to systems and methods for performing spinal fixation and, in particular, to cervical plates and inserters.

Description of the Related Art

Advancing age, as well as injury, can lead to degenerative changes in the bones, discs, joints and ligaments of the spine, producing pain and instability. Under certain circumstances, alleviation of the problems can be provided by performing spinal fusion. Spinal fusion is a surgical technique where two or more vertebrae of the spinal column are fused together to eliminate the motion between the fused vertebrae. Spinal fusion is used to treat conditions where the spine exhibits instability. Spine instability may result from causes such as fracture, scoliosis and spondylolisthesis, where one or more vertebrae move in a forward direction relative to the other vertebrae. Spinal fusion with discectomy is also performed for herniation of the discs. This surgery involves removal of the affected disc and fusion of the adjacent vertebrae. Traditionally, bone grafts have been used to fuse the vertebrae, but various types of vertebral implants have also been used.

The use of bone plate and bone screw fixation systems for treating injuries to bones is well established. In most instances, a bone plate is positioned over and surrounding the bone injury area and secured to the bone. The bone plate is secured to the bone by bone screws or other similar fasteners inserted through holes in the bone plate and into the bone itself. The screws are tightened so that the bone plate holds the bone to be treated in place in order to insure proper healing. Notwithstanding the foregoing, there remains a need for improved methods and devices for treating spinal instability.

SUMMARY

Devices and methods are disclosed for treating the vertebral column. In some embodiments, a cervical plate for treating the spine is provided. In some embodiments, an interbody spacer is provided. In some embodiments, an inserter is provided.

In some embodiments, a cervical plate with an inserter tool or inserter is provided. The cervical plate with an inserter tool are provided for combined attachment to an interbody spacer. The design allows for simultaneous insertion of the cervical plate and interbody spacer using the inserter tool. The design allows for high angle screw insertion. In some embodiments, the high angle screw insertion is 35 degrees. The inserter features the ability to rotate the inner shaft to attach to the interbody implant. The inserter features the ability to translate the outer shaft independently of the rotation of the inner shaft. In some embodiments, the inner shaft may extend through the cervical plate and into the interbody spacer. In some embodiments, the outer barrel translates to engage notches or lumens in the cervical plate. In some embodiments, the outer barrel translates to engage notches or lumens in the interbody spacer. The inserter features the ability to remove the outer shaft to use a screw guide. In some embodiments, the advantages include decreased operating room time and increased operating room efficiency. In some embodiments, a kit includes an interbody spacer and cervical plate, sterile-packaged and pre-assembled with an inserter.

In some embodiments, a cervical plate is provided with high screw angles. An inserter is provided with rotation and translation features to allow for simultaneous insertion of the cervical plate and interbody spacer. In some embodiments, the inserter includes an anchor guide. A cervical plate is provided with a prominence of material on the underside of the plate that enables high angle screw insertion for purchase of a screw into a corner or edge of a vertebral body. In some embodiments, the high angle screw insertion is between 30° and 70°. The screw is inserted into the harder cortical bone of a corner or edge of a vertebral body without affecting biomechanics. The high angle screw insertion allows at least a portion of the screw hole to be located adjacent the disc space region. In some embodiments, the high angle screw insertion allows at least a portion of the screw hole to be located below a corner or edge of a superior vertebral body or above a corner or edge of an inferior vertebral body. The cervical plate overcomes difficulties with a constrained screw angle to facilitate secure screw hold. The cervical plate overcomes difficulties with prior screw holes wherein enlargement of the screw hole would allow for consequent failure of screw hold due to enlargement of the screw hole.

In some embodiments, a cervical plate for treating the spine is provided. The cervical plate can include an access surface and a bone facing surface. The cervical plate can include a hole between the access surface and the bone facing surface, wherein the hole comprises a trajectory surface configured to guide an anchor into a vertebral body. The cervical plate can include a ledge disposed within the hole, wherein the ledge extends from the bone facing surface toward the access surface, wherein the ledge is configured to allow a portion of the hole to extend into the disc space region.

In some embodiments, the hole comprises a trajectory surface configured to guide an anchor into a corner or edge of a vertebral body. In some embodiments, an anchor is configured to be inserted into the hole at an angle between 15° and 25°. In some embodiments, an anchor is configured to be inserted into the hole at an angle between 25° and 35°. In some embodiments, an anchor head of the anchor is configured to abut the ledge. In some embodiments, an anchor head of the anchor is configured to be completely recessed in the cervical plate when the anchor head abuts the ledge. In some embodiments, the bone facing surface near the hole comprises a concave curvature. In some embodiments, a portion of the cervical plate extends into the disc space region below the surface of the vertebral body.

In some embodiments, a kit is provided. The kit can include the cervical plate. The kit can include an interbody spacer.

In some embodiments, the cervical plate comprises a concave portion and the interbody spacer comprises a convex portion, wherein the concave portion and the convex portion are configured to mate. In some embodiments, the ledge extends below the convex portion of the interbody spacer when the cervical plate is within the disc space region. In some embodiments, the cervical plate is configured to be flush within the disc space region.

In some embodiments, a cervical plate for treating the spine is provided. The cervical plate can include an access surface and a bone facing surface. The cervical plate can include a first hole between the access surface and the bone facing surface, the first hole disposed on a superior portion of the cervical plate, wherein the first hole is configured to guide a first anchor into a superior vertebral body. The cervical plate can include a second hole between the access surface and the bone facing surface, the second hole disposed on an inferior portion of the cervical plate, wherein the second hole is configured to guide a second anchor into an inferior vertebral body. In some embodiments, a portion of the first hole and the second hole extend into the disc space region between the superior vertebral body and the inferior vertebral body.

In some embodiments, the first hole is configured to guide a first anchor into a corner or edge of a superior vertebral body. In some embodiments, the second hole is configured to guide a second anchor into a corner or edge of an inferior vertebral body. In some embodiments, the first anchor is configured to be inserted into the first hole at an angle between 15° and 25°. In some embodiments, the first anchor is configured to be inserted into the first hole at an angle between 25° and 35°. The cervical plate can include a third hole between the access surface and the bone facing surface, the third hole disposed on the superior portion of the cervical plate, wherein the third hole is configured to guide a third anchor into the superior vertebral body. The cervical plate can include a fourth hole between the access surface and the bone facing surface, the fourth hole disposed on the inferior portion of the cervical plate, wherein the fourth hole is configured to guide a fourth anchor into the inferior vertebral body. In some embodiments, a portion of the third hole and the fourth hole extend into the disc space region between the superior vertebral body and the inferior vertebral body. In some embodiments, the third hole is configured to guide a third anchor into the corner or edge of the superior vertebral body. In some embodiments, the fourth hole is configured to guide a fourth anchor into a corner or edge of the inferior vertebral body. In some embodiments, the first anchor and the third anchor are configured to be parallel when inserted into the first hole and the third hole. In some embodiments, the first anchor and the second anchor are configured to be skewed when inserted into the first hole and the second hole. In some embodiments, the cervical plate can include at least one additional hole disposed between the first hole and the second hole. In some embodiments, the cervical plate can include at least two additional holes disposed between the first hole and the second hole. In some embodiments, the cervical plate can include at least four additional holes disposed between the first hole and the second hole. In some embodiments, the cervical plate can include at least six additional holes disposed between the first hole and the second hole. In some embodiments, the cervical plate can include least eight additional holes disposed between the first hole and the second hole. In some embodiments, the cervical plate is a two-level cervical plate. In some embodiments, the cervical plate is a three-level cervical plate. In some embodiments, the cervical plate is a four-level cervical plate. In some embodiments, the cervical plate is a five-level cervical plate.

In some embodiments, a cervical plate for treating the spine is provided. The cervical plate can include an access surface and a bone facing surface. The cervical plate can include a first hole between the access surface and the bone facing surface, the first hole disposed on a superior portion of the cervical plate, wherein the first hole is configured to guide a first anchor into a superior vertebral body. The cervical plate can include a second hole between the access surface and the bone facing surface, the second hole disposed on a middle portion of the cervical plate, wherein the second hole is configured to guide a second anchor into a middle vertebral body. The cervical plate can include a third hole between the access surface and the bone facing surface, the third hole disposed on an inferior portion of the cervical plate, wherein the third hole is configured to guide a third anchor into an inferior vertebral body. In some embodiments, a portion of the first hole extends into the disc space region between the superior vertebral body and the middle vertebral body, wherein a portion of the third hole extends into the disc space region between the middle vertebral body and the inferior vertebral body.

In some embodiments, the first hole is configured to guide a first anchor into a corner or edge of a superior vertebral body. In some embodiments, the third hole is configured to guide a third anchor into a corner or edge of an inferior vertebral body. In some embodiments, the first anchor is configured to be inserted into the first hole at an angle between 15° and 25°. In some embodiments, the second anchor is configured to be inserted into the second hole at an angle between 25° and 35°.

In some embodiments, a method for treating the spine is provided. The method can include positioning a cervical plate relative to a vertebral body and a disc space region, the cervical plate comprising an access surface, a bone facing surface, and a hole between the access surface and the bone facing surface, wherein a portion of the hole extends into the disc space region. The method can include advancing an anchor body into the hole, wherein the anchor comprises an anchor body and an anchor head. The method can include advancing the anchor body into a vertebral body.

In some embodiments, advancing the anchor body into a vertebral body further comprises inserting the anchor body into a corner or edge of a vertebral body. In some embodiments, advancing the anchor body into a corner or edge of a vertebral body further comprises inserting the anchor body at an angle between 15° and 25°. The method can include advancing the anchor head against a ledge within the hole. The method can include positioning an interbody spacer in the disc space region. The method can include coupling an interbody spacer to the bone facing surface.

In some embodiments, an inserter assembly is provided. The inserter assembly can include an interbody implant inserter comprising a first retention feature and an anti-rotation feature, an interbody implant inserter comprising a proximal position along the length and a distal position along the length. The inserter assembly can include a cervical plate comprising an engagement portion, wherein the engagement portion comprises a complementary retention feature and a complementary anti-rotation feature. The inserter assembly can include an interbody spacer. In some embodiments, the interbody implant inserter is configured to couple with the interbody spacer. In some embodiments, the cervical plate is disposed at the proximal position and is configured to translate along the interbody implant inserter toward the distal position.

In some embodiments, the first retention feature comprises a leaf spring. In some embodiments, the first retention feature comprises a flexible region. In some embodiments, the complementary retention feature comprises a groove. In some embodiments, the anti-rotation feature comprises a ridge. In some embodiments, the interbody implant inserter comprises a second retention feature. In some embodiments, the cervical plate is retained at the distal position by the second retention feature. In some embodiments, the second retention feature is a ridge. In some embodiments, the interbody implant inserter comprises an internal shaft and an outer shaft. In some embodiments, the first retention feature and the anti-rotation feature are disposed on the outer shaft. In some embodiments, the cervical plate is a two-level cervical plate. In some embodiments, the cervical plate is a three-level cervical plate. In some embodiments, the cervical plate is a four-level cervical plate. In some embodiments, the cervical plate is a five-level cervical plate. In some embodiments, the first retention feature comprises a lever. In some embodiments, the first retention feature comprises a projection. In some embodiments, the first retention feature comprises a spring. In some embodiments, the interbody implant inserter comprises a second retention feature comprising a ridge. In some embodiments, the complementary retention feature comprises a groove. In some embodiments, the anti-rotation feature comprises a ridge and the complementary anti-rotation feature comprises a groove. In some embodiments, the retention feature and the anti-rotation feature are located on a temporary alignment fixation pin. In some embodiments, the temporary alignment fixation pin remains coupled to the interbody spacer when a portion of the interbody implant inserter is removed. In some embodiments, a portion of the interbody implant inserter is removed from the temporary alignment fixation pin before positioning the cervical plate. In some embodiments, the inserter assembly can include a second interbody implant inserter; and a second interbody spacer, wherein the second interbody implant inserter is configured to couple with the second interbody spacer. In some embodiments, the second interbody implant inserter comprises a second temporary alignment fixation pin. In some embodiments, the second temporary alignment fixation pin remains coupled to the second interbody spacer when a portion of the second interbody implant inserter is removed. In some embodiments, a portion of the second interbody implant inserter is removed from the second temporary alignment fixation pin before positioning the cervical plate.

BRIEF DESCRIPTION OF THE DRAWINGS

The structure and method of use will be better understood with the following detailed description of embodiments, along with the accompanying illustrations, in which:

FIG. 34 is a perspective view of an outer shaft and an internal shaft of the interbody implant inserter of FIG. 29.

DETAILED DESCRIPTION

Although certain preferred embodiments and examples are disclosed below, it will be understood by those in the art that the disclosure extends beyond the specifically disclosed embodiments and/or uses of the invention and obvious modifications and equivalents thereof. Thus, it is intended that the scope should not be limited by the particular disclosed embodiments described below.

The systems and methods described herein relate to embodiments of interbody implant inserters, embodiments of interbody implants, and embodiments of cervical plates. The interbody implant inserters can facilitate insertion of interbody implants and cervical plates. The interbody implants can be inserted between adjacent vertebrae. The cervical plates can be secured to the adjacent vertebrae using anchors inserted through the cervical plate.

1. Anatomy of the Spine

The vertebral column comprises a series of alternating vertebrae and fibrous discs that provide axial support and movement to the upper portions of the body. The vertebral column typically comprises thirty-three vertebrae, with seven cervical (C1-C7), twelve thoracic (T1-T12), five lumbar (L1-15), five fused sacral (S1-S5) and four fused coccygeal vertebrae. Each vertebra includes an anterior body with a posterior arch. The posterior arch comprises two pedicles and two laminae that join posteriorly to form a spinous process. Projecting from each side of the posterior arch is a transverse, superior and inferior articular process. The facets of the superior and inferior articular processes form facet joints with the articular processes of the adjacent vertebrae.

The typical cervical vertebrae differ from the other vertebrae with relatively larger spinal canals, oval shaped vertebral bodies, bifid spinous processes and foramina in their transverse processes. These foramina transversaria contain the vertebral artery and vein. The first and second cervical vertebrae are also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

Bone is typically classified as cortical bone or cancellous bone. Cortical bone is much denser than cancellous bone. Cancellous bone is spongy bone tissue which is not as strong as cortical bone. In the vertebrae, cortical bone is the dense outer shell or surface of the vertebra.

2. Interbody Implant Inserter

Figure 1:
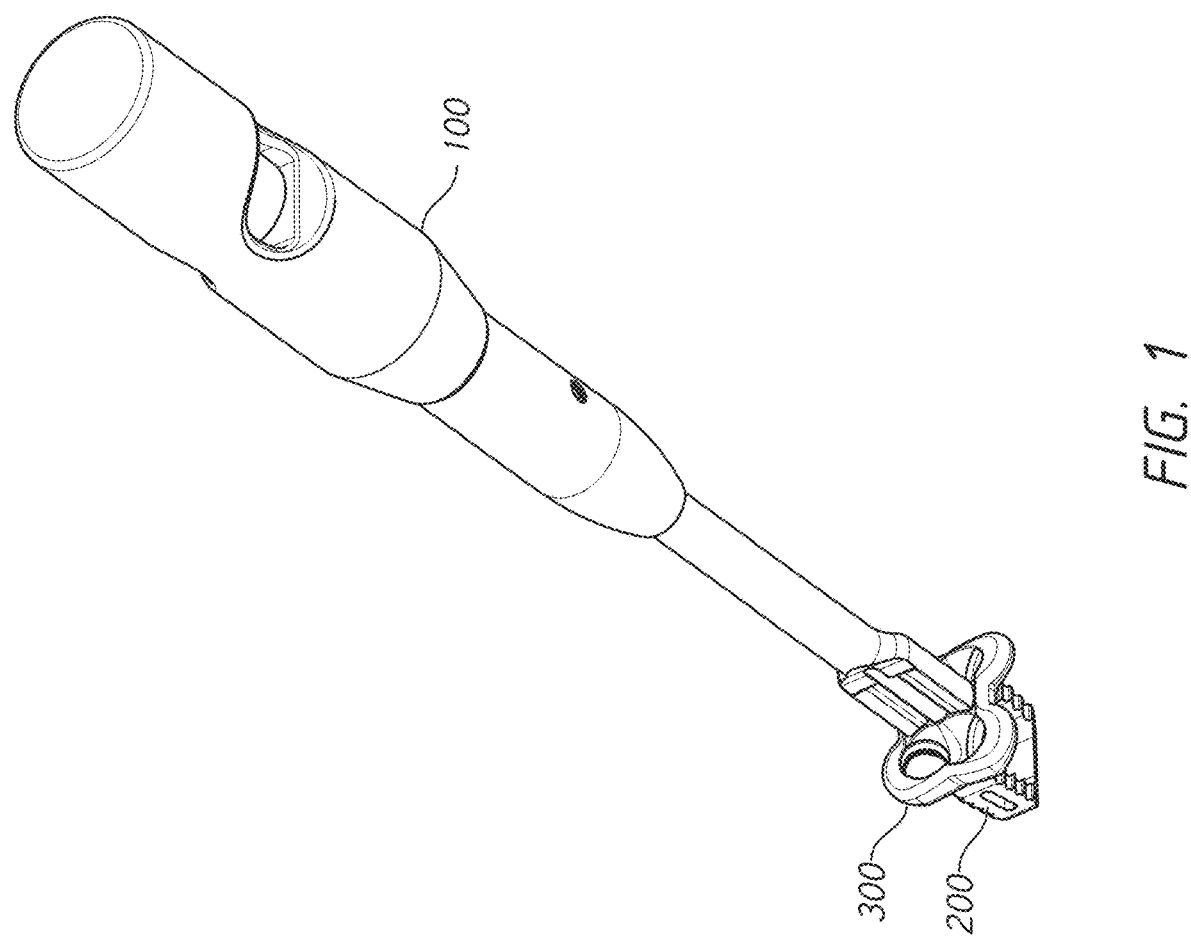
FIG. 1 is a perspective view of an embodiment of an interbody implant inserter, an embodiment of interbody implant, and an embodiment of cervical plate.
Figure 2:
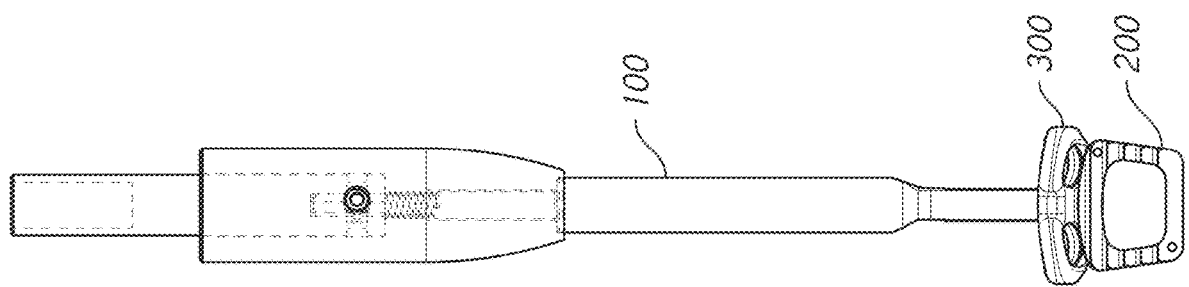
FIG. 2 is a side view of the interbody implant inserter, the interbody implant, and the cervical plate of FIG. 1.
Figure 3:
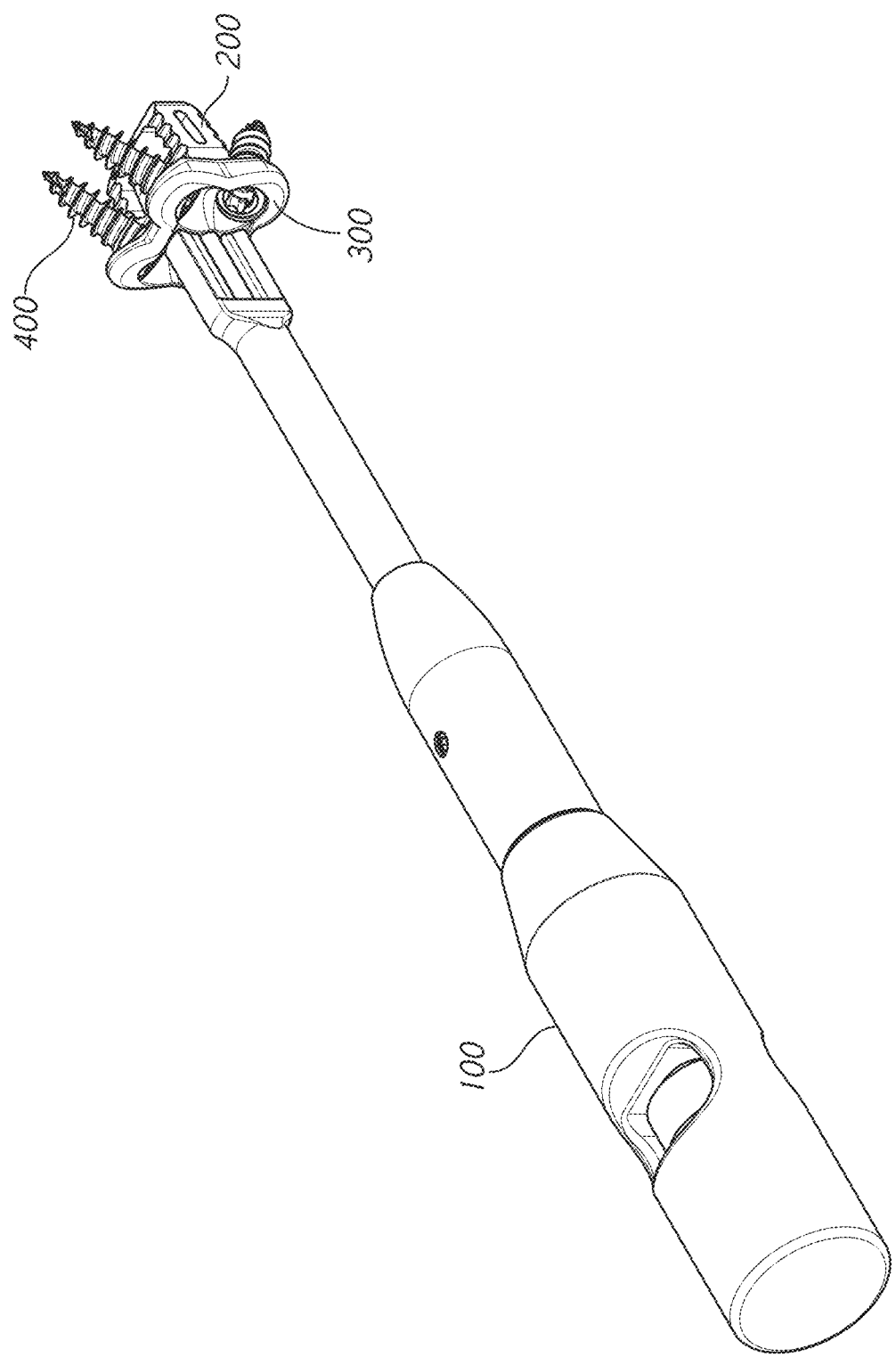
FIG. 3 is a perspective view of the interbody implant inserter, the interbody implant, and the cervical plate of FIG. 1, further including anchors.
Figure 4:
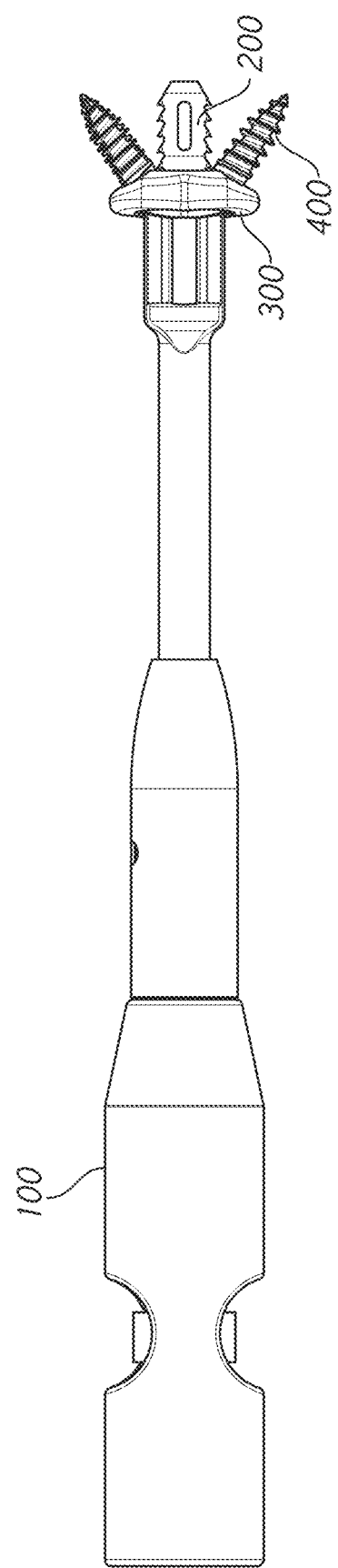
FIG. 4 is a side view of the interbody implant inserter, the interbody implant, the cervical plate, and the anchors of FIG. 3.

FIGS. 1-4 depict views of an embodiment of an interbody implant inserter 100, an interbody spacer 200, and a cervical plate 300. FIG. 1 illustrates a perspective view. FIG. 2 illustrates a side view. FIG. 3 illustrates a perspective view with anchors 400. FIG. 4 illustrates a side view with anchors 400. The systems and methods described herein can include one or more of these components.

Figure 5:
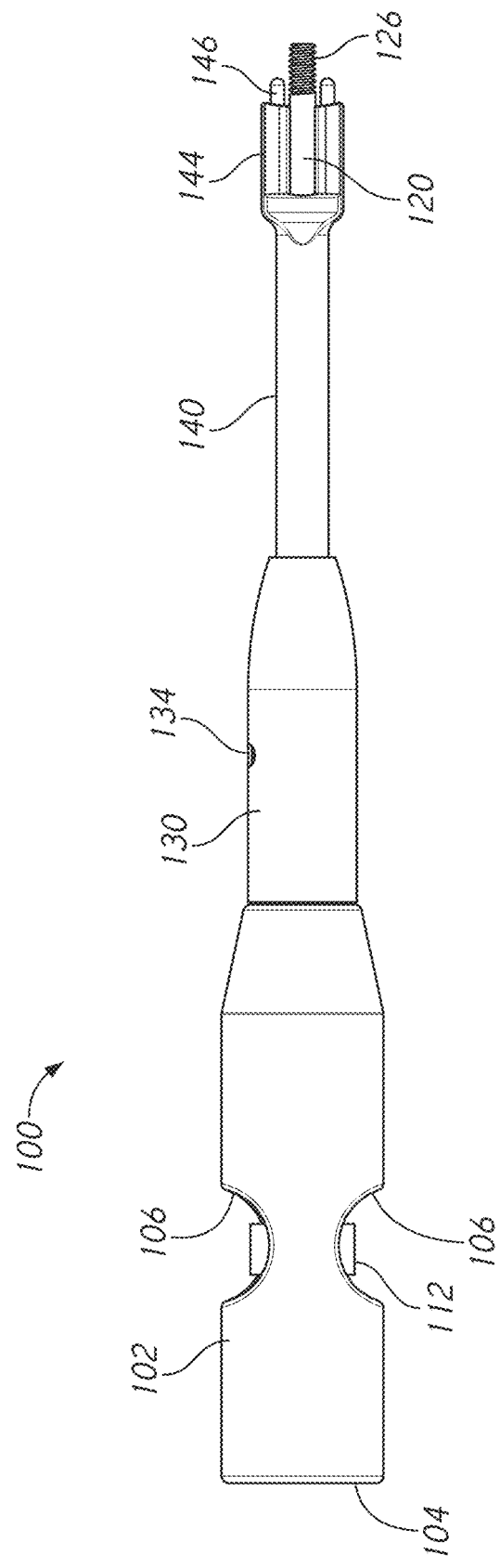
FIG. 5 is a side view of the interbody implant inserter of FIG. 1.
Figure 6:
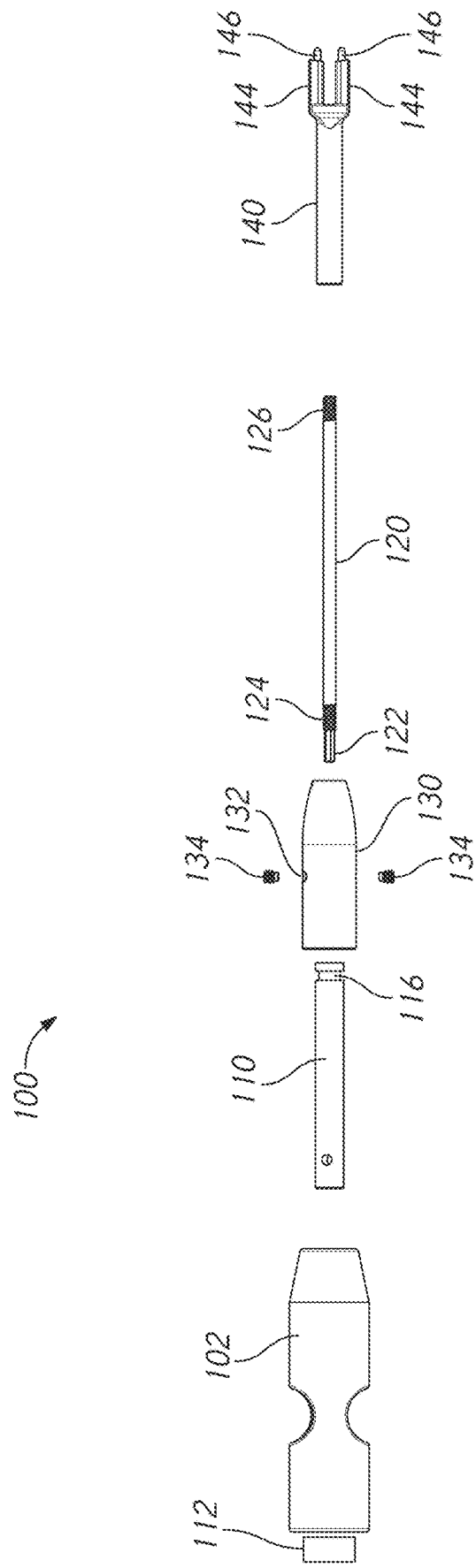
FIG. 6 is an exploded view of the interbody implant inserter of FIG. 1.
Figure 7:
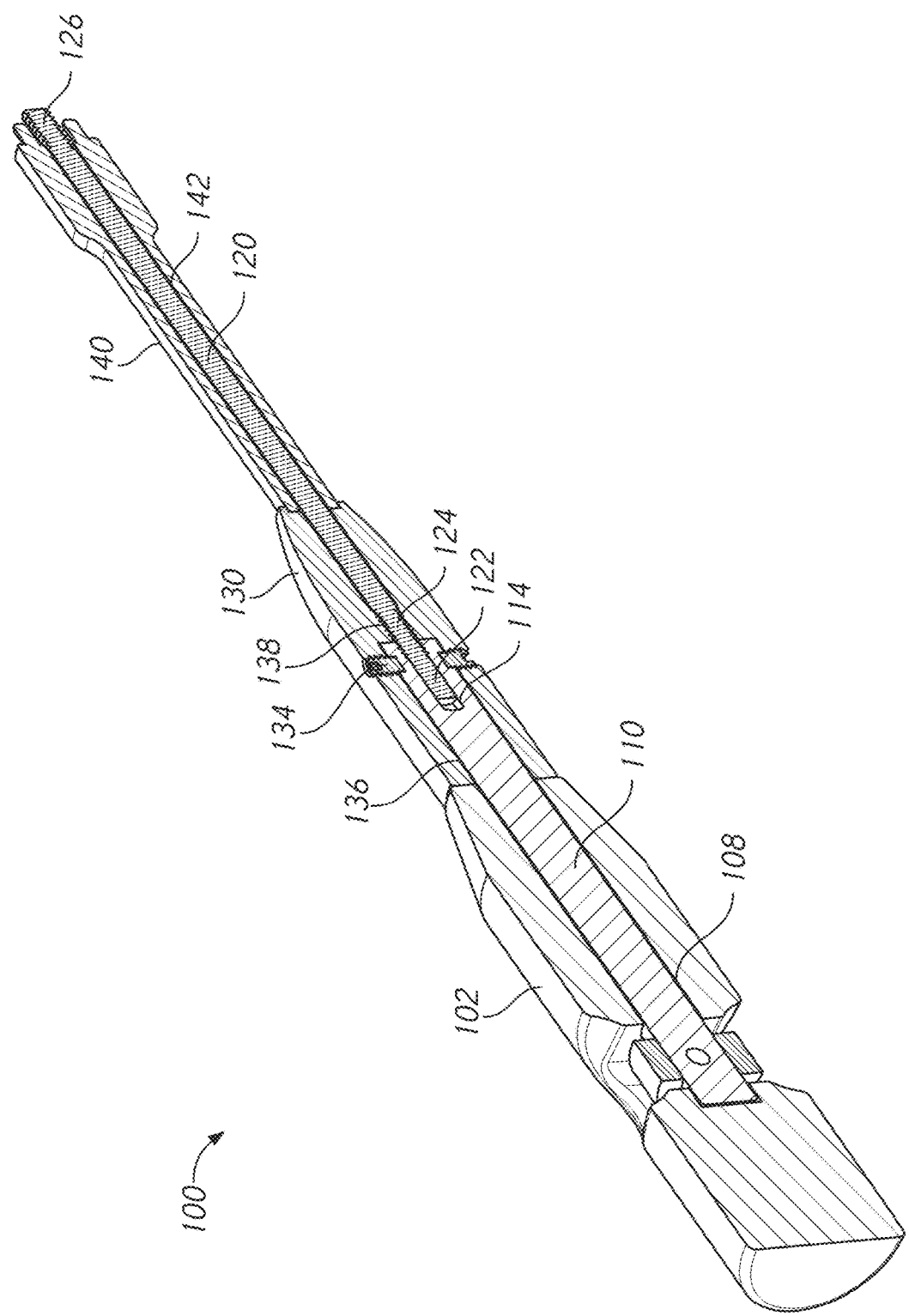
FIG. 7 is a cross-sectional view of the interbody implant inserter of FIG. 1.

FIGS. 5-7 illustrate the interbody implant inserter 100. FIG. 5 illustrates a side view. FIG. 6 illustrates an exploded view. FIG. 7 illustrates a cross-sectional view. The interbody implant inserter 100 can comprise an impact cap 102. The impact cap 102 can allow the user to apply a force to position an interbody implant between adjacent vertebrae. The impact cap 102 can have a flat proximal end 104 to allow a force to be applied. The impact cap 102 can include a window 106. In the illustrated embodiment, the impact cap 102 can include two windows 106. The two windows 106 can be diametrically opposed on the body of the impact cap 102. While the impact cap 102 is illustrated as an elongate cylindrical shape, other configurations are contemplated. The impact cap 102 can include a lumen 108. The lumen 108 can extend from a distal end of the impact cap 102 toward the proximal end 104. In the illustrated embodiment, the lumen 108 extends only partially through the impact cap 102.

The interbody implant inserter 100 can include a handle shaft 110. The handle shaft 110 can be coupled to a thumbscrew 112. The thumbscrew 112 can be manipulated by the user through the window 106 of the impact cap 102. In some embodiments, rotational movement of the thumbscrew 112 by the user can cause rotational movement of the handle shaft 110. The handle shaft 110 can include a keyed lumen 114. The keyed lumen 114 can extend from a distal end of the handle shaft 110. In some embodiments, the keyed lumen 114 is hexagonal. Other non-circular shapes are contemplated including triangular, square, rectangular, elliptical, polygonal, etc. The handle shaft 110 can include a slot 116. The slot 116 can be circumferential extending around the handle shaft 110. The slot 116 can be near the distal end of the handle shaft 110. The lumen 108 of the impact cap 102 can be sized to accommodate the proximal end of the handle shaft 110.

The interbody implant inserter 100 can include an internal shaft 120. The internal shaft 120 can include a keyed projection 122. The keyed projection 122 can be near or at the proximal end of the internal shaft 120. The keyed projection 122 can have a corresponding shape to the keyed lumen 114. The keyed lumen 114 can be sized to accommodate the keyed projection 122. In some embodiments, rotational movement of the handle shaft 110 can cause rotational movement of the internal shaft 120. In some embodiments, the keyed projection 122 is hexagonal. Other non-circular shapes are contemplated including triangular, square, rectangular, elliptical, polygonal, etc. In some embodiments, the handle shaft 110 can include a keyed projection and the internal shaft 120 can include a keyed lumen. The internal shaft 120 can include a first threaded portion 124. The first threaded portion 124 can be distal to the keyed projection 122. The internal shaft 120 can include a second threaded portion 126. The second threaded portion 126 can be distal to the keyed projection 122. The second threaded portion 126 can be near or at the distal end of the internal shaft 120.

The interbody implant inserter 100 can include a handle lock 130. The handle lock 130 can include a cored hole 132. In the illustrated embodiment, the handle lock 130 can include two cored holes 132. The two cored holes 132 can be diametrically opposed on the body of the handle lock 130. The handle lock 130 can include a set screw 134. In the illustrated embodiment, the handle lock 130 can include two set screws 134. The handle lock 130 can include a set screw 134 for each cored hole 132. The set screw 134 can be an extended point set screw. The set screw 134 can include a threaded portion and a non-threaded tip portion. The slot 116 of the handle shaft 110 can be sized to accommodate the non-threaded tip portion of the set screw 134. The set screw 134 can allow rotation of the handle shaft 110 relative to the handle lock 130. The set screw 134 can limit or prevent translation of the handle shaft 110 relative to the handle lock 130. The one or more set screws 134 can be loosened and removed. Once the set screws 134 are removed, the handle lock 130, the handle shaft 110, and the impact cap 102 can be removed from the internal shaft 120.

The handle lock 130 can include a lumen 136. The lumen 136 can be sized to accommodate the handle shaft 110. The handle shaft 110 can be configured to rotate relative to the handle lock 130 as the thumbscrew 112 is rotated. The lumen 136 can be sized to accommodate the internal shaft 120. The handle lock 130 can include a third threaded portion 138. The third threaded portion 138 can couple with the first threaded portion 124 of the internal shaft 120. The internal shaft 120 can be configured to rotate relative to the handle lock 130 as the thumbscrew 112 is rotated. While the handle lock 130 is illustrated as an elongate cylindrical shape, other configurations are contemplated.

The interbody implant inserter 100 can include an outer shaft 140. The outer shaft 140 can include a lumen 142. The lumen 142 can be sized to accommodate the internal shaft 120. The internal shaft 120 can be configured to rotate relative to the outer shaft 140 as the thumbscrew 112 is rotated. While the outer shaft 140 is illustrated as an elongate cylindrical shape, other configurations are contemplated. The outer shaft 140 can include a support 144. In the illustrated embodiment, the outer shaft 140 can include two supports 144. The two supports 144 can be diametrically opposed on the body of the outer shaft 140. The two supports 144 can be diametrically opposed relative to the lumen 142. The two supports 144 can include a surface contiguous with the lumen 142. The support 144 can have a substantially rectangular shape. The support 144 can have a taper from an outer portion toward the lumen 142.

The outer shaft 140 can include a projection 146. In the illustrated embodiment, the outer shaft 140 can include two projections 146. The outer shaft 140 can include a projection 146 for each support 144. In some embodiments, each support 144 can include one or more projections 146. The projection 146 can be an extended point. The projection 146 can have a circular cross-sectional shape. The projection 146 can have a non-circular cross-sectional shape.

The outer shaft 140 can function to couple to the cervical plate 300, as described herein. In some embodiments, the one or more projections 146 can couple with corresponding lumens in the cervical plate 300. The internal shaft 120 can function to couple to the interbody implant 200, as described herein. The distal end of the internal shaft 120 can extend through the cervical plate 300. The distal end of the internal shaft 120 can include the second threaded portion 126. The second threaded portion 126 can couple with a corresponding threaded lumen in the interbody spacer 200.

The interbody implant inserter 100 can function as an implant holder. The interbody implant inserter 100 can releasably hold a cervical plate and a corresponding interbody spacer. In some embodiments, a first support 144 can be identical or substantially similar to a second support 144. The interbody implant inserter 100 can couple to the cervical plate in one of two orientations. In other embodiments, the first support 144 is different than the second support 144. The interbody implant inserter 100 can couple to the cervical plate in only one orientation.

The interbody implant inserter 100 has the ability to rotate the inner internal shaft 120. The user can rotate the thumbscrew 112. The thumbscrew 112 can rotate independently of the impact cap 102. As the thumbscrew 112 is rotated, the handle shaft 110 is rotated. The handle shaft 110 can rotate independently of the handle lock 130. The two set screws 134 rotate within the slot 116 of the handle shaft 110. As the thumbscrew 112 and the handle shaft 110 are rotated, the internal shaft 120 is rotated. The keyed projection 122 of the internal shaft 120 can have a corresponding shape to the keyed lumen 114 of the handle shaft 110. The internal shaft 120 can include a second threaded portion 126. As the internal shaft 120 is rotated, the internal shaft 120 can thread into the interbody implant 200.

The interbody implant inserter 100 has the ability to translate. The interbody implant inserter 100 can comprise the impact cap 102. The interbody implant inserter 100 can include the handle lock 130. In some embodiments, the impact cap 102 and the handle lock 130 can be coupled. The interbody implant inserter 100 can include the outer shaft 140. In some embodiments, the handle lock 130 and the outer shaft 140 can be coupled. The impact cap 102, the handle lock 130, and the outer shaft 140 can translate together as a unit. The impact cap 102, the handle lock 130, and the outer shaft 140 can be rigidly coupled. The impact cap 102, the handle lock 130, and the outer shaft 140 can translate independently of the rotation of the internal shaft 120. The interbody implant inserter 100 has the ability to translate the outer shaft 140 independent of the rotation of the internal shaft 120.

The interbody implant inserter 100 has the ability to remove the outer shaft 140. The outer shaft 140 can be removed when the one or more set screws 134 are removed. One or more of the impact cap 102, the handle shaft 110, the handle lock 130, and the outer shaft 140 can all be removed as a unit. In some embodiments, the impact cap 102, the handle shaft 110, the handle lock 130, and the outer shaft 140 can all be removed as a unit. Once one or more set screws 134 are removed, the outer shaft 140 can be removed from the internal shaft 120.

The interbody implant inserter 100 has the ability to couple with an anchor guide (not shown). The anchor guide can couple with the interbody implant inserter 100 when the outer shaft 140 is removed. The anchor guide can couple with the interbody implant inserter 100 when the outer shaft 140 remains in place. The anchor guide can couple with the interbody implant inserter 100 when one or more of the impact cap 102, the handle shaft 110, the handle lock 130, and the outer shaft 140 are removed. The anchor guide can couple with the interbody implant inserter 100 when one or more of the impact cap 102, the handle shaft 110, the handle lock 130, and the outer shaft 140 remain in place. The anchor guide can couple with the internal shaft 120. The anchor guide can couple to the cervical plate 300 when the internal shaft 120 is coupled to the interbody implant 100.

3. Interbody Implant

The interbody implant inserter 100 can couple with an interbody implant 200. In some methods of use, the interbody implant 200 can be placed between the endplates of the superior and the inferior vertebra. In some embodiments, the interbody implant 200 can be retained between the superior vertebra and the inferior vertebra by the cervical plate 300.

Figure 8:
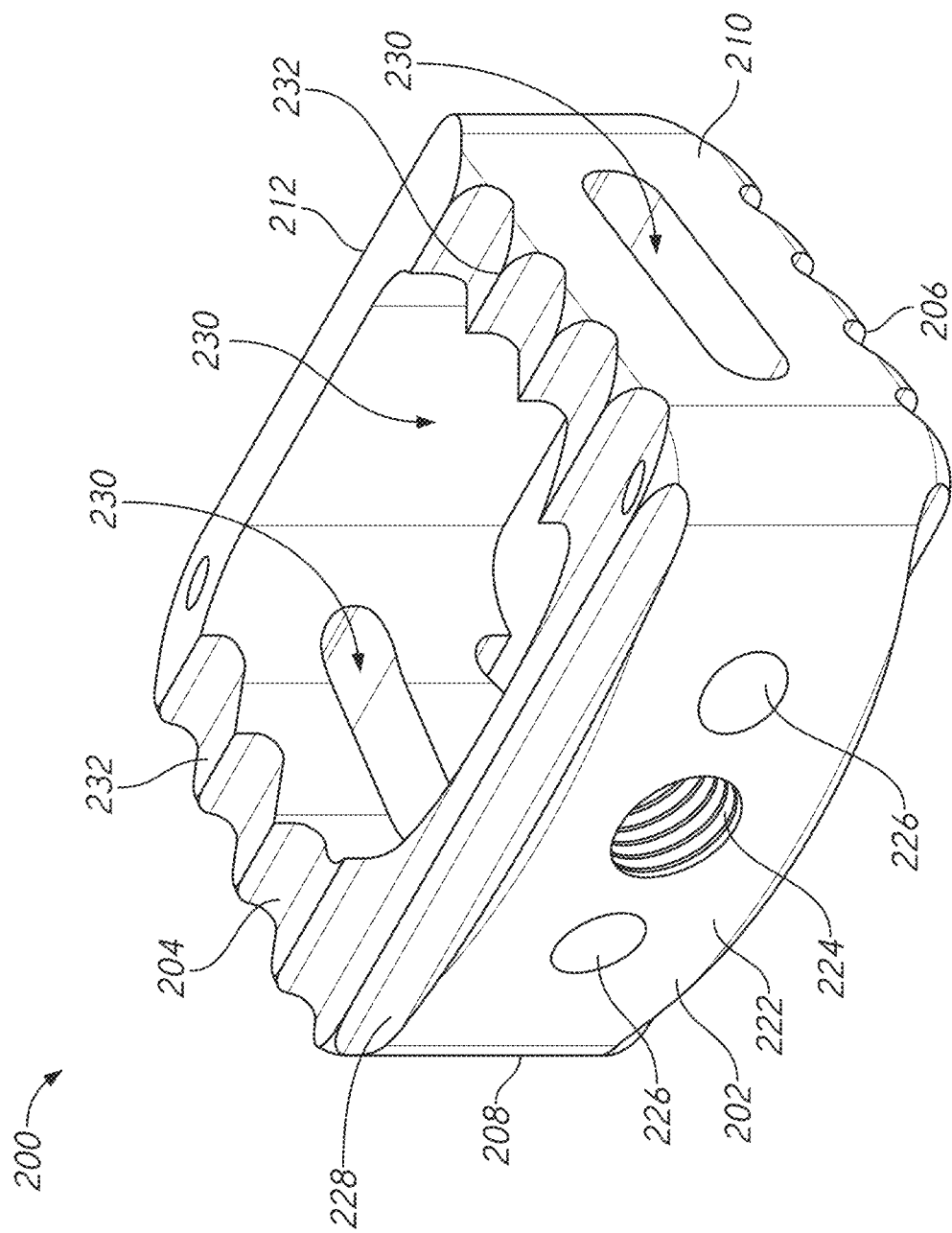
FIG. 8 is a perspective view of the interbody implant of FIG. 1.
Figure 9:
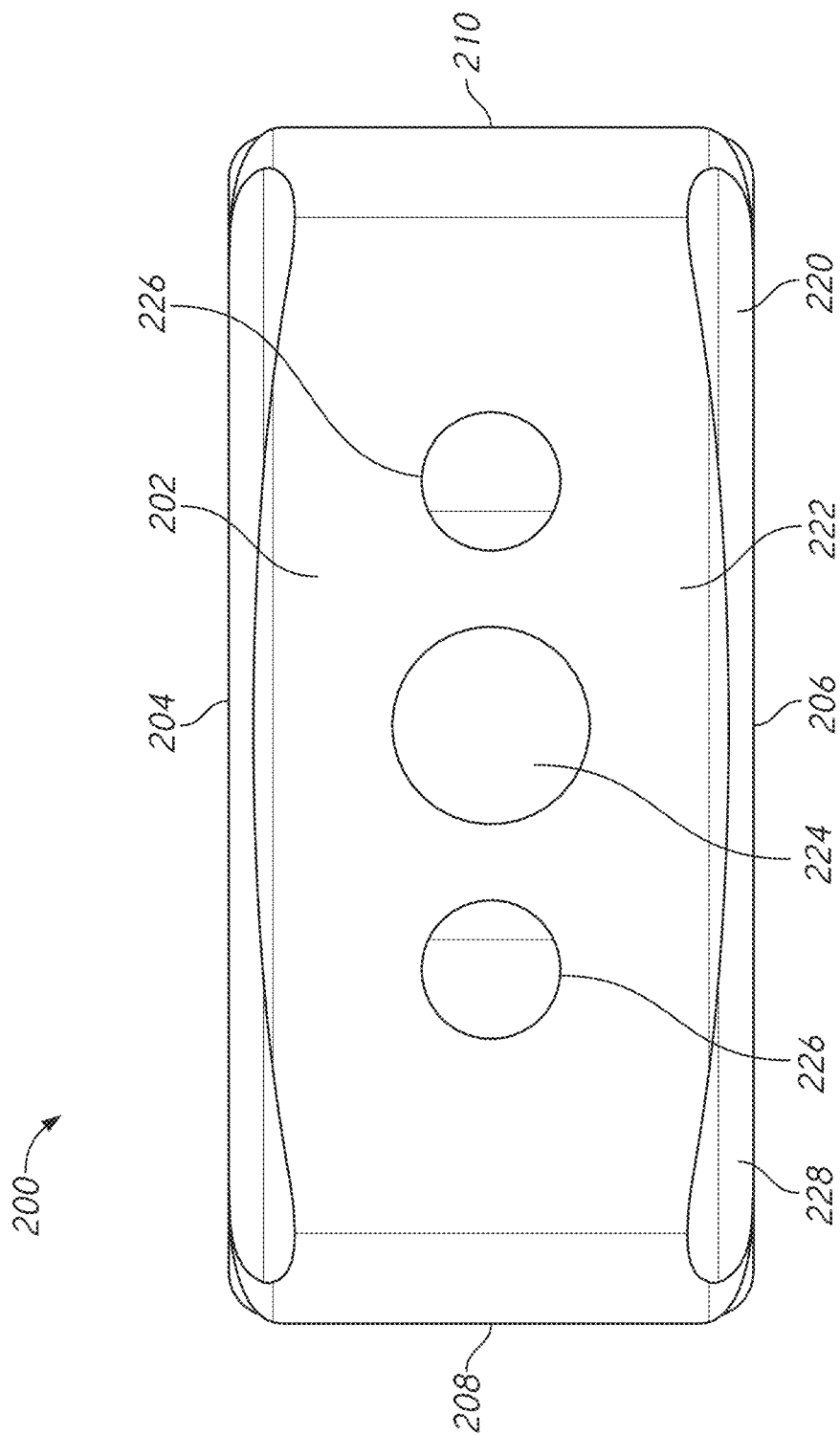
FIG. 9 is a top view of the interbody implant of FIG. 1.

FIGS. 8-9 shows an embodiment of the interbody implant 200. FIG. 8 illustrates a perspective view. FIG. 9 illustrates the top view. The interbody implant 200 can comprise any structure configured to maintain a separation and resist compression between two adjacent vertebral bodies. The interbody implant 200 can have any of a variety of overall shapes, including but not limited to a rectangular box, a trapezoidal box, H-shaped, O-shaped, or V-shaped, etc. As shown in FIG. 8, the interbody implant 200 can have an anterior surface 202, a superior surface 204 and an inferior surface 206, and side surfaces 208, 210, and a posterior surface 212. Each surface 202, 204, 206, 208, 210, 212 need not be flat, and can be curved or undulating or any combination thereof. The superior and inferior surfaces 204, 206 can be configured for facing the superior and inferior vertebral bodies. When viewed from the superior surface 204, the side surfaces 208, 210 can taper from the anterior surface 202 to the posterior surface 212. The posterior end of each side surface 208, 210 can be tapered to facilitate insertion.

FIG. 9 illustrates the anterior surface 202. The anterior surface 202 can have a generally flat configuration, curved configuration or combination thereof. In the illustrated embodiment, the anterior surface 202 comprises a generally flat portion 220 and a convex portion 222. The anterior surface 202 can include a threaded lumen 224. The distal end of the internal shaft 120 can include the second threaded portion 126. The second threaded portion 126 can couple with the corresponding threaded lumen 224 in the interbody spacer 200. In the illustrated embodiment, the convex portion 222 of the anterior surface 202 can include the threaded lumen 224.

The anterior surface 202 can include a guide lumen 226. In the illustrated embodiment, the anterior surface 202 can include two guide lumens 226. The two guide lumens 226 can be diametrically opposed relative to the threaded lumen 224. In the illustrated embodiment, the convex portion 222 of the anterior surface 202 can include the one or more guide lumens 226.

The flat portion 220 and the convex portion 222 forms a cutout 228. In some embodiments, the cutout 228 can accommodate features of the cervical plate 300. The cutout 228 can allow a portion of the cervical plate 300 to extend into the disc space region. The cervical plate 300 can include one or more holes, as described herein. The holes can align with the cutout 228 such that the interbody spacer 200 does not obstruct the trajectory of the anchor. The hole thus has a portion directly over the interbody spacer 200 when the interbody spacer 200 is disposed within the disc space region. In some embodiments, the ledge of the hole rests on the convex portion 222 of the anterior surface 202 when the interbody spacer 200 is disposed within the disc space region.

The edges of the anterior surface 202 can optionally be angled, rounded or curved. The edges of the anterior surface 202 can be smoothed or polished. In some embodiments, the anterior surface 202 of the interbody implant 200 can have a general square or rectangular shape. In other embodiments, the anterior surface 202 can comprise any of a variety of other shapes, including trapezoids, circles, ovals, polygons or other closed shapes. The anterior surface 202 is dimensioned to allow stable connection to the cervical plate 300, as described herein. The convex portion 222 of the anterior surface 202 can have a curvature to match or mate with a curvature of the cervical plate 300, as described herein.

Referring to FIG. 8, the interbody implant 200 can have any number of lumens 230, e.g., one, two, three, four, five, etc. The lumens 230 can extend between any surface of the interbody implant 200. The lumens 230 may be oriented in different directions. For instance, a first lumen 230 may be oriented between the superior surface 204 and the inferior surface 206. The first lumen 230 may promote bone ingrowth between the superior vertebra and the inferior vertebra. For instance, a second lumen 230 may be oriented between the side surfaces 208, 210. The second lumen 230 may allow visualization of bony ingrowth. The lumens 230 can allow bony growth into the interbody implant 200. The lumens 230 can also be filled with graft materials (not shown). The graft material can be an autograft, allograft, xenograft or synthetic material. Synthetic graft material can be ceramic-based, silicon-based or calcium-based. The graft material can also include osteoinductive factors to promote bone ingrowth. One skilled in the art will appreciate that there are many varieties of synthetic graft materials and constituents that can be used.

Each lumen 230 need not have the same configuration or size. In some embodiments, the lumen 230 can be round in cross-sectional shape. The lumen 230 can comprise any of a variety of shapes including square, rectangular, trapezoids, circles, ovals, polygons or other closed shapes. In some embodiments, at least a portion of the lumen 230 can have a non-round cross-sectional shape.

The relative configuration of the superior surface 204 and the inferior surface 206 can vary, depending upon the relative position desired between the two adjacent vertebrae, the anatomical shape of the vertebrae, ease of insertion of the interbody implant 200 and other factors. For example, if a neutral vertical alignment is desired between two vertebrae, the superior and inferior surfaces 204, 206 can have generally parallel planar orientations. If a non-neutral alignment is desired, for instance to maintain a natural spinal curvature in the cervical region, the superior and inferior surfaces 204, 206 can have a wedge-like relationship to allow fixation of the vertebrae in the desired non-neutral position. A non-neutral alignment with respect to the anterior-posterior direction can also be used to compensate for excessive lordosis or kyphosis in other portions of the vertebral column. The height of the interbody implant 200 at any section between the superior and inferior surfaces 204, 206 can be further configured to accommodate degenerative changes or anatomical anomalies to provide fixation in the desired relative position. Likewise, the side surfaces 208, 210 of the interbody implant 200 can be generally parallel or skewed. In some embodiments, the side surfaces 208, 210 of the interbody implant 200 taper with increasing distance from the anterior surface 202 of the interbody implant 200. A tapered interbody implant 200 can facilitate insertion of the interbody implant 2000 into the intervertebral space. In some embodiments, the one or more side surfaces 208, 210 can flare distally or have both tapering and flaring portions.

One or more surfaces of the interbody implant 200 can have surface projections, indentations, or holes or pores that can further alter the characteristics of the interbody implant 200. Referring to FIG. 8, in some embodiments, the interbody implant 200 can include one or more engagement features 232 designed to engage the adjacent anatomical features. The engagement features 232 can include angled projections, barbs, teeth, or ramped surfaces which incline outwardly from one or more surface of the interbody implant 200. In some embodiments, the engagement features 232 are provided on the superior surface 204, the inferior surface 206 or both the superior and inferior surfaces 204, 206. Other surfaces of the interbody implant 200 can also include one or more engagement features 232. In some embodiments, the engagement features 232 can be combined with indentations, holes or pores for allowing bony ingrowth which may enhance insertion and stabilization of the interbody implant 200.

The engagement features 232 can allow insertion of the interbody implant 200 in one direction but resist movement in the opposite direction. The engagement features 232 can be advantageous in reducing the migration of the interbody implant 200 out of the intervertebral space. The engagement features 232 can maintain the position of the interbody implant 200. When the cervical plate 300 is mated to the interbody spacer 200, the engagement features 232 can facilitate the positioning of the cervical plate 300. The engagement features 232 can maintain the position of the interbody implant 200 and the cervical plate 300 during drilling of the pilot holes into the vertebral bodies or inserting the anchors.

In some embodiments, the interbody implant 200 can have a height between the superior surface 204 and the inferior surface 206 of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 30 mm, 35 mm, 40 mm, 45 mm, 50 mm, between 0 mm and 10 mm, between 10 mm and 20 mm, between 4 mm and 50 mm, between 4 mm and 12 mm, between 6 mm and 9 mm, or any range of the foregoing values. In some embodiments, the interbody implant 200 can have a length as measured from the anterior surface 202 to the posterior surface 212 of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 30 mm, 35 mm, between 5 mm and 25 mm, between 10 mm and 20 mm, between 10 mm and 20 mm, between 10 mm and 15 mm, or any range of the foregoing values. In some embodiments, the interbody implant 200 can have a width between the side surfaces 208, 210 of the interbody implant 200 of 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, between 0 mm and 30 mm, between 5 mm and 25 mm, between 10 mm and 15 mm, or any range of the foregoing values. One skilled in the art can dimension the interbody implant 200 based upon the implantation location and specific vertebral morphology, neurological anatomy and disease state.

The interbody implant 200 can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cortical bone. The interbody implant 200 can also be formed of material such as metal including, but not limited to, titanium and its alloys, surgical grade plastics, plastic composites, ceramics, or other materials suitable for use as a spinal fusion implant. In some embodiments, the interbody implant 200 can comprise a radiolucent material, a radio-opaque material, or a combination thereof. An interbody implant 200 that is partially or completely radiolucent can be advantageous when evaluating the effect of the interbody implant 200 post-implantation. Many existing interbody implants obscure visualization of the vertebrae, which can complicate post-operative treatment, diagnosis and prognosis of the patient's condition. In some embodiments, the interbody implant 200 can include materials that are bioabsorbable in the body.

The interbody implant 200 of the described embodiments can be formed of a porous material or can be formed of a material that intrinsically participates in the growth of bone from one of adjacent vertebral bodies to the other of adjacent vertebral bodies. The interbody implant 200 can be treated with, coated with, or used in combination with substances to inhibit scar tissue formation. The interbody implant 200 can be modified, or used in combination with materials to provide antibacterial properties, such as, but not limited to, electroplating or plasma spraying with silver ions or other substance. The interbody implant 200 can optionally comprise an electrical source to provide iontophoresis of the silver ions into the surrounding tissue to prevent infection. The antibacterial properties can include bactericidal and/or bacteriostatic characteristics. Similarly, anti-fungal characteristics can also be provided.

4. Cervical Plate

FIGS. 10-14 depict views of an embodiment of the cervical plate 300.

Figure 10:
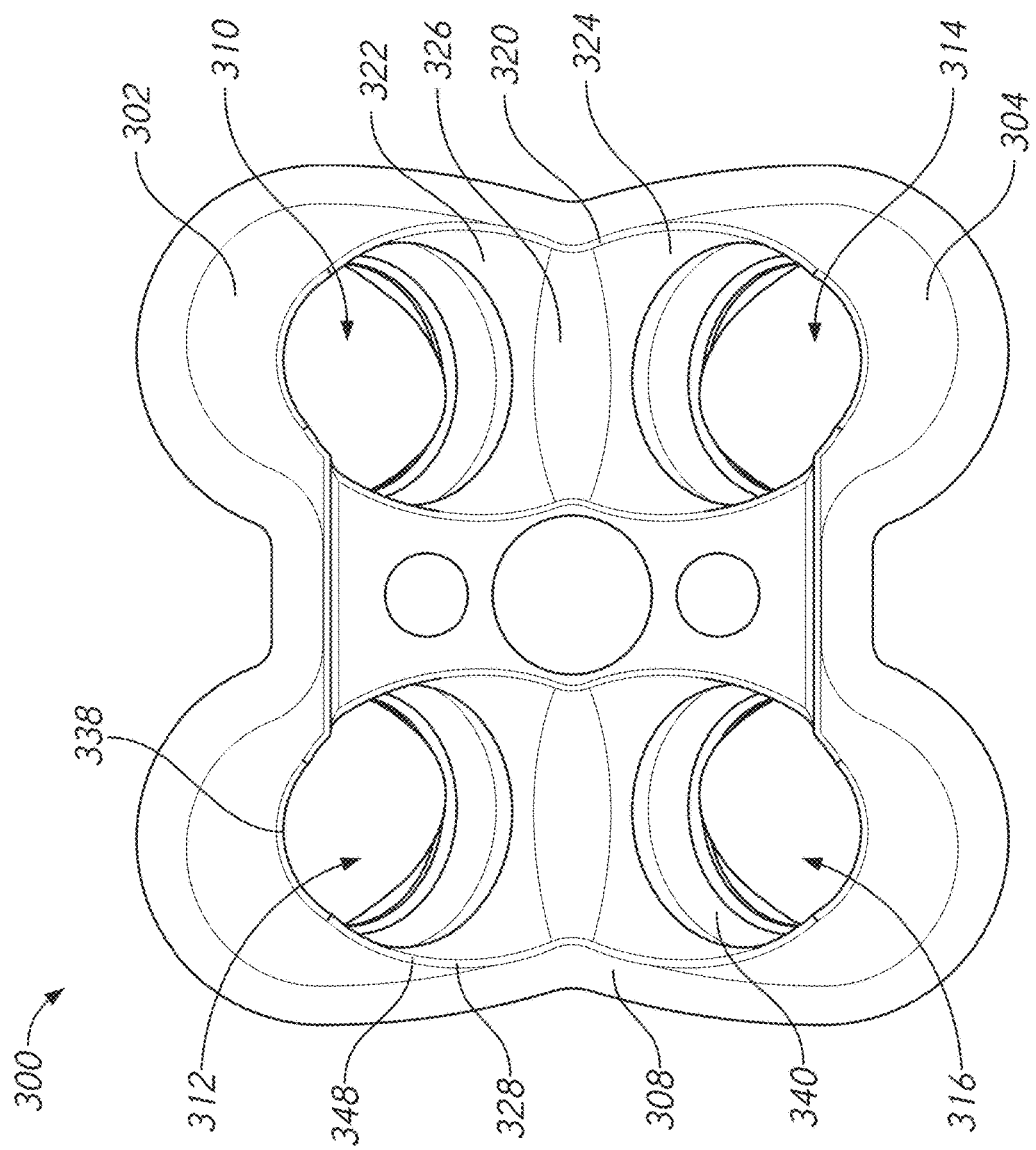
FIG. 10 is a top view of the cervical plate of FIG. 1.
Figure 11:
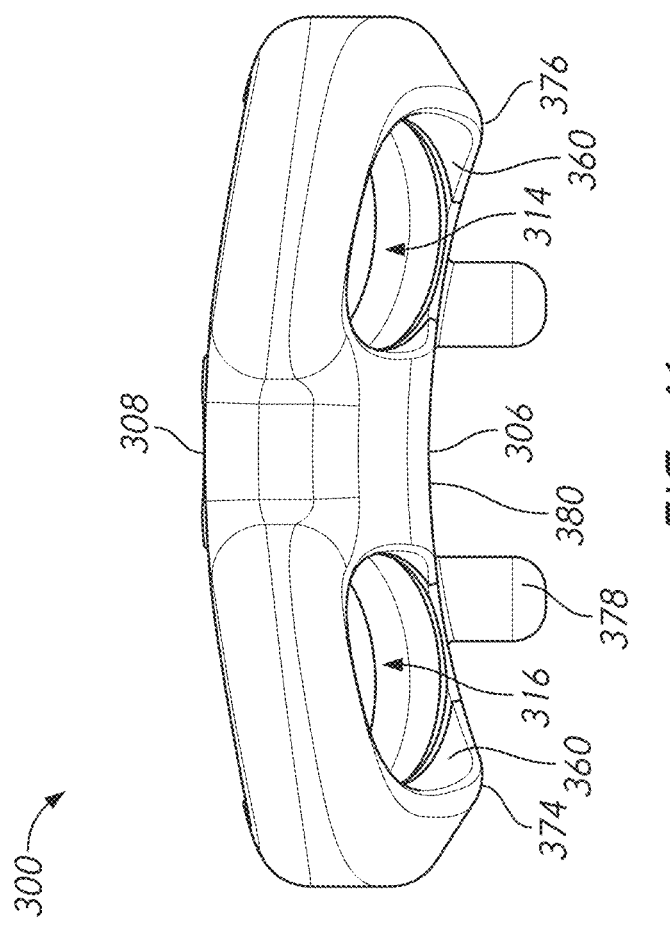
FIG. 11 is a side view of the cervical plate of FIG. 1.
Figure 12:
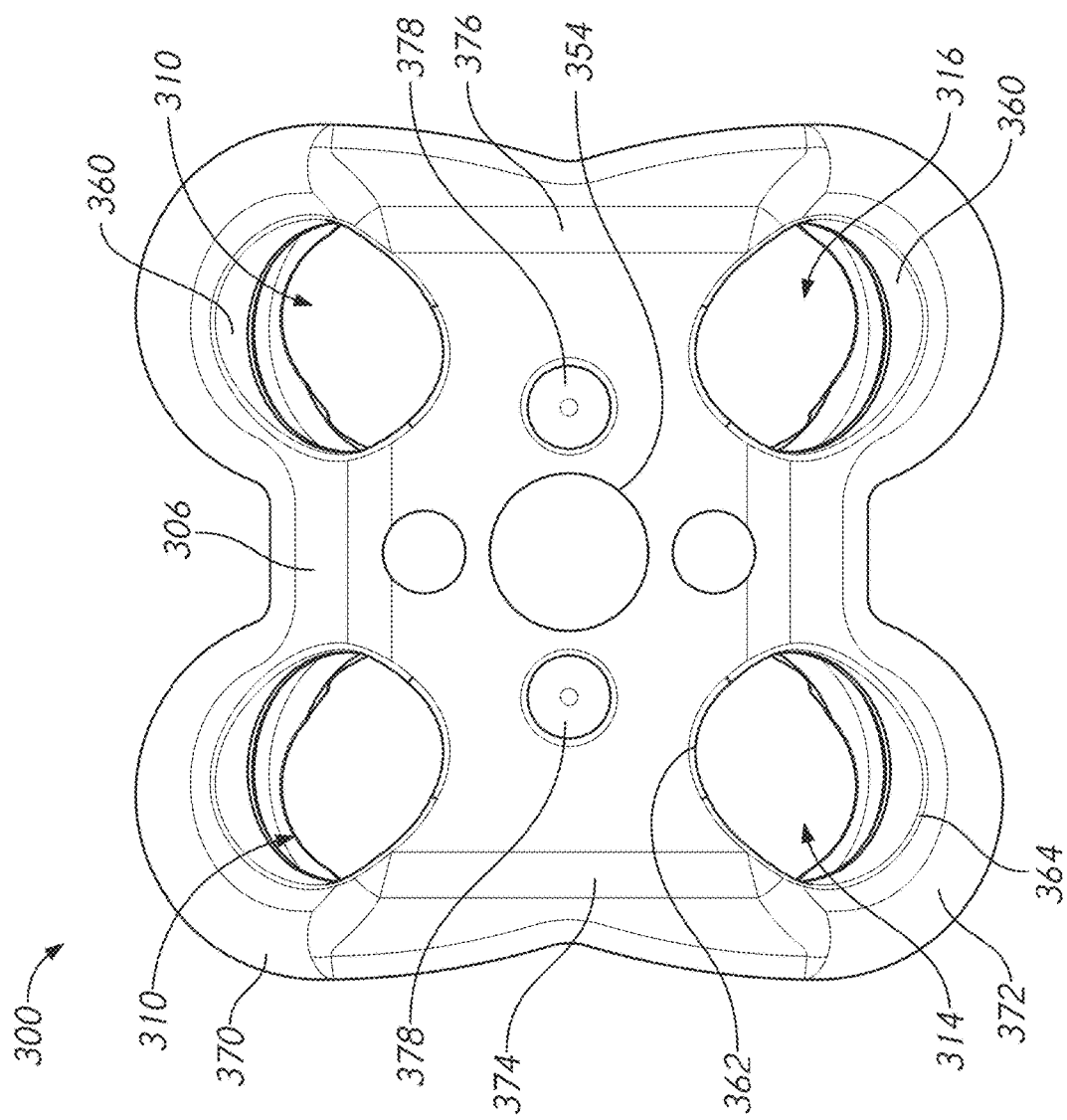
FIG. 12 is a bottom view of the cervical plate of FIG. 1.
Figure 13:
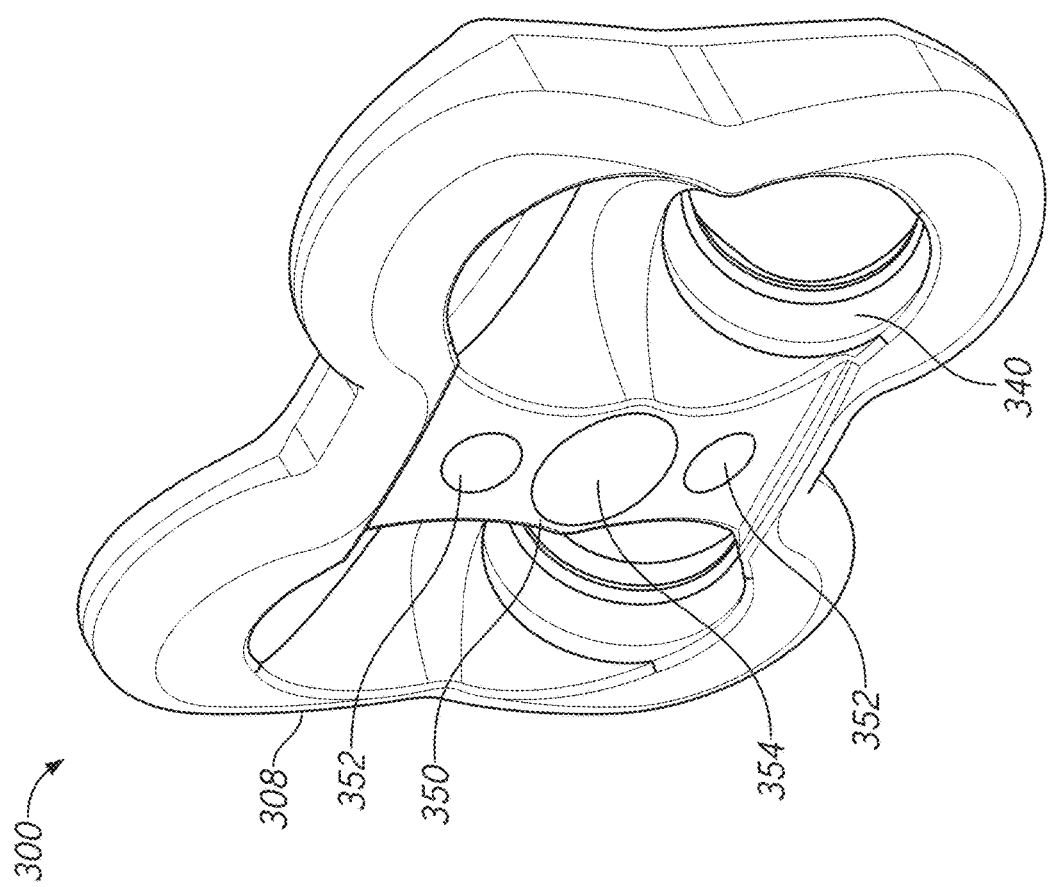
FIG. 13 is a perspective top view of the cervical plate of FIG. 1.
Figure 14:
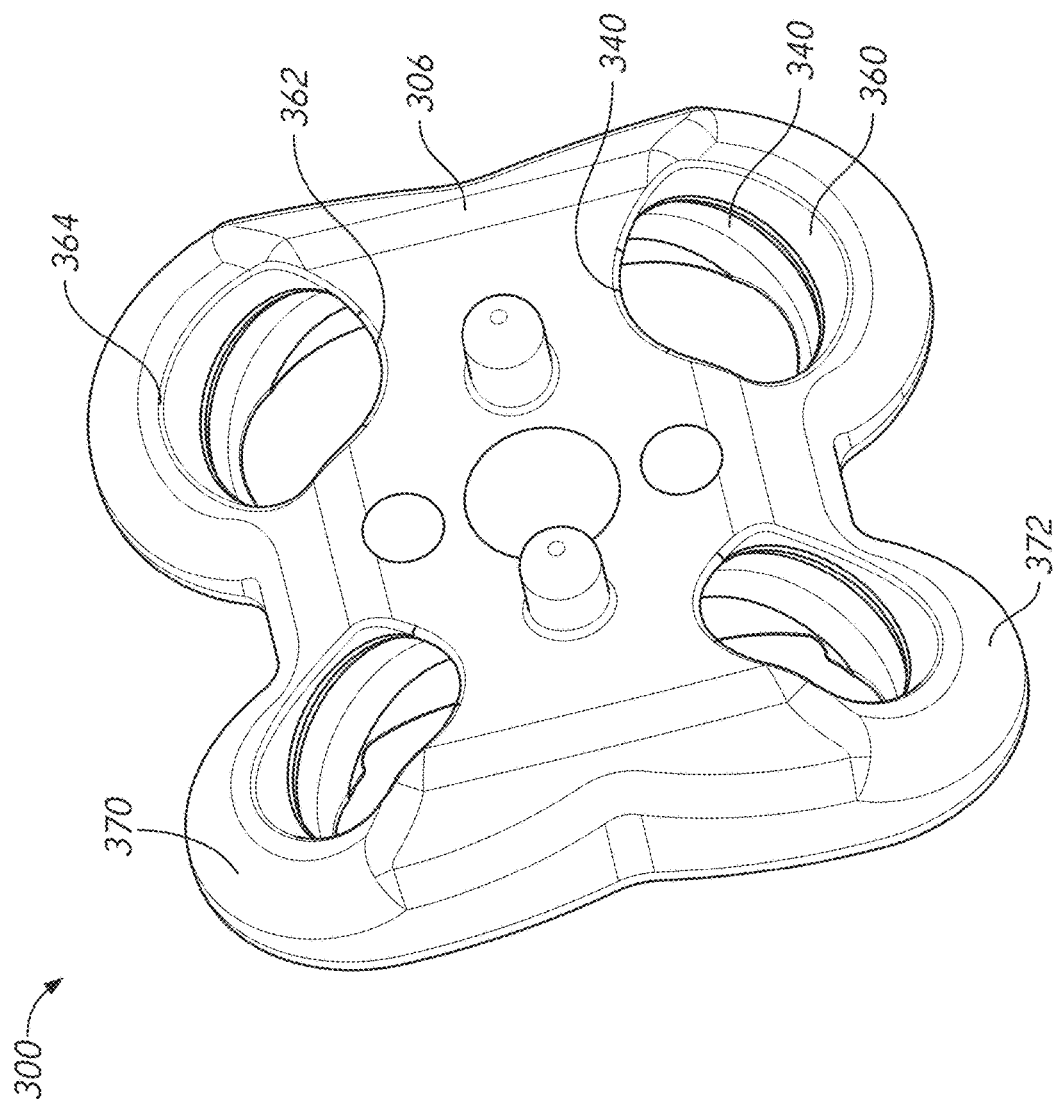
FIG. 14 is a perspective bottom view of the cervical plate of FIG. 1.

FIG. 10 illustrates a top view. FIG. 11 illustrates a side view. FIG. 12 illustrates a bottom view. FIG. 13 illustrates a top perspective view. FIG. 14 illustrates a bottom perspective view.

Figure 15:
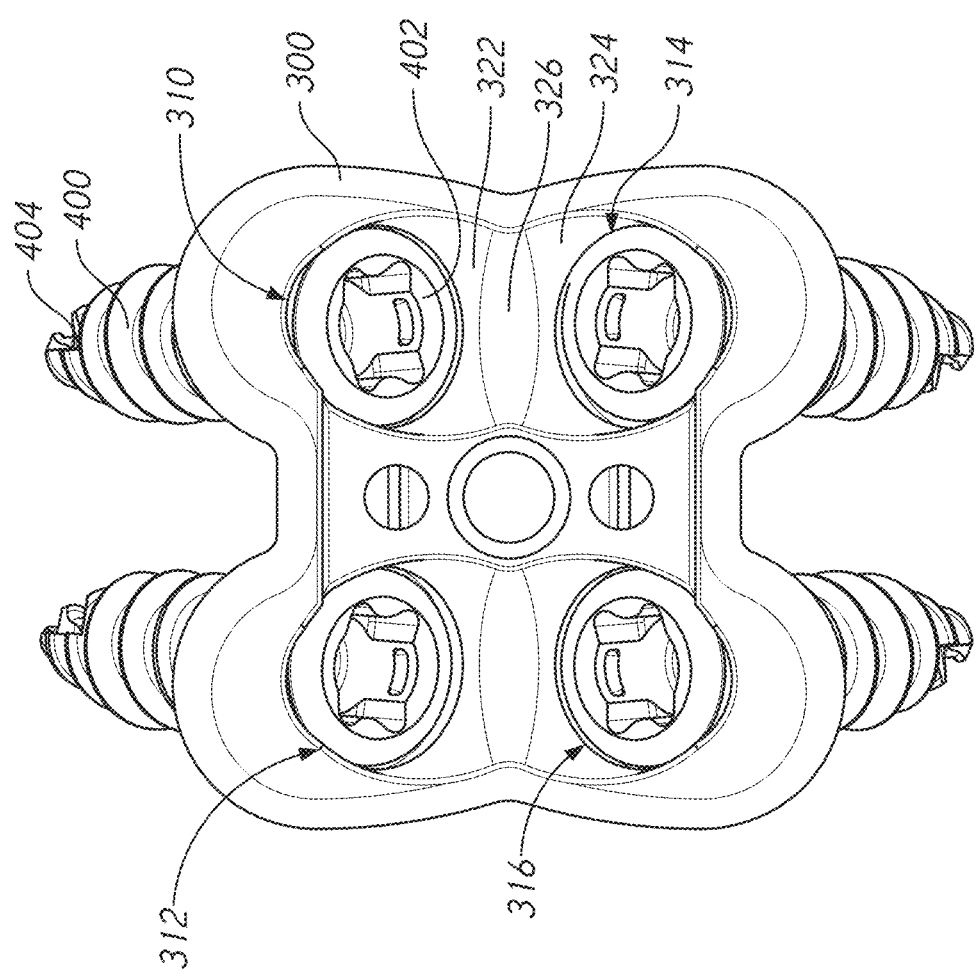
FIG. 15 is a top view of the cervical plate, the anchors, and the interbody implant of FIG. 1.
Figure 16:
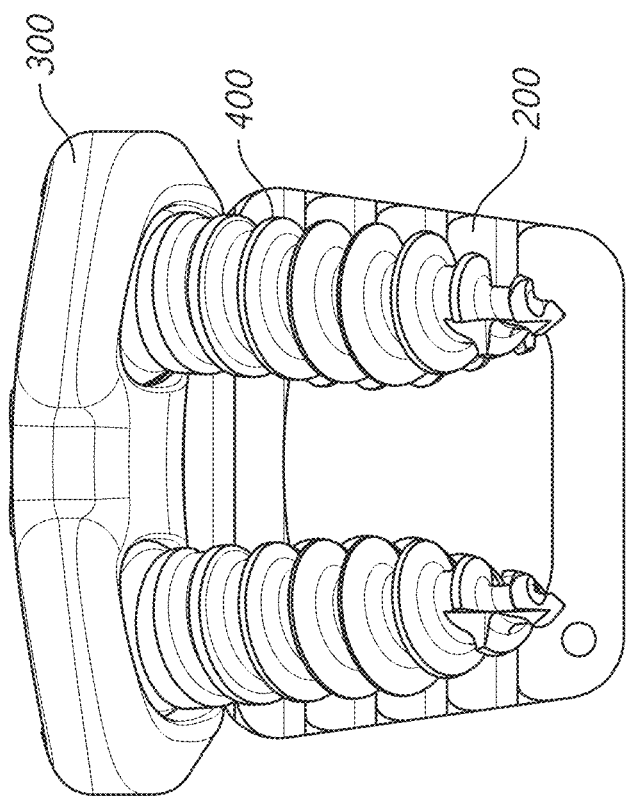
FIG. 16 is a side view of the cervical plate, the anchors, and the interbody implant of FIG. 1.
Figure 17:
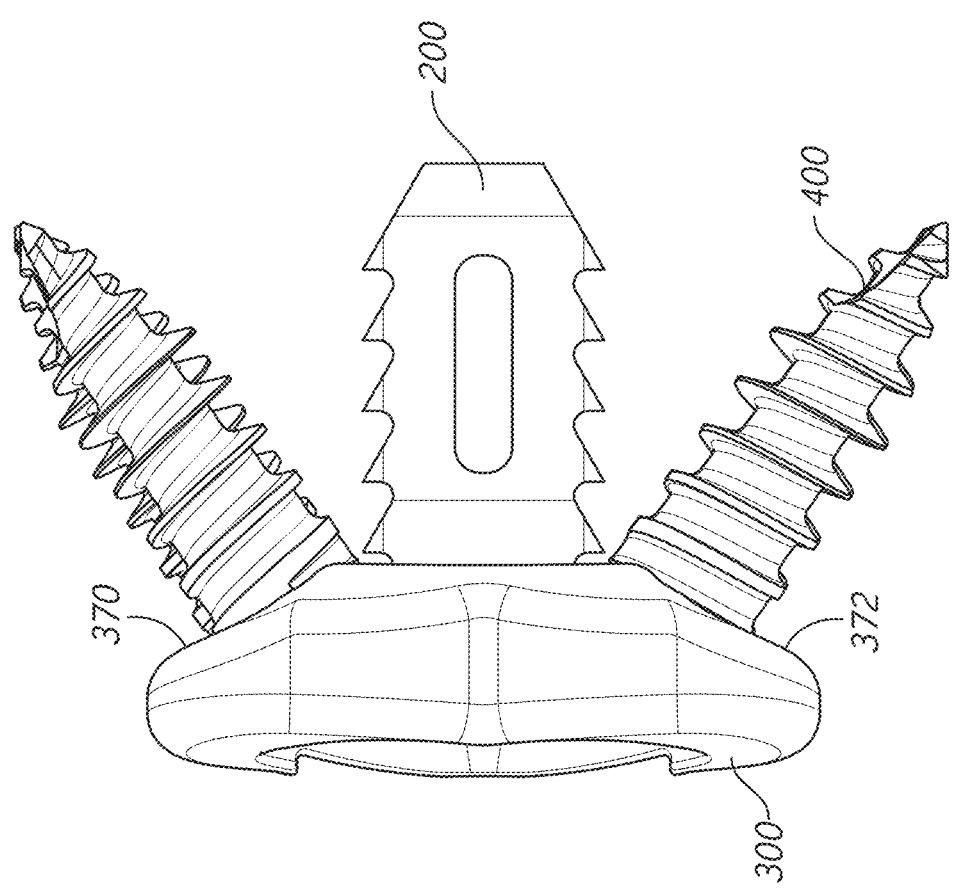
FIG. 17 is a side view of the cervical plate, the anchors, and the interbody implant of FIG. 1.
Figure 18:
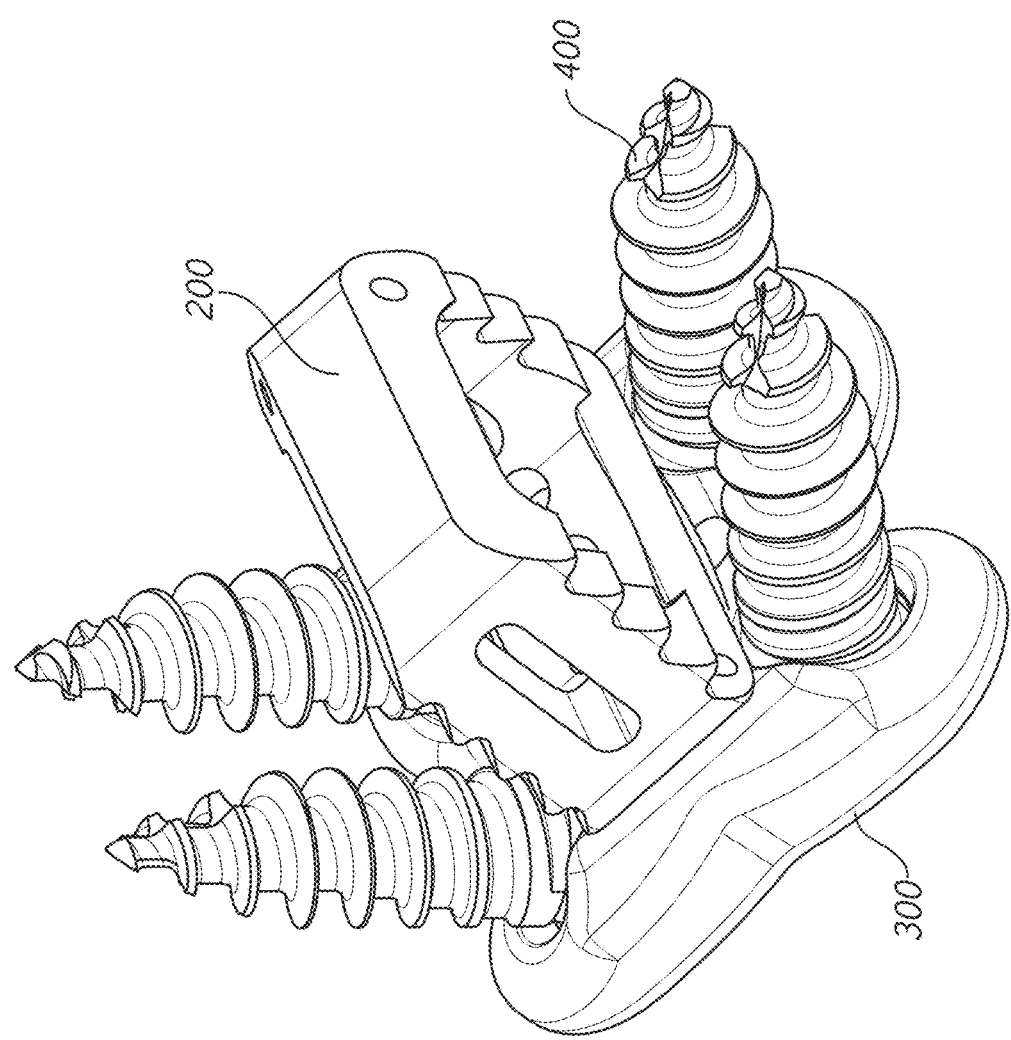
FIG. 18 is a bottom view of the cervical plate, the anchors, and the interbody implant of FIG. 1.

FIGS. 15-18 illustrate the interbody implant 200, the cervical plate 300, and anchors 400. FIG. 15 illustrates a top view. FIG. 16 illustrates a side view. FIG. 17 illustrates a side view. FIG. 18 illustrates a bottom perspective view.

Figure 19:
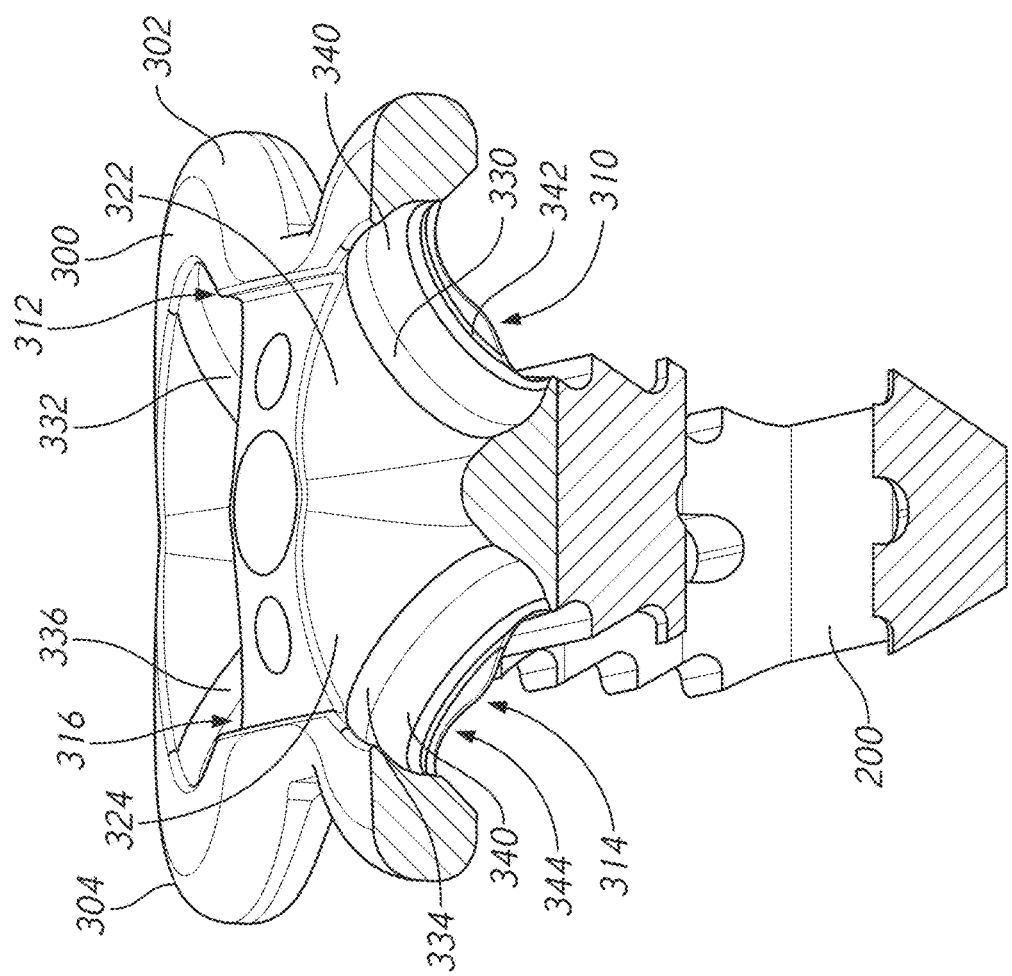
FIG. 19 is a cross-sectional view of the cervical plate and the interbody implant of FIG. 1.
Figure 20:
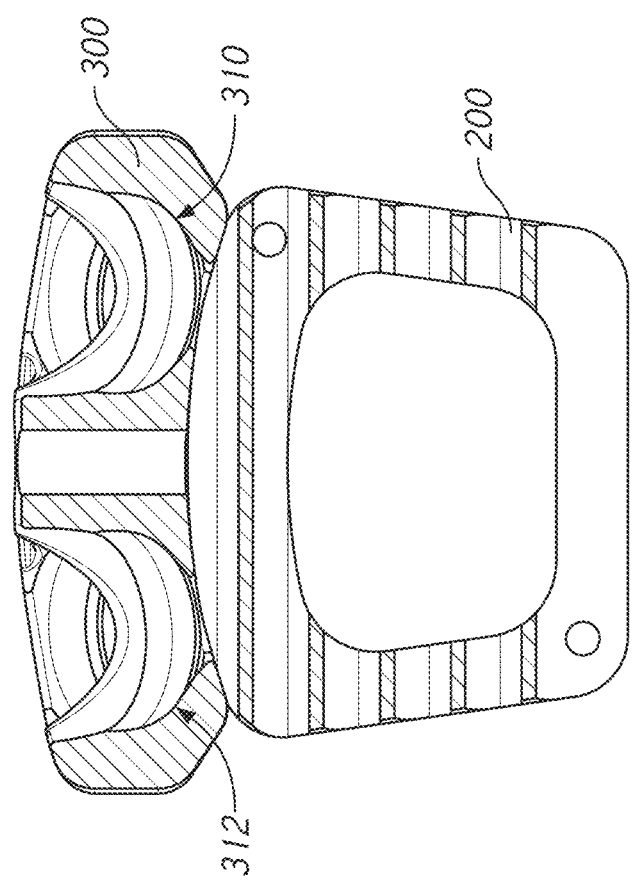
FIG. 20 is a cross-sectional view of the cervical plate and the interbody implant of FIG. 1.

FIGS. 19-20 illustrate cross-sectional views of the interbody implant 200 and the cervical plate 300. FIG. 19 illustrates a cross-sectional view through opposed holes. FIG. 20 illustrates a cross-sectional view through adjacent holes.

The cervical plate 300 can be designed to allow high angle anchor insertion. The anchor 400 can be inserted at any angle including 30°, 35°, 40°, 45°, 50°, 55°, 60°, 65°, 70°, between 30° and 35°, between 35° and 40°, between 40° and 45°, between 45° and 50°, between 30° and 40°, between 40° and 50°, between 50° and 60°, between 55° and 65°, between 60° and 70°, or any range of the foregoing values. The insertion angle can be an acute angle (e.g., 5°, 10°, 15°, 20°, 25°, 30°, 35°, 40°, 45°, 50°, 55°, 60°, 65°, 70°, 80°, 85°, between 30° and 40°, between 30° and 50°, between 60° and 70°, or any range of the foregoing values). The insertion angle can be within a range from 18° to 25°. The insertion angle can be within a range from 25° to 35°. The insertion angle can be within a range from 18° to 30.5°. The anchor 400 can be inserted at any of the foregoing angles relative to an anterior-posterior direction. The anchor 400 can be inserted at any of the foregoing angles relative to a horizontal axis. The anchor 400 can be inserted at any of the foregoing angles relative to a cranial-caudal direction. The anchor 400 can be inserted at any of the foregoing angles relative to a vertical axis.

The cervical plate 300 can be designed to be at least partially inserted within a disc space. The cervical plate 300 can couple to the interbody spacer 200. The cervical plate 300 can include a concavity to accept the interbody spacer 200 at least partially therewithin. The cervical plate 300 can include a lower surface which includes a concavity. The interbody spacer 200 can include a corresponding convexity. The cervical plate 300 can extend from the interbody space and at least partially around the corner or edge of adjacent vertebrae. The cervical plate 300 can be partially disposed within and flush with the intervertebral space. The cervical plate 300 can include a superior and inferior curve to match the curvature of the adjacent vertebrae. The cervical plate 300 can extend from the interbody space toward the edges or corners of the superior and inferior vertebra.

In some methods of use, the cervical plate 300 is configured to be placed adjacent to cervical vertebrae. These vertebrae have vertebral bodies which are oblong with a greater dimension side-to-side than anterior-to-posterior. The anterior and posterior surfaces of the bodies are generally flattened. The upper surface of the body is curved and has a projection. This upper projection can be formed of thicker cortical bone. The lower surface of the body is curved to accept the adjacent vertebra. The outer surface of the vertebra comprises corners or edges which transition from the anterior surface to the upper surface and the lower surface. The outer surface of the vertebra comprises corners or edges which transition from the posterior surface to the upper surface and the lower surface. The outer surface of the vertebra comprises corners or edges which transition from the anterior or posterior surface to the side surfaces. The corners or edges transition from a first surface or curvature to a second surface or curvature. The corners or edges can be rounded, concave, convex, curved, flat, generally flat, or any other shaped surface. The corners or edges can partially extend within the disc space. The corners or edges can be between the disc space and the anterior surface of the vertebra. The corners or edges can transition from a generally horizontal direction to a generally vertical direction. The corners or edges can transition from the anterior-posterior direction to the cranial-caudal direction.

The outer surface of a vertebra comprises cortical bone. Cortical bone can be denser and stronger than cancellous bone. Cancellous bone is spongy bone tissue which is disposed within the outer surface of the vertebra. Typically, the corners or edges of the vertebra include dense cortical bone. The corners or edges can include a thick layer of cortical bone.

The cervical plate 300 can be designed to facilitate insertion of the anchor into the edge or corner of the vertebra. The cervical plate 300 can include holes configured to guide the anchor 400 at the high angle toward the edge or corner. The anchor 400 can be guided into harder cortical bone. The anchor 400 can be inserted without impacting biomechanics.

The cervical plate 300 can be designed such that at least a portion of the hole is located within the disc space region.

The cervical plate 300 can include a ledge that supports the anchor head in the high angle position. The ledge can extend from the interbody space toward the adjacent vertebrae. The cervical plate 300 can be designed to completely recess the anchor head. In some embodiments, at least a portion of the anchor head is within the disc space region.

The cervical plate 300 can be considered a stabilization or fixation plate. The cervical plate 300 can include a superior portion 302 and an inferior portion 304. The cervical plate 300 can include a bone facing surface 306 and an access surface 308. In some embodiments, the bone facing surface 306 can contact the vertebral bone surface. In some embodiments, other structures or components may lie in between the bone facing surface 306 and the bone surface of the vertebra. The superior portion 302 can include one or more holes 310, 312 oriented between the bone facing surface 306 and the access surface 308. The inferior portion 304 can include one or more holes 314, 316 oriented between the bone facing surface 306 and the access surface 308.

The holes 310, 312, 314, 316 are configured to accept screws and/or other attachment devices for anchoring the cervical plate 300 to the vertebral bone. One or more anchors 400 configured for insertion through one or more holes 310, 312, 314, 316 in the cervical plate 300 can be provided. As shown in FIG. 15, each bone anchors 400 typically comprises an anchor head 402 and an anchor body 404. The bone anchors 400 may or may not be self-tapping. The anchor head 402 is adapted to interface with the cervical plate 300 to hold the cervical plate 300 against the adjacent vertebral bone structures. The anchor body 404 comprises threads or barbs for piercing or inserting into bone and fixing the position of the anchor head 402. The anchor head 402 may or may not form a mechanical interfit with the holes 310, 312, 314, 316 of the cervical plate 300 to further fix the position of the cervical plate 300 with respect to the vertebral bone.

Each hole 310, 312, 314, 316 of the cervical plate 300 need not have the same configuration or size. The hole 310, 312, 314, 316 is typically round in cross-section and dimensioned to allow passage of the anchor body 404 therethrough while resisting passage of the anchor head 402 completely through the hole 310, 312, 314, 316. In some embodiments, however, at least a portion of the hole 310, 312, 314, 316 may have a non-round cross-section, such as an oval, square, rectangle, polygonal or other closed shape. In some embodiments, the inside surface of the holes 310, 312, 314, 316 may be polished or coated to facilitate insertion and/or movement of the anchor 400.

The cervical plate 300 can include a first inside surface 320. The first inside surface 320 can be adjacent to the access surface 308. The first inside surface 320 can extend from the access surface 308 toward the holes 310, 314. The first inside surface 320 can connect to the holes 310, 314 below the surface of the access surface 308. The first inside surface 320 can be oblong. The first inside surface 320 can include a first lobe directed toward the hole 310 and a second lobe directed toward the hole 314. The first inside surface 320 can include a first curvature 322 directed toward the hole 310 and a second curvature 324 directed toward the hole 314. The first curvature 322 can be a mirror image of the second curvature 324. The first inside surface 320 can include a saddle 326. The saddle 326 can be disposed between the holes 310, 314. The saddle 326 can have a curvature to allow entry of the anchor 400 into either hole 310, 314.

In some embodiments, the cervical plate 300 can include a second inside surface 328. The second inside surface 328 can be adjacent to the access surface 308. The second inside surface 328 can extend from the access surface 308 toward the holes 312, 316. In some embodiments, the second inside surface 328 can be a mirror image of the first inside surface 320. The second inside surface 328 can have any of the features of the first inside surface 320. In some embodiments, either one or both of the first inside surface 320 and second inside surface 328 may be dimensioned to allow entry of the anchor 400 in a corresponding hole 310, 312, 314, 316.

FIG. 19 illustrates a cross-sectional view with the anchors removed to illustrate additional features of the holes 310, 312, 314, 316. The holes 310 and 314 are illustrated in cross-section. In some embodiments, the hole 312 can have the same configuration as hole 310. The holes 310, 312 can be located on the superior portion 302. In some embodiments, the hole 316 can have the same configuration as hole 314. In some embodiments, the hole 314 can have the mirror image configuration as the hole 310. In some embodiments, the hole 316 can have the mirror image configuration as the hole 312. The holes 314, 316 can be located on the inferior portion 304. FIG. 20 illustrates another cross-sectional view illustrating the holes 310 and 312.

The cervical plate 300 can include a trajectory surface 330, 332, 334, 336 corresponding to each hole 310, 312, 314, 316. The trajectory surface 330 of hole 310 and the trajectory surface 334 of hole 314 are illustrated in FIG. 19 in cross-section. In some embodiments, each trajectory surface 330, 332, 334, 336 corresponds to the trajectory of the anchor inserted through the hole 310, 312, 314, 316. In some embodiments, the hole 312 can have the same angle of trajectory as hole 310. In some embodiments, the hole 316 can have the same angle of trajectory as hole 314. In some embodiments, the trajectory surface 330, 332, 334, 336 has a diameter or cross-section to accommodate the anchor head 402. Each trajectory surface 330, 332, 334, 336 can have a constant diameter. Each trajectory surface 330, 332, 334, 336 can be a bored hole. Each trajectory surface 330, 332, 334, 336 can be shaped to allow the anchor 400 to maintain a constant trajectory from the access surface 308 to the bone facing surface 306 of the cervical plate 300. In some embodiments, the trajectory surface 330, 332, 334, 336 may be dimensioned to allow entry of the anchor 400 in generally one particular orientation or trajectory. In some embodiments, the trajectory surface 330, 332, 334, 336 may be dimensioned to allow entry of the anchor 400 in a range of trajectories.

In some embodiments, the trajectory surface 330, 332, 334, 336 can be dimensioned to allow for adjustment of the anchor 400. In some embodiments, the trajectory surface 330, 332, 334, 336 can have a diameter greater than the diameter of the anchor head 402. The trajectory surface 330, 332, 334, 336 can allow deviation from the trajectory by +/−3°, +/−5°, +/−10°, e.g. 0°, 1°, 2°, 3°, 4°, 5°, 6°, 7°, 8°, 9°, 10°, −1°, −2°, −3°, −4°, −5°, −6°, −7°, −8°, −9°, −10°, or any range of the foregoing values. For example, if the trajectory surface 330, 332, 334, 336 is designed with a screw insertion angle of 60°+/−3°, then the trajectory surface 330, 332, 334, 336 can accommodate anchors 400 inserted between 57° and 63°. Other configurations are contemplated.

In some embodiments, the trajectory surface 330, 332, 334, 336 extends to the access surface 308. Referring to FIG. 10, the interface 338 between the trajectory surface 330, 332, 334, 336 and the access surface 308 can have a curvature. In some embodiments, the curvature of the interface 338 matches the curvature of the corresponding trajectory surface 330, 332, 334, 336. The curvature of the interface 338 can flow or extend directly from the trajectory surface 330, 332, 334, 336. The interface 338 can be linearly aligned with the trajectory surface 330, 332, 334, 336. The interface 338 can be coaxial with the trajectory surface 330, 332, 334, 336. The interface 338 and the corresponding trajectory surface 330, 332, 334, 336 can form a continuous throughbore. The interface 338 allows the corresponding trajectory surface 330, 332, 334, 336 to extend to the access surface 308. In some embodiments, the interface 338 allows the anchor head 402 to be fully recessed. In some embodiments, the interface 338 allows the anchor head 402 to be inserted within the corresponding hole 310, 312, 314, 316 without changing the trajectory of the anchor 400 during insertion. The interface 346 between the first inside surface 320 and the access surface 308 can have a different curvature than the interface 338. The interface 348 between the second inside surface 328 and the access surface 308 can have a different curvature than the interface 338. The interface 338 can allow the anchor 400 to maintain a constant trajectory from the access surface 308 to the bone facing surface 306. The interface 338 can have a smaller radius of curvature than the interface 346, 348.

Referring back to the cross-sectional view of FIG. 19, the cervical plate 300 can include a ledge 340 corresponding to each hole 310, 312, 314, 336. The ledge 340 can be located below the trajectory surface 330, 332, 334, 336. The ledge 340 can be flat, curved, or tapered. The ledge 340 can include a curvature that corresponds to the curvature of the anchor head 402.

In some embodiments, the ledge 340 can be dimensioned to allow for adjustment of the anchor 400. In some embodiments, the ledge 340 can have a curved or poly-axial surface configured to accept the anchor head 402. In some embodiments, the ledge 340 can be concave. In some embodiments, the ledge 340 can have a concavity that corresponds to a convexity of the anchor head 402. The concavity of the ledge 340 can allow the anchor head 402 to have slight variations in insertion angle while still supporting the anchor head 402. The ledge 340 can allow deviation from the trajectory by +/−3°, +/−5°, +/−10°, e.g. 0°, 1°, 2°, 3°, 4°, 5°, 6°, 7°, 8°, 9°, 10°, −1°, −2°, −3°, −4°, −5°, −6°, −7°, −8°, −9°, −10°, or any range of the foregoing values. For example, if the ledge 340 is designed with a screw insertion angle of 35°+/−5°, then the ledge 340 can accommodate anchors 400 inserted between 30° and 40°. Other configurations are contemplated. In some embodiments, the ledge 340 may be dimensioned to allow entry of the anchor 400 in generally one particular orientation or trajectory. In some embodiments, the ledge 340 may be dimensioned to allow entry of the anchor 400 in a range of trajectories.

The ledge 340 can include a taper 342. The taper 342 can facilitate the entry of the anchor body 404. The ledge 340 surrounds an opening 344. The ledge 340 can be shaped to allow the anchor body 404 to pass through the opening 344. The ledge 340 can be shaped to prevent the anchor head 402 from passing through the opening 344. The ledge 340 can be sized according to the corresponding anchor 400. The ledge 340 can extend inward from the corresponding trajectory surface 330, 332, 334, 336. The opening 344 can have a smaller diameter or cross-section than the corresponding trajectory surface 330, 332, 334, 336. The ledge 340 can be disposed between the trajectory surface 330, 332, 334, 336 and the opening 344. In some embodiments, the taper 342 can be dimensioned to allow for adjustment of the anchor 400. The taper 342 can facilitate the passage of the anchor body 404 at slight variations in insertion angle. In some embodiments, the opening 344 can be dimensioned to allow for adjustment of the anchor 400. The opening 344 can have a diameter greater than the diameter of the anchor body 404. In some embodiments, one or more of the trajectory surface 330, 332, 334, 336, the ledge 340, the taper 342, and/or the opening 344 can be dimensioned to allow for adjustment of the angle of trajectory. In some embodiments, the hole 310, 312, 314, 316 allows for a range of trajectories, e.g., +/−3°, +/−5°, +/−10° from the axis of the hole 310, 312, 314, 316. In some embodiments, the hole 310, 312, 314, 316 allows movement of the anchor 400 within the hole 310, 312, 314, 316 during insertion. In some embodiments, the hole 310, 312, 314, 316 allows movement of the anchor 400 to better align with the corner or edge of the vertebral body. In some embodiments, the hole 310, 312, 314, 316 allows adjustment of the trajectory within a range.

In some embodiments, the ledge 340 can extend from the bone facing surface 306 toward the access surface 308. In some embodiments, the ledge 340 and the corresponding trajectory surface 330, 332, 334, 336 can extend from the bone facing surface 306 toward the access surface 308. In some embodiments, the ledge 340 can be a prominence of material on the underside of the cervical plate 300. In some embodiments, the bone facing surface 308 comprises a prominence of material near the hole 310, 312, 314, 316. In some embodiments, the prominence of material on the underside of the cervical plate 300 enables high angle screw insertion. In some embodiments, the prominence of material on the underside of the cervical plate 300 enables a portion of the cervical plate 300 to fit within the disc space. In some embodiments, the prominence of material on the underside of the cervical plate 300 enables the cervical plate 300 to curve around the natural geometry of the vertebra.

In some embodiments, the anchor 400 can travel along a constant trajectory from the access surface 308 to the bone facing surface 306 until the anchor head 402 contacts the ledge 340. The ledge 340 can limit or prevent further movement along the trajectory. The anchor 400 can be tightened until the anchor head 402 provides a compressive force on the ledge 340. The ledge 340 can be configured to have direct surface contact with at least a portion of the anchor head 402.

The ledge 340 can function to orient the anchor 400 within the corresponding hole 310, 312, 314, 336. The ledge 340 can function to support the anchor 400 at the high insertion angle. The anchor 400 is typically selected so that the largest diameter of the anchor head 402 is larger than the diameter or cross-section of the opening 344. In some embodiments, the largest diameter of the anchor head 402 may be equal or less than the diameter of the trajectory surface 330, 332, 334, 336. In some embodiments, the largest diameter of the anchor head 402 is smaller than the trajectory surface 330, 332, 334, 336 but larger than the opening 344.

The anchor 400 is typically selected so that the thickness of the anchor head 402 is equal to or less than the thickness of trajectory surface 330, 332, 334, 336. In the illustrated embodiment, the anchor 400 is configured to be flush or completely recessed within the cervical plate 300. In some embodiments, the anchor 400 is configured to be partially recessed within the cervical plate 300. In some embodiments, the anchor 400 is a non-recessed anchor.

In some embodiment, each hole 310, 312, 314, 316 may have a diameter of the trajectory surface 330, 332, 334, 336 of about 3 mm to about 10 mm. In some embodiments, each hole 310, 312, 314, 316 may have a diameter of the opening 344 of about 2 mm to about 8 mm. The ledge 340 can have a radial measurement of between 2 mm and 4 mm. In some embodiments, the hole 310, 312, 314, 316 may have a diameter of the opening 344 of about 0.1 mm to about 4.0 mm smaller than the trajectory surface 330, 332, 334, 336. In some embodiments, the anchor head 402 may have a diameter of about 3 mm to about 10 mm.

In some embodiments, the trajectory surface 330, 332, 334, 336 may be partial or incomplete. The trajectory surface 330, 332, 334, 336 may be adapted for partial recessed positioning of the anchor head 402. In some embodiments, the trajectory surface 330, 332, 334, 336 may be complete, forming a bored hole. The trajectory surface 330, 332, 334, 336 may be adapted for completed recessed positioning of the anchor head 402. In some embodiments, the ledge 340 may be partial or incomplete. In some embodiments, the ledge 340 may be complete and circumferential. With partial recessed positioning, only a portion of the inserted anchor 400 lies below the access surface 308 of the cervical plate 300. With complete recessed positioning, the entire anchor head 402 lies at or below the access surface 308 of the cervical plate 300.

Referring to FIGS. 15-17, the anchor 400 can be configured for complete recessed positioning. In some embodiments, the anchors 400 inserted within the holes 310, 312 are parallel. In some embodiments, the anchors 400 inserted within the holes 310, 314 are skewed. The angle between the anchors inserted within the holes 310, 314 can be 75°, 80°, 85°, 90°, 95°, 100°, 105°, 110°, 115°, 120°, 125°, 130°, 135°, 140°, 145°, 150°, between 80° and 100°, between 90° and 110°, or any range of the foregoing values).

In some embodiments, the ledge 340 is configured to align the anchor 400 having a general angled or skewed orientation with respect to either or both the access surface 308 or bone facing surface 306 of the cervical plate 300. In some embodiments, the ledge 340 is configured to align the anchor 400 at a superior or inferior angle, depending upon whether the hole 310, 312, 314, 316 is located on the superior portion 302 or inferior portion 304, respectively. The ledge 340 provides support for the anchor 400 in the skewed orientation. The skewed orientation of the anchor 400 may allow the anchor 400 to engage the adjacent vertebrae to increase purchase into stronger cortical bone.

In some embodiments, the ledge 340 can support the anchor 400 in an orientation that is within the range of about 0° to about 60° with respect to the coronal plane. In one embodiment, the hole is configured to accept the anchor 400 in an orientation that is within the range of about 30° to about 40° to the coronal plane. In some embodiments, the ledge 340 can support the anchor 400 in an orientation that is within the range of about 0° to about 60° with respect to the transverse plane. In one embodiment, the hole is configured to accept the anchor 400 in an orientation that is within the range of about 30° to about 40° to the transverse plane. In some embodiments, the ledge 340 can support the anchor 400 in an orientation that is within the range of about 0° to about 60° with respect to the sagittal plane. In one embodiment, the hole is configured to accept the anchor 400 in an orientation that is within the range of about 30° to about 40° to the sagittal plane. The particular orientation of the anchor 400 may be determined by inclination of the ledge 340.

In some embodiments, one or more additional structures are provided to further interact with the anchor. In some embodiments, the anchor may include an expandable or collapsible retainer ring. The trajectory surface 330, 332, 334, 336 can include a corresponding recess or indentation to accept the retainer ring. The retainer ring may be positioned within one or more holes 310, 312, 314, 316 with a recess or indentation along at least a portion of its circumference capable of accepting at least the outside diameter portion of the retainer ring. The recess or indentation typically comprises a circumferential channel having a diameter greater than the diameter of the trajectory surface 330, 332, 334, 336.

The retainer ring allows insertion of the anchor 400 in one direction but resists movement of the anchor 400 in the opposite direction. The retainer ring can resist backout of the anchor 400. The backout forces acting on the anchor 400 may be insufficient to cause movement of the retainer ring and the anchor 400. In some embodiments, the retainer ring has a completely closed configuration. The cross-sectional shape of the retainer structure may be any of a variety shapes, including a circle, oval, squares, rectangles, polygonal or other closed shape.

Referring to FIG. 13, the access surface 308 can include an engagement portion 350. The engagement portion 350 can be recessed. The engagement portion 350 can be configured to engage the outer shaft 140 of the interbody implant inserter 100. The engagement portion 350 can include a lumen 352. In the illustrated embodiment, the engagement portion 350 can include two lumens 352. The engagement portion 350 can include a lumen 352 for each projection 146 of the outer shaft 140 of the interbody implant inserter 100. The lumen 352 can have a circular cross-sectional shape. The lumen 352 can have a non-circular cross-sectional shape.

The outer shaft 140 can couple to the engagement portion 350 of the cervical plate 300. In some embodiments, the one or more projections 146 can couple with corresponding lumens 352 in the cervical plate 300. The engagement portion 350 can be flat, tapered, or curved. The engagement portion 350 can have a corresponding shape as the supports 144 of the outer shaft 140. The supports 144 of the outer shaft 140 can be shaped to fit within the recessed engagement portion 350.

The engagement portion 350 can include an interbody lumen 354. In the illustrated embodiment, the engagement portion 350 can include one interbody lumen 354. The interbody lumen 354 can be centrally located. The interbody lumen 354 can have a circular cross-sectional shape. The interbody lumen 354 can have a non-circular cross-sectional shape. The interbody lumen 354 can be threaded. In the illustrated embodiment, the interbody lumen 354 is not threaded.

The internal shaft 120 of the interbody implant inserter 100 can couple to the interbody implant 200. The distal end of the internal shaft 120 can extend through the interbody lumen 354 of the cervical plate 300. The distal end of the internal shaft 120 can include the second threaded portion 126. The second threaded portion 126 can couple with the threaded lumen 224 in the interbody spacer 200. The interbody lumen 354 can have a greater diameter or cross-sectional measurement than the second threaded portion 126 of the internal shaft 120. In some embodiments, the threaded lumen 224 of the interbody spacer 200 is adapted to form a rotatable mechanical interfit with the second threaded portion 126 on the internal shaft 120 inserted through the interbody lumen 354. When the internal shaft 120 is coupled to the interbody spacer 200, the outer shaft 140 can be firmly seated against the engagement portion 350 of the cervical plate 300.

The engagement portion 350 of the cervical plate 300 can be oriented perpendicular to the anterior surface 202 of the interbody implant 200 when the interbody implant 200 is coupled to the cervical plate 300. The interbody implant 200 can be configured to occupy the disc space between adjacent vertebrae. The interbody implant 200 extends between the superior and inferior vertebra. The interbody implant inserter 100 can be oriented perpendicular to the anterior surface 202 of the interbody implant 200. The interbody implant inserter 100 can be oriented in a general inferior-superior direction. The outer shaft 140 can be oriented in a general inferior-superior direction. The interbody implant inserter 100 can be oriented in any manner. In some embodiments, the interbody implant inserter 100 is oriented to allow access to the holes 310, 312, 314, 316.

In use, the interbody implant 200 extends from the bone facing surface 306 of the cervical plate 300. The interbody implant 200 is illustrated as a separate component. In some embodiments, the interbody implant 200 can integrated with the bone facing surface 306 of the cervical plate 300. In some embodiments, the interbody implant 200 and the cervical plate 300 can form a unitary or monolithic structure.

FIGS. 11 and 12 illustrate the bone facing surface 306 of the cervical plate 300. Each hole 310, 312, 314, 316 can include a bone facing inside surface 360. The bone facing inside surface 360 can be adjacent to the bone facing surface 306. The bone facing inside surface 360 can extend from the bone facing surface 306 to the ledge 340. The bone facing inside surface 360 can have a larger diameter or cross-sectional opening than the opening 344 of the ledge 340. The bone facing inside surface 360 can be oblong. The bone facing inside surface 360 can include a curvature. The bone facing inside surface 360 can extend to bone facing surface 306 at a location toward an outward facing section of the hole 310, 312, 314, 316.

The ledge 340 can be skewed in order to support the anchor 400 in a high angle orientation. In some embodiments, the ledge 340 can extend to bone facing surface 306. In the illustrated embodiment, a portion of the ledge 340 extends to bone facing surface 306, for instance 90 degrees of the ledge extends to the bone facing surface 306. In some embodiments, the ledge 340 does not extend to the bone facing surface 306. The bone facing inside surface 360 can be provided between the entire ledge 340 and the bone facing surface 306, or a portion thereof. The ledge 340 can extend to bone facing surface 306 at a location toward an inward facing section of the hole 310, 312, 314, 316. The interface 362 between the ledge 340 and the bone facing surface 306 can have a curvature corresponding to the curvature of the ledge 340. The interface 364 between the bone facing surface 306 and the bone facing inside surface 360 can have a different curvature than the interface 362.

The bone facing surface 306 can include a superior curvature 370. The superior curvature 370 can extend from a portion of the holes 310, 312. The superior curvature 370 can curve inward toward the access surface 308. The superior curvature 370 can follow the direction of the ledge 340. The superior curvature 370 can extend from the interface 364 between the bone facing surface 306 and the bone facing inside surface 360. The superior curvature 370 can reduce the thickness of the cervical plate 300. The superior curvature 370 can correspond or match the curvature of the superior vertebra. The superior curvature 370 can allow the bone facing surface 306 to lie flush against the superior vertebra. The superior curvature 370 can have any shape to match the general shape of the edge or corner of the corresponding vertebra. The superior curvature 370 can have any shape that allows the cervical plate 300 to be flush with a surface of the vertebra.

The bone facing surface 306 can include an inferior curvature 372. The inferior curvature 372 can extend from a portion of the holes 314, 316. The inferior curvature 372 can be the mirror image of the superior curvature 370. The inferior curvature 372 can be non-symmetric relative to the superior curvature 370. The inferior curvature 372 can be shaped to allow contouring of the superior curvature 370 and inferior curvature 372 to the corresponding cervical vertebrae. The inferior curvature 372 can be the same or similar to the superior curvature 370. The inferior curvature 372 can be different than the superior curvature 370. The inferior curvature 372 can have a larger radius of curvature than the superior curvature 370. The inferior curvature 372 can have a smaller radius of curvature than the superior curvature 370. The inferior curvature 372 can have any of the features of the superior curvature 370. The inferior curvature 372 can correspond or match the curvature of the inferior vertebra. The inferior curvature 372 can allow the bone facing surface 306 to lie flush against the inferior vertebra. The inferior curvature 372 can have any shape to match the general shape of the edge or corner of the corresponding vertebra. The inferior curvature 372 can have any shape that allows the cervical plate 300 to be flush with a surface of the vertebra. FIG. 17 illustrates a side view of the superior curvature 370 and the inferior curvature 372. In some embodiments, the superior curvature 370 and the inferior curvature 372 are not planar. Rather, the superior curvature 370 and the inferior curvature 372 form curved surfaces designed to match the curved surface of the anatomy. The superior curvature 370 and the inferior curvature 372 extend distally and inwardly forming concave surfaces. The superior curvature 370 and the inferior curvature 372 form an abutting surface with at least a portion of the native anatomy, for instance, a corner or edge of the vertebral body.

The bone facing surface 306 can include a first interbody ledge 374. The first interbody ledge 374 can extend from a portion of the holes 310, 314. The bone facing surface 306 can include a second interbody ledge 376. The second interbody ledge 376 can extend from a portion of the holes 312, 316. The first interbody ledge 374 and the second interbody ledge 376 can curve outward such that the first interbody ledge 374 and the second interbody ledge 376 form a distal portion of the bone facing surface 306. The first interbody ledge 374 and the second interbody ledge 376 can be convex.

The bone facing surface 306 can include a projection 378. In the illustrated embodiment, the bone facing surface 306 can include two projections 378. Referring to FIG. 8, the anterior surface 202 of interbody implant 200 can include two guide lumens 226. The two guide lumens 226 can be diametrically opposed relative to the threaded lumen 224. The projection 378 and the corresponding guide lumen 226 can have a circular cross-sectional shape. The projection 378 and the corresponding guide lumen 226 can have a non-circular cross-sectional shape. The projection 378 and the corresponding guide lumen 226 can function to couple the cervical plate 300 to the interbody implant 200.

The bone facing surface 306 can include a central curvature 380. The central curvature 380 can extend between the first interbody ledge 374 and the second interbody ledge 376. The central curvature 380 can be concave. The central curvature 380 can accommodate the anterior surface 202 of the interbody spacer 200. In the illustrated embodiment, the anterior surface 202 comprises the convex portion 222. The central curvature 380 of the bone facing surface 306 and the convex portion 222 of the interbody spacer 200 can be correspondingly curved.

The cervical plate 300 can have a generally flat configuration, curved configuration, or combination thereof.

Optionally, each surface of the cervical plate 300 may also have a generally flat or curved configuration or combination thereof. Each surface of the cervical plate 300 need not have the same configuration. The edges of the cervical plate 300 may optionally be rounded, smoothed or polished. In some embodiments, the cervical plate 300 is dimensioned to extend generally about 1 mm to about 20 mm beyond an edge of a perimeter of the interbody implant 200 at its interface with the cervical plate 300. The cervical plate 300 may or may not extend uniformly along the edges of the interbody implant 200. The shape of the cervical plate 300 may be larger in perimeter than the interbody implant 200.

In some embodiments, the average thickness of the cervical plate 300 is within the range of about 1 mm to about 5 mm. In other embodiments, the average thickness of the cervical plate 300 is within the range of about 1.5 mm to about 3.0 mm. The thicknesses of the cervical plate 300 need not to be uniform. In some embodiments, the cervical plate 300 is conformable to the vertebral surfaces of the implantation sites.

The cervical plate 300 can be made from a material that is the same or different from the interbody implant 200. In some embodiments, a cervical plate 300 and an interbody implant 200 having different materials may be beneficial because the interbody implant 200 may be configured to withstand compressive forces while the cervical plate 300 is configured to withstand primarily tension forces.

In some embodiments, the interbody implant 200 comprises a polyaryl polymer, including but not limited to PEK, PEEK, PEKK, PEKEKK or a blend thereof, and the cervical plate 300 comprises a titanium or titanium alloy. Other combination may also be used as is known by those with skill in the art.

5. Two-Level Cervical Plate

Figure 21:
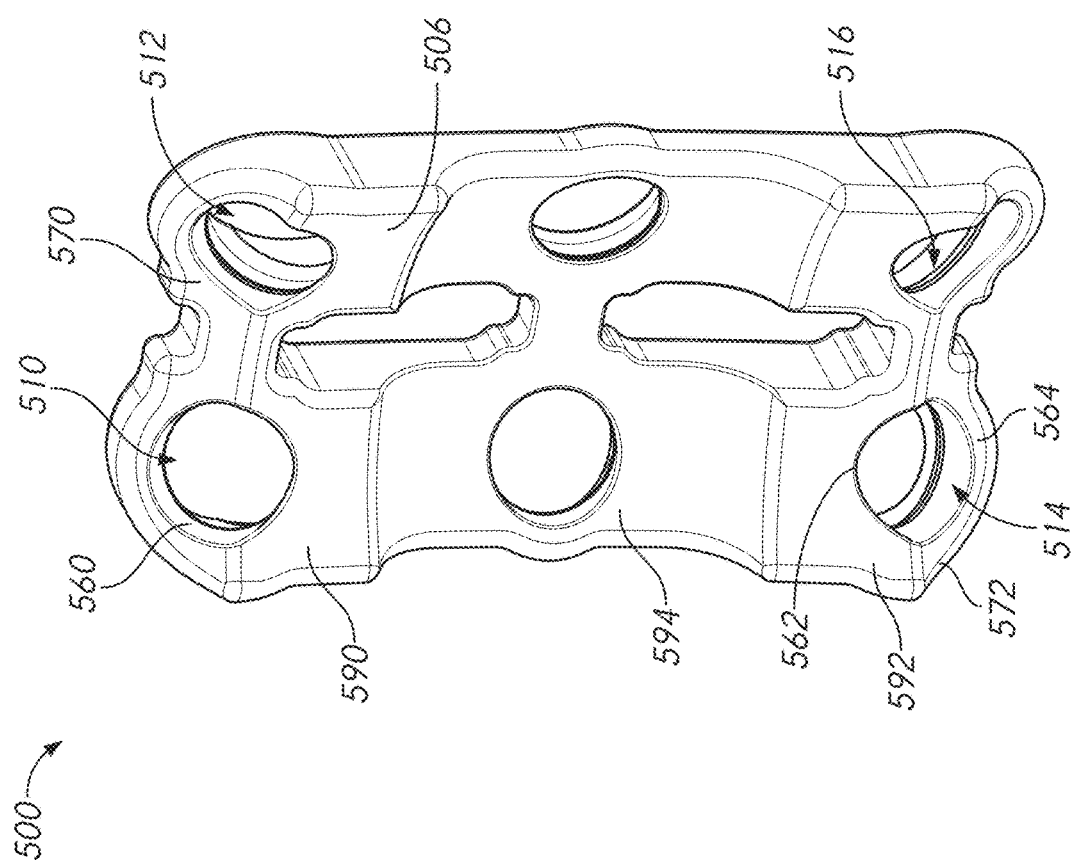
FIG. 21 is a perspective top view of an embodiment of a cervical plate.
Figure 22:
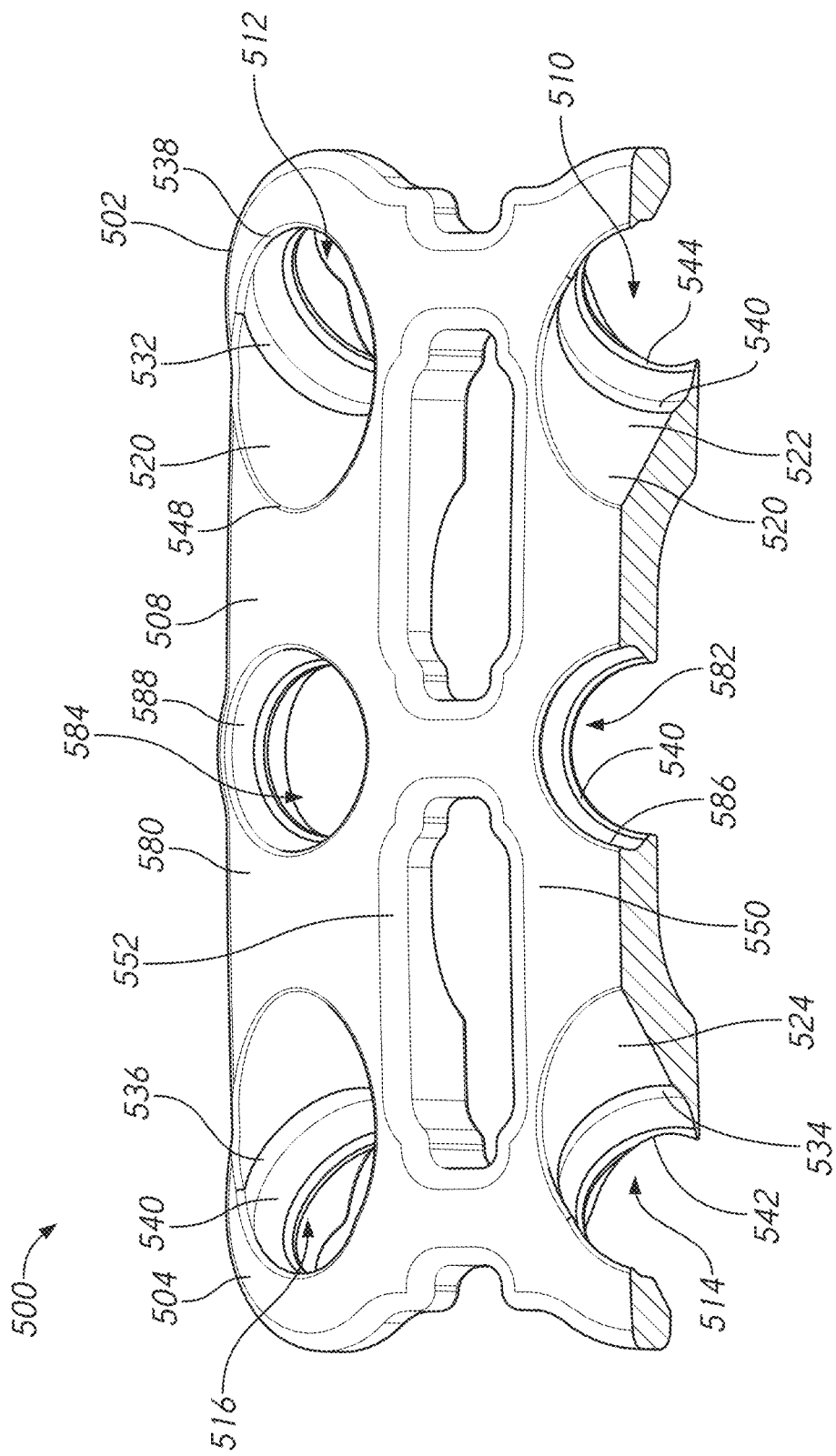
FIG. 22 is a cross-sectional view of the cervical plate of FIG. 21.
Figure 23:
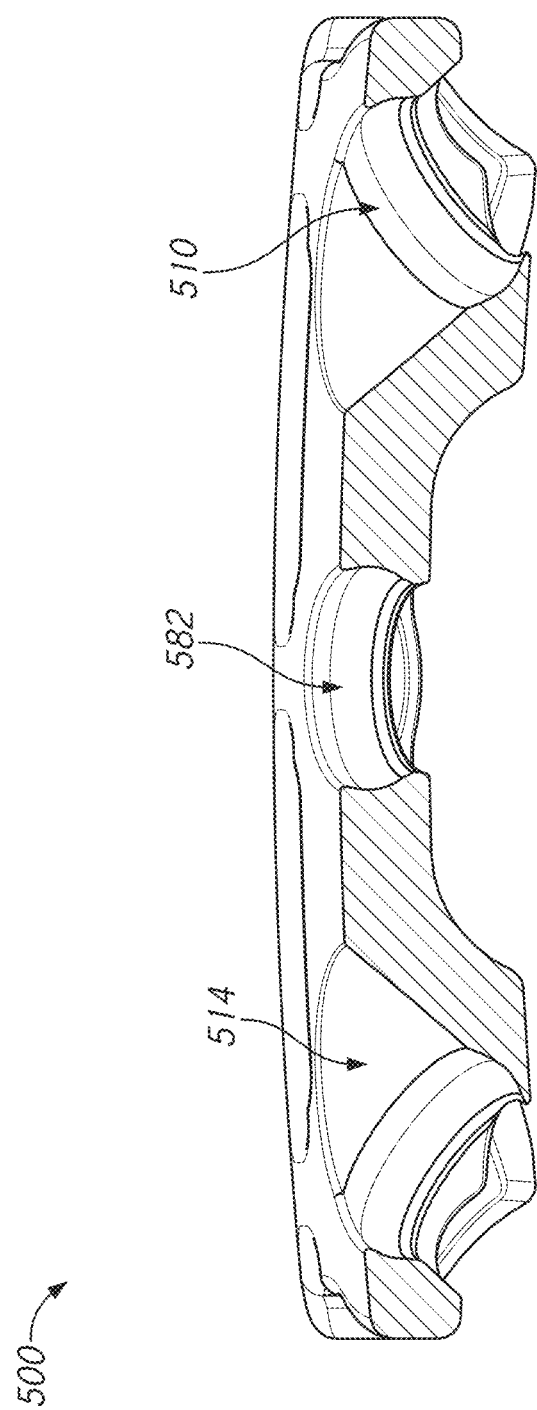
FIG. 23 is a cross-sectional view of the cervical plate of FIG. 21.
Figure 24:
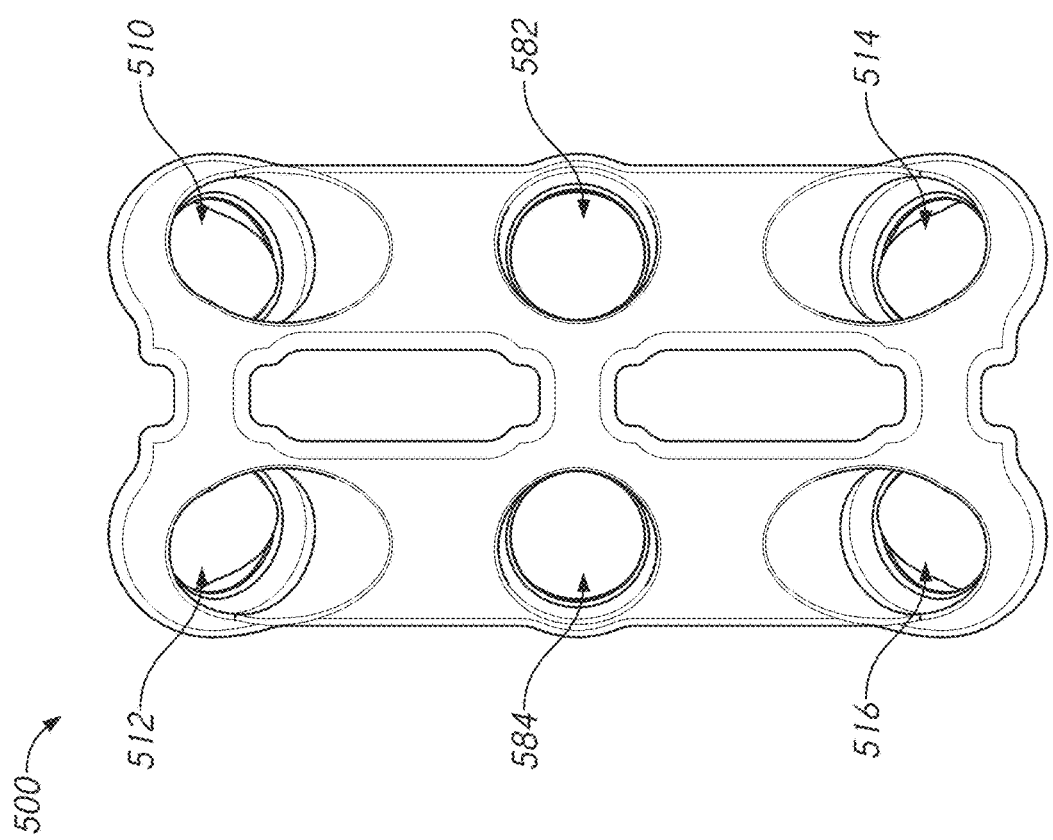
FIG. 24 is a top view of the cervical plate of FIG. 21.
Figure 25:
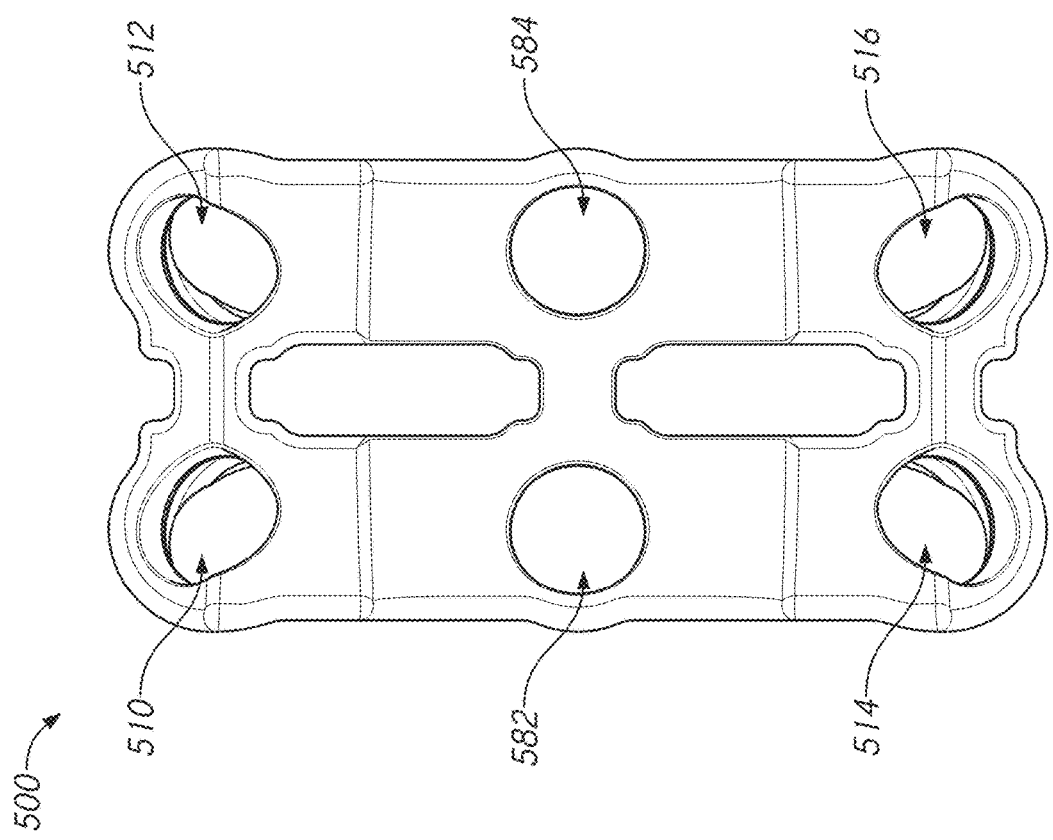
FIG. 25 is a bottom view of the cervical plate of FIG. 21.

FIGS. 21-25 depict views of an embodiment of the two-level cervical plate 500. FIG. 21 illustrates a perspective view. FIG. 22 illustrates a top cross-sectional view. FIG. 23 illustrates a side cross-sectional view. FIG. 24 illustrates a top view. FIG. 25 illustrates a bottom view.

The two-level cervical plate 500 can be designed to allow high angle anchor insertion. The anchor 400 can be inserted at 30°, 35°, 40°, between 30° and 35°, between 35° and 40°, between 30° and 40°, or any range of the foregoing values. The two-level cervical plate 500 can have any of the features of the cervical plate 300 described herein.

The two-level cervical plate 500 can include a superior portion 502 and an inferior portion 504. The two-level cervical plate 500 can include a bone facing surface 506 and an access surface 508. In some embodiments, the bone facing surface 506 can contact the vertebral bone surface. In some embodiments, other structures or components may lie inbetween the bone facing surface 506 and the bone surface of the vertebra. The superior portion 502 can include one or more holes 510, 512 oriented between the bone facing surface 506 and the access surface 508. The inferior portion 504 can include one or more holes 514, 516 oriented between the bone facing surface 506 and the access surface 508.

The two-level cervical plate 500 can include a middle portion 580. The middle portion 580 can be disposed between the superior portion 502 and an inferior portion 504. The middle portion 580 can include one or more holes 582, 584 oriented between the bone facing surface 506 and the access surface 508.

The holes 510, 512, 514, 516, 582, 584 are configured to accept screws and/or other attachment devices for anchoring the two-level cervical plate 500 to the vertebral bone. One or more anchors 400 configured for insertion through one or more holes 510, 512, 514, 516, 582, 584 in the two-level cervical plate 500 can be provided. The anchors 400 can have any of the features described herein including the anchor head 402 and the anchor body 404.

Each hole 510, 512, 514, 516, 582, 584 of the cervical plate 500 need not have the same configuration or size. The holes 510, 512, 514, 516, 582, 584 are typically rounded or oblong in cross-section and dimensioned to allow passage of the anchor body 404 therethrough while resisting passage of the anchor head 402 completely through the hole 510, 512, 514, 516, 582, 584.

FIGS. 22-23 illustrate a cross-sectional view. The holes 510, 582, and 514 are illustrated in cross-section. In some embodiments, the hole 512 can have the same configuration as hole 510. The holes 510, 512 can be located on the superior portion 502. In some embodiments, the hole 516 can have the same configuration as hole 514. In some embodiments, the hole 514 can have the mirror image configuration as the hole 510. In some embodiments, the hole 516 can have the mirror image configuration as the hole 512. The holes 514, 516 can be located on the inferior portion 504. In some embodiments, the hole 584 can have the same configuration as hole 582. The holes 582, 584 can be located on the middle portion 580.

In some embodiments, each hole 510, 512, 514, 516 can include an inside surface 520. The inside surfaces 520 can be adjacent to the access surface 508. The inside surfaces 520 can extend from the access surface 508 toward each hole 510, 512, 514, 516. The inside surfaces 520 corresponding to the holes 510, 512 can be identical or substantially similar. The inside surfaces 520 corresponding to the holes 514, 516 can be identical or substantially similar. The inside surfaces 520 can be an angled entry from the access surface 508. The inside surfaces 520 can be oblong. In some embodiments, the inside surface 520 can have a first diameter or cross-sectional shape. The inside surface 520 can include a first curvature 522 directed toward the hole 510 and a second curvature 524 directed toward the hole 514. In some embodiments, the first curvature 522 can be a mirror image of the second curvature 524.

In some embodiments, the two-level cervical plate 500 can include a trajectory surface 530, 532, 534, 536 corresponding to each hole 510, 512, 514, 516. The trajectory surface 530 of hole 510 and the trajectory surface 534 of hole 514 are illustrated in FIG. 22. In some embodiments, each trajectory surface 530, 532, 534, 536 corresponds to the trajectory of the anchor 400 inserted through the hole 510, 512, 514, 516. The hole 512 can have the same or similar angle of trajectory as hole 510. The hole 516 can have the same or similar angle of trajectory as hole 514. In some embodiments, the trajectory surface 530, 532, 534, 536 has a diameter or cross-section to accommodate the anchor head 402. Each trajectory surface 530, 532, 534, 536 can have a constant diameter. Each trajectory surface 530, 532, 534, 536 can be a bored hole. Each trajectory surface 530, 532, 534, 536 can be shaped to allow the anchor 400 to maintain a constant trajectory from the access surface 508 toward the bone facing surface 506.

In some embodiments, the trajectory surface 530, 532, 534, 536 extends to the access surface 508 along at least part of the trajectory surface 530, 532, 534, 536. The interface 538 between the trajectory surface 530, 532, 534, 536 and the access surface 508 can have a curvature corresponding to the trajectory surface 530, 532, 534, 536. The interface 548 between the first inside surface 520 and the access surface 508 can have a different curvature than the interface 558. The interface 538 can allow the anchor 400 to maintain a constant trajectory from the access surface 508 toward the bone facing surface 506.

In some embodiments, the two-level cervical plate 500 can include a trajectory surface 586, 588 corresponding to each hole 582, 584. The trajectory surface 586 of hole 582 is illustrated in FIG. 22 in cross-section. In some embodiments, each trajectory surface 586, 588 corresponds to the trajectory of the anchor 400 inserted through the hole 582, 584. In some embodiments, the hole 582 can have the same or similar angle of trajectory as hole 584. In some embodiments, the trajectory surface 586, 588 has a diameter or cross-section to accommodate the anchor head 402. Each trajectory surface 586, 588 can have a constant diameter. Each trajectory surface 586, 588 can be a bored hole. The trajectory surface 586, 588 can be adjacent to the access surface 508. In some embodiments, the trajectory surface 586, 588 can be substantially perpendicular to the access surface 508.

In some embodiments, the two-level cervical plate 500 can include a ledge 540 corresponding to each hole 510, 512, 514, 516, 582, 584. The ledge 540 can be located below the trajectory surface 530, 532, 534, 536, 586, 588. The ledge 540 can be flat, curved, or tapered. The ledge 540 can include a curvature that corresponds to the curvature of the underside of the anchor head 402. The ledge 540 can include a taper 542 near an opening 544. The taper 542 can facilitate centering of the anchor body 404. The anchor body 404 is sized to pass through the opening 544. The ledge 540 can be configured to prevent the anchor head 402 from passing through the opening 544. The ledge 540 can be sized according to the corresponding anchor 400 to span a distance from the anchor head 402 toward the anchor body 404. The opening 544 can have a smaller diameter or cross-section than the corresponding trajectory surface 530, 532, 534, 536, 586, 588. The ledge 540 can transition from the trajectory surface 530, 532, 534, 536, 582, 584 to the opening 544.

The anchor 400 can travel along a desired trajectory from the access surface 508 to the bone facing surface 506 until the anchor head 402 contacts the ledge 540. The ledge 540 can limit or prevent further movement in the direction of travel. The anchor 400 can be tightened into a vertebral body until the anchor head 402 provides a compressive force on the ledge 540. The ledge 540 can be configured to be in contact with the anchor head 402 when the two-level cervical plate 500 is secured to the vertebral body.

The ledge 540 can function to orient the anchor 400 at a desired angle within the corresponding hole 510, 512, 514, 516, 582, 584. In the illustrated embodiment, the anchor 400 is configured to be flush or completely recessed within the two-level cervical plate 500. In some embodiments, the trajectory surface 530, 532, 534, 536, 582, 584 may be complete forming a bored hole. The trajectory surface 530, 532, 534, 536, 582, 584 may be adapted for complete recessed positioning of the anchor head 402. In some embodiments, the ledge 540 may be complete and circumferential. With complete recessed positioning, the entire anchor head 402 lies at or below the access surface 508 of the cervical plate 500.

In some embodiments, the ledge 540 is configured to align the anchor 400 to have a general angled or skewed orientation for holes 510, 512, 514, 516. In some embodiments, the ledge 540 is configured to align the anchor 400 at a superior or inferior angle, depending upon whether the hole 510, 512, 514, 516 is located on the superior portion 502 or inferior portion 504, respectively. The ledge 540 provides support for the anchor 400 in the skewed orientation. The skewed orientation of the anchor 400 may allow the anchor 400 to engage the cortical bone of the vertebra, as described herein.

In some embodiments, the ledge 540 is configured to align the anchor 400 having a general straight orientation for holes 582, 584. In some embodiments, the ledge 540 is configured to align the anchor 400 generally perpendicular to the plane of the vertebrae. The ledge 540 provides support for the anchor 400 in this orientation. This orientation of the anchor 400 may allow the anchor 400 to engage the vertebra disposed under the middle portion 580.

In some embodiments, the ledge 540 can support the anchor 400 in an orientation that is within the range of about 0° to about 60° with respect to the coronal plane. In one embodiment, the hole is configured to accept the anchor 400 in an orientation that is within the range of about 30° to about 40° to the coronal plane. In some embodiments, the ledge 540 can support the anchor 400 in an orientation that is within the range of about 0° to about 60° with respect to the transverse plane. In one embodiment, the hole is configured to accept the anchor 400 in an orientation that is within the range of about 30° to about 40° to the transverse plane. In some embodiments, the ledge 540 can support the anchor 400 in an orientation that is within the range of about 0° to about 60° with respect to the sagittal plane. In one embodiment, the hole is configured to accept the anchor 400 in an orientation that is within the range of about 30° to about 40° to the sagittal plane. The particular orientation of the anchor 400 may be determined by inclination of the ledge 540.

The access surface 508 can include an engagement portion 550. The engagement portion 550 can be configured to engage an outer shaft of the inserter tool (not shown). The engagement portion 550 can include a lumen 552. In the illustrated embodiment, the engagement portion 550 can include two lumens 552. The engagement portion 550 can include a lumen 552 for each projection of an outer shaft of an inserter tool. The lumen 552 can have an oblong cross-sectional shape. The lumen 552 can have a non-circular cross-sectional shape.

The outer shaft can couple to the engagement portion 550 of the cervical plate 500. In some embodiments, the one or more projections can couple with corresponding lumens 552 in the cervical plate 500. The engagement portion 550 can be flat, tapered, or curved. The engagement portion 550 can have a corresponding shape as the support 144 of the outer shaft 140.

FIG. 21 illustrates the bone facing surface 506 of the cervical plate 500. Each hole 510, 512, 514, 516 can include a bone facing inside surface 560. The bone facing inside surface 560 can be adjacent to the bone facing surface 506. The bone facing inside surface 560 can extend from the bone facing surface 506 to the ledge 540. The bone facing inside surface 560 can have a larger diameter or cross-sectional opening than the opening 544 of the ledge 540. The bone facing inside surface 560 can be oblong. The bone facing inside surface 560 can include a curvature. In some embodiments, a portion of the ledge 540 of the hole 582, 584 is adjacent to the bone facing surface 506. In some embodiments, a portion of the holes 582, 584 do not include a bone facing inside surface 560.

The bone facing inside surface 560 can be provided in relation to a skewed ledge 540. The ledge 540 can be skewed in order to support the anchor 400 in a high angle orientation for holes 510, 512, 514, 516. In some embodiments, at least a portion of the ledge 540 can extend to bone facing surface 506. In some embodiments, the ledge 540 does not extend to the bone facing surface 506. The ledge 540 can extend to bone facing surface 506 at a location toward an inward facing section of the hole 510, 512, 514, 516. The interface 562 between the ledge 540 and the bone facing surface 506 can have a curvature corresponding to the curvature of the ledge 540. The interface 564 between the bone facing surface 506 and the bone facing inside surface 560 can have a different curvature than the interface 562.

The bone facing surface 506 can include a superior curvature 570. The superior curvature 570 can extend from a portion of the holes 510, 512. The superior curvature 570 can curve inward toward the access surface 508. The superior curvature 570 can follow the direction of the ledge 540. The superior curvature 570 can extend from the interface 564. The superior curvature 570 can reduce the thickness of the cervical plate 500. The superior curvature 570 can correspond or match the curvature of the superior vertebra. The superior curvature 570 can allow the bone facing surface 506 to lie flush against the superior vertebra. The superior curvature 570 can allow at least a portion of the bone facing surface 506 to be disposed within the disc space.

The bone facing surface 506 can include an inferior curvature 572. The inferior curvature 572 can extend from a portion of the holes 514, 516. In some embodiments, the inferior curvature 572 can be the mirror image of the superior curvature 570. The inferior curvature 572 can have any of the features of the superior curvature 570. The inferior curvature 572 can correspond or match the curvature of the inferior vertebra. The inferior curvature 572 can allow the bone facing surface 506 to lie flush against the inferior vertebra. The inferior curvature 572 can allow at least a portion of the bone facing surface 506 to be disposed within the disc space.

The bone facing surface 506 can include a first interbody portion 590. The first interbody portion 590 can extend from a portion of the holes 510, 512. The bone facing surface 506 can include a second interbody portion 592. The second interbody portion 592 can extend from a portion of the holes 514, 516. The first interbody portion 590 and the second interbody portion 592 can be concave. The first interbody portion 590 and the second interbody portion 592 can be shaped to fit within the disc space between adjacent vertebrae.

The bone facing surface 506 can include a central curvature 594. The central curvature 594 can extend between the first interbody portion 590 and the second interbody portion 592. The central curvature 594 can be concave. The central curvature 594 can accommodate the anterior surface of the middle vertebra. The central curvature 594 of the bone facing surface 506 and the middle vertebra can be correspondingly curved. The central curvature 594 can allow the bone facing surface 506 to lie flush against the middle vertebra.

6. Implantation Procedure

Figure 26:
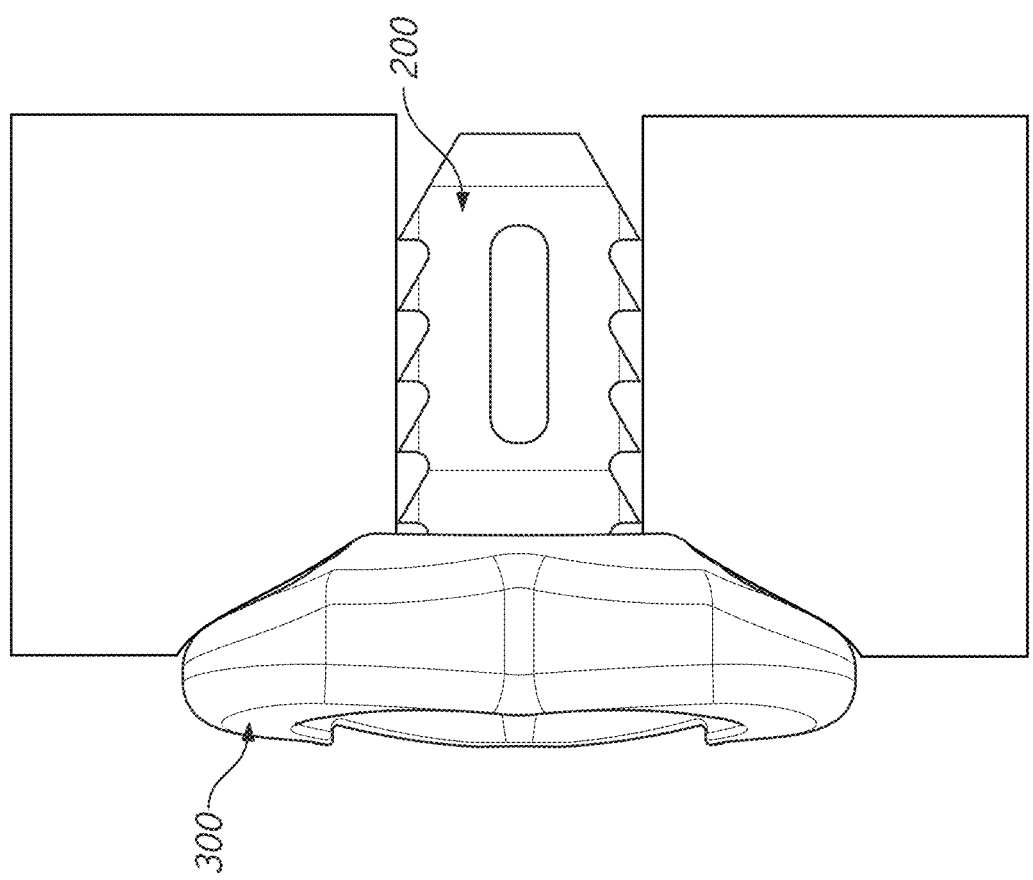
FIG. 26 is a view of the cervical plate of FIG. 1.
Figure 27:
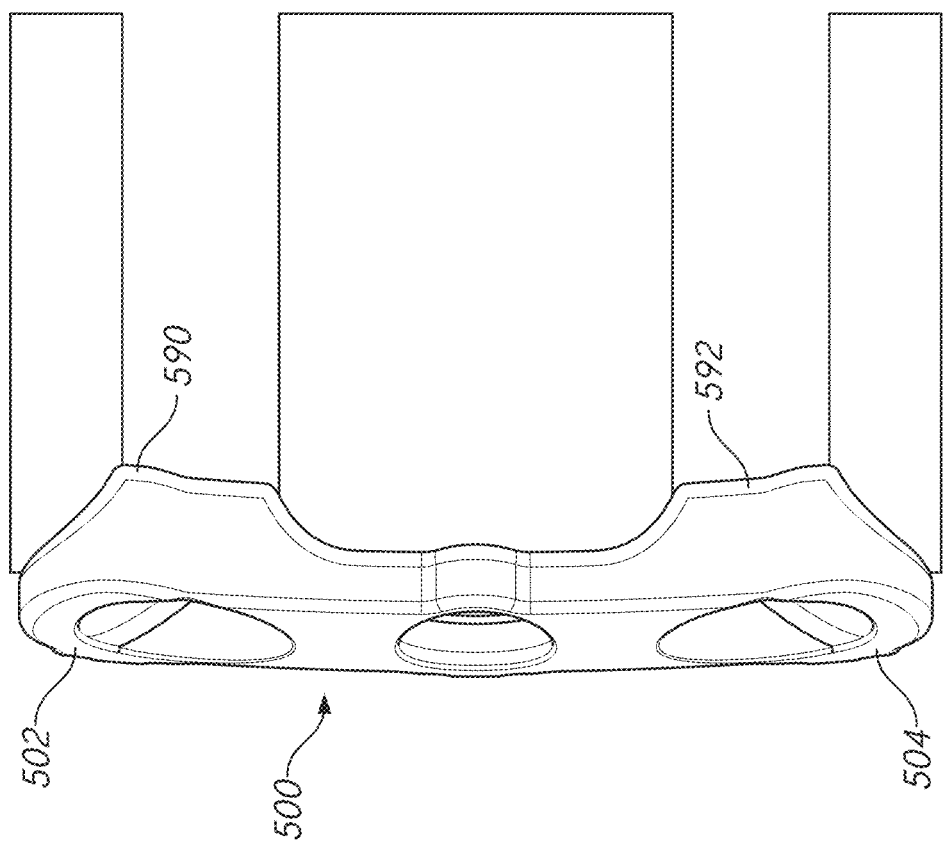
FIG. 27 is a view of the cervical plate of FIG. 21.

FIGS. 26-27 illustrate an embodiment of implanted configurations. FIG. 26 illustrates the cervical plate 300. FIG. 26 illustrates the two-level cervical plate 500. The vertebrae are illustrated.

The cervical plate 300 and the two-level cervical plate 500 can be designed for independent insertion of anchors 400. The cervical plate 300 and the two-level cervical plate 500 can be designed for separate insertion of anchors 400. The cervical plate 300 and the two-level cervical plate 500 can be designed for the user to place the anchors 400. The cervical plate 300 and the two-level cervical plate 500 can be designed for simultaneous alignment of anchors 400 with two or more holes of the cervical plate 300 and the two-level cervical plate 500, for example through the use of anchor guides. The cervical plate 300 and the two-level cervical plate 500 can be designed for simultaneous insertion of anchors 400. For example, robotics or other mechanical instruments can facilitate simultaneous insertion of anchors 400. For example, two or more users can simultaneously insert anchors 400. In some embodiments, two anchors 400 are simultaneously inserted into the inferior vertebra. In some embodiments, two anchors 400 are simultaneously inserted into the superior vertebra. In some embodiments, two anchors 400 are simultaneously inserted into the middle vertebra with use of the two-level cervical plate 500. In some embodiments, two anchors 400 are simultaneously inserted into the inferior vertebra and the superior vertebra. In some embodiments, four anchors 400 are simultaneously inserted into the inferior vertebra and the superior vertebra.

In some embodiments, two anchors 400 are simultaneously inserted into the inferior vertebra and the middle vertebra with use of the two-level cervical plate 500. In some embodiments, four anchors 400 are simultaneously inserted into the inferior vertebra and the middle vertebra with use of the two-level cervical plate 500. In some embodiments, two anchors 400 are simultaneously inserted into the middle vertebra and the superior vertebra with use of the two-level cervical plate 500. In some embodiments, four anchors 400 are simultaneously inserted into the middle vertebra and the superior vertebra with use of the two-level cervical plate 500.

The cervical plate 300 and the two-level cervical plate 500 can be designed for high angle anchor insertion. The cervical plate 300 and the two-level cervical plate 500 can support the anchor at an angle between 30° and 50°. The cervical plate 300 and the two-level cervical plate 500 can include the ledge 340, 540. The ledge 340, 540 can enable high angle anchor insertion. In some embodiments, the cervical plate 300 and the two-level cervical plate 500 can support the anchor at a range of trajectories. The holes of the cervical plate 300 and the two-level cervical plate 500 can accommodate slight variations in trajectories. The holes of the cervical plate 300 and the two-level cervical plate 500 can allow slight poly-axial movement.

The cervical plate 300 and the two-level cervical plate 500 can guide the anchor 400 toward an edge or corner of the vertebral body. The cervical plate 300 and the two-level cervical plate 500 can guide the anchor 400 for purchase of the anchor 400 into the corner of the vertebral body. The cervical plate 300 and the two-level cervical plate 500 can guide the anchor 400 into harder, denser cortical bone. The cervical plate 300 and the two-level cervical plate 500 can guide the anchor 400 into a corner or edge. The cervical plate 300 and the two-level cervical plate 500 can allow slight variations of trajectory within the holes. The variations in trajectory can allow the user to insert the anchor 400 into the edge or corner. The variations in trajectory can accommodate variations in the anatomy of the patient.

The cervical plate 300 and the two-level cervical plate 500 can include holes designed to be at least partially located in the disc space region. Referring back to FIG. 18, at least a portion of the holes 310, 312, 314, 316 extend above the interbody implant 100. At least a portion of the holes 310, 312, 314, 316 are located within the disc space region when the cervical plate 300 is implanted. In some embodiments, the cervical plate 300 and the two-level cervical plate 500 extend below the surface of the vertebral body. The cervical plate 300 and the two-level cervical plate 500 can include a prominence of material that extends into the disc space region. The prominence of material supports the high angle insertion of the anchors 400. The prominence of material supports the anchor 400 along a path toward the corner or edge of the vertebral body.

The patient can be prepared for insertion of the interbody implant 200 and the cervical plate 300. The patient can be prepared for insertion of the two-level cervical plate 500. In some embodiments, the patient can be intubated and general anesthesia can be achieved. The patient can be prepped and draped in the usual sterile fashion. An anterior approach to the spine can be used to expose the anterior vertebral bodies. In some embodiments, the upper cervical spine can be accessed. The anterior upper cervical spine can be accessed by a transoral or retropharyngeal route, or by using a subtotal or extended maxillotomy. In other embodiments, the lower cervical spine, cervicothoracic junction, thoracic spine, thoracolumbar junction, lumbar region, lumbosacral junction, sacrum or combination of the above regions can be accessed. The intervertebral space can be debrided. The disc space can be prepared for insertion of the interbody implant 200. The disc space can be prepared for insertion of a portion of the cervical plate 300. The disc space can be prepared for insertion of a portion of the two-level cervical plate 500.

In some embodiments, the vertebral bodies remain intact. For example, the cervical plate 300 and the two-level cervical plate 500 can have a bend, angle or curve to generally match the natural shape of the vertebral bodies. The cervical plate 300 and the two-level cervical plate 500 may have curvatures to generally match the natural anatomy of the patient. In some embodiments, the cervical plate 300 and the two-level cervical plate 500 are configured to be implanted over and/or within the corresponding disc space. In some embodiments, the cervical plate 300 and the two-level cervical plate 500 extend beyond the disc space to rest against adjacent vertebrae. The cervical plate 300 and the two-level cervical plate 500 are designed to be secured to the cortical bone. The cervical plate 300 and the two-level cervical plate 500 are designed to be used without substantial invasion or disruption of the cortical bone. The cervical plate 300 and the two-level cervical plate 500 are designed to maintain the integrity of the vertebral body. The cervical plate 300 and the two-level cervical plate 500 are designed to be used without removal of cortical bone. The cervical plate 300 and the two-level cervical plate 500 are designed to curve around the native bone.

The interbody implant inserter 100 can be at least partially assembled. The outer shaft 140 can couple to the cervical plate 300. In some embodiments, the one or more projections 146 can couple with corresponding lumen 352 in the cervical plate 300. The interbody implant 200 can be coupled to the cervical plate 300. The bone facing surface 306 can include projections 378. The anterior surface 202 of the interbody implant 200 can include two guide lumens 226. The projection 378 and the corresponding guide lumen 226 can function to couple the cervical plate 300 to the interbody implant 200. The internal shaft 120 of the interbody implant inserter 100 can function to couple to the interbody implant 200. The distal end of the internal shaft 120 can extend through the interbody lumen 354 of the cervical plate 300. The distal end of the internal shaft 120 can include the second threaded portion 126. The second threaded portion 126 can couple with the corresponding threaded lumen 224 in the interbody spacer 200. The second threaded portion 126 can be rotated until the interbody implant inserter 100, the interbody implant 200, and the cervical plate 300 form a unitary, sturdy structure. The interbody implant inserter 100 features the ability to rotate the internal shaft 120 to attach to the interbody spacer 200. The interbody implant inserter 100 features the ability to translate the outer shaft 140 into engagement with the cervical plate 300.

The interbody implant inserter 100 can comprise the impact cap 102. The user can apply a force to the impact cap 102 to insert the interbody implant 200 in the disc space. The user can apply a force to the impact cap 102 to insert the cervical plate 300 at least partially in the disc space. The user can apply a force to the impact cap 102 until the cervical plate 300 is flush with the corners or edges of the adjacent vertebrae. The interbody implant 200 can include features to facilitate insertion of the interbody implant 200. In some embodiments, the interbody implant 200 is packed with one or more materials to facilitate fusion. In some embodiments, the interbody implant 200 can be packed with natural or artificial bone matrix and/or other osteogenesis factors. The interbody implant 200 can be inserted into an intervertebral space between the superior vertebra and the inferior vertebra. The superior surface 302 can be adjacent to the superior vertebra and the inferior surface 304 can be adjacent to the inferior vertebra. In some embodiments, the cervical plate 300 and the interbody spacer 200 are configured for simultaneous insertion. In some embodiments, a portion of the cervical plate 300 extends into the intervertebral space. In some embodiments, a portion of the cervical plate 300 extends over the interbody implant 200. In some embodiments, the cervical plate 300 and the interbody implant 200 are coupled during insertion. In some embodiments, the cervical plate 300 and the interbody implant 200 are coupled within the intervertebral space In some embodiments, the cervical plate 300 is positioned relative to the vertebrae. In some embodiments, a portion of the holes 310, 312, 314, 316 of the cervical plate 300 extends into the intervertebral space. In some embodiments, the superior curvature 370 can rest on at least two surfaces of a corresponding vertebra. The superior curvature 370 rests on an intervertebral surface of the disc space. In some embodiments, the superior curvature 370 rests on an anterior surface of the superior vertebral body. The superior curvature 370 matches the native curvature of the superior vertebral body from a surface inside the disc space to a surface outside of the disc space. The inferior curvature 372 can rest on at least two surfaces of a corresponding vertebra. The inferior curvature 372 rests on an intervertebral surface of the disc space. In some embodiments, the inferior curvature 372 rests on anterior surface of the vertebral body. The inferior curvature 372 matches the native curvature of the inferior vertebral body from a surface inside the disc space to a surface outside of the disc space.

The superior curvature 370 and the inferior curvature 372 can assist in placement of the cervical plate 300. The user can impact the interbody spacer 200 until cervical plate 300 is resting against at least two surfaces of each corresponding vertebrae. The superior curvature 370 and the inferior curvature 372 may assist with selection of cervical plate sizing. The cervical plate 300 can facilitate a desired distance of separation of adjacent vertebrae. The superior curvature 370 and the inferior curvature 372 can be selected based on this desired distance. The prominence of material on the underside of the cervical plate 300 can extend into the disc space. The size and shape of the prominence of material can distract the adjacent vertebrae. The cervical plate 300 can be inserted between adjacent vertebrae with the insertion of the interbody spacer 200. The cervical plate 300 and the interbody spacer 200 can maintain a distraction distance. The cervical plate 300 and the interbody spacer 200 can restore a native or natural distraction. The cervical plate 300 and the interbody spacer 200 can impart a desired angle between adjacent vertebrae. The cervical plate 300 can provide support that is in addition to support provided from the interbody spacer 200.

In some embodiments, the cervical plate 300 can be designed to be inserted a pre-set depth into the disc space until the superior curvature 370 and inferior curvature 372 abut the adjacent vertebrae. In some embodiments, the cervical plate 300 can be designed to allow for a pre-set distraction of the disc space. In some embodiments, the cervical plate 300 is not inserted a variable distance into the disc space. Rather, the insertion depth is determined by the superior curvature 370 and the inferior curvature 372.

In some embodiments, a portion of the interbody implant inserter 100 is disassembled after insertion of the interbody implant 200. The interbody implant inserter 100 can include the handle lock 130. The handle lock 130 can include one or more set screws 134. Once one or more set screws 134 are removed, the handle shaft 110 can be removed from the internal shaft 120. In some embodiments, the handle shaft 110 is removed for placement of the anchors. In some embodiments, the handle shaft 110 remains coupled to the interbody implant 200 and the cervical plate 300 during placement of the anchors. The interbody implant inserter 100 can include the internal shaft 120. The internal shaft 120 can include a second threaded portion 126. The second threaded portion 126 can remain in threaded engagement with the interbody implant 200. The interbody implant inserter 100 features the ability to remove the outer shaft 140 to use anchor guides.

In some embodiments, an anchor guide is provided. In some embodiments, the anchor guide can include at least one lumen aligned with the hole 310. In some embodiments, the anchor guide can include at least two lumens aligned with the holes 310, 312. In some embodiments, the anchor guide can include at least two lumens aligned with the holes 310, 314. In some embodiments, the anchor guide can include at least two lumens aligned with the holes 310, 316. In some embodiments, the anchor guide can include at least four lumens aligned with the holes 310, 312, 314, 316. The alignment facilitates the placement of the anchors 400 through the corresponding holes 310, 312, 314, 316.

One or more anchors can be guided along the trajectories of the trajectory surface 330, 332, 334, 336 of holes 310, 312, 314, 316. The trajectory can be along the axis of the hole 310, 312, 314, 316. The trajectory surface 330, 332, 334, 336 can allow a range of trajectories. The trajectory surface 330, 332, 334, 336 can be dimensioned to be greater than the diameter of the anchor head 402. The trajectory surface 330, 332, 334, 336 can allow slight poly-axial movement to better align the anchor 400 with the desired surface of the bone. Each anchor 400 can be coupled to a driver to facilitate insertion of the anchor 400 into the bone. The lumen of the anchor guide, if provided, can guide the anchor 400 through the hole 310. The tip of the anchor 400 can contact dense cortical bone. The native cortical bone can remain intact after disc preparation. The tip of the anchor 400 contacts the edge or corner of the vertebral body. The tip of the anchor 400 can contact a surface disposed between the disc space and the anterior surface of the superior vertebral body. The anchor 400 can be guided into the superior vertebra. The anchor 400 can travel along the trajectory surface 330 until at least a portion of the anchor head 402 contacts the ledge 340. The ledge 340 can support the anchor head 402 in a range of trajectories. The ledge 340 can have a concave curvature to support the anchor head 402. In some embodiments, the anchor 400 is perpendicular to the ledge 340. In some embodiments, the anchor 400 is not perpendicular to the ledge 340.

The lumen of the anchor guide, if provided, can guide the anchor 400 through the hole 314. The tip of the anchor 400 contacts the edge or corner of the vertebral body. The tip of the anchor 400 contacts a surface disposed between the disc space and the anterior surface of the inferior vertebral body. The anchor 400 can be guided into the inferior vertebra. The anchor 400 can travel along the trajectory surface 334 until the anchor head 402 contacts the ledge 340. These steps can be repeated for the anchors 400 guided by the trajectory surfaces 332, 336 of holes 312, 316. In some embodiments, one or more tools are passed along the trajectory surface 330, 332, 334, 336 of holes 310, 312, 314, 316. In some embodiments, a pilot hole can be drilled in the vertebra to facilitate the proper trajectory of the anchor 400.

The anchor 400 can follow the trajectory of the hole 310, 312, 314, 316. In some embodiments, the anchor 400 can follow the trajectory of trajectory surface 330, 332, 334, 336. In some embodiments, the anchor 400 can deviate from the trajectory of trajectory surface 330, 332, 334, 336 over a small range. In some embodiments, the anchor 400 can have poly-axial movement within the corresponding hole 310, 312, 314, 316. The ledge 340 can provide a stop for the anchor 400. The anchor 400 can form any insertion angle described herein. The insertion angle can be an acute angle (e.g., 5°, 10°, 15°, 20°, 25°, 30°, 35°, 40°, 45°, 50°, 55°, 60°, 65°, 70°, 80°, 85°, between 30° and 40°, between 30° and 50°, or any range of the foregoing values). The hole 310, 312, 314, 316, including features therein, can guide the anchor 400 into a vertebral body. The anchor 400 can extend from the hole 310, 312, 314, 316 at a variety of trajectories.

FIG. 26 illustrates the interbody implant 200 and the cervical plate 300. The interbody implant 200 can be disposed between the superior vertebra and the inferior vertebra. The interbody implant 200 can be disposed in the disc space region. A portion of the cervical plate 300 can be disposed between the superior vertebra and the inferior vertebra. The portion of the cervical plate 300 can be disposed in the disc space region. In some embodiments, a portion of the ledge 340 can be disposed in the disc space region. In some embodiments, a portion of the hole 310, 312, 314, 316 can be disposed in the disc space region. In some embodiments, the portion of the cervical plate 300 can be disposed in the disc space region to facilitate the high angle insertion of the anchor. In some embodiments, the portion of the cervical plate 300 can be disposed in the disc space region to orient the anchor 400 toward the corner of the vertebral body.

Figure 28:
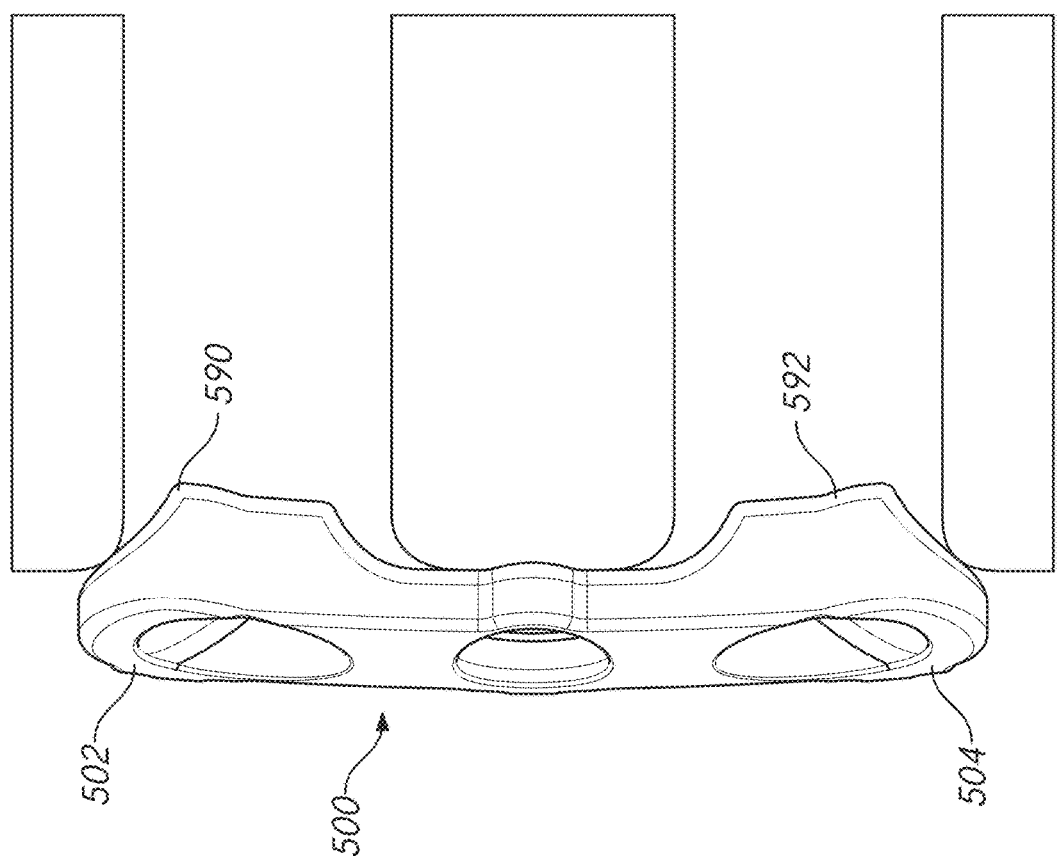
FIG. 28 is a view of the cervical plate of FIG. 21.

FIG. 27 illustrates the two-level cervical plate 500. FIG. 28 illustrates another placement of the two-level cervical plate 500. The middle portion 580 can be disposed over a middle vertebra. The superior region 502 can be oriented toward a superior vertebra. The inferior region 504 can be oriented toward an inferior vertebra. The first interbody portion 590 of the two-level cervical plate 500 can be disposed between the superior vertebra and the middle vertebra. The second interbody portion 592 of the two-level cervical plate 500 can be disposed between the middle vertebra and the inferior vertebra. The portion of the two-level cervical plate 500 can be disposed in the disc space region. In some embodiments, a portion of the ledge 540 can be disposed in the disc space region. In some embodiments, a portion of the hole 510, 512, 514, 516 can be disposed in the disc space region. In some embodiments, the portion of the two-level cervical plate 500 can be disposed in the disc space region to facilitate the high angle insertion of the anchor. In some embodiments, the portion of the two-level cervical plate 500 can be disposed in the disc space region to orient the anchor 400 toward the corner of the vertebral body.

7. Interbody Implant Inserter

Figure 29:
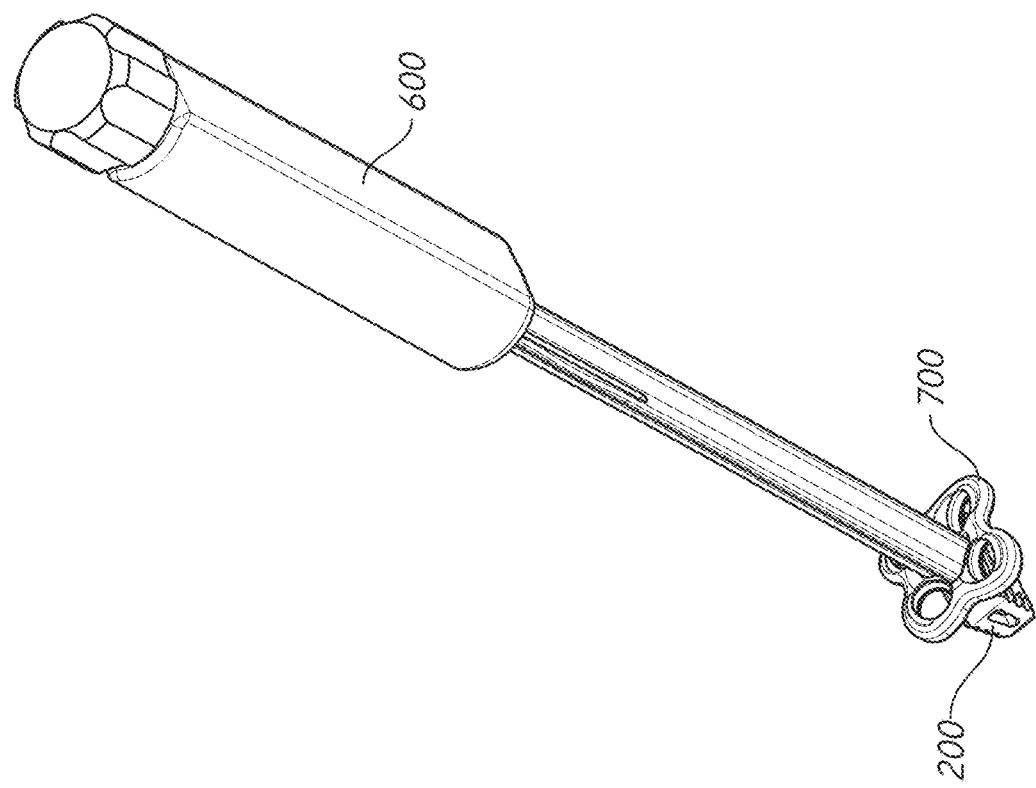
FIG. 29 is a perspective view of an embodiment of an interbody implant inserter, an embodiment of an interbody implant, and an embodiment of a cervical plate.
Figure 30:
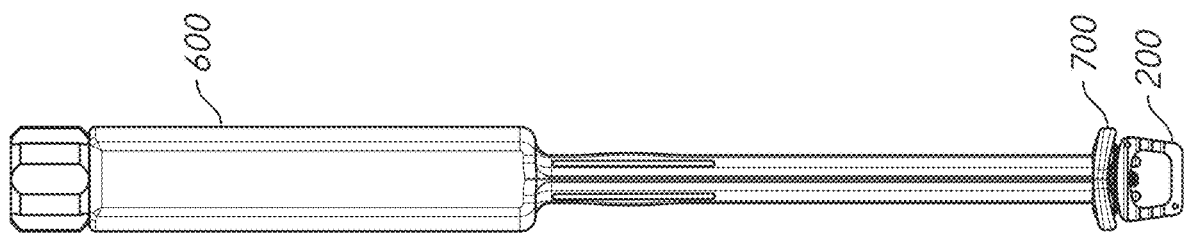
FIG. 30 is a side view of the interbody implant inserter, the interbody implant, and the cervical plate of FIG. 29.
Figure 31:
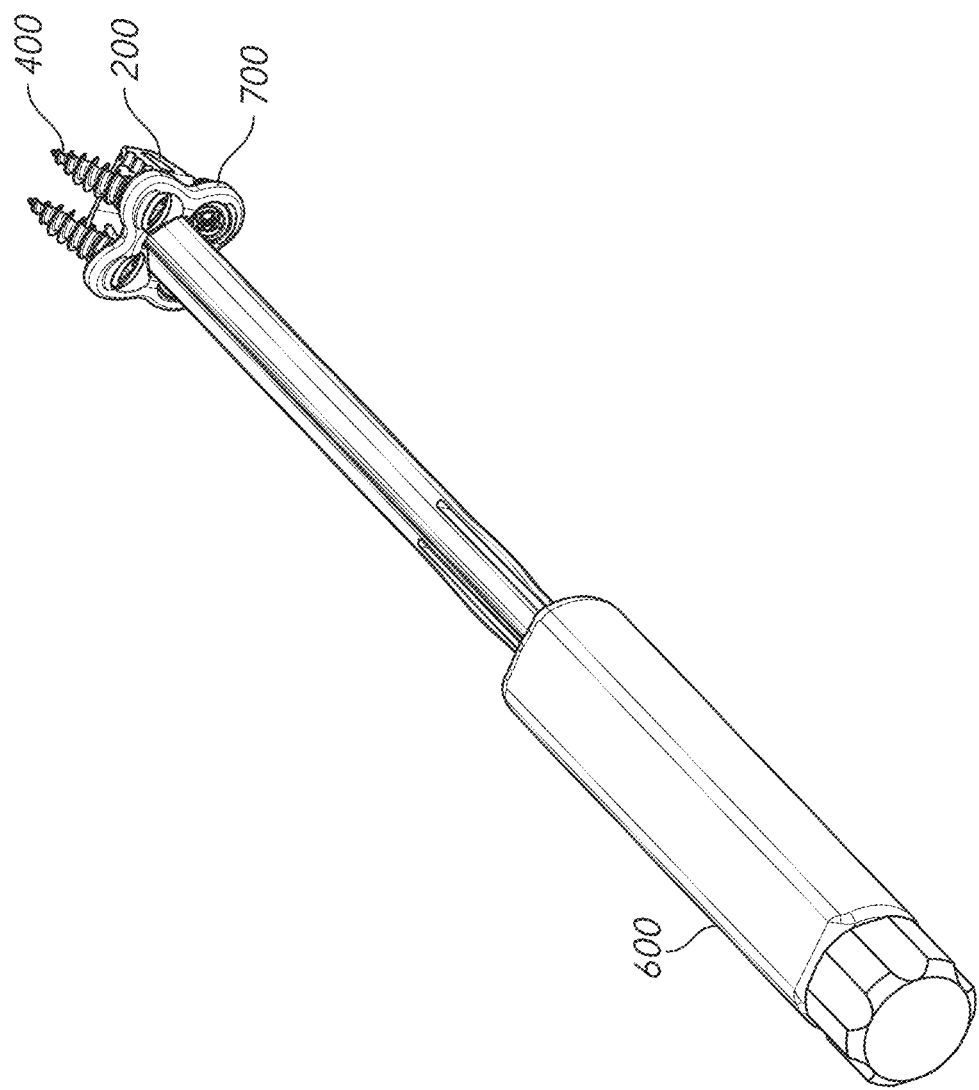
FIG. 31 is a perspective view of the interbody implant inserter, the interbody implant, and the cervical plate of FIG. 29, further including anchors.
Figure 32:
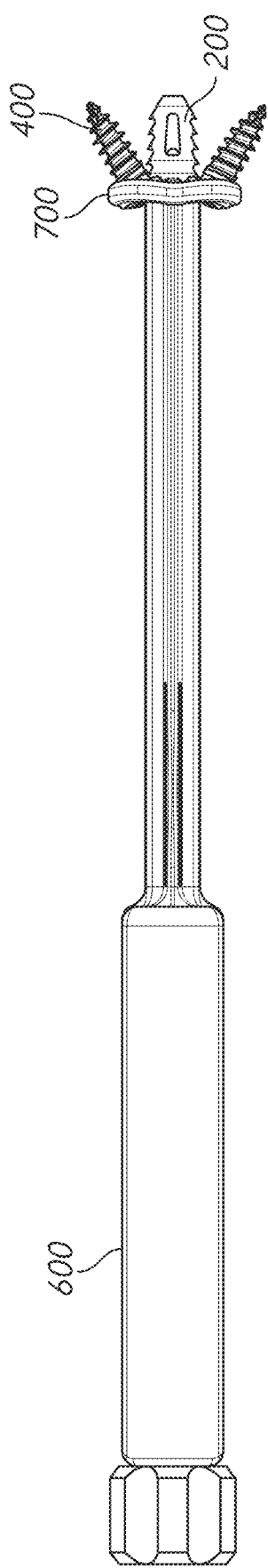
FIG. 32 is a side view of the interbody implant inserter, the interbody implant, the cervical plate, and the anchors of FIG. 31.

FIGS. 29-32 depict views of an embodiment of an interbody implant inserter 600, the interbody spacer 200, and a cervical plate 700. FIG. 29 illustrates a perspective view. FIG. 30 illustrates a side view. FIG. 31 illustrates a perspective view with anchors 400. FIG. 32 illustrates a side view with anchors 400. The systems and methods described herein can include one or more of these components. The interbody implant inserter 600 can be used in combination with the cervical plate 700. The interbody implant inserter 600 can be used in combination with the cervical plate 300 or the two-level cervical plate 500, described herein. The interbody implant inserter 600 can be used in combination with the interbody implant 200. The interbody implant inserter 600 can be used in combination with one or more anchors 400. The interbody implant 200 can include any features described herein. The cervical plate 700 can have any features of the cervical plate 300 or the two-level cervical plate 500, described herein. The interbody implant inserter 600, the interbody spacer 200, and the cervical plate 700 can form an assembly.

Figure 33:
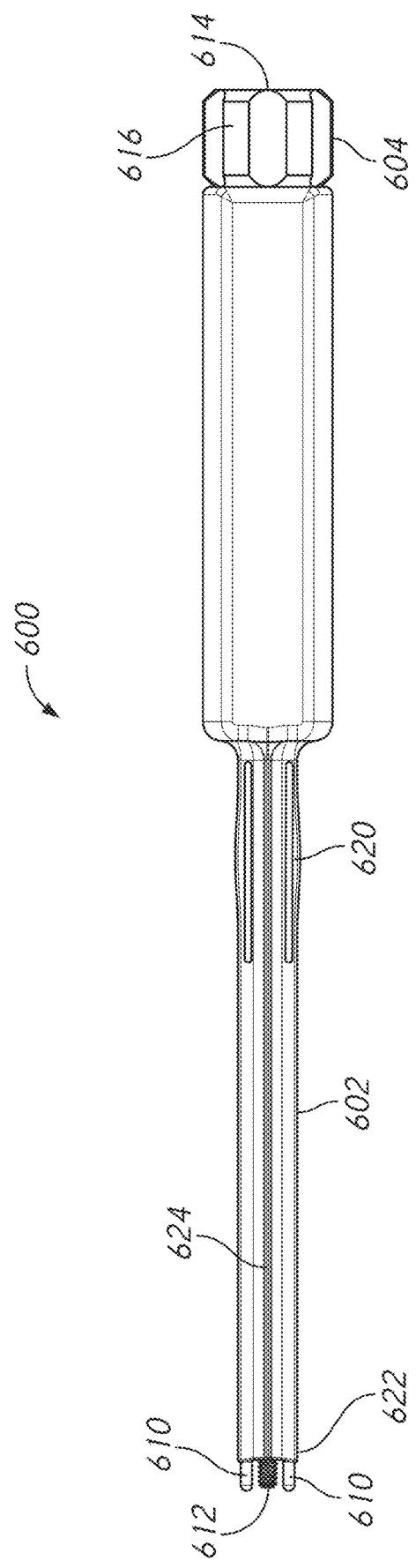
FIG. 33 is a side view of the interbody implant inserter of FIG. 29.
Figure 35:
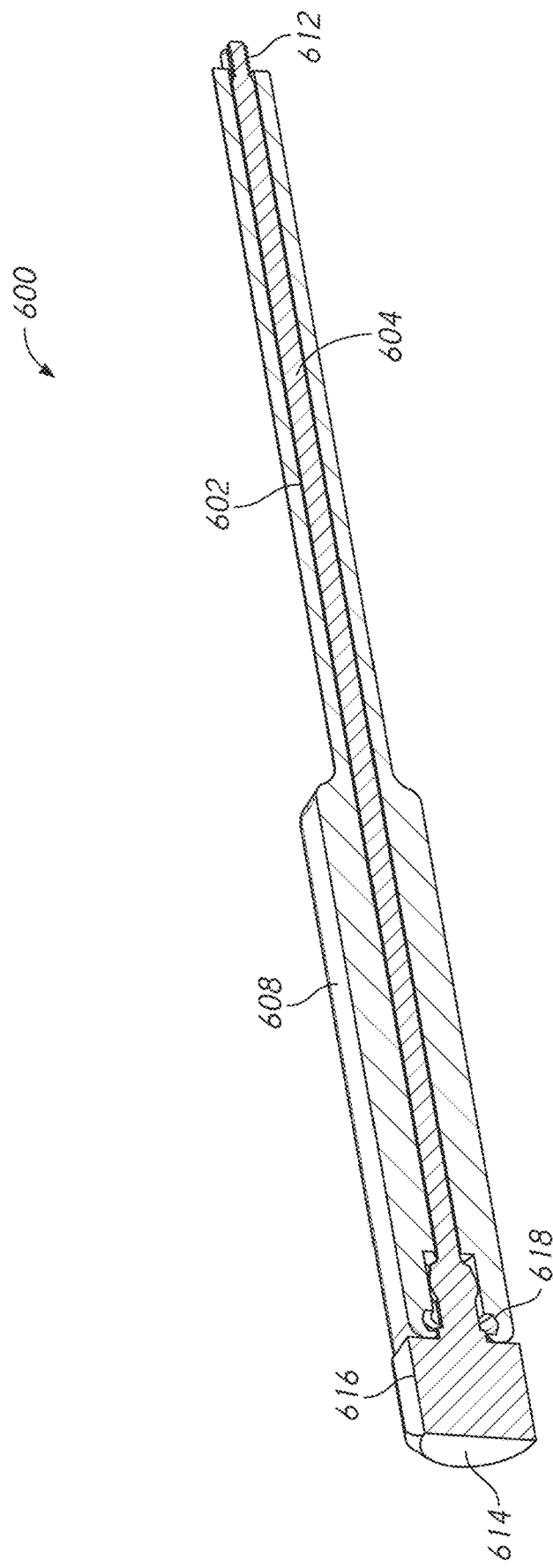
FIG. 35 is a cross-sectional view of the interbody implant inserter of FIG. 29.

FIGS. 33-35 illustrate the interbody implant inserter 600. FIG. 33 illustrates a side view. FIG. 34 illustrates a perspective view of an outer shaft 602 and a perspective view of an internal shaft 604. FIG. 35 illustrates a cross-sectional view.

The interbody implant inserter 600 can comprise the outer shaft 602 and the internal shaft 604. The outer shaft 602 can include a lumen 606. The lumen 606 can be sized to accommodate the internal shaft 604. The internal shaft 604 can be configured to rotate relative to the outer shaft 602 when the internal shaft 604 is disposed within the outer shaft 602. While the internal shaft 604 is illustrated as an elongate cylindrical shape, other configurations are contemplated. The outer shaft 602 can include a handle 608. In the illustrated embodiment, the handle 608 comprises a cylindrical portion. The handle 608 can be located along a proximal portion of the outer shaft 602. The cervical plate 700 can translate proximally to the handle 608.

The outer shaft 602 can include a projection 610. In the illustrated embodiment, the outer shaft 602 can include two projections 610. The two projections 610 can be diametrically opposed on the body of the outer shaft 602. The two projections 610 can be diametrically opposed relative to the lumen 606. The projection 610 can be an extended point. The projection 610 can have a circular cross-sectional shape. The projection 610 can have a non-circular cross-sectional shape. The projection 610 can be any interface configured to couple with the interbody implant 200.

The internal shaft 604 can function to couple to the interbody implant 200, as described herein. The distal end of the internal shaft 604 can include a second threaded portion 612. The second threaded portion 612 can couple with a corresponding threaded lumen in the interbody spacer 200. The second threaded portion 612 can be near or at the distal end of the internal shaft 604.

The internal shaft 604 can comprise an impact cap 614. The impact cap 614 can allow the user to apply a force to position the interbody implant 200 between adjacent vertebrae. The impact cap 614 can have a flat proximal end to allow a force to be applied. While the impact cap 614 is illustrated as an elongate cylindrical shape, other configurations are contemplated.

The internal shaft 604 can include a thumbscrew 616. The thumbscrew 616 can be manipulated by the user to rotate the internal shaft 604. The thumbscrew 616 can be considered a handle. In some embodiments, rotational movement of the thumbscrew 616 by the user can cause rotational movement of the internal shaft 604 relative to the outer shaft 602. The thumbscrew 616 can extend proximally from the outer shaft 602 when the internal shaft 604 is disposed within the outer shaft 602.

The outer shaft 602 and the internal shaft 604 can be coupled via a connection 618. In some embodiments, the internal shaft 604 can be easily removed from the outer shaft 602. The interbody implant inserter 600 can include a quick release connection. The connection 618 can allow the internal shaft 604 to rotate relative to the outer shaft 602. In some embodiments, the connection 618 can allow the internal shaft 604 to rotate but not translate relative to the outer shaft 602. The interbody implant inserter 600 can include any mechanical coupling or disconnect. The interbody implant inserter 600 can include any connection mechanism. The outer shaft 602 and the internal shaft 604 can be coupled via any releasable mechanism.

The interbody implant inserter 600 can function as an implant holder. The interbody implant inserter 600 can releasably hold the interbody implant 200. In some embodiments, the first projection 610 can be identical or substantially similar to the second projection 610. The interbody implant inserter 600 can couple to the interbody implant 200 in one of two orientations. In other embodiments, the first projection 610 is different than the second projection 610. The interbody implant inserter 600 can couple to the interbody implant 200 in only one orientation.

The interbody implant inserter 600 has the ability to rotate the internal shaft 604. The user can rotate the thumbscrew 616. The thumbscrew 616 can rotate independently of the outer shaft 602. The first projection 610 and the second projection 610 of the outer shaft 602 can engage corresponding lumens in the interbody implant 200, as described herein. As the thumbscrew 616 is rotated, the internal shaft 604 is rotated. As the internal shaft 604 is rotated, the internal shaft 604 can thread into a threaded lumen of the interbody implant 200, as described herein. In some embodiments, the internal shaft 604 rotates but does not translate relative to the outer shaft 602.

The interbody implant inserter 600 has the ability to be impacted. The internal shaft 604 can include an impact cap 614 configured to allow the interbody implant 200 to be impacted. The outer shaft 602, the internal shaft 604, and the interbody implant 200 can translate together as a unit. The internal shaft 604 and the interbody implant 200 can be rigidly coupled via threaded portions. The outer shaft 602 and the internal shaft 604 can be rigidly coupled via the connection 618, as described herein.

The internal shaft 604 can be detached from the outer shaft 602. The internal shaft 604 can be considered a detachable shaft. The interbody implant inserter 600 has the ability to remove the internal shaft 604. In some embodiments, the internal shaft 604 can be removed by a quick-release connection to decouple from the interbody implant 200. In some embodiments, the internal shaft 604 can be removed by any suitable mechanism to decouple from the interbody implant 200. The internal shaft 604 can be removed by rotating the internal shaft 604 to decouple from the interbody implant 200. In some methods of use, the outer shaft 602 can remain coupled to the interbody implant 200 as the internal shaft 604 is removed. The internal shaft 604 can be rotated to decouple from the interbody implant 200.

The internal shaft 604 can be pulled proximally after decoupling from the interbody implant 200. The internal shaft 604 can be pulled proximally to decouple from connection 618.

In some embodiments, the thumbscrew 616 can be detached from the internal shaft 604. In some embodiments, the thumbscrew 616 can be considered a detachable thumbscrew or detachable handle. In some embodiments, the interbody implant inserter 600 has the ability to remove the thumbscrew 616 from the internal shaft 604. In some embodiments, the thumbscrew 616 can be removed by a quick-release connection to decouple from the internal shaft 604. In some embodiments, the thumbscrew 616 can be removed by any suitable mechanism to decouple from the internal shaft 604. In some methods of use, the internal shaft 604 can remain coupled to the outer shaft 602 as the thumbscrew 616 is removed. In some methods of use, the internal shaft 604 does not remain coupled to the outer shaft 602 as the thumbscrew 616 is removed. In some methods of use, the thumbscrew 616 can be pulled proximally after decoupling from the internal shaft 604.

In some embodiments, the handle 608 can be detached from the outer shaft 602. In some embodiments, the handle 608 can be considered a detachable handle. In some embodiments, the interbody implant inserter 600 has the ability to remove the handle 608 from the outer shaft 602. In some embodiments, the handle 608 can be removed by a quick-release connection to decouple from the outer shaft 602. In some embodiments, the handle 608 can be removed by any suitable mechanism to decouple from the outer shaft 602. In some embodiments, the handle 608 can retain the cervical plate 700 when the handle 608 is removed from the outer shaft 602. In some embodiments, the handle 608 can include a distal projection that retains the cervical plate 700 when the handle 608 is removed from the outer shaft 602. In some embodiments, the handle 608 can include arms or grips that hold the cervical plate 700 on the outer edge when the handle 608 is removed from the outer shaft 602. In some embodiments, the handle 608 can be pulled proximally after decoupling from the outer shaft 602. In some embodiments, the handle 608 and the outer shaft 602 can be decoupled to allow removal of cervical plate 700 for introduction of a different cervical plate. In some embodiments, the handle 608 and the outer shaft 602 can be decoupled to allow removal of cervical plate 700 over the outer shaft 602 for introduction of a different cervical plate. In some embodiments, the handle 608 and the outer shaft 602 can be decoupled after the interbody implant 200 has been impacted. In some embodiments, the outer shaft 602 can be decoupled from the interbody implant 200. In some embodiments, the internal shaft 604 can remain coupled to the interbody implant 200.

In some embodiments, one or more of the thumbscrew 616, internal shaft 604, handle 608, outer shaft 602, and cervical plate 700 can be removed to allow introduction of a different (e.g., larger) cervical plate, before or after the interbody implant 200 has been impacted. In some embodiments, one or more of the thumbscrew 616, internal shaft 604, handle 608, and outer shaft 602 can be recoupled to interbody implant inserter 600 after introduction of a different (e.g., larger) cervical plate, before or after the interbody implant 200 has been impacted.

The interbody implant inserter 600 has the ability to couple with an anchor guide. In some embodiments, the anchor guide can couple with the interbody implant inserter 600 when the internal shaft 604 is removed. In some embodiments, the anchor guide can couple with the interbody implant inserter 600 when the internal shaft 604 remains in place. In some embodiments, the anchor guide can couple to the internal shaft 604. In some embodiments, the anchor guide can couple with the interbody implant inserter 600 when the outer shaft 602 is removed. In some embodiments, the anchor guide can couple with the interbody implant inserter 600 when the outer shaft 602 remains in place. In some embodiments, the anchor guide can couple to the outer shaft 602.

The outer shaft 602 can function to couple to the cervical plate 700. The outer shaft 602 can include a first retention feature 620 configured to couple with a corresponding feature of the cervical plate 700, as described herein. In some embodiments, the first retention feature 620 can be configured to couple with an interior and/or exterior portion of the cervical plate 700. In some embodiments, the first retention feature 620 can be configured to couple with a proximal and/or distal portion of the cervical plate 700. The first retention feature 620 can be a keyed projection. The first retention feature 620 can be near the proximal end of the outer shaft 602. The first retention feature 620 can be distal to the handle 608. In some embodiments, the first retention feature 620 can extend from the handle between the handle 608 and the outer shaft 602. In some embodiments, the first retention feature 620 can retain the cervical plate 700 when the handle 608 is removed from the outer shaft 602, as described herein. The first retention feature 620 can include one or more ridges. The first retention feature 620 can include one or more flexible portions. The first retention feature 620 can include one or more leaf springs. In some embodiments, the first retention feature 620 can include one or more hooks. In some embodiments, the first retention feature 620 can include one or more clips. The first retention feature 620 can be a solid, shaped surface. The first retention feature 620 can provide a frictional fit. The first retention feature 620 can provide an interference fit. In some embodiments, the first retention feature 620 can include one or more locking and/or release mechanisms. In some embodiments, the first retention feature 620 can include a button or lever release mechanism. The first retention feature 620 can include two or more diametrically opposed structures. The first retention feature 620 can include two or more structures equally spaced around the outer shaft 602. In the illustrated embodiment, the first retention feature 620 includes two structures. Other configurations are contemplated, e.g. one structure, three structures, four structures, etc.

The first retention feature 620 can include one or more springs. The first retention feature 620 can include one or more leaf springs. A leaf spring is a simple spring comprising a thin, flexible arc. The leaf spring can have any cross-sectional shape such as rectangular, circular, elliptical, polygonal, etc. The leaf spring can be attached to the outer shaft 602 at both ends of the leaf spring. The leaf spring can be attached to the outer shaft 602 at only one end of the leaf spring. In the illustrated example, the first retention feature 620 comprises a leaf spring attached at both ends of the leaf spring. The first retention feature 620 can include a longitudinal slot. The first retention feature 620 can flex toward and away from the longitudinal axis of the outer shaft 602. In the illustrated embodiment, the first retention feature 620 includes two leaf springs. Other configurations are contemplated, e.g. one leaf spring, three leaf springs, four leaf springs, etc. The first retention feature 620 can extend for a portion of the length of the outer shaft 602. The first retention feature 620 can extend a length along the outer shaft 602 equal to the thickness of the cervical plate 700. The first retention feature 620 can extend a length along the outer shaft 602 greater than the thickness of the cervical plate 700.

The first retention feature 620 can extend a length along the outer shaft 602 less than the thickness of the cervical plate 700. The first retention feature 620 can have a length of 1 to 10 mm. The first retention feature 620 can have any length along the outer shaft 602.

The first retention feature 620 can include one or more tabs. The first retention feature 620 can include one or more projections. The first retention feature 620 can include one or more detents. The first retention feature 620 can include one or more ball detents. The first retention feature 620 can include one or more flexible mechanisms. The first retention feature 620 can include one or more structure configured to flex away from the longitudinal axis of the outer shaft 602. The first retention feature 620 can be any mechanical arrangement configured to hold the cervical plate 700 in a temporarily fixed position relative to the outer shaft 602. The first retention feature 620 can be any mechanical arrangement configured to prevent or limit sliding or translating of the cervical plate 700 relative to the outer shaft 602. The first retention feature 620 can be any mechanical arrangement configured to prevent or limit rotating of the cervical plate 700 relative to the outer shaft 602. The first retention feature 620 can apply pressure to the cervical plate 700. The first retention feature 620 can push against the cervical plate 700. In some embodiments, additional force applied to the cervical plate 700 will overcome the retention force of the first retention feature 620. In some embodiments, the cervical plate 700 is released from the first retention feature 620.

The outer shaft 602 can include a second retention feature 622 configured to couple with a corresponding feature of the cervical plate 700, as described herein. The second retention feature 622 can be a keyed projection. The second retention feature 622 can be near or at the distal end of the outer shaft 602. The second retention feature 622 can include one or more ridges. The second retention feature 622 can include one or more flexible portions. The second retention feature 622 can be a solid, shaped surface. The second retention feature 622 can provide a frictional fit. The second retention feature 622 can provide an interference fit. The second retention feature 622 can include two or more diametrically opposed structures. The second retention feature 622 can include two or more structures equally spaced around the outer shaft 602. In the illustrated embodiment, the second retention feature 622 includes two structures. Other configurations are contemplated, e.g. one structure, three structures, four structures, etc.

The second retention feature 622 can include one or more tapered surfaces. The second retention feature 622 can include one or more wedges. The second retention feature 622 can form an interference fit, press fit, or friction fit. The second retention feature 622 can retain the cervical plate 700 with friction. The second retention feature 622 and the cervical plate 700 can be pushed together. The tightness of the fit is determined by the amount of interference between the second retention feature 622 and the cervical plate 700. The tolerance or allowance between the second retention feature 622 and the cervical plate 700 determines the amount of strength or hold of this connection. The second retention feature 622 can have any cross-sectional shape such a rectangular, circular, elliptical, polygonal, etc. The second retention feature 622 can be a solid structure. In some embodiments, the second retention feature 622 does not include a longitudinal slot. In some embodiments, the second retention feature 622 does not flex toward and away from the longitudinal axis of the outer shaft 602. The second retention feature 622 can extend for a portion of the length of the outer shaft 602. The second retention feature 622 can extend a length along the outer shaft 602 equal to the thickness of the cervical plate 700. The second retention feature 622 can extend a length along the outer shaft 602 greater than the thickness of the cervical plate 700. The second retention feature 622 can extend a length along the outer shaft 602 less than the thickness of the cervical plate 700. The second retention feature 622 can have a length of 1 to 4 mm. The second retention feature 622 can have a length of 1 to 4 mm to maintain the cervical plate 700 in position to secure to the vertebral bodies after the interbody implant 200 has been impacted and recessed between the vertebral bodies. The second retention feature 622 can have any length along the outer shaft 602.

The second retention feature 622 can be any mechanical arrangement configured to hold the cervical plate 700 in a temporarily fixed position relative to the outer shaft 602. The second retention feature 622 can be any mechanical arrangement configured to prevent or limit sliding or translating of the cervical plate 700 relative to the outer shaft 602. The second retention feature 622 can be any mechanical arrangement configured to prevent or limit rotating of the cervical plate 700 relative to the outer shaft 602. The second retention feature 622 can apply pressure to the cervical plate 700. The second retention feature 622 can push against the cervical plate 700. In some embodiments, additional force applied to the cervical plate 700 will overcome the retention force of the second retention feature 622. In some embodiments, after insertion of the anchors 400, the outer shaft 602 is withdrawn and the second retention feature 622 slides relative to the cervical plate 700. The second retention feature 622 can be shaped to allow the outer shaft 602 to be removed proximally relative to the cervical plate 700. In some embodiments, a force is applied to the cervical plate 700 to remove the cervical plate 700 from the outer shaft 602.

The first retention feature 620 can have any feature of the second retention feature 622, as described herein. The second retention feature 622 can have any feature of the first retention feature 620, as described herein. The first retention feature 620 can be the only retention feature of the interbody implant inserter 600. The second retention feature 622 can be the only retention feature of the interbody implant inserter 600. The interbody implant inserter 600 can include both the first retention feature 620 and the second retention feature 622. The first retention feature 620 and the second retention feature 622 can be the same or similar. The first retention feature 620 and the second retention feature 622 can be different. The first retention feature 620 and the second retention feature 622 can be coaxial. The first retention feature 620 and the second retention feature 622 can be spaced along the length of the outer shaft 602. The first retention feature 620 and the second retention feature 622 can engage the same corresponding feature of the cervical plate 700, as described herein.

The outer shaft 602 can include an anti-rotation feature 624 configured to couple with a corresponding feature of the cervical plate 700, as described herein. The anti-rotation feature 624 can be a keyed projection. The anti-rotation feature 624 can be distal to the handle 608. The anti-rotation feature 624 can extend longitudinally. The anti-rotation feature 624 can be near or at the proximal end of the outer shaft 602. The anti-rotation feature 624 can be near or at the distal end of the outer shaft 602. The anti-rotation feature 624 can be along the length of the outer shaft 602. The anti-rotation feature 624 can be along a portion of the length of the outer shaft 602 about which the cervical plate 700 translates.

The anti-rotation feature 624 can include one or more ridges. The anti-rotation feature 624 can be a solid, shaped surface. In some embodiments, the anti-rotation feature 624 can form a point. Other shapes are contemplated including triangular, square, rectangular, elliptical, polygonal, etc. The anti-rotation feature 624 can include two or more diametrically opposed structures. The anti-rotation feature 624 can include two or more structures equally spaced around the outer shaft 602. In the illustrated embodiment, the anti-rotation feature 624 includes two structures. Other configurations are contemplated, e.g. one structure, three structures, four structures, etc. The anti-rotation feature 624 can engage a different feature of the cervical plate 700 than the first retention feature 620 and the second retention feature 622, as described herein. The anti-rotation feature 624 can engage the same feature of the cervical plate 700 as the first retention feature 620 and the second retention feature 622, as described herein.

The anti-rotation feature 624 can limit or prevent rotation of the cervical plate 700 relative to the outer shaft 602 of the interbody implant inserter 600. The anti-rotation feature 624 can prevent or limit rotation of the cervical plate 700. The anti-rotation feature 624 can prevent or limit rotation of the cervical plate 700 during translation of the cervical plate 700. The anti-rotation feature 624 can prevent or limit rotation of the cervical plate 700 along a portion of the length of the outer shaft 602.

In some embodiments, the anti-rotation feature 624 is not configured to hold the cervical plate 700 in a temporarily fixed position relative to the outer shaft 602. In some embodiments, the anti-rotation feature 624 is not configured to prevent or limit sliding or translating of the cervical plate 700 relative to the outer shaft 602. In some embodiments, the anti-rotation feature 624 does not apply pressure to the cervical plate 700 or push against the cervical plate 700. The anti-rotation feature 624 can limit or prevent the rotation of the cervical plate 700 relative to the outer shaft 602. The anti-rotation feature 624 can have any cross-sectional shape that resists rotation with respect to a complementary feature of the cervical plate 700.

In some embodiments, the outer shaft 602 and the cervical plate 700 are coupled by one or more of the first retention feature 620, the second retention feature 622, and the anti-rotation feature 624. In some embodiments, rotational movement of the outer shaft 602 can cause the same or similar rotational movement of the cervical plate 700.

The outer shaft 602 can include one or more retention features 620, 622. The outer shaft 602 can include one or more retention features 620, 622 configured to couple with a complementary retention feature of the cervical plate 700, as described herein. The one or more retention features 620, 622 can be near or at the proximal end of the outer shaft 602, near the distal end of the outer shaft 602, or at any position along the length of the outer shaft 602. The one or more retention features 620, 622 can have a corresponding shape to the cervical plate 700 as described herein. The cervical plate 700 can be sized to accommodate the retention features 620, 622.

The outer shaft 602 can include the anti-rotation feature 624 configured to couple with a complementary anti-rotation feature in the cervical plate 700, as described herein. The anti-rotation feature 624 can be along the length of the outer shaft 602, or a portion thereof. The anti-rotation feature 624 can have a corresponding shape to the cervical plate 700 as described herein. The cervical plate 700 can be sized to accommodate the anti-rotation feature 624.

8. Interbody Implant

Figure 36:
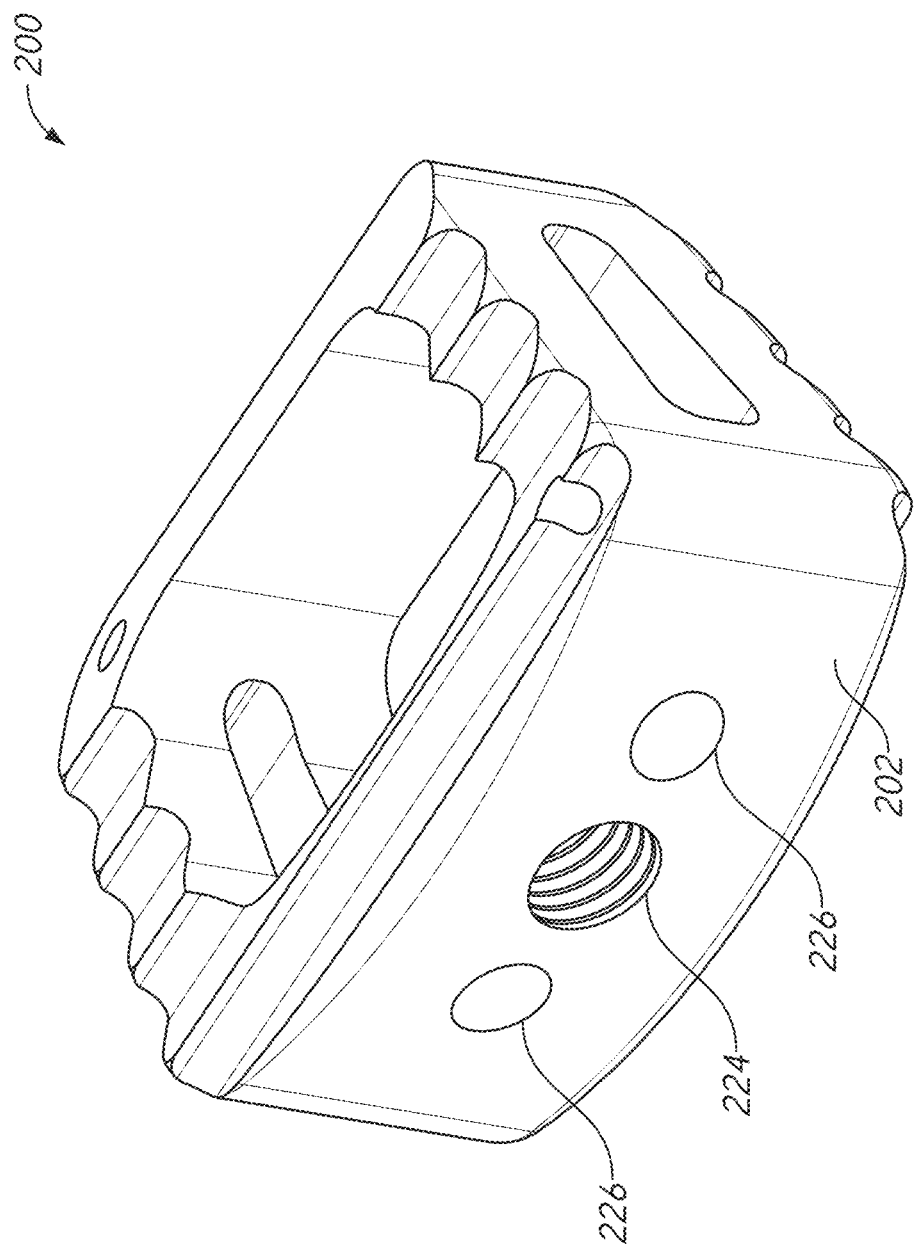
FIG. 36 is a perspective view of the interbody implant of FIG. 29.
Figure 37:
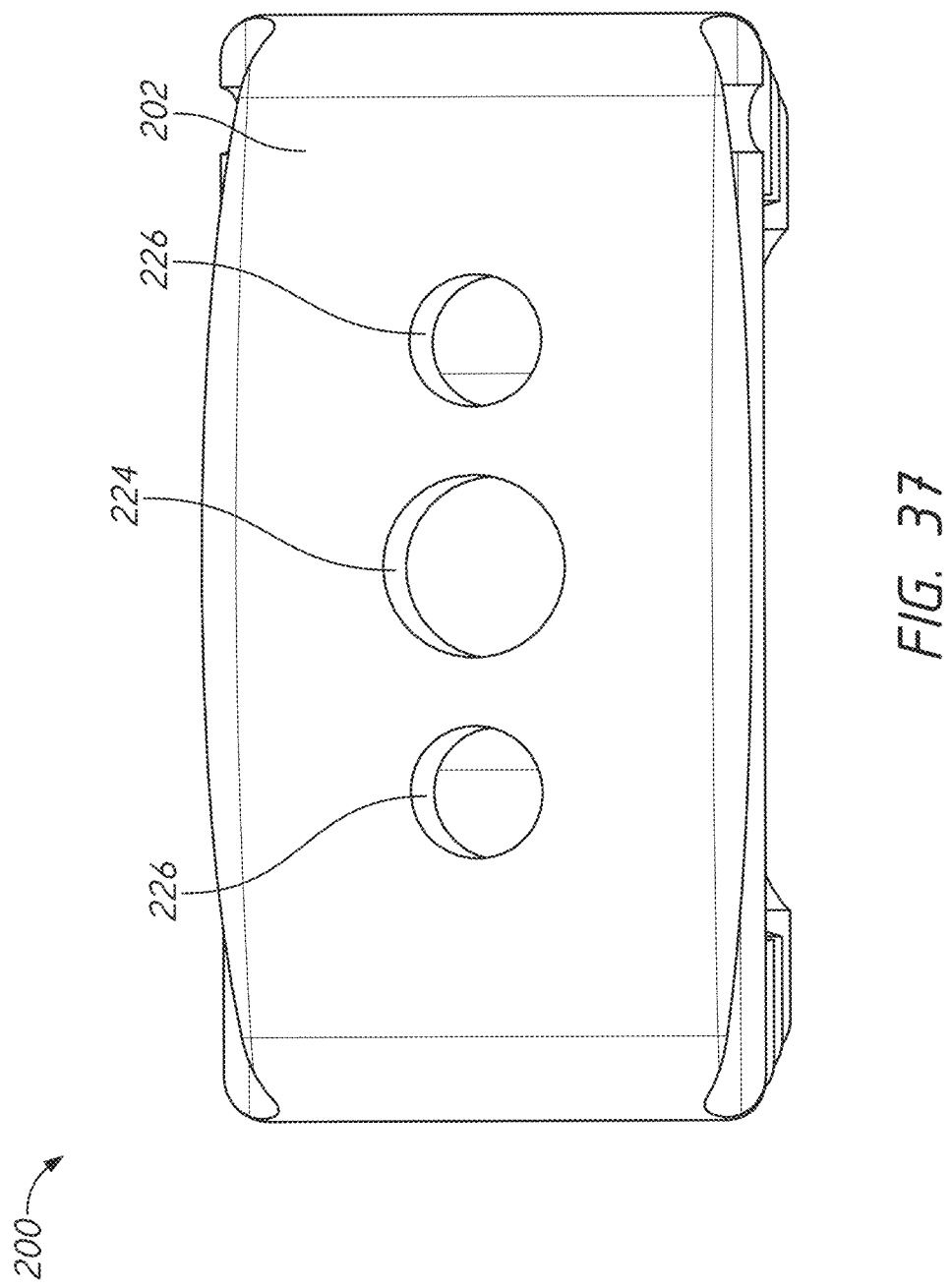
FIG. 37 is a top view of the interbody implant of FIG. 29.

The interbody implant inserter 600 can couple with the interbody implant 200. In some methods of use, the interbody implant 200 can have any feature described herein. FIGS. 36-37 show an embodiment of the interbody implant 200. FIG. 36 illustrates a perspective view. FIG. 37 illustrates a top view.

The anterior surface 202 of the interbody implant 200 can include the threaded lumen 224. The distal end of the internal shaft 604 can include the second threaded portion 612. The second threaded portion 612 can couple with the corresponding threaded lumen 224 in the interbody spacer 200. The anterior surface 202 can include one or more guide lumens 226. In the illustrated embodiment, the anterior surface 202 can include two guide lumens 226. The two guide lumens 226 can be diametrically opposed relative to the threaded lumen 224.

9. Cervical Plate

Figure 38:
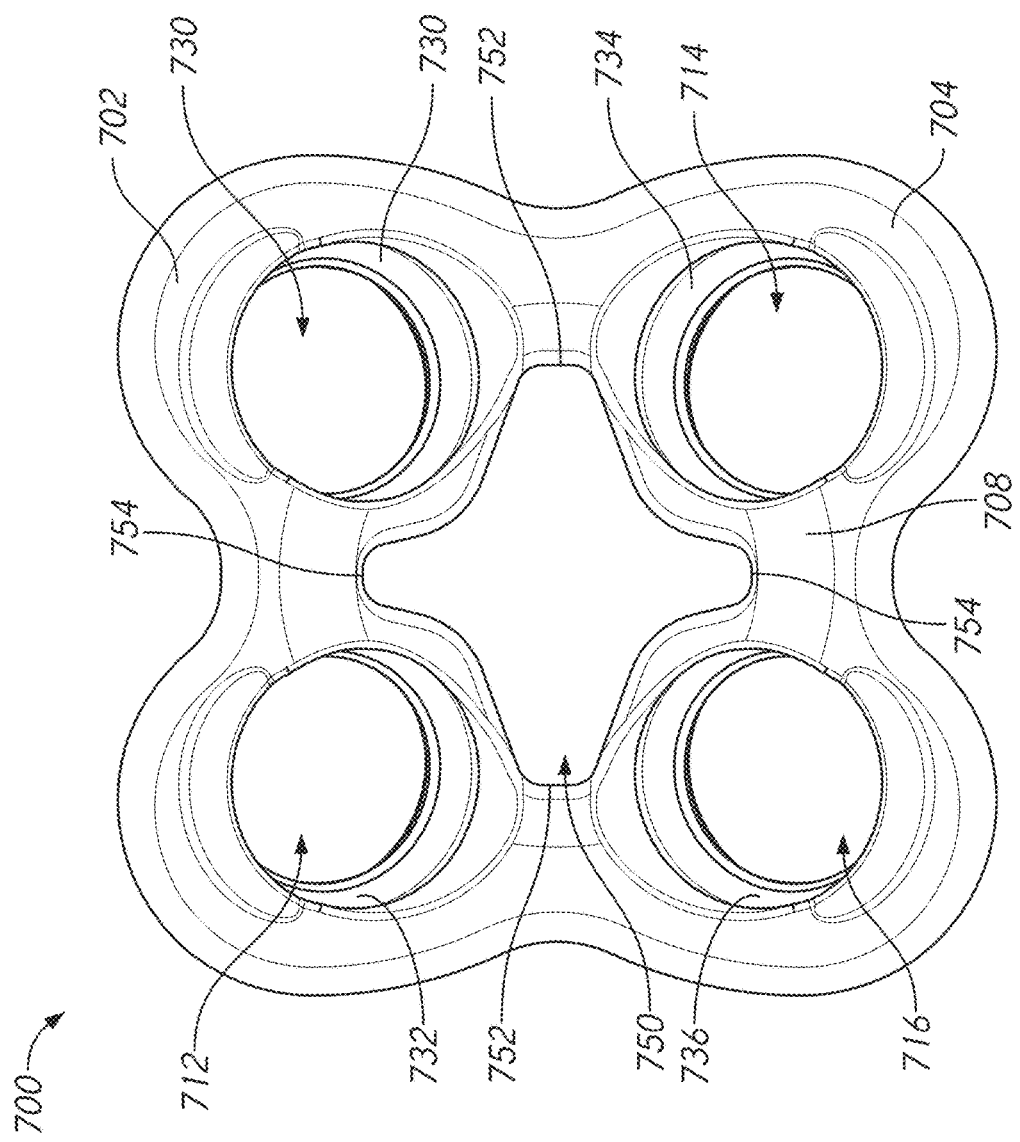
FIG. 38 is a top view of the cervical plate of FIG. 29.
Figure 39:
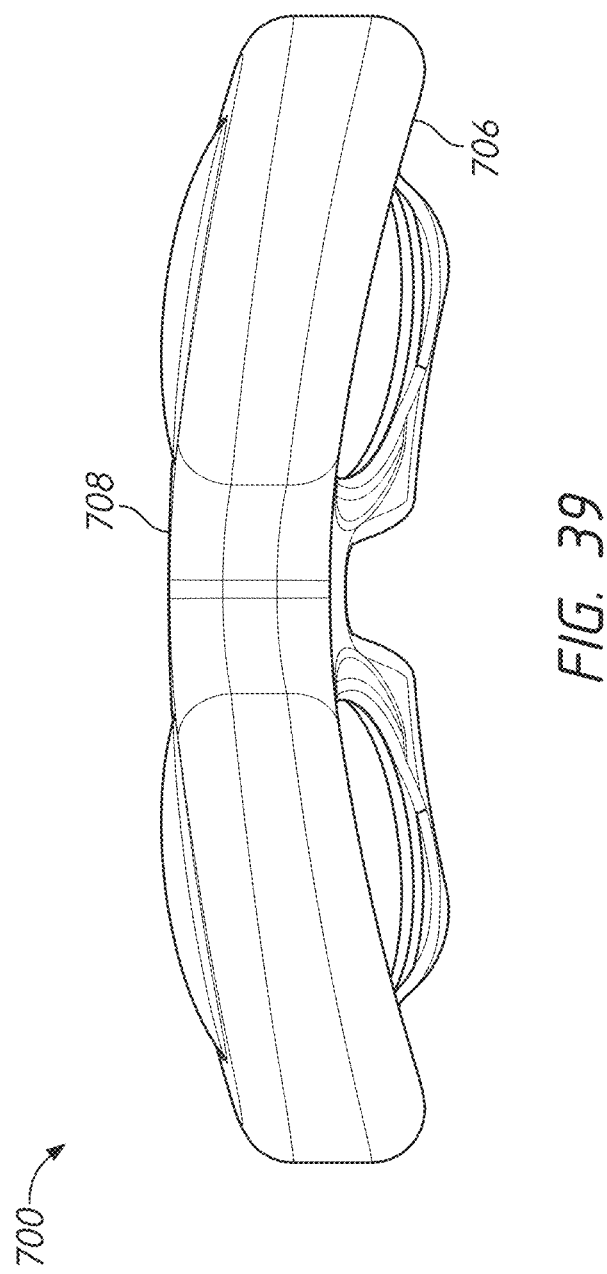
FIG. 39 is a side view of the cervical plate of FIG. 29.
Figure 40:
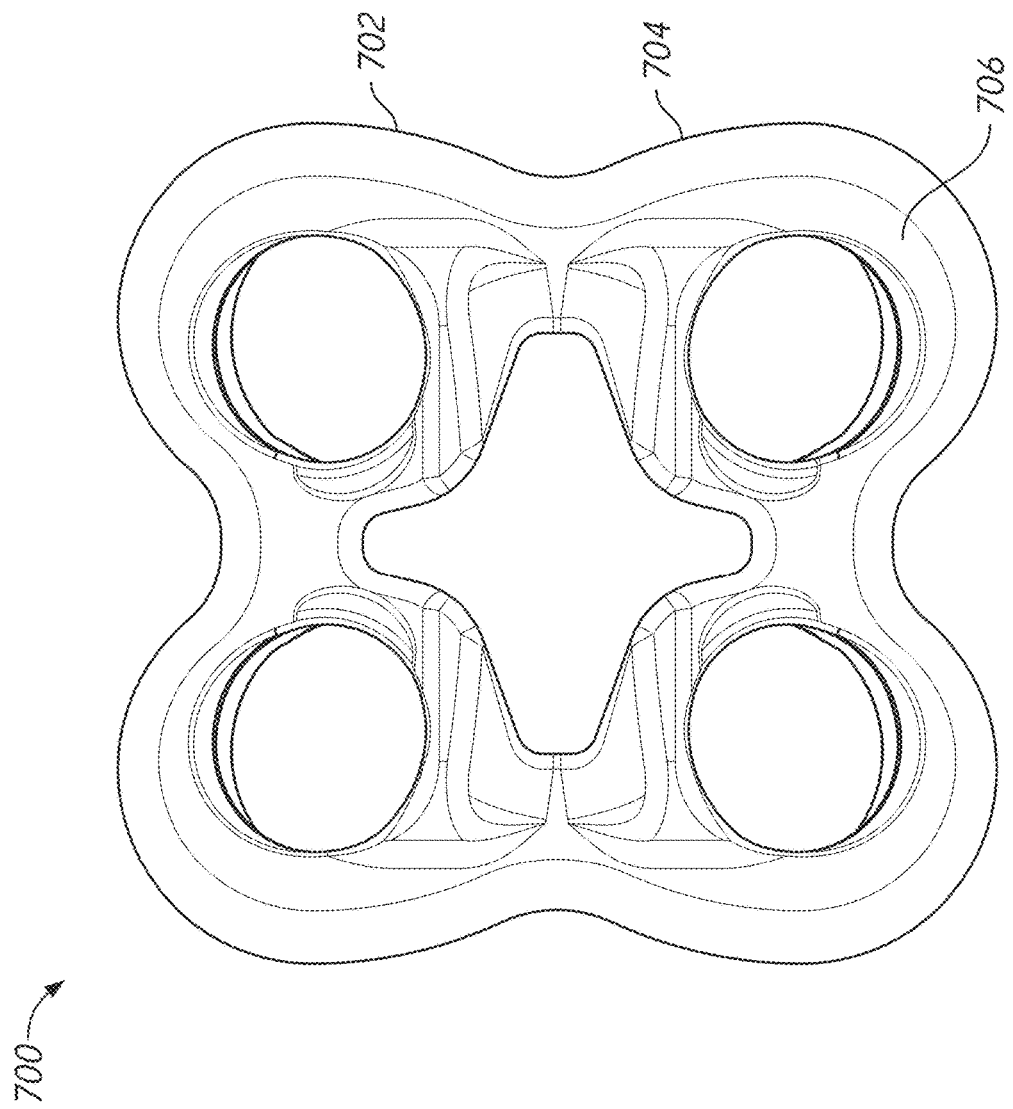
FIG. 40 is a bottom view of the cervical plate of FIG. 29.
Figure 41:
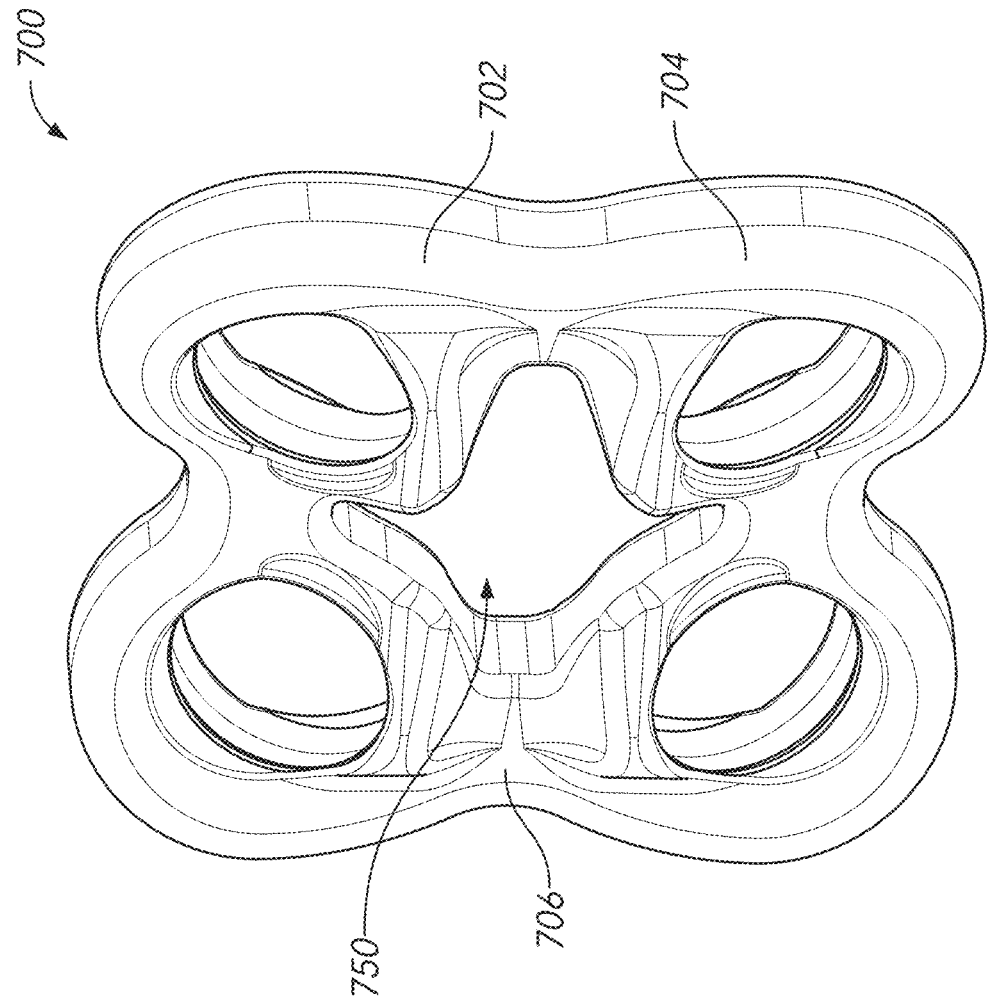
FIG. 41 is a perspective bottom view of the cervical plate of FIG. 29.
Figure 42:
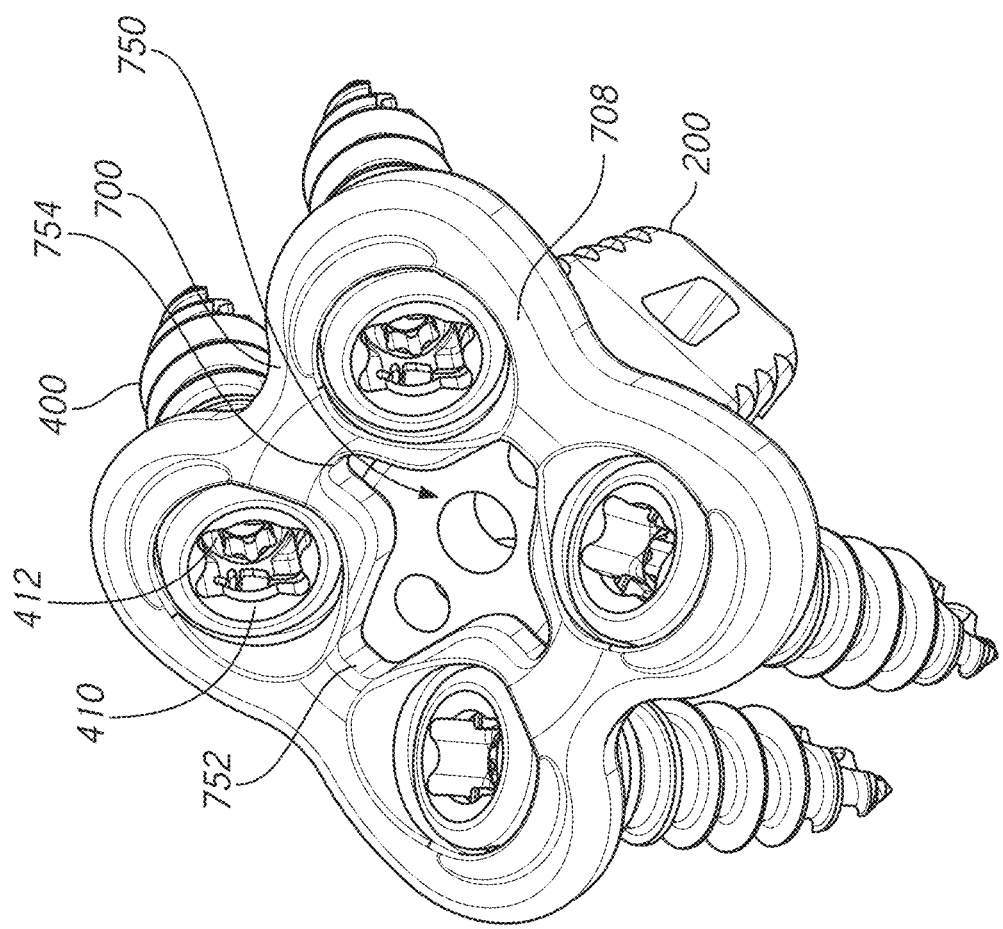
FIG. 42 is a top view of the cervical plate, the anchors, and the interbody implant of FIG. 29.

FIGS. 38-42 depict views of an embodiment of the cervical plate 700. FIG. 38 illustrates a top view. FIG. 39 illustrates a side view. FIG. 40 illustrates a bottom view. FIG. 41 illustrates a bottom perspective view. FIG. 42 illustrates a top perspective view of the interbody implant 200, the cervical plate 700, and the anchors 400.

The cervical plate 700 can include a superior portion 702 and an inferior portion 704. The cervical plate 700 can include a bone facing surface 706 and an access surface 708. In some embodiments, the bone facing surface 706 can contact the vertebral bone surface. In some embodiments, other structures or components may lie in between the bone facing surface 706 and the bone surface of the vertebra. The superior portion 702 can include one or more holes 710, 712 oriented between the bone facing surface 706 and the access surface 708. The inferior portion 704 can include one or more holes 714, 716 oriented between the bone facing surface 706 and the access surface 708.

The cervical plate 700 can be designed to allow high angle anchor insertion. The cervical plate 700 can include any feature described herein. The anchor 400 can be inserted at any angle including 5°, 10°, 15°, 20°, 25°, 30°, 35°, 40°, 45°, 50°, 55°, 60°, 65°, 70°, 80°, 85°, between 30° and 35°, between 35° and 40°, between 40° and 45°, between 45° and 50°, between 30° and 40°, between 40° and 50°, between 50° and 60°, between 55° and 65°, between 60° and 70°, between 30° and 50°, or any range of the foregoing values. The insertion angle can be within a range from 18° to 25°. The insertion angle can be within a range from 25° to 35°. The insertion angle can be within a range from 18° to 30.5°.

The cervical plate 700 can be designed to be at least partially inserted within a disc space as described herein. The cervical plate 700 can couple to the interbody spacer 200. The cervical plate 700 can include a concavity to accept the interbody spacer 200 at least partially therewithin. In some methods of use, the cervical plate 700 is configured to be placed adjacent to cervical vertebrae as described herein. The cervical plate 700 can be designed to facilitate insertion of one or more anchors 400 into the edge or corner of the vertebra.

The holes 710, 712, 714, 716 are configured to accept anchors 400 and/or other attachment devices for anchoring the cervical plate 700 to the vertebral bone. The holes 710, 712, 714, 716 can have any feature described herein.

In some embodiments, one or more additional structures are provided to further interact with the anchor 400. In some embodiments, the anchor 400 can include an expandable or collapsible retainer ring 410. A trajectory surface 730, 732, 734, 736 can include a corresponding recess or indentation to accept the retainer ring 410. The retainer ring 410 can be positioned within one of the holes 710, 712, 714, 716. The retainer ring 410 can be positioned within a recess or indentation along at least a portion of the circumference of the hole 710, 712, 714, 716, wherein the recess or indentation is capable of accepting at least the outside diameter portion of the retainer ring 410. The recess or indentation typically comprises a circumferential channel having a diameter greater than the diameter of the trajectory surface 730, 732, 734, 736.

The retainer ring 410 can allow insertion of the anchor 400 in one direction but can resist movement of the anchor 400 in the opposite direction. The retainer ring 410 can resist backout of the anchor 400. The backout forces acting on the anchor 400 can be insufficient to cause movement of the retainer ring 410 and the anchor 400. In some embodiments, the retainer ring 410 has a completely closed or partially closed configuration. The cross-sectional shape of the retainer structure may be any of a variety shapes, including a circle, semi-circular, oval, squares, rectangles, polygonal or other closed or partially closed shape.

In some embodiments, the anchor may include a secondary anchor 412. The anchor 400 can include a corresponding recess or indentation to accept the secondary anchor 412. The retainer ring 410 can be positioned relative to the secondary anchor 412 with a portion capable of interacting with at least portion of the outside diameter of the secondary anchor 412. The outside diameter of the secondary anchor 412 can be configured to expand the retainer ring 410 when the secondary anchor 412 is inserted within the anchor 400.

Referring to FIGS. 38-42, the cervical plate 700 can include an engagement portion 750. The engagement portion 750 can be recessed. The engagement portion 750 can be configured to engage the outer shaft 602 of the interbody implant inserter 600. The engagement portion 750 can include a lumen. The engagement portion 750 can include a shaped lumen. The engagement portion 750 can include a diamond shaped lumen. The engagement portion 750 can include a complementary retention feature 752. The engagement portion 750 can include a complementary anti-rotation feature 754. In some embodiments, the engagement portion 750 is a graft window. The engagement portion 750 can be configured to be packed with graft material to promote bony growth. The engagement portion 750 can be configured to be packed with material to promote fusion. The engagement portion 750 can be packed after the interbody implant inserter 600 is removed from the engagement portion 750.

The cervical plate 700 can include the complementary retention feature 752 configured to couple with the interbody implant inserter 600, as described herein. The complementary retention feature 752 can be a keyed groove. The complementary retention feature 752 can extend through the cervical plate 700. The complementary retention feature 752 can include one or more grooves. The complementary retention feature 752 can be a solid, shaped surface. The complementary retention feature 752 can provide a frictional fit. The complementary retention feature 752 can provide an interference fit. The complementary retention feature 752 can include two or more diametrically opposed structures. The complementary retention feature 752 can include two or more structures equally spaced around the engagement feature. In the illustrated embodiment, the complementary retention feature 752 includes two structures. Other configurations are contemplated, e.g. one structure, three structures, four structures, etc. In the illustrated embodiment, the complementary retention feature 752 includes two grooves or recesses. The complementary retention feature 752 can be disposed along a midline of the cervical plate 700. The complementary retention feature 752 can be disposed between the superior portion 702 and the inferior portion 704.

The complementary retention feature 752 can be any mechanical arrangement configured to hold the cervical plate 700 in a temporarily fixed position relative to the outer shaft 602. The complementary retention feature 752 can be any mechanical arrangement configured to prevent or limit sliding or translating of the cervical plate 700 relative to the outer shaft 602. The complementary retention feature 752 can apply pressure to the outer shaft 602. The complementary retention feature 752 can push against the outer shaft 602. In some embodiments, additional force applied to the cervical plate 700 will overcome the retention force of the complementary retention feature 752. In some embodiments, the outer shaft 602 is withdrawn relative to the complementary retention feature 752. In some embodiments, the cervical plate 700 can be released from the outer shaft 602 by actuation of a mechanical means.

The cervical plate 700 can include the complementary anti-rotation feature 754 configured to couple with the interbody implant inserter 600, as described herein. The complementary anti-rotation feature 754 can be a keyed groove. The complementary anti-rotation feature 754 can extend through the cervical plate 700. The complementary anti-rotation feature 754 can include one or more grooves. The complementary anti-rotation feature 754 can be a solid, shaped surface. The complementary anti-rotation feature 754 can prevent or limit rotation of the cervical plate 700. The complementary anti-rotation feature 754 can include two or more diametrically opposed structures. The complementary anti-rotation feature 754 can include two or more structures equally spaced around the engagement portion 750. In the illustrated embodiment, the complementary anti-rotation feature 754 includes two structures. Other configurations are contemplated, e.g. one structure, three structures, four structures, etc.

The complementary anti-rotation feature 754 can limit or prevent rotation of the cervical plate 700 relative to the outer shaft 602 of the interbody implant inserter 600. The complementary anti-rotation feature 754 can prevent or limit rotation of the cervical plate 700 during translation of the cervical plate 700. The complementary anti-rotation feature 754 can prevent or limit rotation along a portion of the length of the outer shaft 602 about which the cervical plate 700 translates.

The complementary retention feature 752 and the complementary anti-rotation feature 754 can alternate around an axis from the access surface 708 to the bone facing surface 706. The complementary retention feature 752 and the complementary anti-rotation feature 754 can be the same or similar. The complementary retention feature 752 and the complementary anti-rotation feature 754 can be different. The complementary retention feature 752 and the complementary anti-rotation feature 754 can have different widths. The complementary retention feature 752 and the complementary anti-rotation feature 754 can be perpendicular to each other. In the illustrated embodiment, the complementary retention feature 752 can include two grooves corresponding to the two projections of the first retention feature 620 and the two projections of the second retention feature 622. In the illustrated embodiment, the complementary anti-rotation feature 754 can include two grooves corresponding to the two projections of the anti-rotation features 624.

The outer shaft 602 can couple to the engagement portion 750 of the cervical plate 700. In some embodiments, the one or more features 620, 622, 624 can couple with corresponding, complementary features 752, 754 in the cervical plate 700. The engagement portion 750 can be flat, tapered, or curved. The engagement portion 750 can have a corresponding shape as the features 620, 622, 624 of the outer shaft 602. The features 620, 622, 624 of the outer shaft 602 can be shaped to fit within the engagement portion 750. The features 620, 622, 624 of the outer shaft 602 can be shaped to fit within recesses of the engagement portion 750.

The engagement portion 750 can include a lumen. In the illustrated embodiment, the engagement portion 750 can include one lumen comprising the complementary features 752, 754. The engagement portion 750 can be centrally located. The engagement portion 750 can have a square or rectangular cross-sectional shape. The engagement portion 750 can have a triangular cross-sectional shape. The engagement portion 750 can have a diamond or rhombus cross-sectional shape. The engagement portion 750 can have a star cross-sectional shape (e.g., four pointed star, five pointed star, six pointed star, seven pointed star, etc.). The engagement portion 750 can have a polygonal cross-sectional shape. The engagement portion 750 can have a non-circular cross-sectional shape.

FIG. 42 shows a position of the cervical plate 700 relative to the interbody implant 200. During use, the distal end of the internal shaft 612 can extend through the engagement portion 750 of the cervical plate 700. The distal end of the internal shaft 604 can include the second threaded portion 612, as described herein. The second threaded portion 612 can couple with the threaded lumen 224 in the interbody spacer 200. In some embodiments, the threaded lumen 224 of the interbody spacer 200 is adapted to form a rotatable mechanical interfit with the second threaded portion 612 of the internal shaft 604 inserted through the engagement portion 750. The internal shaft 604 can be coupled to the interbody spacer 200 such that force applied to the internal shaft 604 is transmitted to the interbody spacer 200.

The distal end of the outer shaft 602 can include two projections 610. The two projections 610 can extend through the engagement portion 750 of the cervical plate 700. The two projections 610 can couple with the guide lumens 226 in the interbody spacer 200. In some embodiments, the guide lumens 226 of the interbody spacer 200 are adapted to form a mechanical interfit with the projections 610 on the outer shaft 602 inserted through the engagement portion 750. When the projections 610 are inserted into the interbody implant 200, the features 620, 622, 624 of the interbody implant inserter 600 align with the complementary features 752, 754 of the cervical plate 700. When the internal shaft 604 is coupled to the interbody spacer 200, the thumbscrew 616 can abut the proximal end of the outer shaft 602. The interbody spacer 200 and the interbody implant inserter 600 can form a rigid assembly. The interbody implant inserter 600 can be firmly seated against the interbody spacer 200. The interbody implant inserter 600 can be firmly seated within the engagement portion 750 of the cervical plate 700.

The engagement portion 750 of the cervical plate 700 can be oriented over the anterior surface 202 of the interbody implant 200 when the cervical plate 700 is translated relative to the interbody implant inserter 600 to be in contact with the interbody implant 200. The interbody implant inserter 600 can be oriented in any manner relative to the interbody implant 200 that allows the cervical plate 700 to translate into position. The cervical plate 700 can include one or more recesses or grooves that accommodates the anterior surface 202 of the interbody implant 200. The cervical plate 700 can include one or more recesses or grooves on the bone facing surface 706. In use, the interbody implant 200 can extend from the bone facing surface 706 of the cervical plate 700.

The interbody implant 200 can be configured to occupy the disc space between adjacent vertebrae. The interbody implant 200 can be configured to be recessed within the disc space. In some methods, the interbody implant 200 can be recessed 0 mm, 1 mm, 2 mm, 3 mm, 4 mm, 5 mm, 6 mm, 7 mm, 8 mm, 9 mm, 10 mm, or any range of the foregoing values. The interbody implant 200 extends between the superior and inferior vertebra. In some embodiments, the interbody implant inserter 600 is oriented to allow access to the holes 710, 712, 714, 716. Once the cervical plate 700 is translated into position, one or more anchors 400 can be utilized to secure the cervical plate 700 to the adjacent vertebrae.

In some embodiments, the average thickness of the cervical plate 700 is within the range of about 1 mm to about 5 mm. In other embodiments, the average thickness of the cervical plate 700 is within the range of about 1.5 mm to about 3.0 mm. The thicknesses of the cervical plate 700 need not be uniform. In some embodiments, the cervical plate 700 is conformable to the vertebral surfaces of the implantation sites.

The cervical plate 700 can be made from a material that is the same or different from the interbody implant 200. In some embodiments, a cervical plate 700 and an interbody implant 200 having different materials may be beneficial because the interbody implant 200 can be configured to withstand compressive forces while the cervical plate 300 can be configured to withstand primarily tension forces. In some embodiments, the cervical plate 700 comprises a titanium or titanium alloy. Other material or combination of materials may also be used as is known by those with skill in the art.

10. Two-Level Cervical Plate

Figure 43:
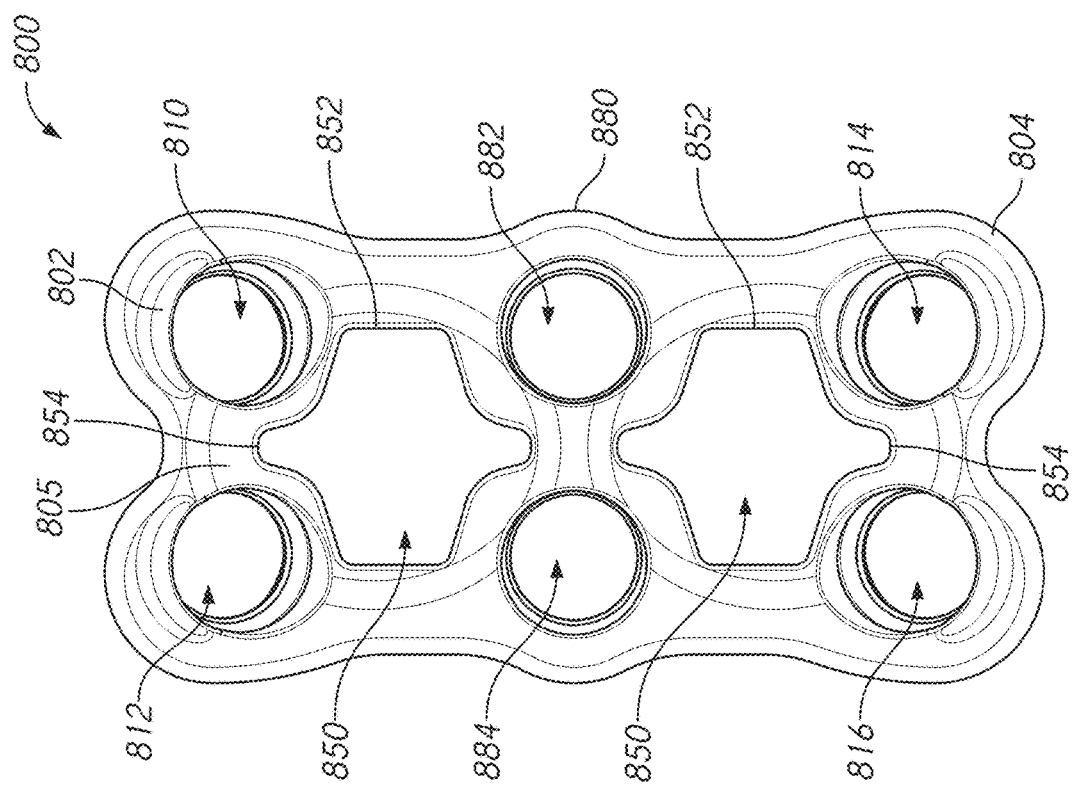
FIG. 43 is a top view of a two-level cervical plate.
Figure 44:
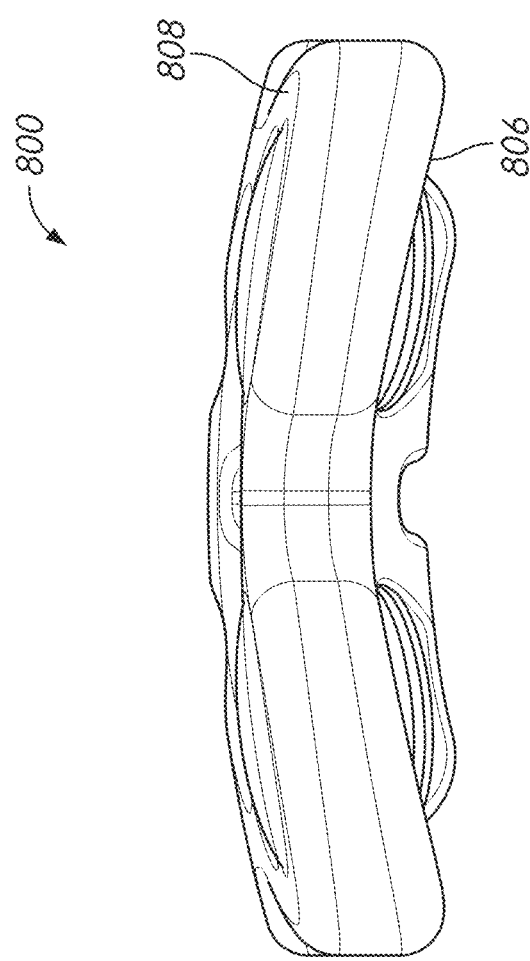
FIG. 44 is a side view of the two-level cervical plate of FIG. 43.
Figure 45:
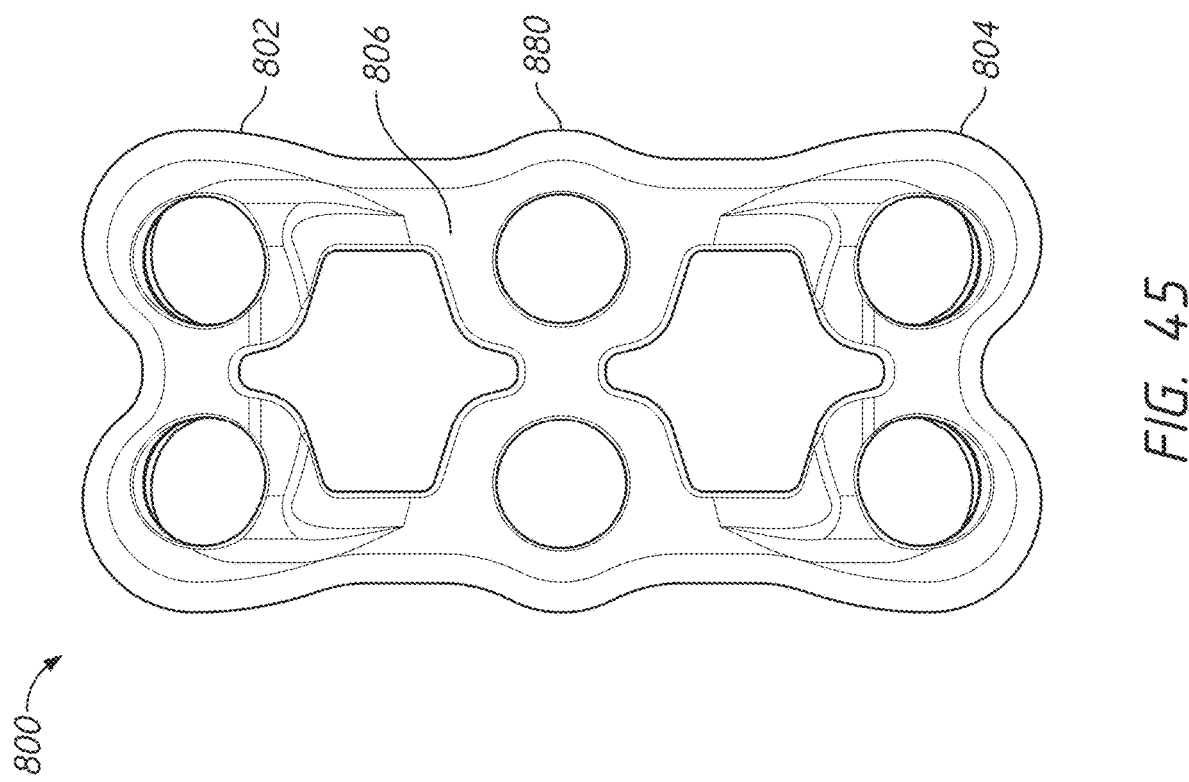
FIG. 45 is a bottom view of the two-level cervical plate of FIG. 43.
Figure 46:
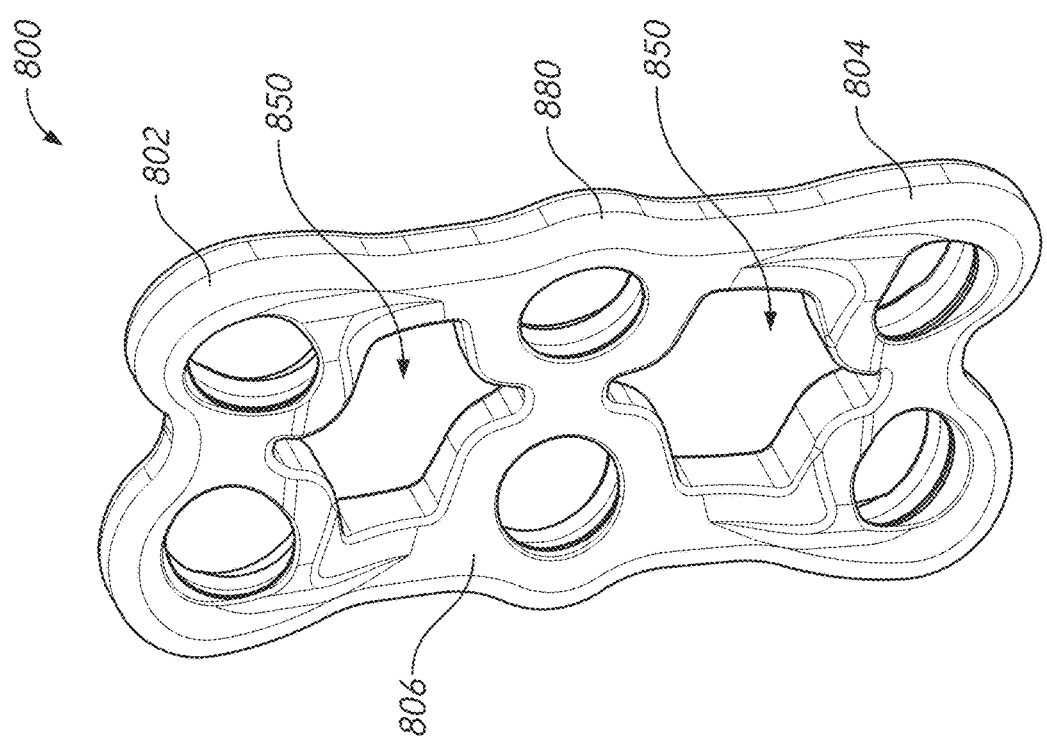
FIG. 46 is a perspective bottom view of the two-level cervical plate of FIG. 43.
Figure 47:
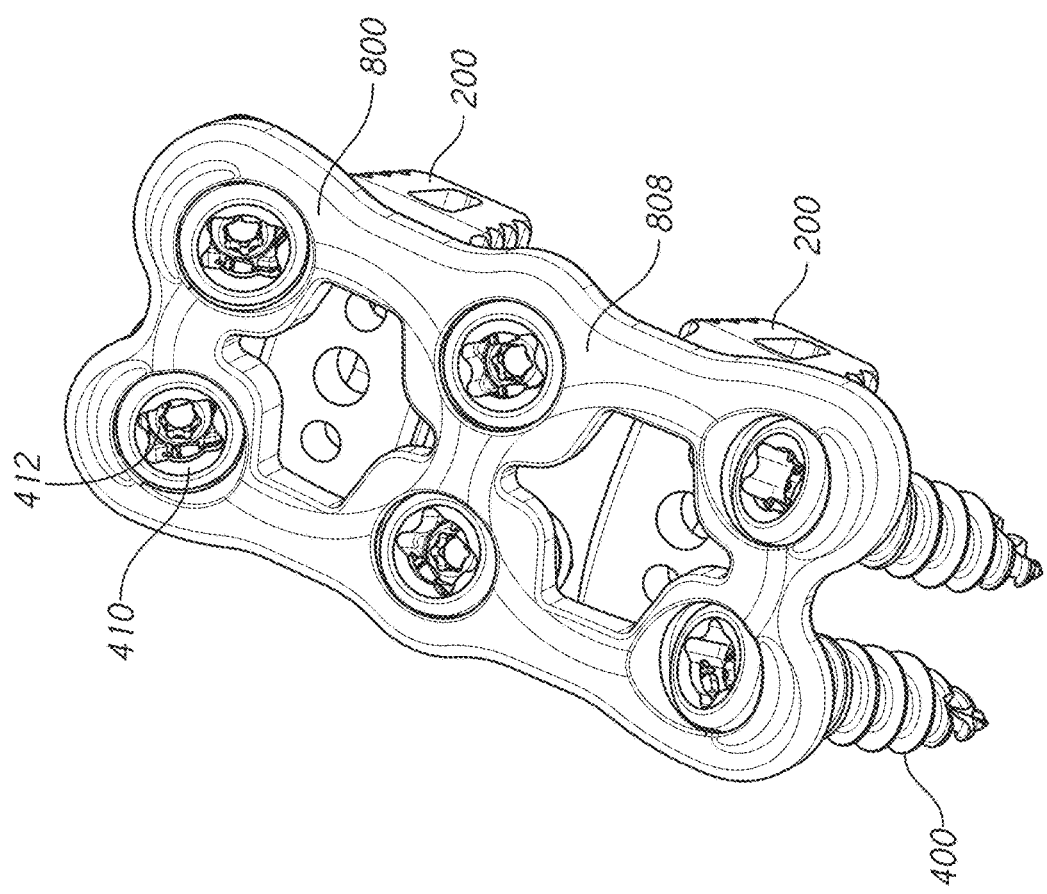
FIG. 47 is a top view of the two-level cervical plate, the anchors, and the interbody implant of FIG. 43.
Figure 48:
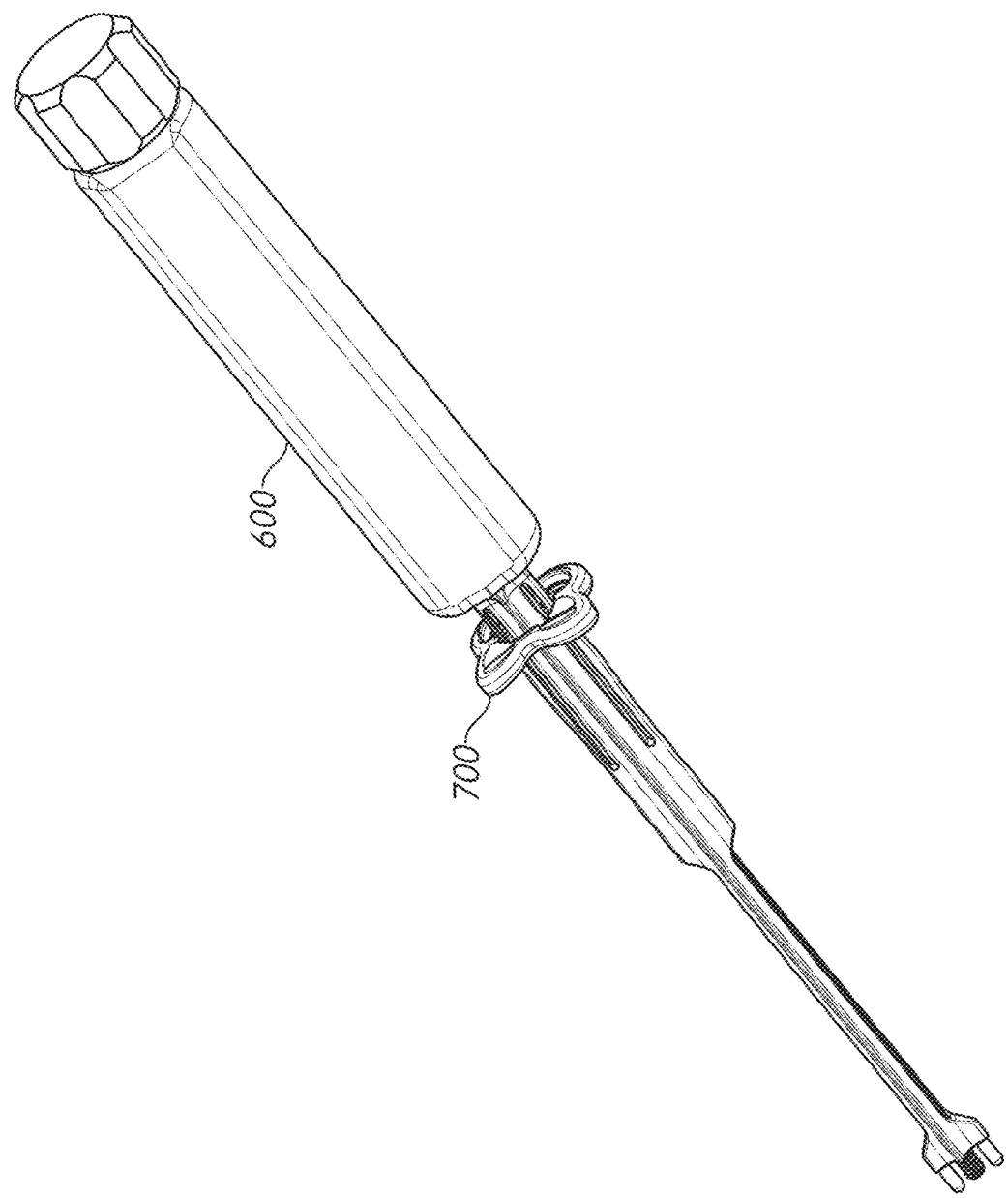
FIG. 48 is a perspective view of the interbody implant inserter and the cervical plate in a proximal position.
Figure 49:
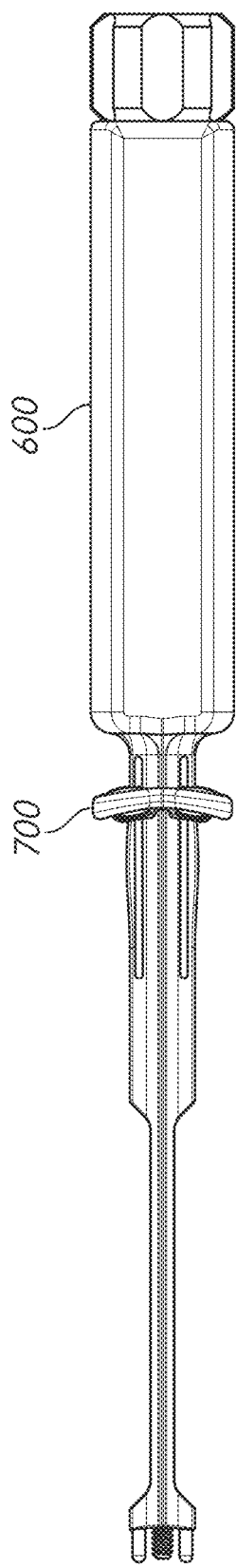
FIG. 49 is a side view of the interbody implant inserter and the cervical plate in the proximal position of FIG. 48.
Figure 50:
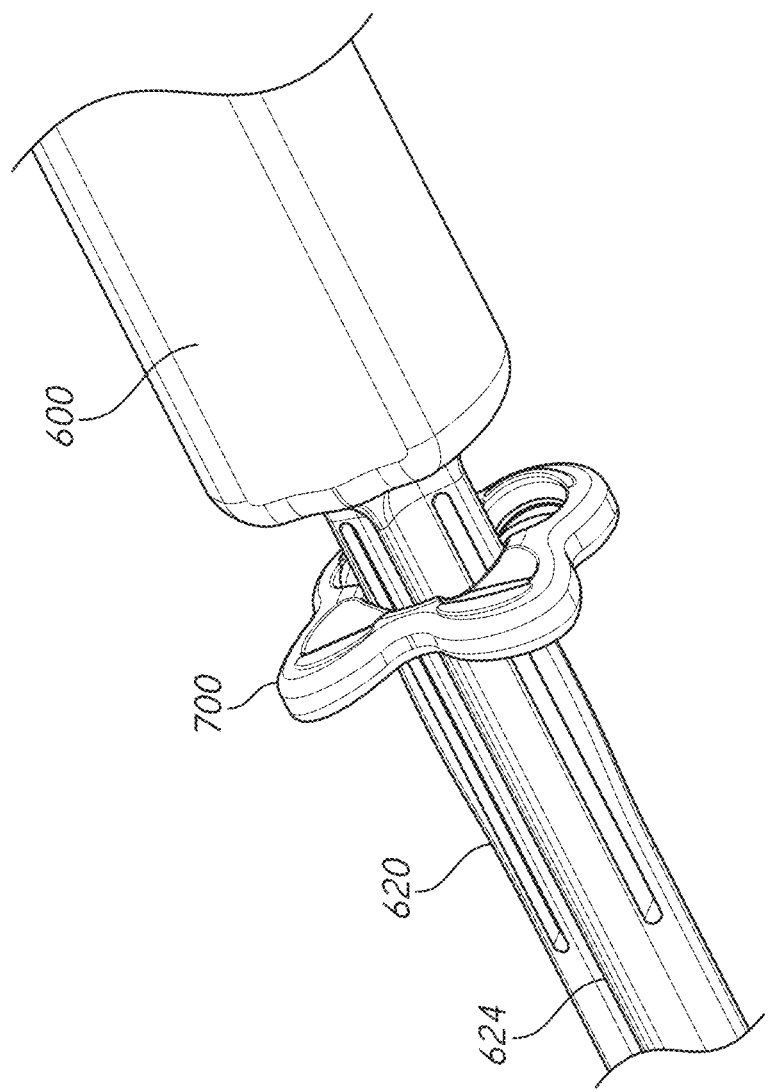
FIG. 50 is an enlarged top perspective view of the interbody implant inserter and the cervical plate in the proximal position of FIG. 48.
Figure 51:
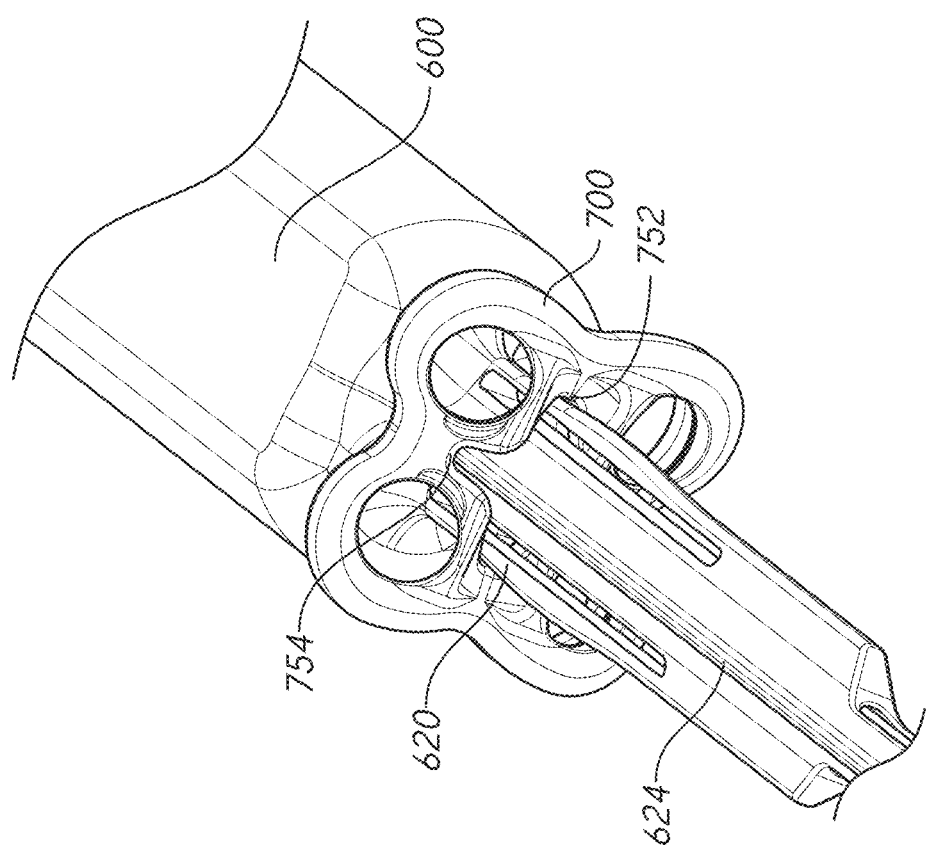
FIG. 51 is an enlarged bottom perspective view of the interbody implant inserter and the cervical plate in the proximal position of FIG. 48.
Figure 52:
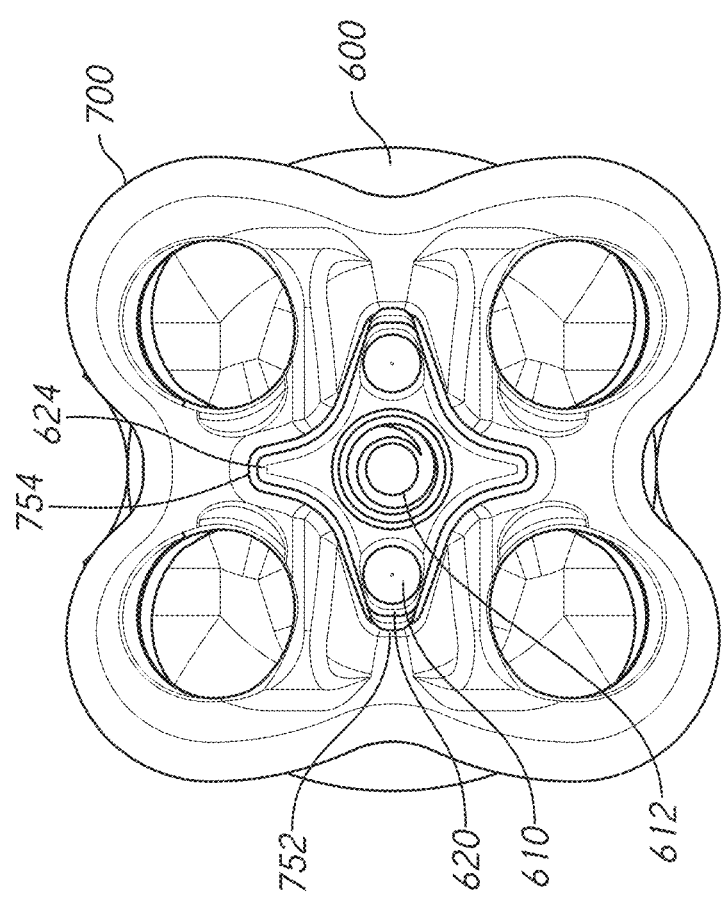
FIG. 52 is an enlarged bottom view of the interbody implant inserter and the cervical plate in the proximal position of FIG. 48.

FIGS. 43-47 depict views of an embodiment of the two-level cervical plate 800. FIG. 43 illustrates a top view. FIG. 44 illustrates a side view. FIG. 45 illustrates a bottom view. FIG. 46 illustrates a bottom perspective view. FIG. 47 illustrates the interbody implant 200, the two-level cervical plate 800, and anchors 400.

The two-level cervical plate 800 can be designed to allow high angle anchor insertion. The anchor 400 can be inserted at 30°, 35°, 40°, between 30° and 35°, between 35° and 40°, between 30° and 40°, or any range of the foregoing values. The insertion angle can be within a range from 18° to 25°. The insertion angle can be within a range from 25° to 35°. The insertion angle can be within a range from 18° to 30.5°. The two-level cervical plate 800 can have any of the features of the cervical plate 300, the cervical plate 700, or the two-level cervical plate 500 described herein.

The two-level cervical plate 800 can include a superior portion 802 and an inferior portion 804. The two-level cervical plate 800 can include a bone facing surface 806 and an access surface 808. The superior portion 802 can include one or more holes 810, 812 oriented between the bone facing surface 806 and the access surface 808. The inferior portion 804 can include one or more holes 814, 816 oriented between the bone facing surface 806 and the access surface 808.

The two-level cervical plate 800 can include a middle portion 880. The middle portion 880 can be disposed between the superior portion 802 and the inferior portion 804. The middle portion 880 can include one or more holes 882, 884 oriented between the bone facing surface 806 and the access surface 808.

The holes 810, 812, 814, 816, 882, 884 are configured to accept anchors 400 and/or other attachment devices for anchoring the two-level cervical plate 800 to the vertebral bone. One or more anchors 400 configured for insertion through one or more holes 810, 812, 814, 816, 882, 884 in the two-level cervical plate 800 can be provided.

Referring to FIGS. 43-47, the two-level cervical plate 800 can include one or more engagement portion 850. Each engagement portion 850 can be recessed. Each engagement portion 850 can be configured to engage the outer shaft 602 of the interbody implant inserter 600. Each engagement portion 850 can include a lumen. Each engagement portion 850 can include a shaped lumen. Each engagement portion 850 can include a diamond shaped lumen. Each engagement portion 850 can include a first complementary retention feature 852. Each engagement portion 850 can include a second complementary retention feature 854. In some embodiments, the engagement portion 850 is a graft window. The engagement portion 850 can have any feature of the engagement portion 750 described herein.

The cervical plate 800 can include a complementary retention feature 852 configured to couple with the interbody implant inserter 600, as described herein. The complementary retention feature 852 can have any features of the complementary retention feature 752 described herein. The complementary retention feature 852 can be a keyed groove. The complementary retention feature 852 can extend through the cervical plate 800. The complementary retention feature 852 can include one or more grooves.

The complementary retention feature 852 can be any mechanical arrangement configured to hold the cervical plate 800 in a temporarily fixed position relative to the outer shaft 602. The complementary retention feature 852 can be any mechanical arrangement configured to prevent or limit sliding or translating of the cervical plate 800 relative to the outer shaft 602. In some embodiments, additional force applied to the cervical plate 800 will overcome the retention force of the complementary retention feature 852.

The cervical plate 800 can include the complementary anti-rotation feature 854 configured to couple with the interbody implant inserter 600, as described herein. The complementary anti-rotation feature 854 can have any features of the complementary anti-rotation feature 754 described herein. The complementary anti-rotation feature 854 can be a keyed groove. The complementary anti-rotation feature 854 can extend through the cervical plate 800. The complementary anti-rotation feature 854 can include one or more grooves.

The complementary anti-rotation feature 854 can limit or prevent rotation of the cervical plate 800 relative to the outer shaft 602 of the interbody implant inserter 600. The complementary anti-rotation feature 854 can prevent or limit rotation of the cervical plate 700 during translation of the cervical plate 700.

The complementary retention feature 852 and the complementary anti-rotation feature 854 can alternate around the engagement portion 850. The complementary retention feature 852 and the complementary anti-rotation feature 854 can be the same or similar. The complementary retention feature 852 and the complementary anti-rotation feature 854 can be different. The complementary retention feature 852 and the complementary anti-rotation feature 854 can have different widths.

The outer shaft 602 can couple to the engagement portion 850 of the cervical plate 800. In some embodiments, the one or more features 620, 622, 624 can couple with corresponding, complementary features 852, 854 in the two-level cervical plate 800. The engagement portion 850 can have a corresponding shape as the features 620, 622, 624 of the outer shaft 602. The features 620, 622, 624 of the outer shaft 602 can be shaped to fit within the recessed engagement portion 850.

In the illustrated embodiment, each engagement portion 850 can include a lumen comprising the complementary features 852, 854. One engagement portion 850 can be disposed between the superior portion 802 and the middle portion 880. One engagement portion 850 can be disposed between the middle portion 880 and the inferior portion 804. Other configurations are contemplated depending on the number and configuration of interbody implants 200.

11. Implantation Procedure

Figure 53:
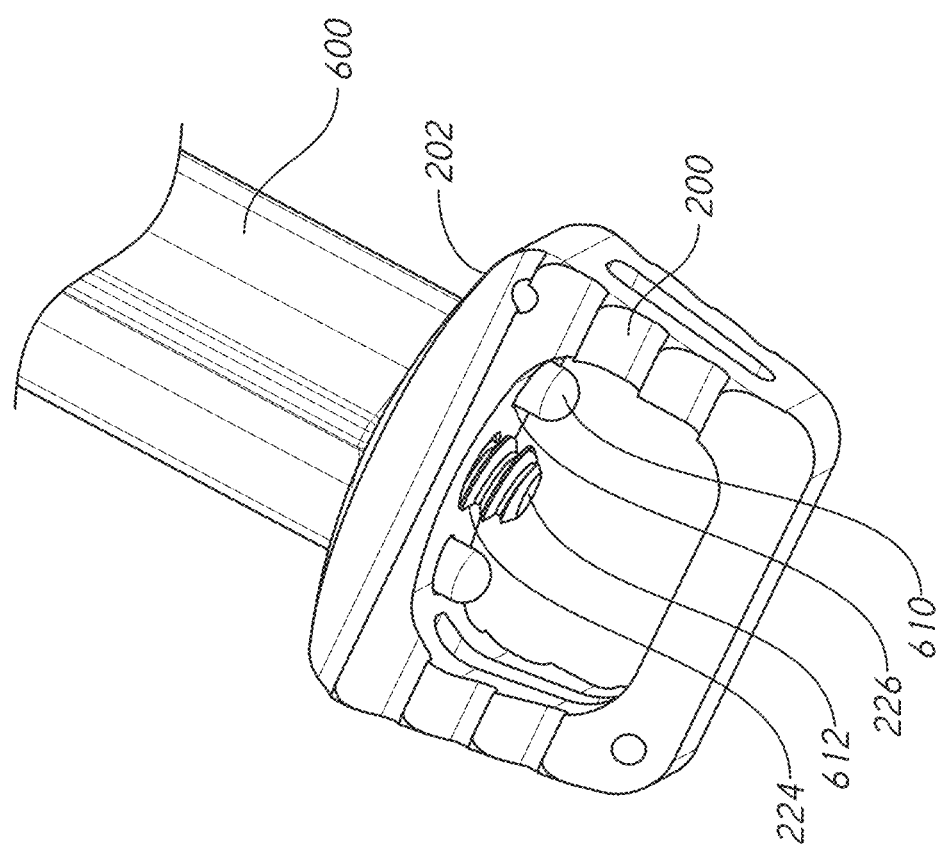
FIG. 53 is an enlarged perspective view of the interbody implant inserter and the interbody implant.
Figure 54:
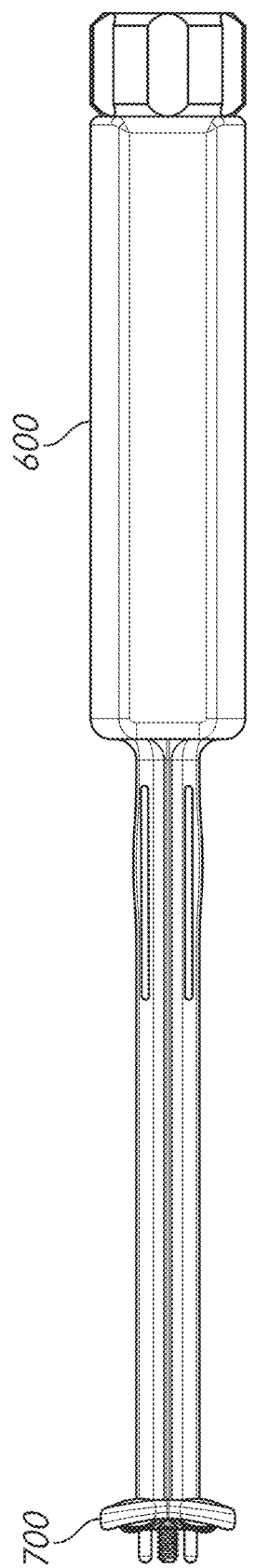
FIG. 54 is a side view of the interbody implant inserter and the cervical plate in a distal position.
Figure 55:
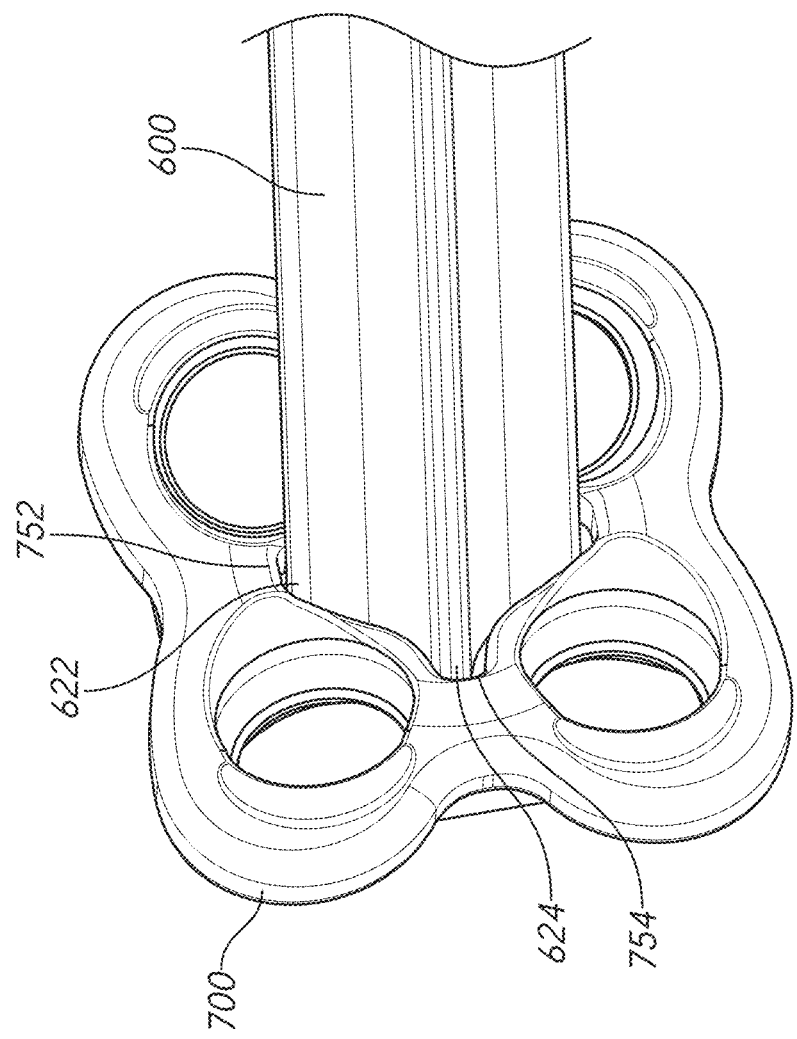
FIG. 55 is an enlarged top perspective view of the interbody implant inserter and the cervical plate in the distal position of FIG. 54.
Figure 56:
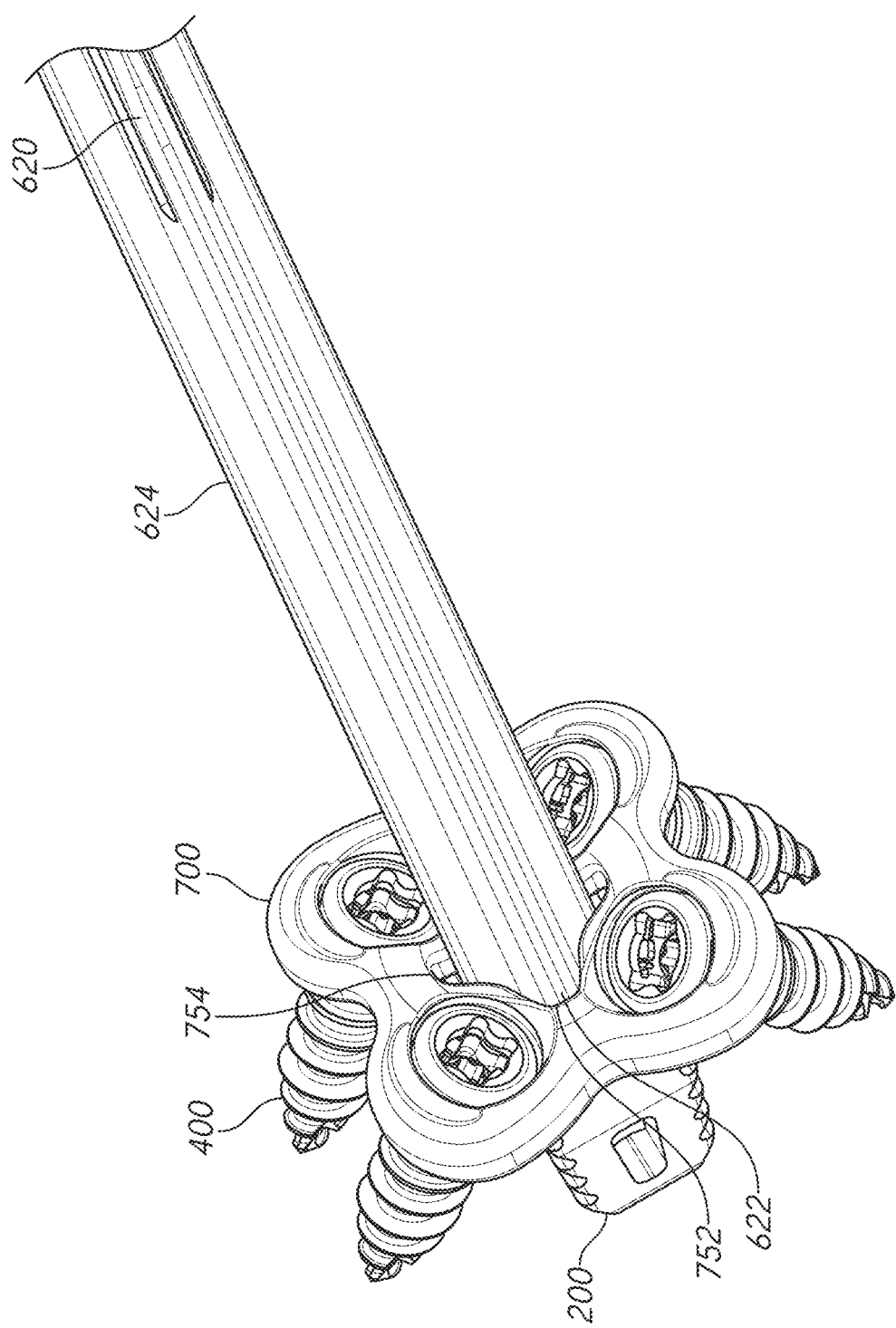
FIG. 56 is an enlarged top perspective view of the interbody implant inserter, the interbody implant, the cervical plate, and the anchors in the distal position of FIG. 54.
Figure 57:
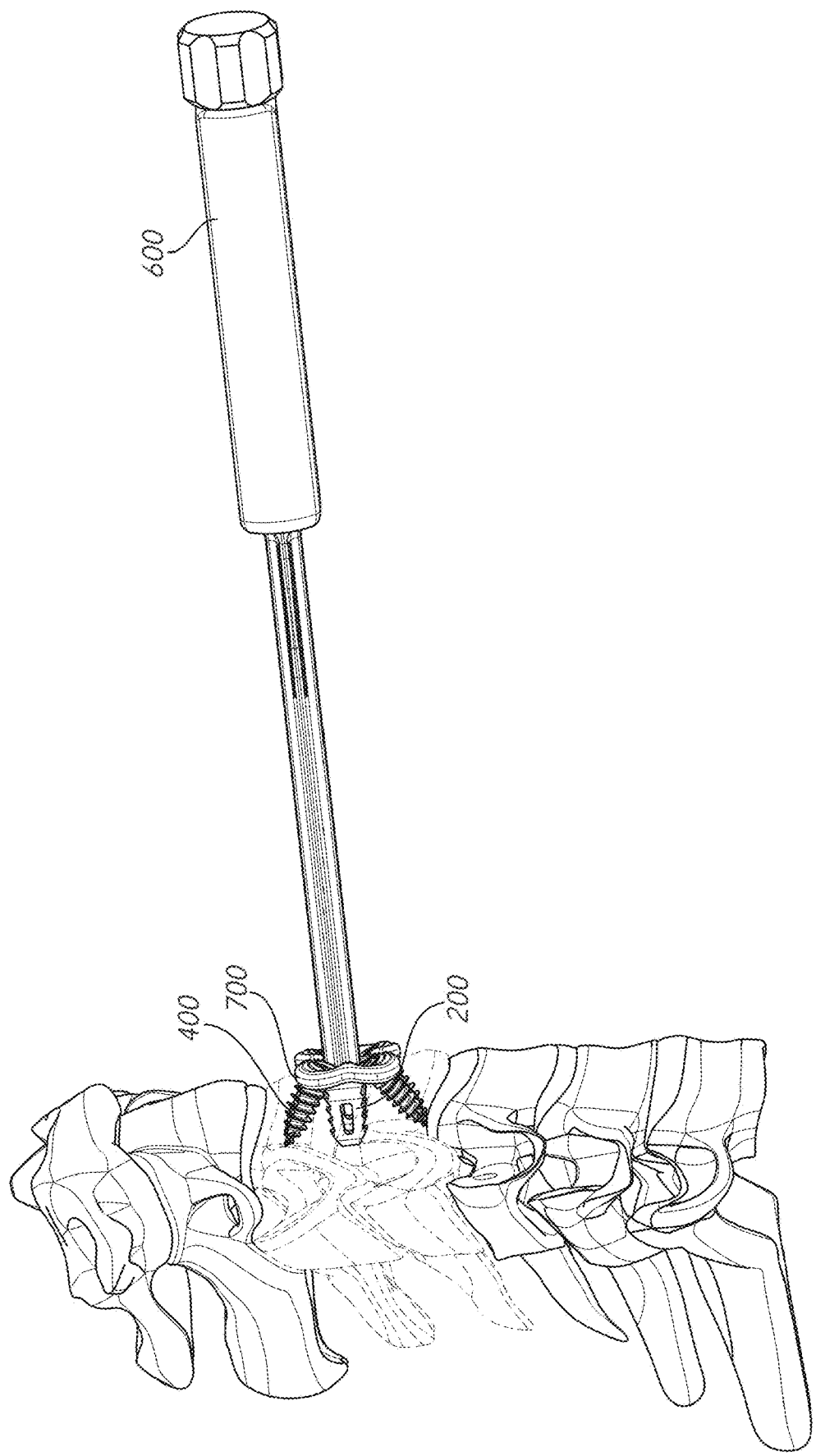
FIG. 57 is a side view of the interbody implant inserter, the interbody implant, the cervical plate, and the anchors in the distal position of FIG. 54.
Figure 58:
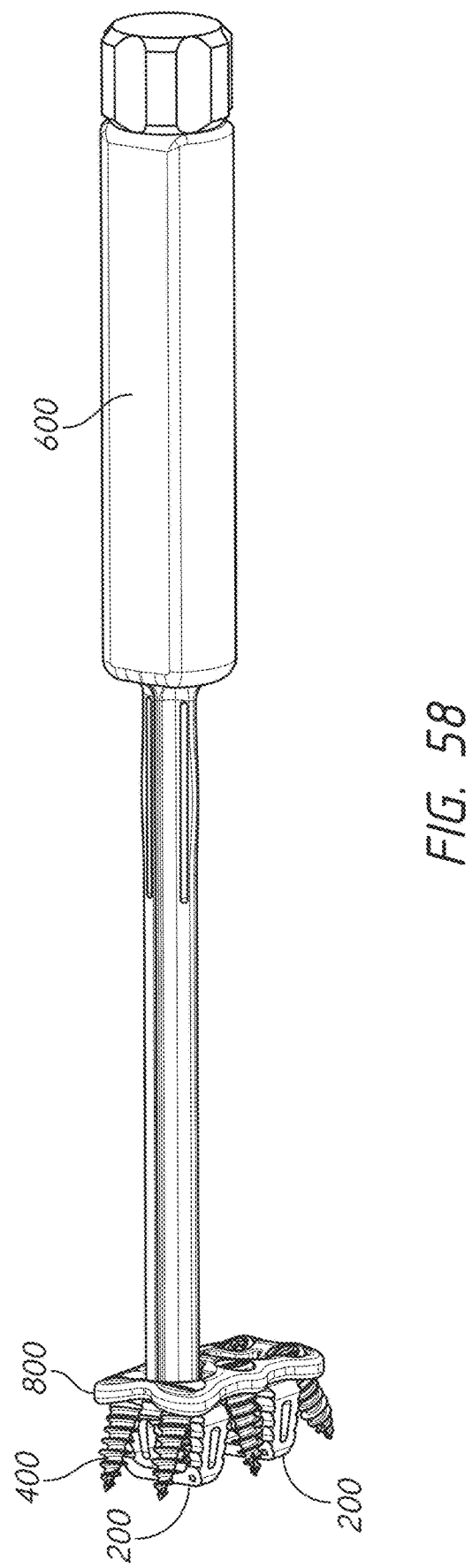
FIG. 58 is a side perspective view of the interbody implant inserter, the interbody implant, the two-level cervical plate, and the anchors in a distal position.
Figure 59:
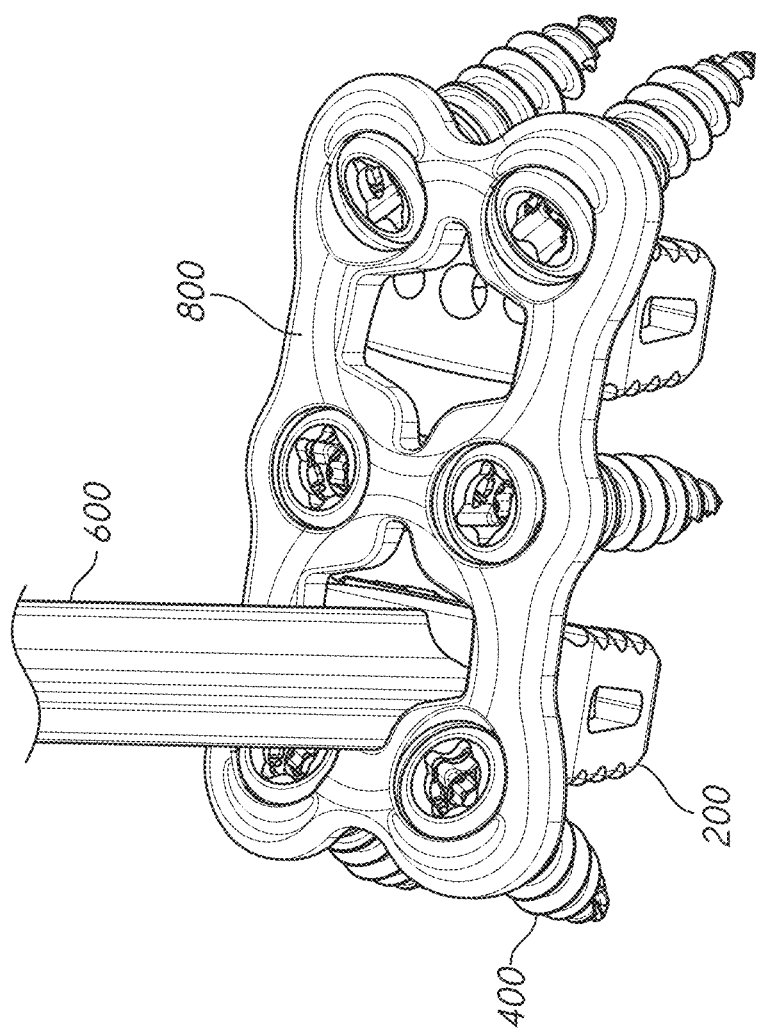
FIG. 59 is a top perspective view of the interbody implant inserter, the interbody implant, the two-level cervical plate, and the anchors in the distal position of FIG. 58.
Figure 60:
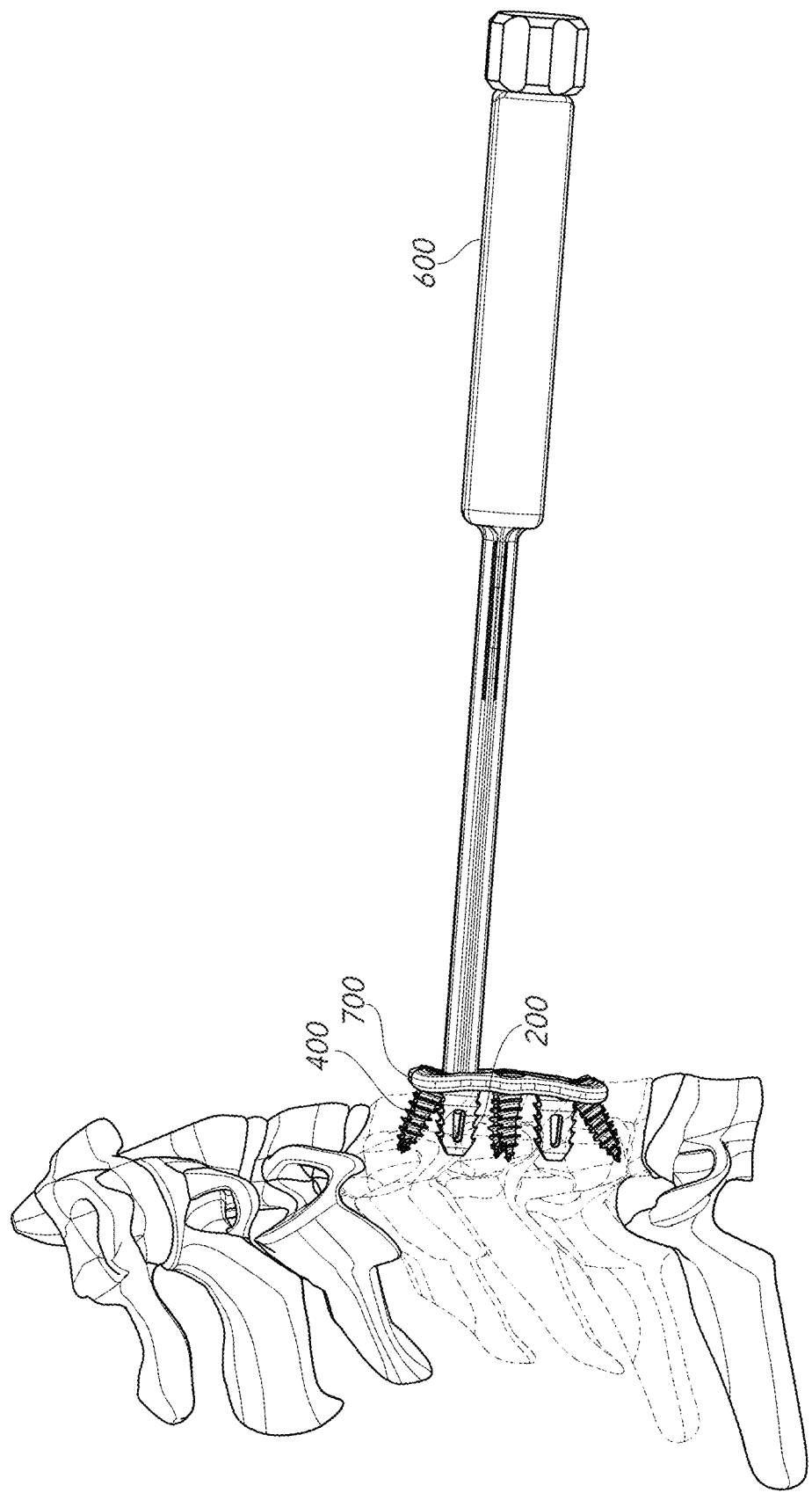
FIG. 60 is a side view of the interbody implant inserter, the interbody implant, the two-level cervical plate, and the anchors in the distal position of FIG. 58.

FIGS. 48-52 illustrate an embodiment of a proximal position of the cervical plate 700. FIG. 53 illustrates the interbody implant inserter 600 coupled to the interbody spacer 200. FIGS. 54-57 illustrate an embodiment of a distal position of the cervical plate 700. FIGS. 58-60 illustrate an embodiment of a distal position of the two-level cervical plate 800. The dashed lines in FIGS. 57 and 60 are used to show the outer surface of the vertebrae. The vertebrae are shown in dashed lines to illustrate the bone as transparent so that the location of the anchors 400 inserted into the bone can be illustrated.

FIGS. 48-52 illustrate an embodiment of a proximal position of the cervical plate 700. The cervical plate 700 can be held via frictional fit at the proximal position. The cervical plate 700 can be held at the proximal part of the outer shaft 602. The proximal part of the outer shaft 602 can include the first retention feature 620. The first retention feature 620 can flex toward and away from the longitudinal axis of the outer shaft 602. In the illustrated example, the first retention feature 620 comprises two leaf springs which are diametrically opposed.

The cervical plate 700 can include the complementary retention feature 752 configured to couple with the first retention feature 620 of the interbody implant inserter 600 at the proximal position. The first retention feature 620 and the complementary retention feature 752 can provide a frictional fit. In the illustrated example, the first complementary retention feature 752 comprises two grooves which are diametrically opposed. The complementary retention feature 752 can have any shape corresponding to the first retention feature 620.

The first retention feature 620 and the complementary retention feature 752 can be any mechanical arrangement configured to hold the cervical plate 700 in a temporarily fixed, proximal position relative to the outer shaft 602. The first retention feature 620 and the complementary retention feature 752 can be any mechanical arrangement configured to prevent or limit sliding or translating of the cervical plate 700 from the proximal position.

The cervical plate 700 can be prevented from rotating in the proximal position. The proximal portion of the outer shaft 602 can include the anti-rotation feature 624. In the illustrated example, the anti-rotation feature 624 comprises two ridges which are diametrically opposed. The cervical plate 700 can include the complementary anti-rotation feature 754 configured to couple with the anti-rotation feature 624 of the interbody implant inserter 600. The anti-rotation feature 624 and the complementary retention feature 754 can prevent or limit rotation of the cervical plate 700 relative to the interbody implant inserter 600. In the illustrated example, the complementary anti-rotation feature 754 comprises two grooves which are diametrically opposed. The complementary anti-rotation feature 754 can have any shape corresponding to the anti-rotation feature 624.

In some embodiments, additional force applied to the cervical plate 700 will overcome the retention force of first retention feature 620 relative to the complementary retention feature 752. In some embodiments, the cervical plate 700 is released from the proximal position. In some embodiments, the cervical plate 700 slides distally from the proximal position. The cervical plate 700 can be prevented from rotating while translating relative to the outer shaft 602. The outer shaft 602 can include the anti-rotation feature 624 along the portion of the outer shaft 602 that the cervical plate 700 translates. The first retention feature 620 and the anti-rotation feature can have different widths. The anti-rotation feature can be thinner than the first rotation feature 620. Other configurations are contemplated.

FIG. 53 illustrates the distal end of the interbody implant inserter 600 when the cervical plate 700 is held via frictional fit at the proximal position. The interbody implant 200 can include the threaded lumen 224. The distal end of the internal shaft 604 can include the second threaded portion 612. The second threaded portion 612 can couple with the corresponding threaded lumen 224 in the interbody spacer 200. The interbody implant 200 can include one or more guide lumens 226. The two guide lumens 226 can be diametrically opposed relative to the threaded lumen 224. The distal end of the outer shaft 602 can include two projections 610. The two projections 610 can couple with the guide lumens 226 in the interbody spacer 200. The outer shaft 602 of the interbody implant inserter 600 can be firmly seated against the interbody spacer 200. In some methods of use, the interbody implant 200 is impacted in place when the cervical plate 700 is held via frictional fit at the proximal position.

FIGS. 54-57 illustrate an embodiment of a distal position of the cervical plate 700. The cervical plate 700 can translate toward the interbody implant 200. The cervical plate 700 can be held via frictional fit at the distal position. The cervical plate 700 can be held at the distal part of the outer shaft 602. The distal part of the outer shaft 602 can include the second retention feature 622. In the illustrated example, the second retention feature 622 comprises two ridges which are diametrically opposed.

The cervical plate 700 can include the complementary retention feature 752 configured to couple with the second retention feature 622 of the interbody implant inserter 600. In the illustrated example, the complementary retention features 752 comprises two grooves which are diametrically opposed. The complementary retention feature 752 can have any shape corresponding to the second retention feature 622.

The second retention feature 622 and the complementary retention feature 752 can be any mechanical arrangement configured to hold the cervical plate 700 in a temporarily fixed, distal position relative to the outer shaft 602. The second retention feature 622 and the complementary retention feature 752 can be any mechanical arrangement configured to prevent or limit sliding or translating of the cervical plate 700 when in the distal position. In some embodiments, withdrawing the interbody implant inserter 600 can overcome the retention force of second retention feature 622 relative to the complementary retention feature 752. The second retention features 622 can maintain the cervical plate 700 in position for securing the cervical plate 700 with anchors to vertebral bodies. The second retention features 622 can limit movement during anchor insertion.

The cervical plate 700 can be prevented from rotating in the distal position. The distal part of the outer shaft 602 can include the anti-rotation feature 624. The anti-rotation feature 624 can extend along a portion of the length of the interbody implant inserter 600, from the proximal location to the distal location. The anti-rotation feature 624 can extend along a portion of the length of the interbody implant inserter 600 about which the cervical plate 700 translates. The cervical plate 700 can include the complementary anti-rotation feature 754 configured to couple with the anti-rotation feature 624 of the interbody implant inserter 600 in the distal position.

FIGS. 58-60 illustrate an embodiment of a distal position of the two-level cervical plate 800. The two-level cervical plate 800 can be held via frictional fit at a proximal position. The first retention feature 620 and the complementary retention feature 852 can be any mechanical arrangement configured to hold the cervical plate 800 in a temporarily fixed, proximal position relative to the outer shaft 602.

The two-level cervical plate 800 can be prevented from rotating in the proximal position. The two-level cervical plate 800 can be held at the proximal part of the outer shaft 602. The proximal part of the outer shaft 602 can include the anti-rotation feature 824. The two-level cervical plate 800 can include the complementary anti-rotation feature 854 configured to couple with the anti-rotation feature 624 of the interbody implant inserter 600.

The two-level cervical plate 800 can translate toward the interbody implant 200 along the interbody implant inserter 600. The anti-rotation feature 624 can prevent or limit rotation while the two-level cervical plate 800 translates. The two-level cervical plate 800 can be held via frictional fit at a distal position. The distal part of the outer shaft 602 can include the second retention feature 622. In the illustrated example, the second retention feature 622 comprises two ridges which are diametrically opposed. The second retention feature 622 can be equally spaced around the circumference of the interbody implant inserter 600. The second retention feature 622 can create a frictional fit with the complementary retention features 852. The second retention features 622 can maintain the two-level cervical plate 800 in the distal position for securing the two-level cervical plate 800 with anchors to vertebral bodies.

In some methods of use, one interbody implant inserter 600 can be utilized. The interbody implant inserter 600 can seat a first interbody implant within a first disc space. The interbody implant inserter 600 can be removed from the first interbody implant. The interbody implant inserter 600 can be coupled to a second interbody implant. The interbody implant inserter 600 can be coupled to the cervical plate 700, if not already coupled thereto. The interbody implant inserter 600 can seat the second interbody implant within a second disc space. The two-level cervical plate 800 can be released from the first retention feature 622. The two-level cervical plate 800 can be translated distally. The second retention features 622 can maintain the two-level cervical plate 800 in the distal position for securing the two-level cervical plate 800 with anchors to vertebral bodies. One or more anchors 400 can secure the two-level cervical plate 800 to the vertebrae.

In some methods of use, two interbody implant inserters 600 can be utilized. The first interbody implant inserter 600 can be coupled to the two-level cervical plate 800 and a first interbody implant 200. The second interbody implant inserter 600 can be coupled to the two-level cervical plate 800 and a second interbody implant 200. The first interbody implant inserter 600 can seat the first interbody implant within a first disc space. The second interbody implant inserter 600 can seat the second interbody implant 200 within a second disc space. The two-level cervical plate 800 can be released from the first retention feature 620 of the first interbody implant inserter 600 and the first retention feature 620 of the second interbody implant inserter 600. The two-level cervical plate 800 can be translated distally along the first and second interbody implant inserters 600. The two-level cervical plate 800 can be secured to the second retention feature 622 of the first interbody implant inserter 600 and the second retention feature 622 of the second interbody implant inserter 600. One or more anchors 400 can secure the two-level cervical plate 800 to the vertebrae. In some methods of use, two interbody implant inserters 600 are used to position the two-level cervical plate 800. In some methods of use, one inserter is used for each interbody implant 200. In some methods of use, two interbody implants 200 are utilized for the two-level procedure. In some methods of use, one interbody implant 200 is utilized for the two-level procedure.

The interbody spacer 200, the interbody implant inserter 600, and the cervical plate 700 can be coupled in an all-in-one inserter assembly. The methods of use are in the field of cervical and lumbar spine surgery, and include methods for controlling a cervical plate insertion simultaneously with an interbody implant insertion. The interbody implant insertion and the cervical plate insertion can be combined using one instrument that reduces the steps of the surgery. The interbody implant inserter 600 allows a user to insert the interbody implant 200 and secondarily slide the cervical plate 700 using the outer shaft 602 of the interbody implant inserter 600. The interbody implant inserter 600 can include features that prevent the cervical plate 700 from rotating.

The cervical plate 700 and the two-level cervical plate 800 can be designed for independent insertion of anchors 400. The cervical plate 700 and the two-level cervical plate 800 can be designed for high angle anchor insertion. The cervical plate 700 and the two-level cervical plate 800 can support the anchor at an angle between 15° and 35°. The cervical plate 700 and the two-level cervical plate 800 can support the anchor at any angle, as described herein. The cervical plate 700 and the two-level cervical plate 800 can include the ledge, as described herein. The ledge can enable high angle anchor insertion. The cervical plate 700 and the two-level cervical plate 800 can guide the anchor 400 toward an edge or corner of the vertebral body. The cervical plate 700 and the two-level cervical plate 800 can include holes designed to be at least partially located in the disc space region. In some embodiments, at least a portion of the holes are located within the disc space region when the cervical plate 700 or the two-level cervical plate 800 is implanted. In some embodiments, the cervical plate 700 and the two-level cervical plate 800 can extend below the surface of the vertebral body. The cervical plate 700 and the two-level cervical plate 800 can include a prominence of material that extends into the disc space region. The prominence of material supports the high angle insertion of the anchors 400. In some embodiments, the vertebral bodies remain intact. For example, the cervical plate 700 and the two-level cervical plate 800 can have a bend, angle or curve to generally match the natural shape of the vertebral bodies.

The interbody implant inserter 600 can include a mechanism that retains the cervical plate 700 on a proximal part of the interbody implant inserter 600. There are various possibilities in view of the interbody implant delivery. The outer shaft 602 of the interbody implant inserter 600 is configured to slide over the tip of the internal shaft 604 of the implant inserter 600. The outer shaft 602 of the interbody implant inserter 600 is configured to maintain the cervical plate 700 and prevent rotation.

The tip of the internal shaft of the interbody implant inserter 600 is configured to be inserted into the interbody implant 200. The internal shaft 604 of the interbody implant inserter 600 is configured to facilitate placement of the interbody implant 200 into the disc space. The interbody implant 200 can be recessed into the disc space between 1 and 4 mm. The interbody implant 200 can be recessed without having the cervical plate 700 connected to the interbody implant 200. The interbody implant 200 can be recessed while the cervical plate 700 is positioned on the surface of the vertebral body.

The cervical plate 700 can have the engagement portion 750. The engagement portion 750 is designed to allow the interbody implant inserter 600 to fit through the engagement portion 750 to attach to the interbody implant 200. The engagement portion 750 can be a window or lumen through the cervical plate 700. The engagement portion 750 of the cervical plate 700 can allow the interbody implant 200 to be inserted with the cervical plate 700 pre-attached to the interbody implant inserter 600, ready to slide down and install once the interbody implant 200 has been inserted. The cervical plate 700 is retained under the handle 608 of the interbody implant inserter 600 by a mechanism that captures the cervical plate 700 on the outer shaft 602 of the interbody implant inserter 600. The mechanism can include one or more members that capture the cervical plate 700, not allowing the cervical plate 700 to slide down the outer shaft 602 of the interbody implant inserter 600 until released. The interbody implant inserter 600 can include the anti-rotation feature 624. This feature is achieved by having the engagement portion of the cervical plate 700 and the outer shaft 602 of the interbody implant inserter 600 having the same, or similar shape, with clearances so that the cervical plate 700 can slide freely, without rotating. The anti-rotation feature 624 allows the cervical plate 700 to be aligned properly with the interbody implant 200, ensuring the best placement of the cervical plate 700. The interbody implant inserter 600 can act as a cervical plate inserter, allowing the user to secure the cervical plate 700 to the interbody implant inserter 600, dock the interbody implant inserter 600 onto the interbody implant 200, and align the cervical plate 700 with the interbody implant 200.

12. Interbody Implant Inserter

Figure 61:
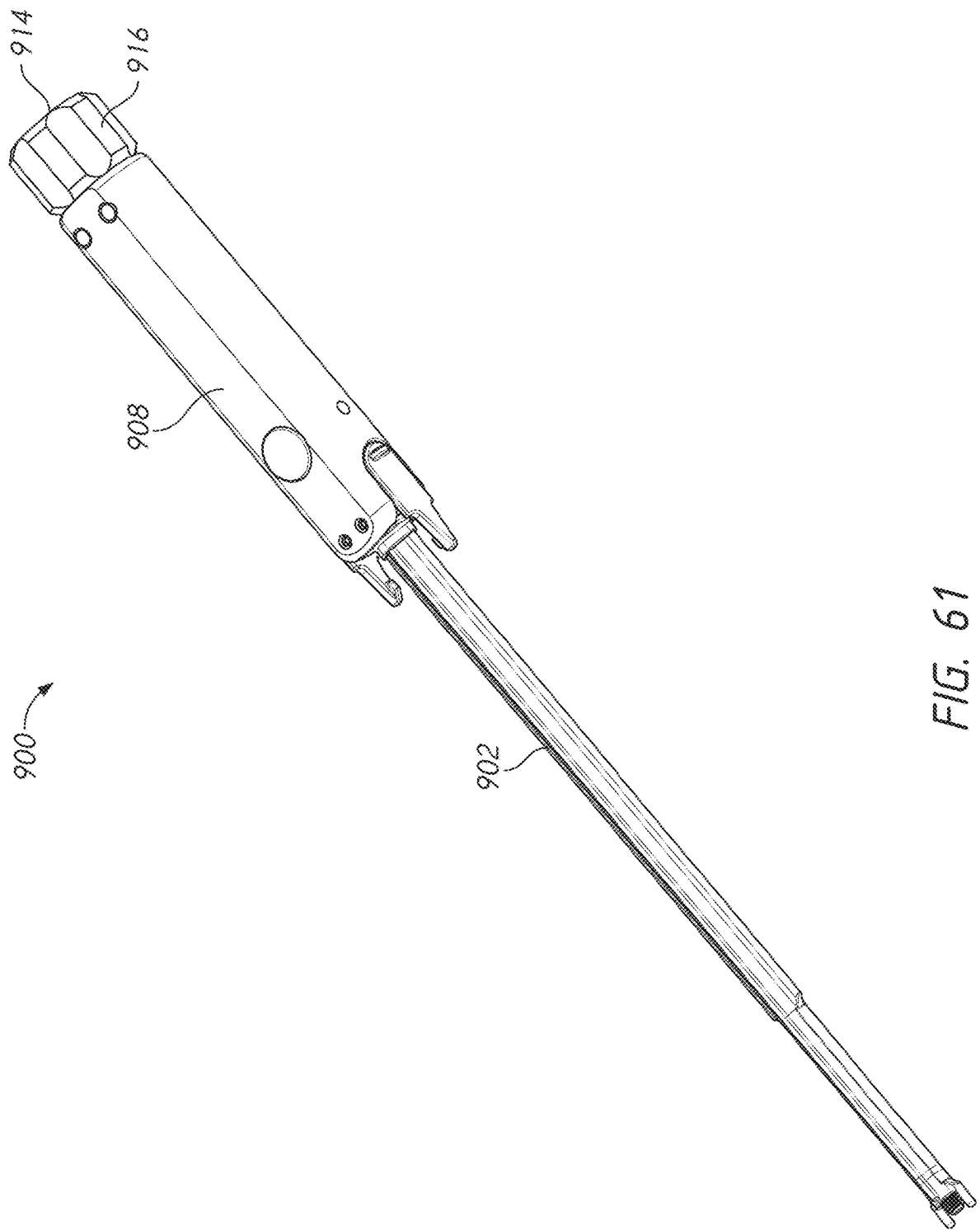
FIG. 61 is a perspective view of an embodiment of an interbody implant inserter.
Figure 62:
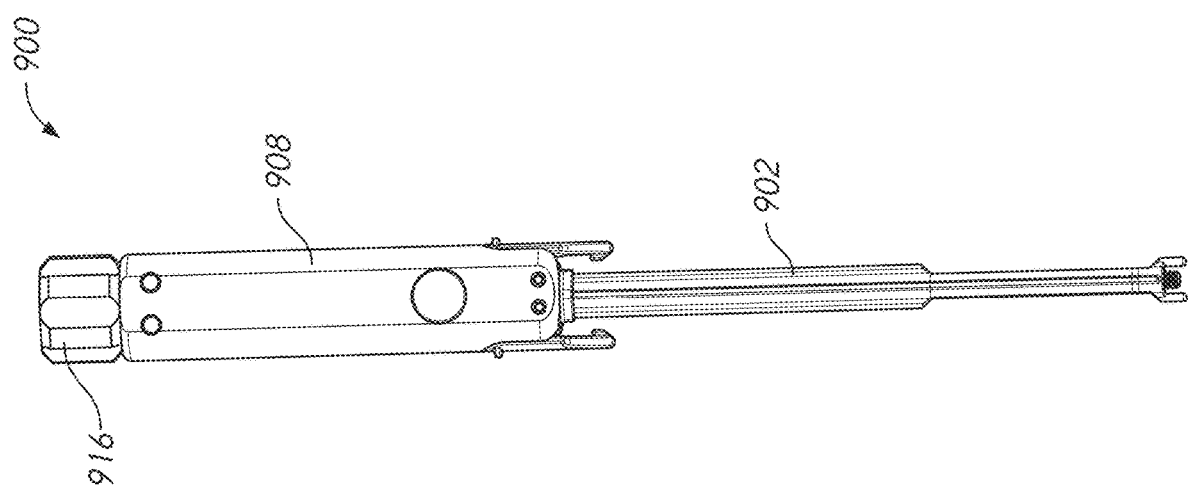
FIG. 62 is a front view of the interbody implant inserter of FIG. 61.
Figure 63:
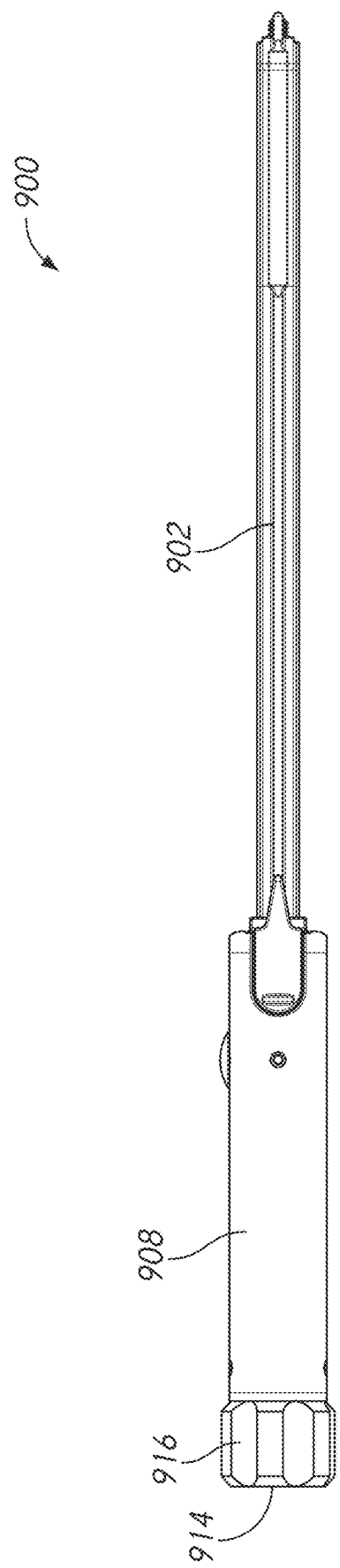
FIG. 63 is a side view of the interbody implant inserter of FIG. 61.
Figure 64:
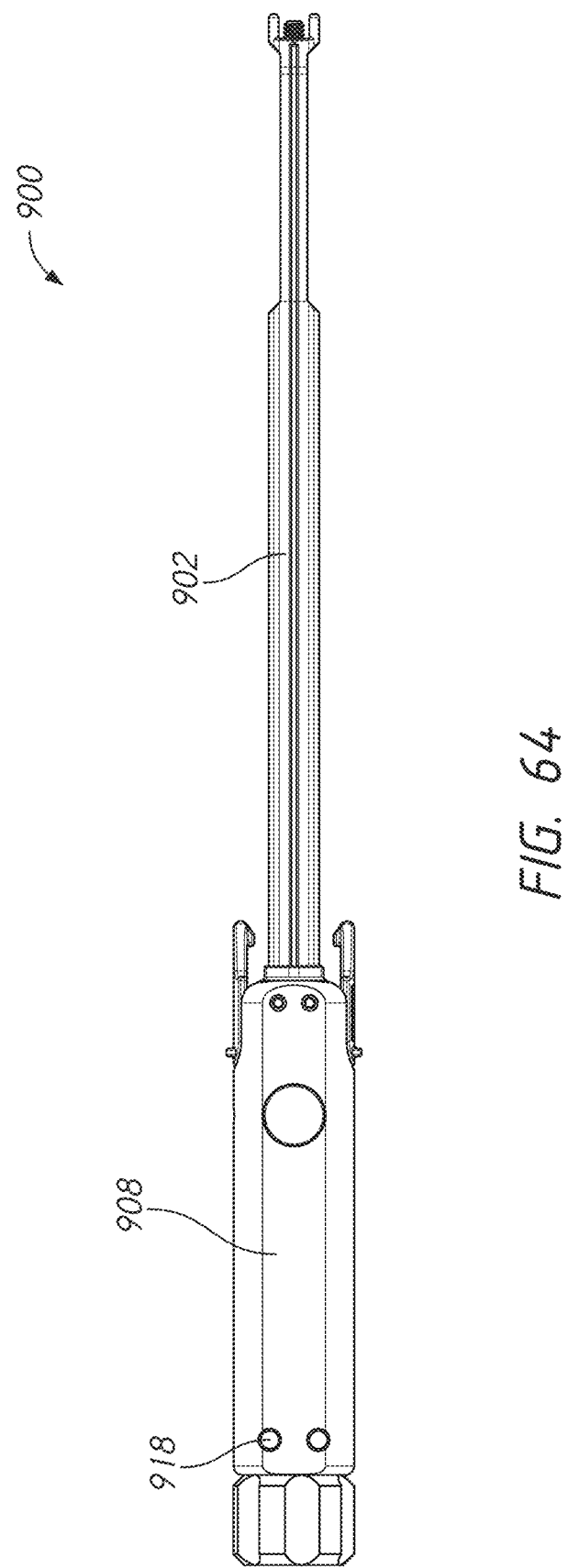
FIG. 64 is a top view of the interbody implant inserter of FIG. 61.
Figure 65:
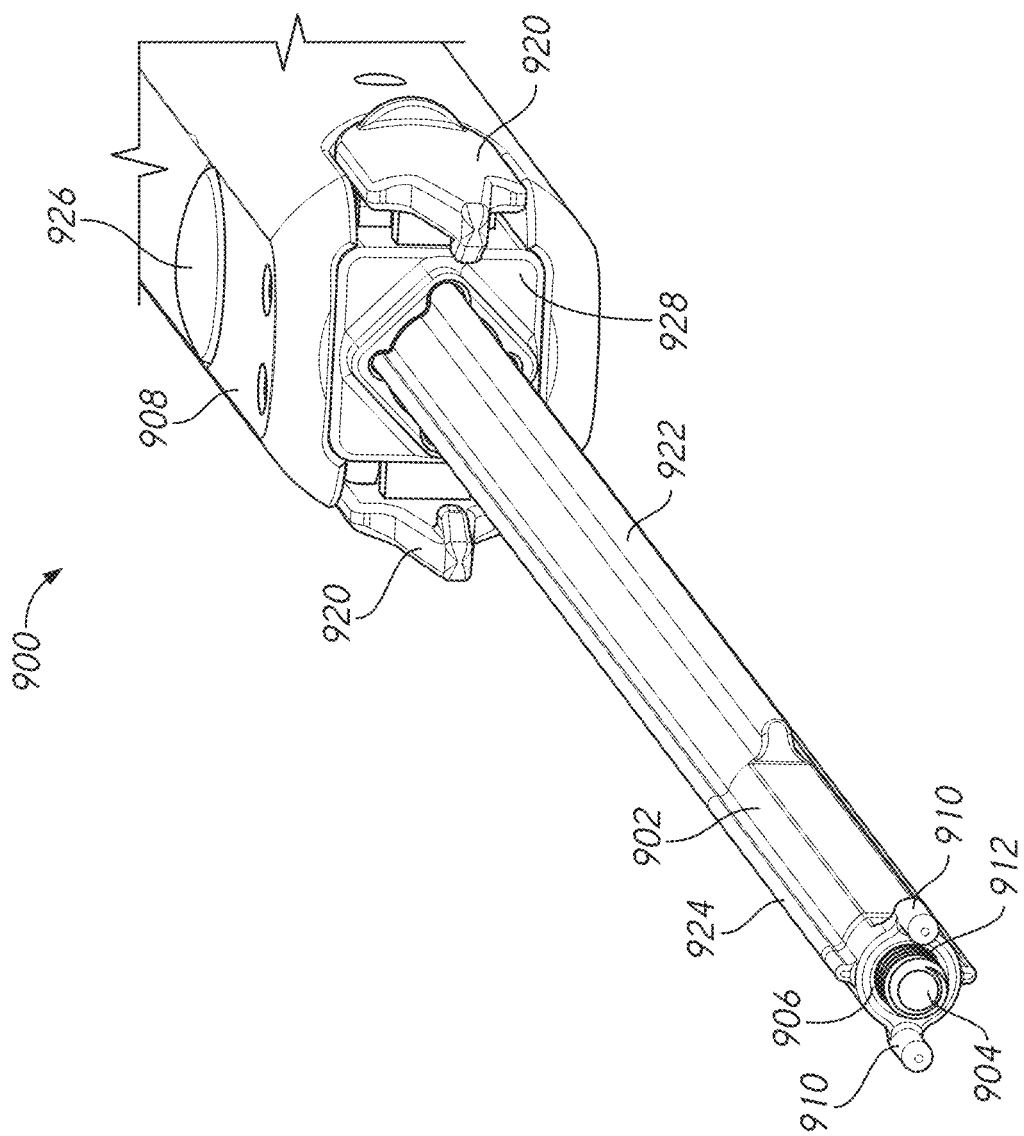
FIG. 65 is a bottom perspective view of the interbody implant inserter of FIG. 61.
Figure 66:
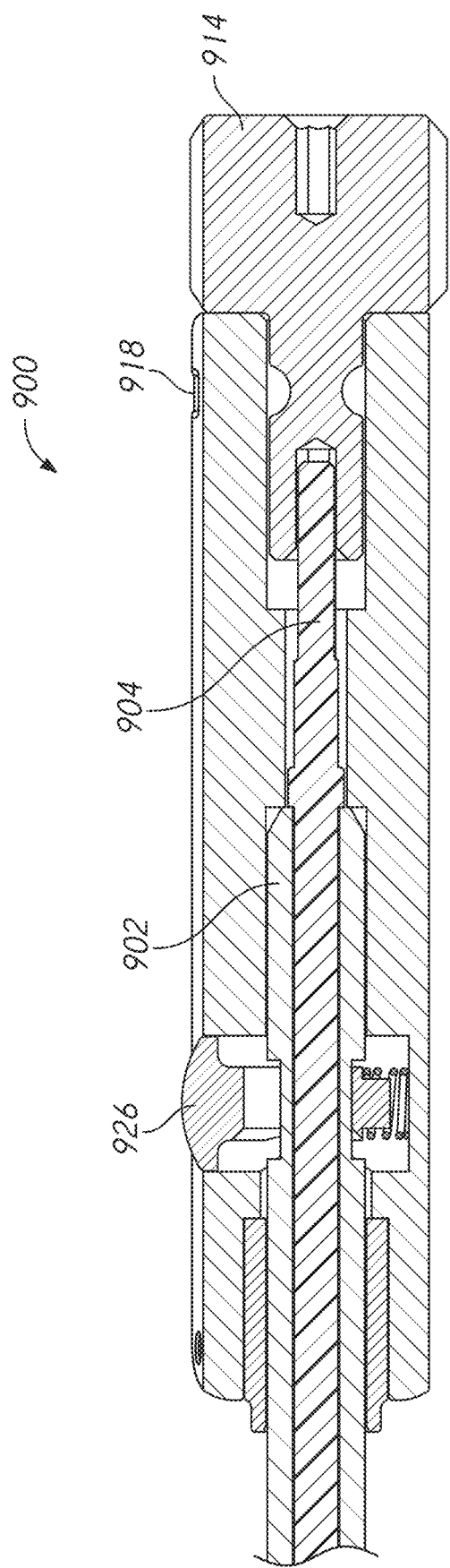
FIG. 66 is a cross-sectional view of the interbody implant inserter of FIG. 61.
Figure 67:
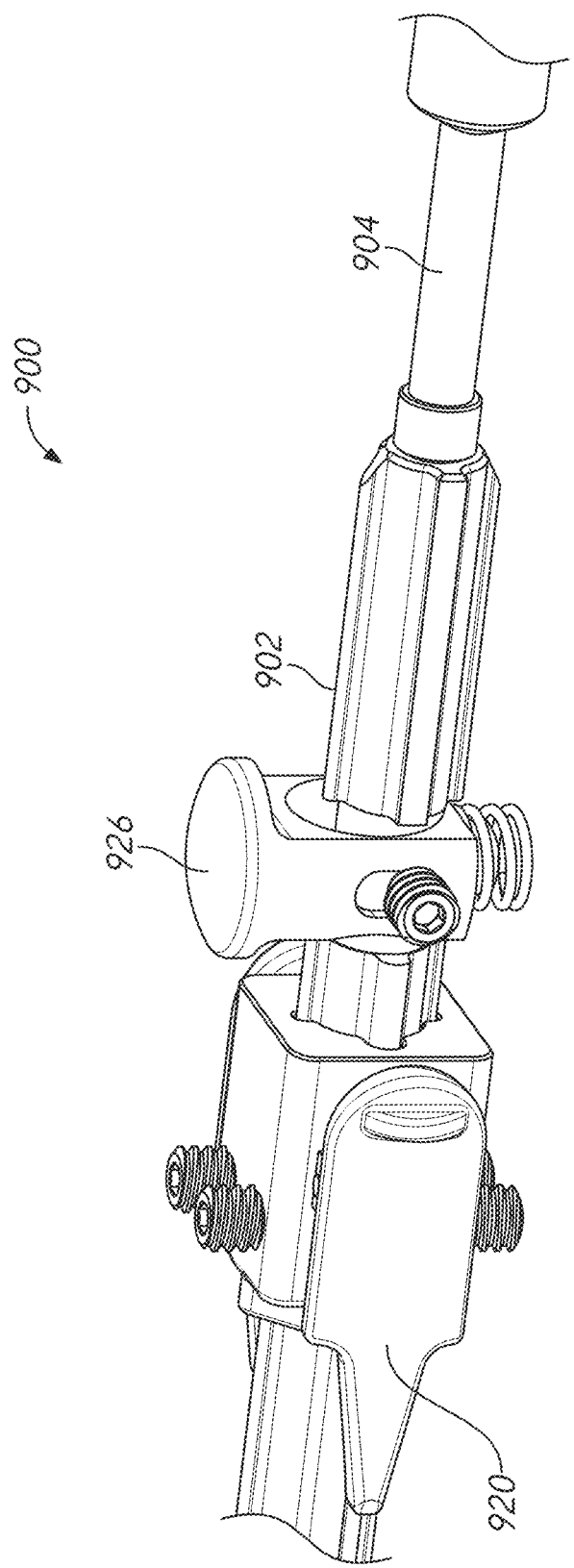
FIG. 67 is an internal view of the handle assembly of the interbody implant inserter of FIG. 61.

FIGS. 61-67 depict views of an embodiment of an interbody implant inserter 900. FIG. 61 illustrates a perspective view. FIG. 62 illustrates a front view. FIG. 63 illustrates a side view. FIG. 64 illustrates a top view. FIG. 65 illustrates a bottom view. FIG. 66 illustrates a cross-sectional view. FIG. 67 illustrates an internal view. The systems and methods described herein can include one or more of these components. The interbody implant inserter 900 can be used in combination with any cervical plate described herein. The interbody implant inserter 900 can be used in combination with the interbody implant 200. The interbody implant inserter 900 can be used in combination with one or more anchors 400. The interbody implant inserter 900 can include any features described herein. The interbody implant inserter 900, the interbody spacer 200, and any cervical plate described herein can form an assembly.

The interbody implant inserter 900 can comprise the outer shaft 902 and the internal shaft 904. The outer shaft 902 can include a lumen 906. The lumen 906 can be sized to accommodate the internal shaft 904. The internal shaft 904 can be configured to rotate relative to the outer shaft 902 when the internal shaft 904 is disposed within the outer shaft 902. While the internal shaft 904 is illustrated as an elongate cylindrical shape, other configurations are contemplated.

The interbody implant inserter 900 can include a handle 908. In the illustrated embodiment, the handle 908 comprises a cylindrical portion. The handle 908 can be separately formed from the outer shaft 902. The outer shaft 902 can be received in the handle 908. The handle 908 can be located along a proximal portion of the outer shaft 902.

The outer shaft 902 can include a projection 910. In the illustrated embodiment, the outer shaft 902 can include two projections 910. The two projections 910 can be diametrically opposed on the body of the outer shaft 902. The two projections 910 can be diametrically opposed relative to the lumen 906. The projection 910 can be an extended point. The projection 910 can have a circular cross-sectional shape. The projection 910 can have a non-circular cross-sectional shape. The projection 910 can be any interface configured to couple with the interbody implant 200.

The internal shaft 904 can function to couple to the interbody implant 200, as described herein. The distal end of the internal shaft 904 can include a second threaded portion 912. The second threaded portion 912 can couple with a corresponding threaded lumen in the interbody spacer 200. The second threaded portion 912 can be near or at the distal end of the internal shaft 904.

The interbody implant inserter 900 can comprise an impact cap 914. The impact cap 914 can allow the user to apply a force to position the interbody implant 200 between adjacent vertebrae. The impact cap 914 can have a flat proximal end to allow a force to be applied. While the impact cap 914 is illustrated as an elongate cylindrical shape, other configurations are contemplated. The internal shaft 904 can couple to the impact cap 914. In some embodiments, the impact cap 914 can include a keyed socket and the internal shaft 904 can include a keyed end.

The impact cap 914 can include a thumbscrew 916. The thumbscrew 916 can be manipulated by the user to rotate the internal shaft 904. In some embodiments, rotational movement of the thumbscrew 916 by the user can cause rotational movement of the internal shaft 904 relative to the outer shaft 902. The thumbscrew 916 can extend proximally from the handle 908 when the internal shaft 904 is disposed within the outer shaft 902 and the outer shaft 902 is disposed within the handle 908.

The handle 908 and the impact cap 914 can be coupled via a connection 918. The connection 918 can allow the impact cap 914 and the internal shaft 904 to rotate and translate relative to the outer shaft 902. In some embodiments, the connection 918 can allow the impact cap 914 and the internal shaft 904 to rotate but not translate relative to the handle 908. The interbody implant inserter 900 can include any mechanical coupling or disconnect. The interbody implant inserter 900 can include any connection mechanism.

The interbody implant inserter 900 can function as an implant holder. The interbody implant inserter 900 can releasably hold the interbody implant 200. In some embodiments, the first projection 910 can be identical or substantially similar to the second projection 910. The interbody implant inserter 900 can couple to the interbody implant 200 in one of two orientations. In other embodiments, the first projection 910 is different than the second projection 910. The interbody implant inserter 900 can couple to the interbody implant 200 in only one orientation.

The interbody implant inserter 900 has the ability to rotate the internal shaft 904. The user can rotate the thumbscrew 916. The thumbscrew 916 can rotate independently of the outer shaft 902. The first projection 910 and the second projection 910 of the outer shaft 902 can engage corresponding lumens in the interbody implant 200, as described herein. As the thumbscrew 916 is rotated, the internal shaft 904 is rotated. As the internal shaft 904 is rotated, the internal shaft 904 can thread into a threaded lumen of the interbody implant 200, as described herein. In some embodiments, the impact cap 914 and the internal shaft 904 rotates but does not translate relative to the outer shaft 902 and the handle 908.

The interbody implant inserter 900 has the ability to be impacted. The internal shaft 904 can include an impact cap 914 configured to allow the interbody implant 200 to be impacted. The impact cap 914, the handle 908, the outer shaft 902, the internal shaft 904, and the interbody implant 200 can translate together as a unit. The internal shaft 904 and the interbody implant 200 can be rigidly coupled via threaded portions.

The interbody implant inserter 900 can function to couple to any cervical plate described herein. The interbody implant inserter 900 can include a first retention feature 920 configured to couple with a corresponding feature of the cervical plate, as described herein. The first retention feature 920 can include an engagement structure. The first retention feature 920 can be depressed to release the cervical plate. In some embodiments, the first retention feature 920 can be configured to couple with an exterior portion of the cervical plate. In some embodiments, the first retention feature 920 can be configured to couple with an interior portion of the cervical plate. In some embodiments, the first retention feature 920 can be configured to couple with a proximal and/or distal portion of the cervical plate. The first retention feature 920 can be a keyed projection. The first retention feature 920 can be near the proximal end of the handle 908. The first retention feature 920 can be distal to the handle 908. The first retention feature 920 can include one or more levers. The first retention feature 920 can include one or more springs. In some embodiments, the first retention feature 920 can include one or more hooks. In some embodiments, the first retention feature 920 can include one or more clips. The first retention feature 920 can be a solid, shaped surface. In some embodiments, the first retention feature 920 can include one or more locking and/or release mechanisms. In some embodiments, the first retention feature 920 can include a button or lever release mechanism. The first retention feature 920 can include two or more diametrically opposed structures. The first retention feature 920 can include two or more structures equally spaced around the handle 908. In the illustrated embodiment, the first retention feature 920 includes two structures. Other configurations are contemplated, e.g. one structure, three structures, four structures, etc.

The first retention feature 920 can be an arm. The first retention feature 920 can be an arm extending from the handle 908. The first retention feature 920 can be a spring-biased arm. The first retention feature 920 can hold a cervical plate. The first retention feature 920 can be a pair of arms. The first retention feature 920 can be squeezed by the user. The first retention feature 920 can be squeezed near a proximal end to pivot the first retention feature 920. The first retention feature 920 can be actuated to attach or release a cervical plate. The first retention feature 920 can be actuated when the handle 908 is removed from the outer shaft 902 and the internal shaft 904. In some methods, the first retention feature 920 can be actuated to couple to the cervical plate when the handle 908 is removed. In some methods, the first retention feature 920 can be actuated to release the cervical plate when the handle 908 is removed. The first retention feature 920 can be actuated when the handle 908 is coupled to the outer shaft 902 and the internal shaft 904. The first retention feature 920 can be actuated with or without the outer shaft 902 and the internal shaft 904 attached. In some methods, the first retention feature 920 can be actuated to release the cervical plate when the handle 908 is coupled to the outer shaft 902 and the internal shaft 904.

The first retention feature 920 can include one or more springs. The spring can bias the first retention feature 920 into engagement with the cervical plate. The first retention feature 920 can flex toward and away from the longitudinal axis of the handle 908. The first retention feature 920 can pivot relative to the handle 908 to release the cervical plate. The first retention feature 920 can extend a length along the outer shaft 902, below the handle 908. The first retention feature 920 can extend a length along the outer shaft 902 greater than the thickness of the cervical plate.

The first retention feature 920 can include one or more tabs. The first retention feature 920 can include one or more projections. The first retention feature 920 can include one or more detents. The first retention feature 920 can include one or more ball detents. The first retention feature 920 can include one or more flexible mechanisms. The first retention feature 920 can include one or more structure configured to flex away from the longitudinal axis of the outer shaft 902. The first retention feature 920 can be any mechanical arrangement configured to hold the cervical plate in a temporarily fixed position relative to the handle 908. The first retention feature 920 can be any mechanical arrangement configured to prevent or limit sliding or translating of the cervical plate 700 relative to the handle 908 during impaction into the disc space. The first retention feature 920 can be any mechanical arrangement configured to prevent or limit rotating of the cervical plate 700 relative to the handle 908. The first retention feature 920 can apply pressure to the cervical plate. The first retention feature 920 can push against the cervical plate. In some embodiments, a force applied to the first retention feature 920 will release the cervical plate. In some embodiments, the cervical plate 700 is released from the first retention feature 920 by depressing a lever.

The outer shaft 902 can include a second retention feature 922 configured to couple with a corresponding feature of the cervical plate 700, as described herein. The second retention feature 922 can be a keyed projection. The second retention feature 922 can include one or more ridges. The second retention feature 922 can be a solid, shaped surface. The second retention feature 922 can provide a frictional fit. The second retention feature 922 can provide an interference fit. The second retention feature 922 can include two or more diametrically opposed structures. The second retention feature 922 can include two or more structures equally spaced around the outer shaft 902. In the illustrated embodiment, the second retention feature 922 includes two structures. In some embodiments, the second retention feature 922 can extend along the length of the outer shaft 902. In some embodiments, the second retention feature 922 can extend along a portion of the length of the outer shaft 902. In some embodiments, the second retention feature 922 can extend along a portion of the length of the outer shaft 902 near the first retention feature 920. Other configurations are contemplated, e.g. one structure, three structures, four structures, etc. The second retention feature 922 can include any features of the retention features described herein.

The outer shaft 902 can include an anti-rotation feature 924 configured to couple with a corresponding feature of the cervical plate, as described herein. The anti-rotation feature 924 can be a keyed projection. The anti-rotation feature 924 can be distal to the handle 908. The anti-rotation feature 924 can extend longitudinally. The anti-rotation feature 924 can be near or at the proximal end of the outer shaft 902. The anti-rotation feature 924 can be along the length of the outer shaft 902. The anti-rotation feature 924 can be along a portion of the length of the outer shaft 902 about which the cervical plate translates. The anti-rotation feature 924 can include any features of the anti-rotation features described herein. In some embodiments, the anti-rotation feature 924 can extend along the length of the outer shaft 902. In some embodiments, the anti-rotation feature 924 can extend along a portion of the length of the outer shaft 902. In some embodiments, the anti-rotation feature 924 can extend along the entire length of the outer shaft 902 that the cervical plate slides.

The interbody implant inserter 900 can include a release 926. The release 926 can be configured to release the handle 908 relative to the outer shaft 902. The release 926 can be a button. The release 926 can be a slide. The release 926 can be a stop. The release 926 can be movable relative to the handle 908. The release 926 can be depressed relative to the handle 908. The release 926 can be depressed by the user. The release 926 can be spaced apart from the first retention feature 920. In some embodiments, the release 926 allows the handle 908 to be slid on and off the outer shaft 902 that is attached to the interbody implant 200. In some embodiments, the release 926 allows the handle 908 to be slid on and off the internal shaft that is attached to the interbody implant 200. In some embodiments, the release 926 allows the handle 908 to be slid on and off the outer shaft 902 and the internal shaft that is attached to the interbody implant 200. In some embodiments, the handle 908 and the impact cap 914 are removed as a unit. In some embodiments, the handle 908 and the impact cap 914 slide relative to the outer shaft 902 and the internal shaft 904. In some embodiments, the handle 908 has an internal guide 928 to facilitate sliding relative to the outer shaft 902. The outer shaft 902 can have a shaped profile and the internal guide 928 of the handle 908 can have a shaped lumen.

The release 926 and the first retention feature 920 can have different configurations. In some embodiments, the release 926 is a button. In some embodiments, the first retention feature 920 is a pair of arms. The release 926 and the first retention feature 920 can have different functions. In some embodiments, the release 926 is actuated to release the handle 908. In some embodiments, the first retention feature 920 is actuated to release the cervical plate.

13. Methods of Use

In some methods of use, the patient is placed in the supine position with the head in a slight extension. In some methods of use, the posterior cervical spine is supported to establish and maintain normal cervical lordosis. In some methods of use, discectomies and spinal decompression are performed using standard surgical techniques. In some methods of use, the anterior osteophytes are removed from the anterior column for the cervical plate to sit evenly on the spine. In some methods of use, the size of the interbody implant 200 is determined by measuring the disc space using the provisional trials. In some methods of use, the user inserts a provisional trial. In some methods of use, the user selects the size of the interbody implant 200 that sufficiently fits the disc space. In some methods of use, plate contouring is optional. In some methods of use, the plate may be contoured to increase or decrease the amount of lordotic curvature by using a plate bender. In some methods of use, bending is performed only on segments of the cervical plate wide enough for the jaws of the plate bender not to touch the screw holes. In some methods of use, bending is performed in small increments.

In some methods of use, the interbody implant inserter 900 is utilized. In some methods of use, the anterior face of the interbody implant 200 is mounted onto the interbody implant inserter 900 using the projections 910. The projection 910 can be two distal pins for the alignment. In some methods of use, while maintaining the interbody implant 200 in place, a user can turn clockwise the thumbscrew 916 until the second threaded portion 912 of the internal shaft 904 is fully engaged with the interbody implant 200. In some methods of use, the interbody implant is secured to both the outer shaft 902 and the internal shaft 904 with the handle 908 attached. In some methods of use, once the interbody implant 200 is secured, the interbody implant 200 is placed into the intervertebral space using a slight impaction. In some methods of use, the interbody implant 200 is positioned. In some methods of use, it may be necessary to tap moderately on the inserter to fully seat the interbody implant 200 posteriorly for final implant seating. In some methods of use, the cervical plate is selected. In some methods of use, the user selects the appropriate cervical plate using preplanning fluoroscopy to determine the plate size. In some methods of use, the user selects the appropriate cervical plate using preplanning fluoroscopy to determine anticipated screw trajectories. In some methods of use, plate length is measured center hole to center hole. In some methods of use, a silver stripe indicates the cranial/caudal orientation which facilitates the correct cervical plate insertion. In some methods of use, the size of the cervical plate is measured using a caliper.

In some methods of use, the handle 908 allows for modular handle release and plate loading. In some methods of use, the handle 908 is modular. In some methods of use, the handle 908 is then removed by pressing the release 926 while maintaining in place the interbody implant 200 attached with the tip of the interbody implant inserter 900. In some methods of use, the handle 908 is removed after positioning of the interbody implant 200. In some methods of use, the handle 908 is removed while the outer shaft 902 remains coupled to the interbody implant 200. In some methods of use, the handle 908 is removed while the internal shaft 904 remains coupled to the interbody implant 200.

In some methods of use, the appropriate cervical plate is loaded into the interbody implant inserter 900 with the cervical plate facing up. In some methods of use, plate sizes are indicated on the face of the cervical plate. In some methods of use, the plate is secured when the first retention feature 920 is coupled to the cervical plate. In some embodiments, the first retention feature 920 are a pair of wings that grab the cervical plate on the side. In some methods of use, the plate is secured when both wings are grabbing the cervical plate on the side. In some methods of use, the silver strip is between the wings. In some methods of use, the first retention feature 920 couples to the cervical plate along a direction perpendicular to the silver strip. In some methods of use, the first retention feature 920 couples to the cervical plate along a direction perpendicular to the cephalad/caudal orientation.

In some methods of use, the handle 908 is reattached with the cervical plate connected onto the handle 908. In some methods of use, the handle 908 is reattached by sliding the handle 908 relative to the outer shaft 902. In some methods of use, the handle 908 is reattached by sliding the handle 908 relative to the internal shaft 904. In some methods of use, the handle 908 is reattached while maintaining the cephalad/caudal orientation. In some methods of use, the handle 908 is reattached once the release 926 relocks on the outer shaft 902. In some methods of use, the handle 908 is reattached when the user receives tactile feedback from the release 926.

In some methods of use, the cervical plate is released once the handle 908 is reattached. In some methods of use, the cervical plate is released by pressing the first retention feature 920. The first retention feature 920 can be two side buttons. The first retention feature 920 can be pressed using two fingers of the user. In some methods of use, the user slides the cervical plate once released. In some methods of use, the cervical plate slides under the influence of gravity. In some methods of use, the user verifies that the cervical plate is fully seated in the correct orientation. In some methods of use, the cervical plate slides while engaging the second retention feature 922. In some methods of use, the cervical plate slides while engaging the anti-rotation feature 924. In some methods of use, the orientation of the cervical plate is maintained as the cervical plate slides toward the interbody implant 200.

In some methods of use, the screw holes are prepared. In some methods of use, a combo drill/awl is used to create a hole by breaking through the cortex of the vertebral body or by advancing into bone. In some methods of use, the user selects the screw length consistent with the drill size. In some methods of use, prior to creating a hole, the tip of the combo drill/awl is seated inside the screw pocket hole. In some methods of use, the user verifies that the combo drill guide is placed in the angle to the desired location. In some methods of use, the user verifies that the angles does not exceed the maximum angle of the cervical plate. In some embodiments, the maximum angle of the cervical plate is 27° range of motion or ROM. Other configurations with additional ranges and other configurations with maximum angle are contemplated. In some methods of use, a variable or fixed drill guide is be used to create the screw hole preparation. In some methods of use, the drill guide is seated into the cervical plate. In some methods of use, the drill is advanced through the variable or the fixed drill guide sleeve until reaching the stop collar located on the drill shaft. In some methods of use, tapping is utilized. In some methods of use, the tap is connected to the quick handle and the desired length is tapped. In some methods of use, the screw is inserted. In some methods of use, the screwdriver is assembled to a modular handle. In some methods of use, the desired screw is loaded onto the screwdriver. In some methods of use, the screw is secured to the screwdriver and inserted into the plate until the head is fully seated. In some methods of use, screws may be loaded, inserted, and driven with straight, flexible screwdrivers depending on patient anatomy. In some methods of use, the screw is locked. In some methods of use, the breakaway driver is inserted into the head of the internal locking screw and turned clockwise until a click is reached. In some methods of use, the locking torque is 2 in-lbs. In some methods of use, prior to final locking, the user confirms screw placement and angulation with x-ray or other imaging techniques. In some methods of use, the user can check the final position of the cervical plate and screws both visually and radiographically. In some methods of use, the user detaches the interbody implant inserter 900 from the interbody implant 200 by turning the thumbscrew 916 counterclockwise. In some methods of use, the user detaches the interbody implant inserter 900 by decoupling the internal shaft 904 by rotating the thumbscrew 916. In some methods of use, the user detaches the interbody implant inserter 900 by sliding the outer shaft 902, the internal shaft 904, the handle 908 and the impact cap 914 away from the interbody implant 200.

14. Cervical Plates Overview

Figure 68:
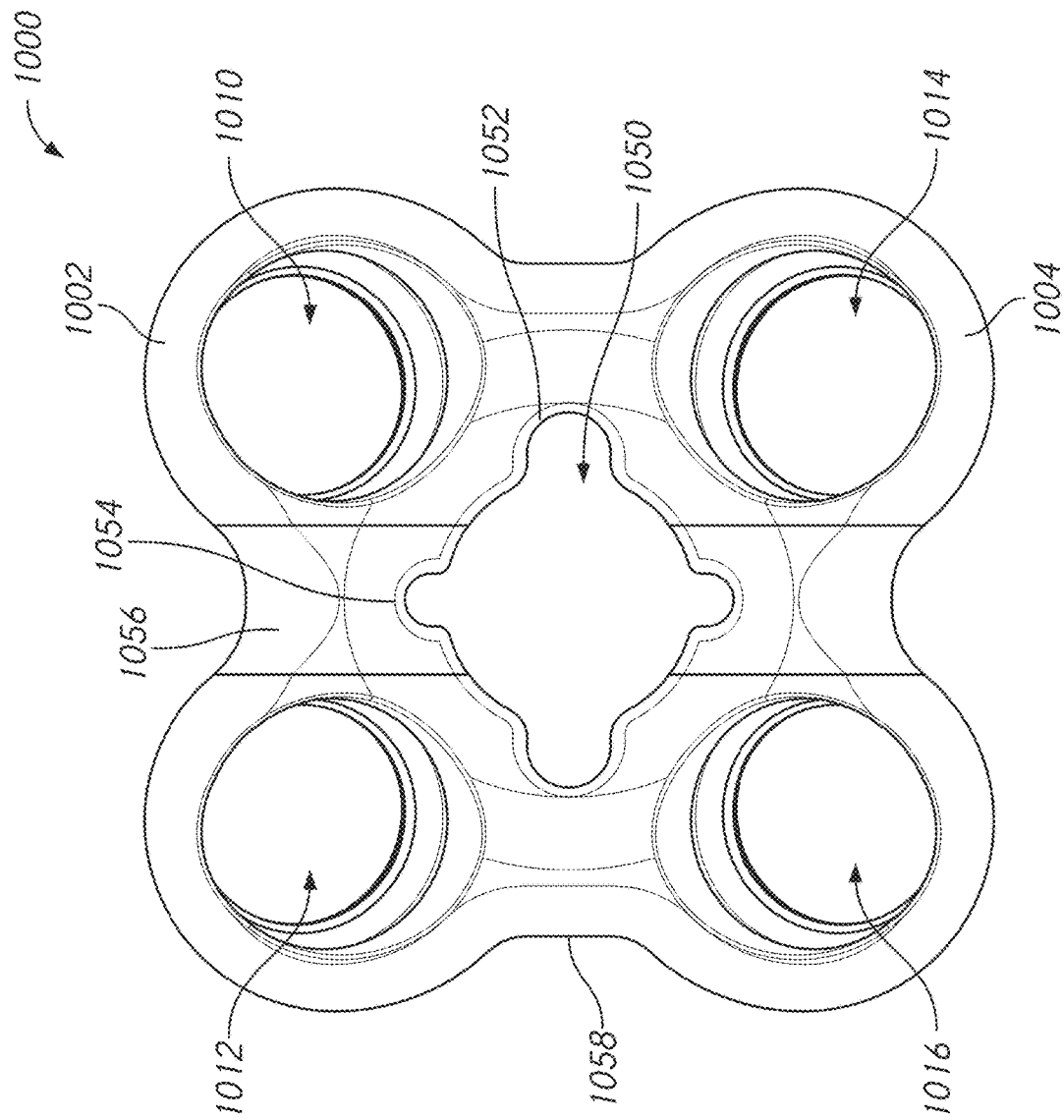
FIG. 68 is a top view of a cervical plate.
Figure 69:
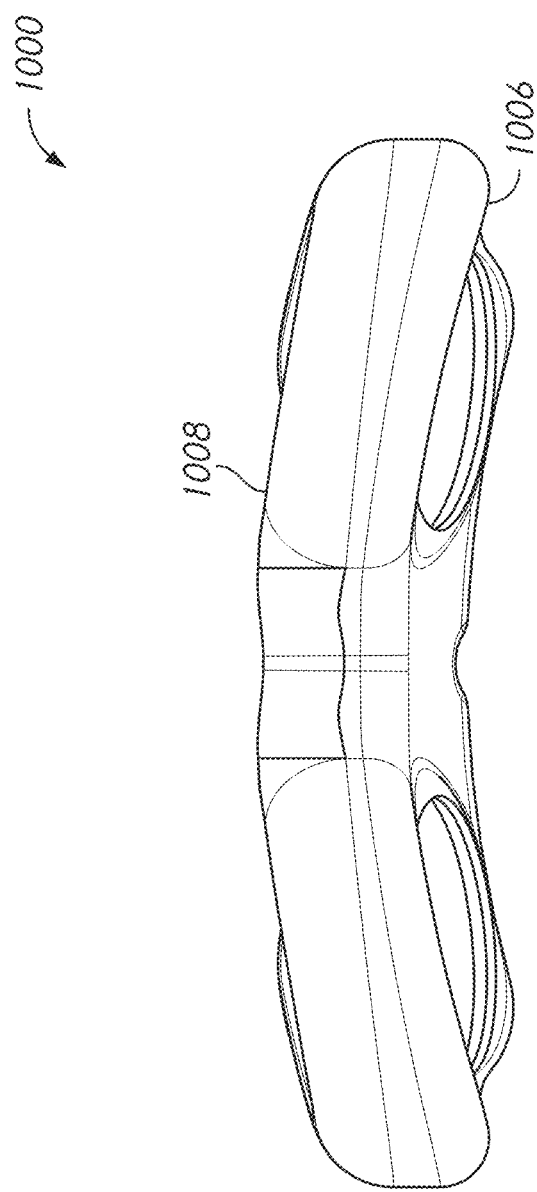
FIG. 69 is a side view of the cervical plate of FIG. 68.
Figure 70:
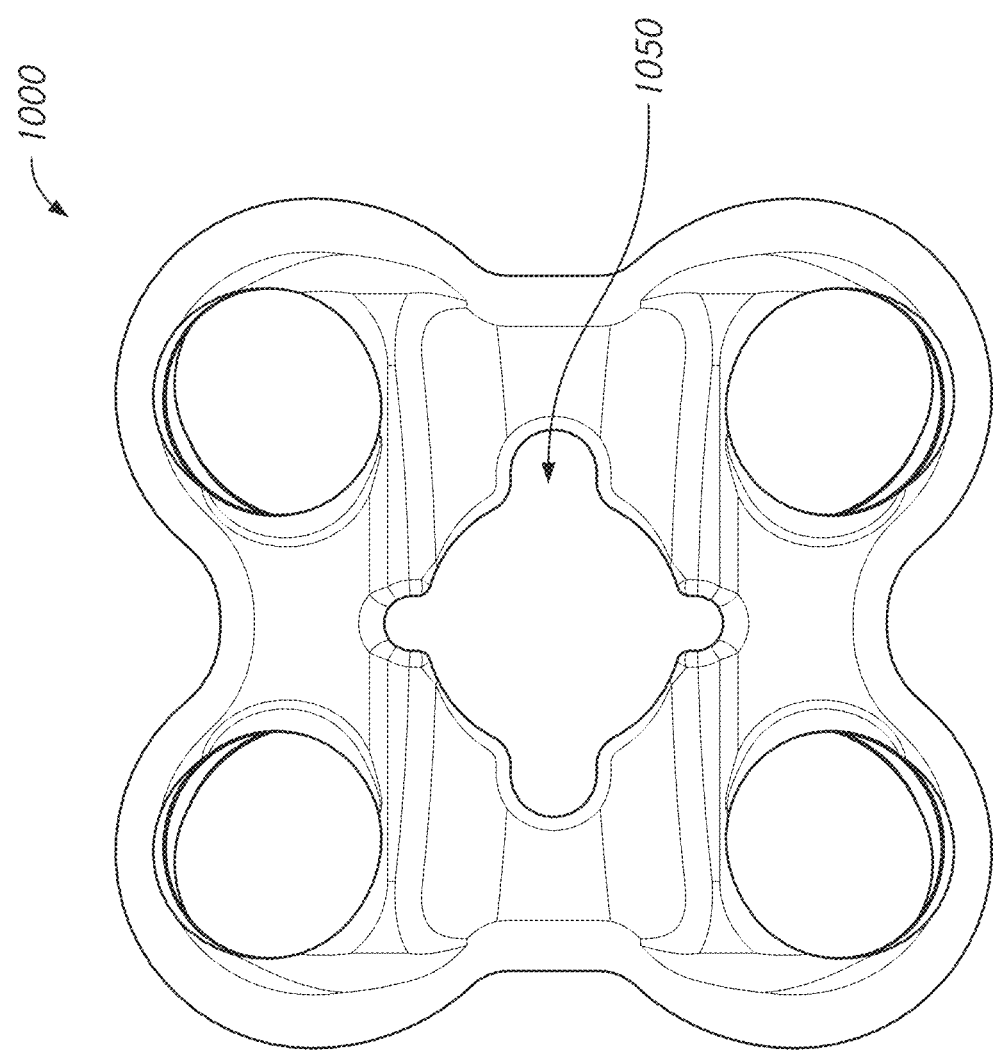
FIG. 70 is a bottom view of the cervical plate of FIG. 68.
Figure 71:
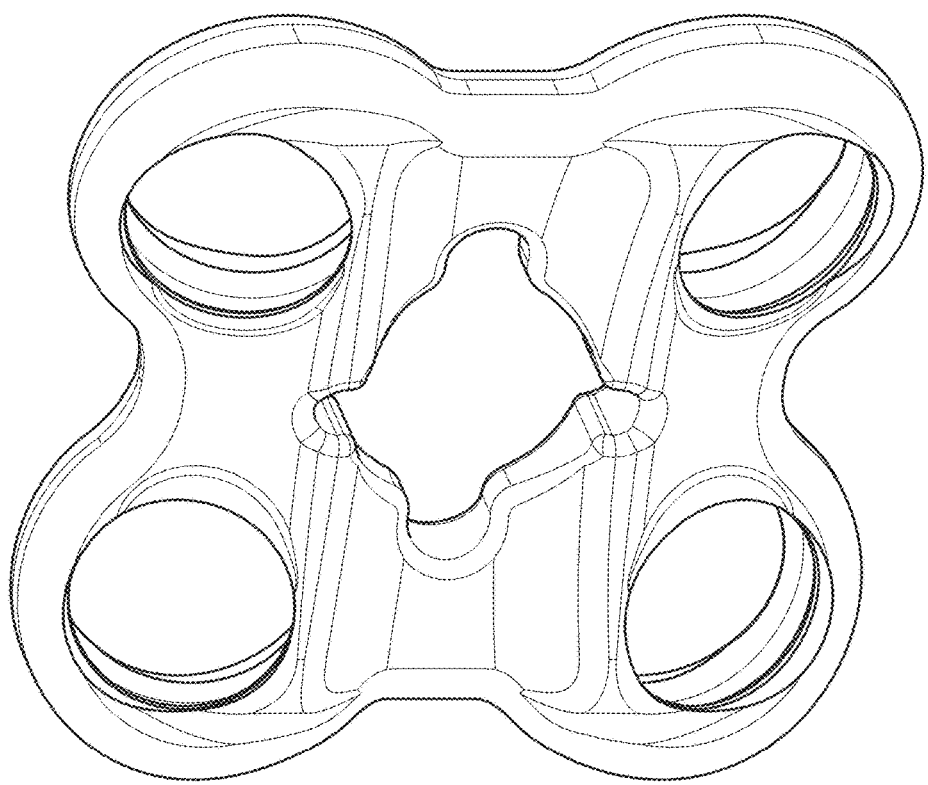
FIG. 71 is a perspective bottom view of the cervical plate of FIG. 68.
Figure 72:
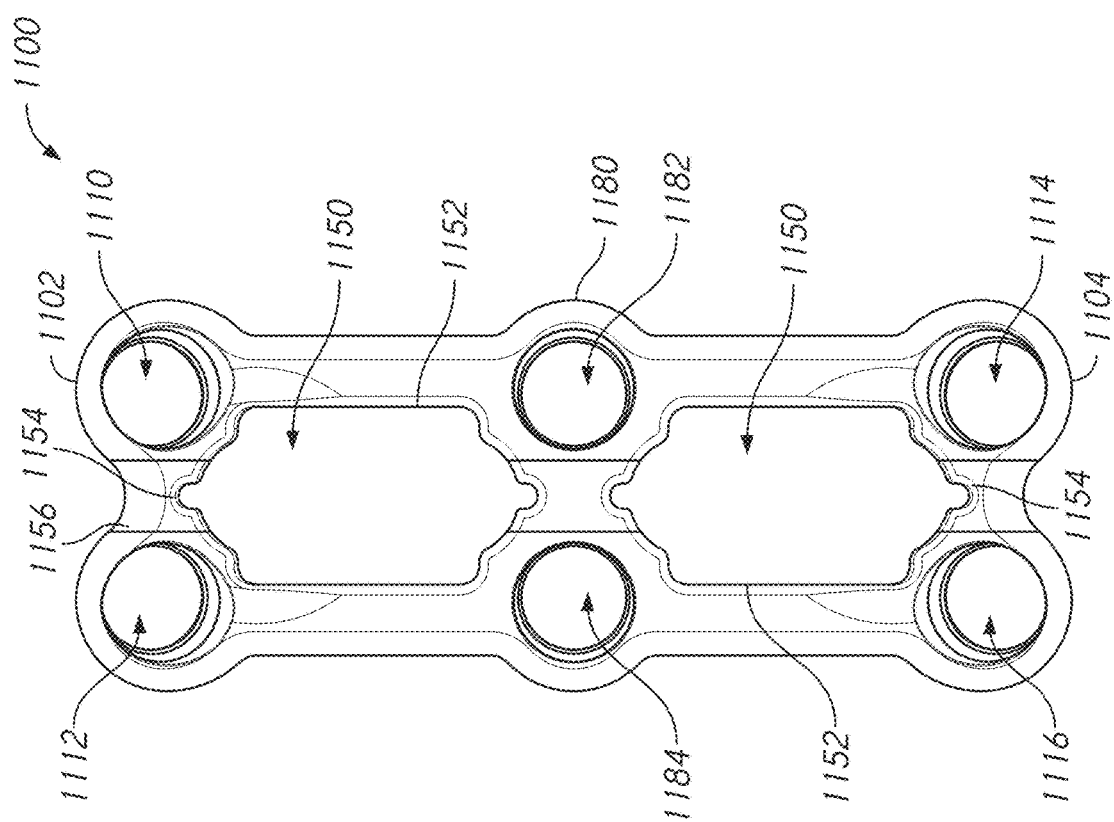
FIG. 72 is a top view of a two-level cervical plate.
Figure 73:
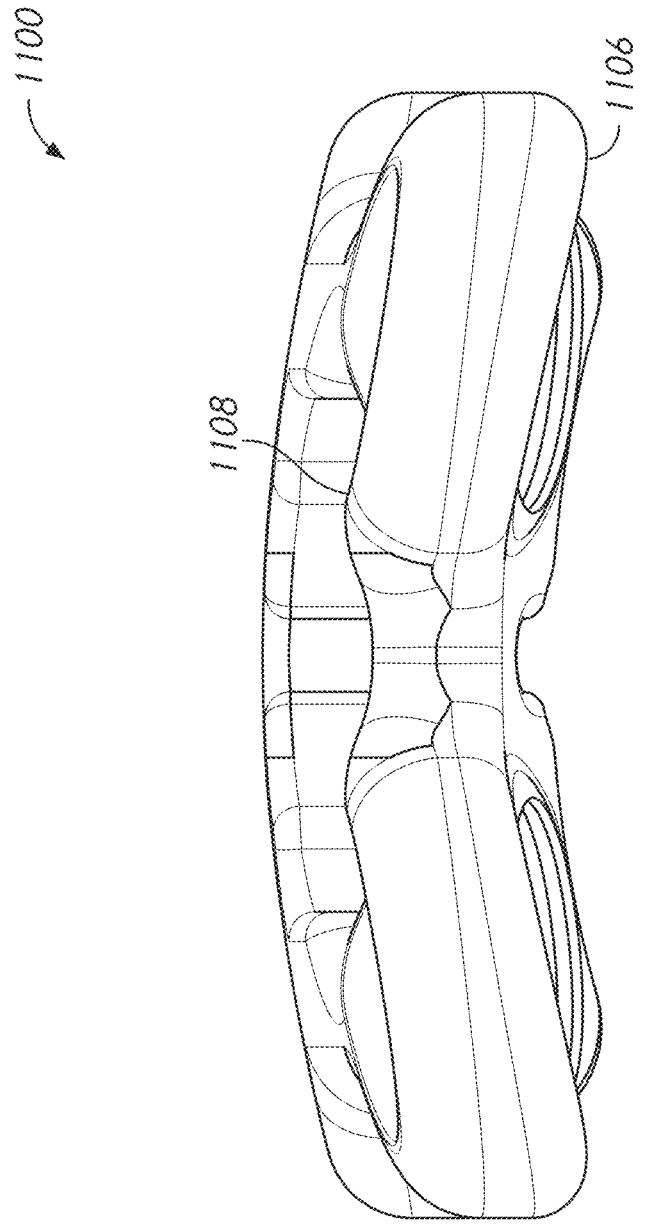
FIG. 73 is a side view of the two-level cervical plate of FIG. 72.
Figure 74:
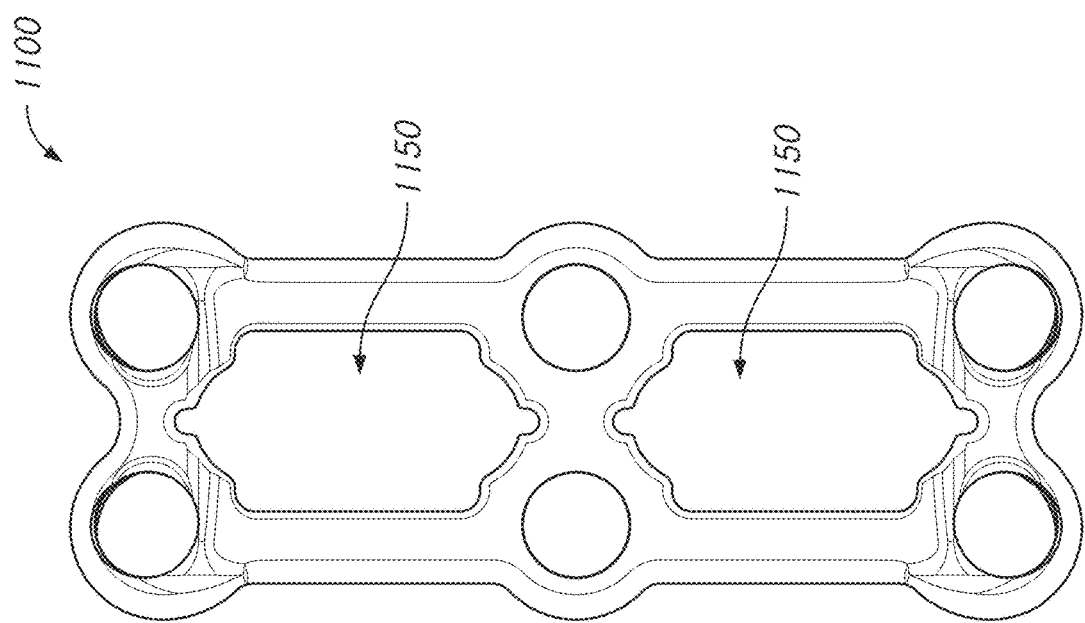
FIG. 74 is a bottom view of the cervical plate of FIG. 72.
Figure 75:
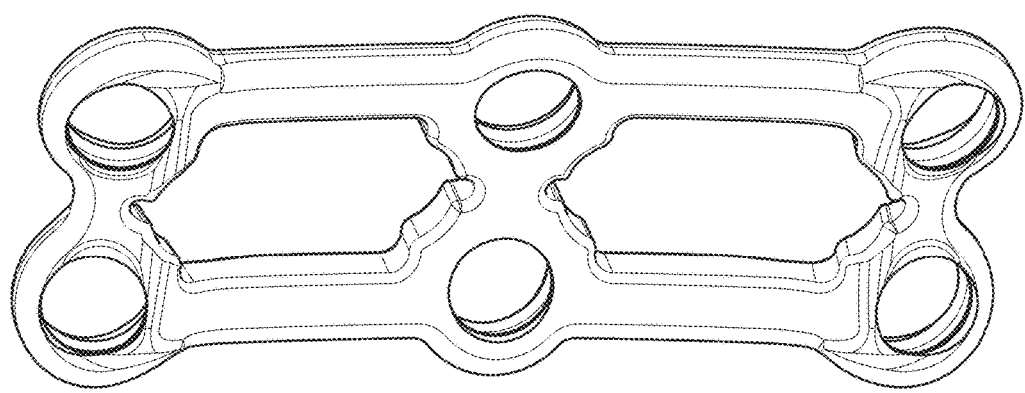
FIG. 75 is a perspective bottom view of the two-level cervical plate of FIG. 72.
Figure 76:
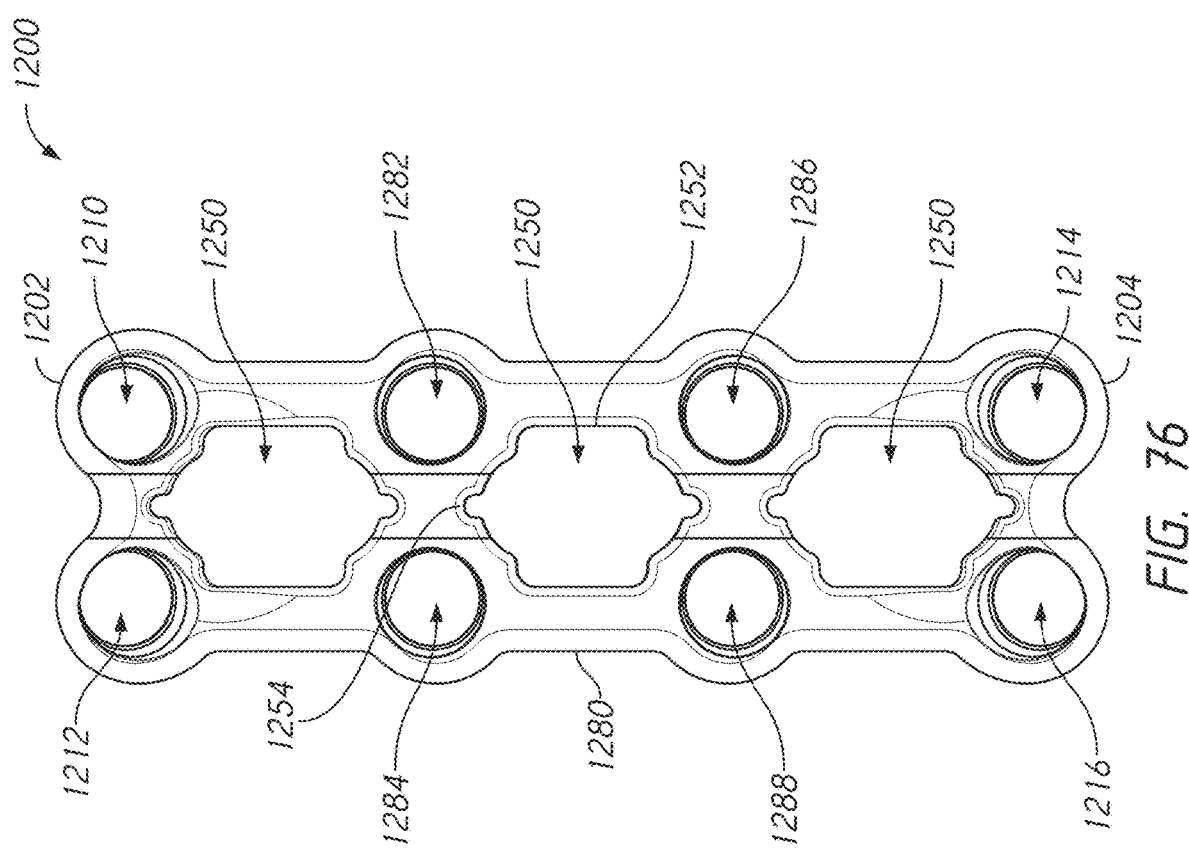
FIG. 76 is a top view of a three-level cervical plate.
Figure 77:
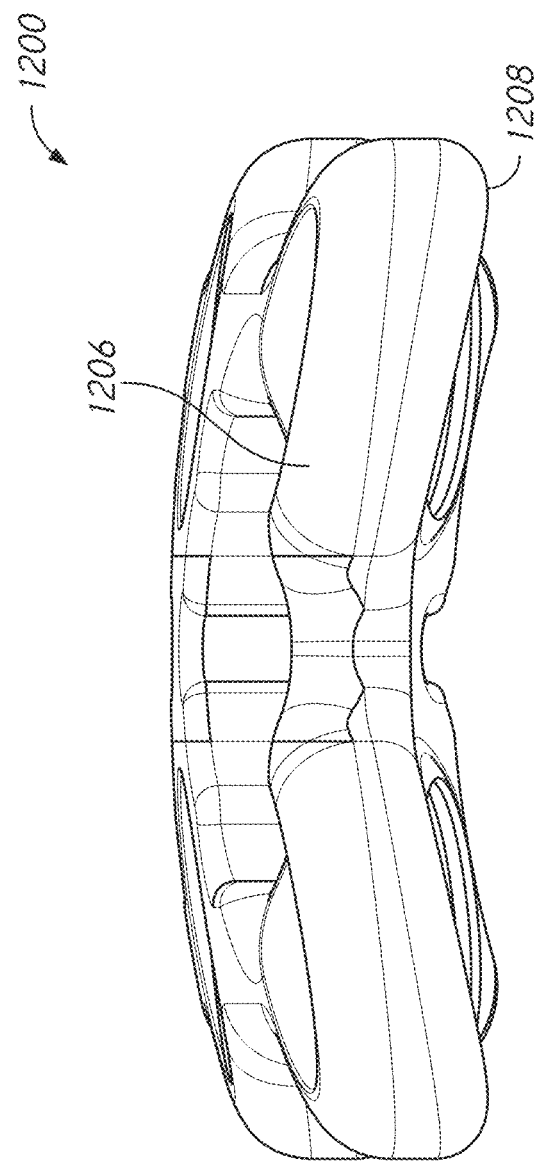
FIG. 77 is a side view of the three-level cervical plate of FIG. 76.
Figure 78:
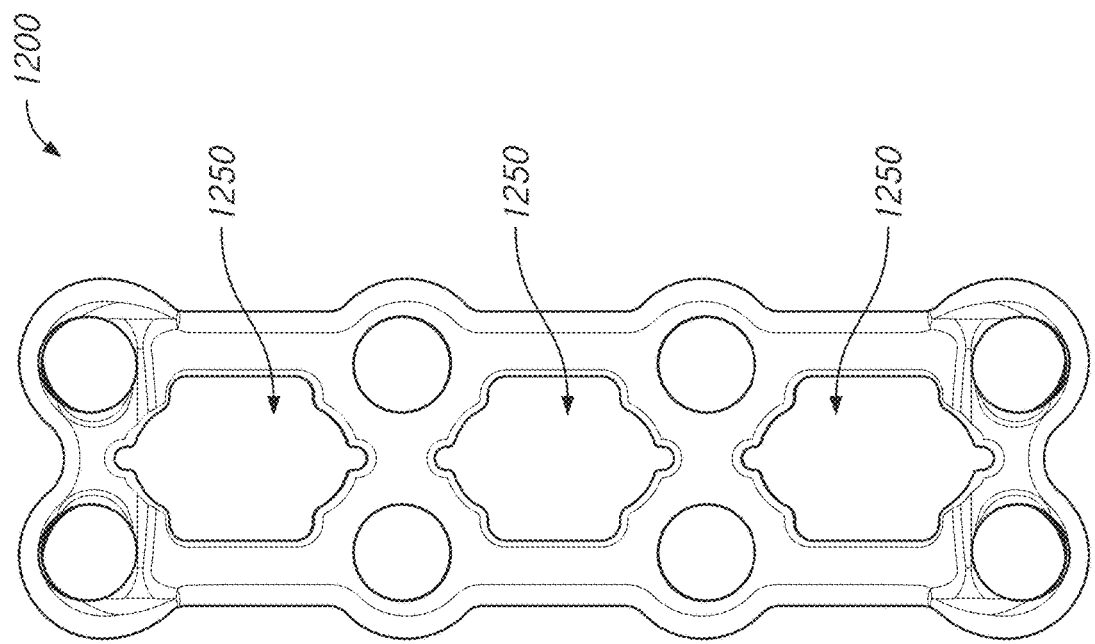
FIG. 78 is a bottom view of the three-level cervical plate of FIG. 76.
Figure 79:
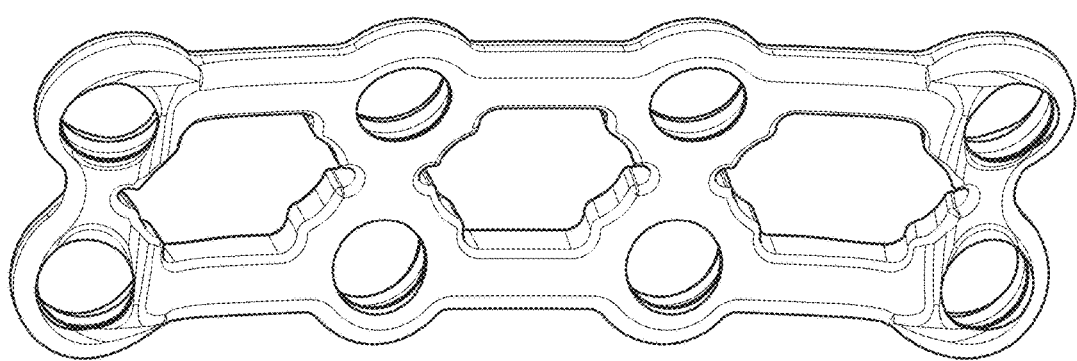
FIG. 79 is a perspective bottom view of the three-level cervical plate of FIG. 76.
Figure 80:
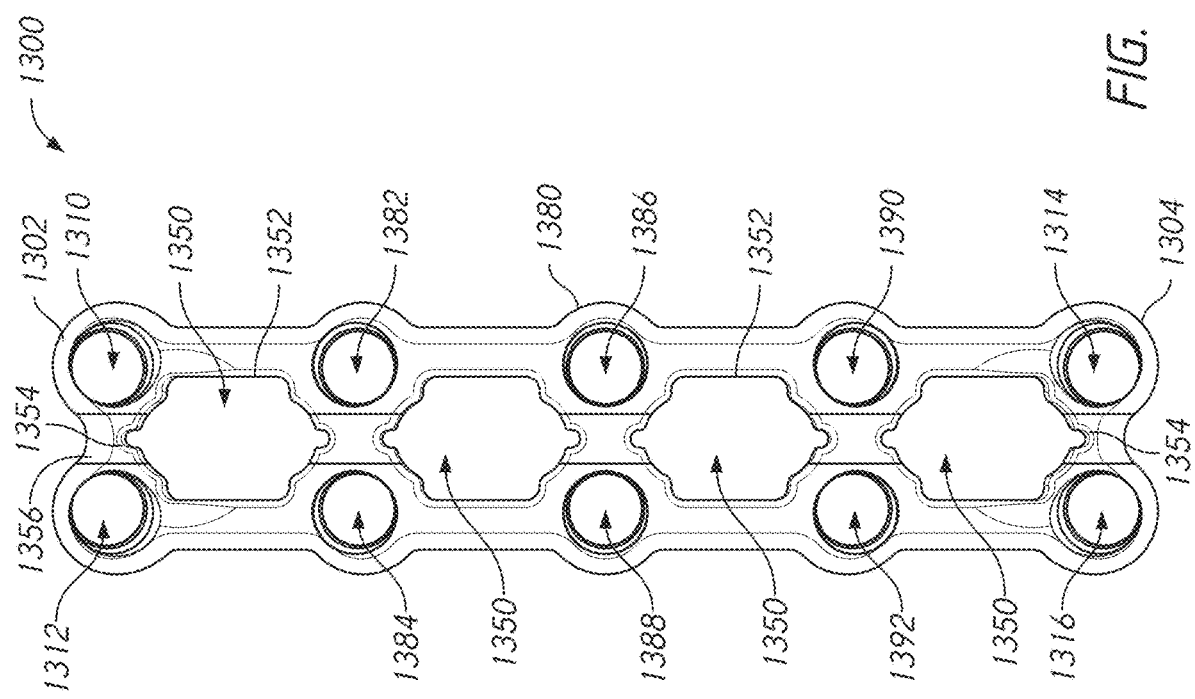
FIG. 80 is a top view of a four-level cervical plate.
Figure 81:
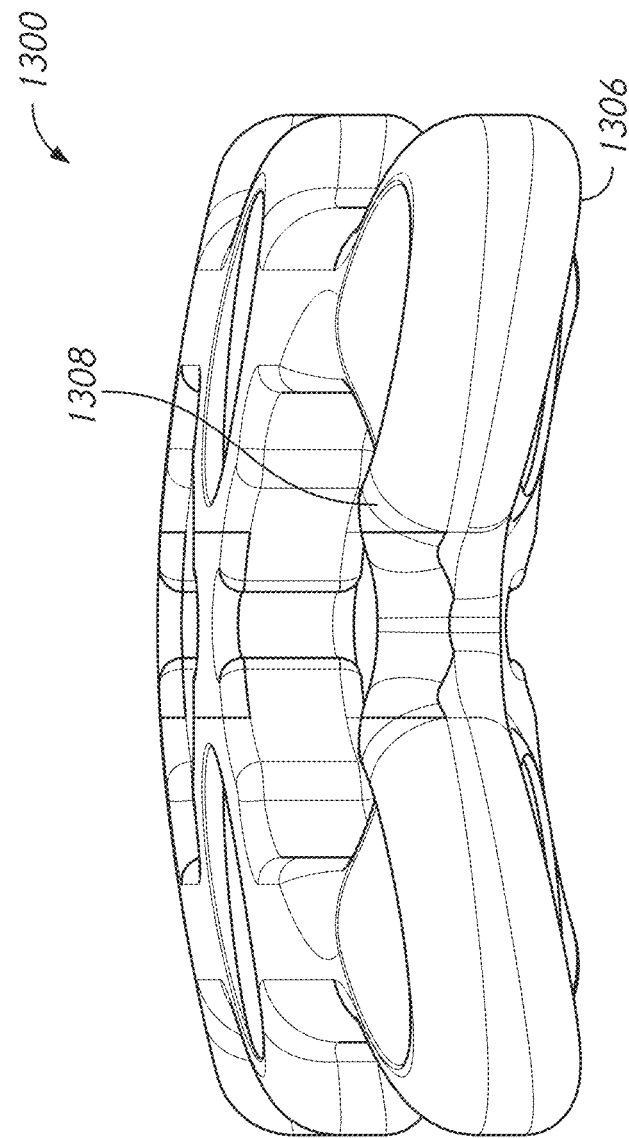
FIG. 81 is a side view of the four-level cervical plate of FIG. 80.
Figure 82:
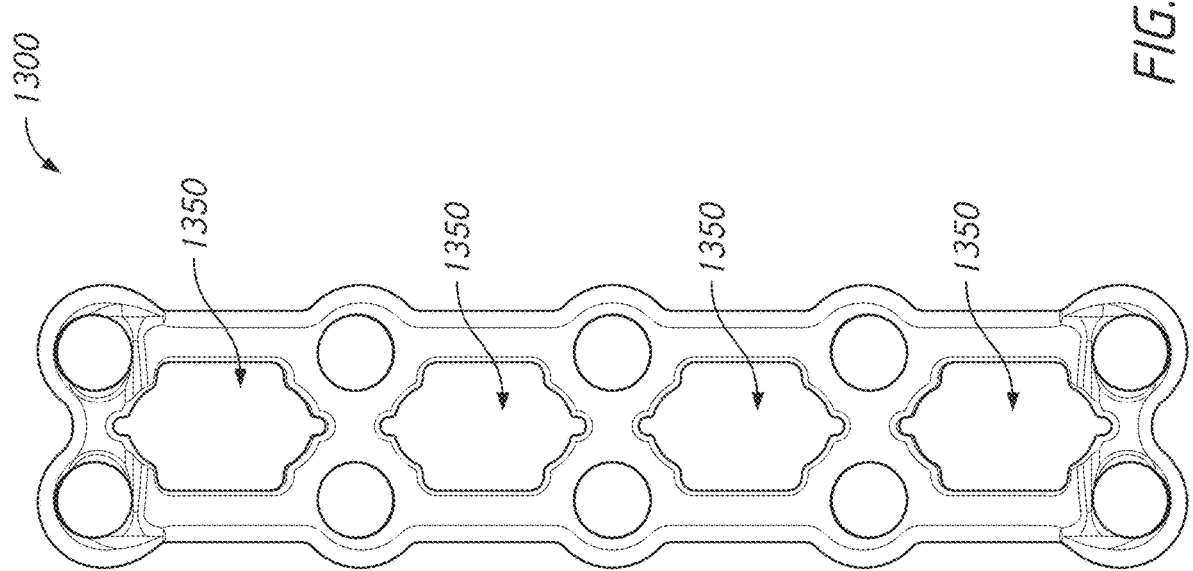
FIG. 82 is a bottom view of the four-level cervical plate of FIG. 80.
Figure 83:
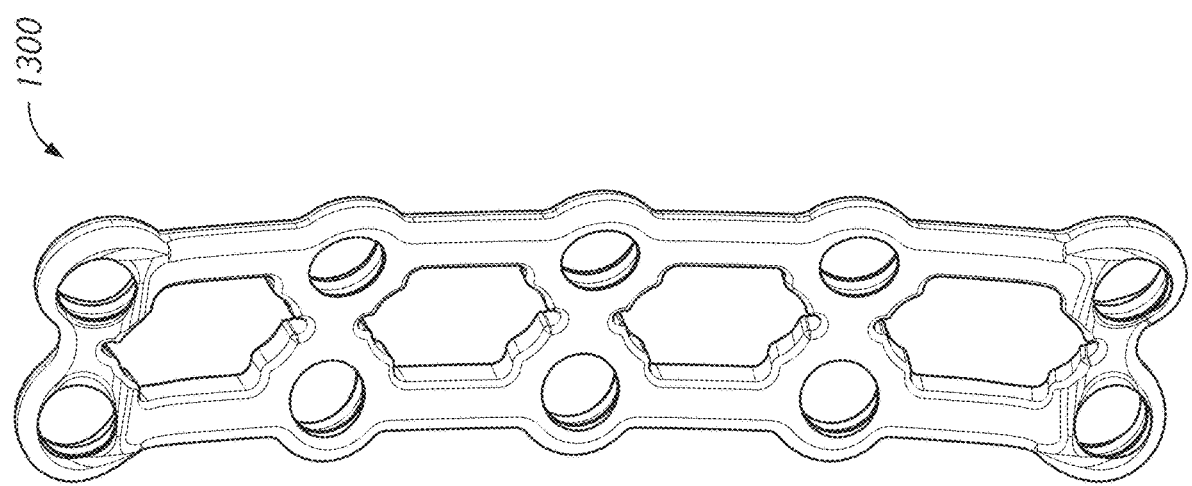
FIG. 83 is a perspective bottom view of the four-level cervical plate of FIG. 80.
Figure 84:
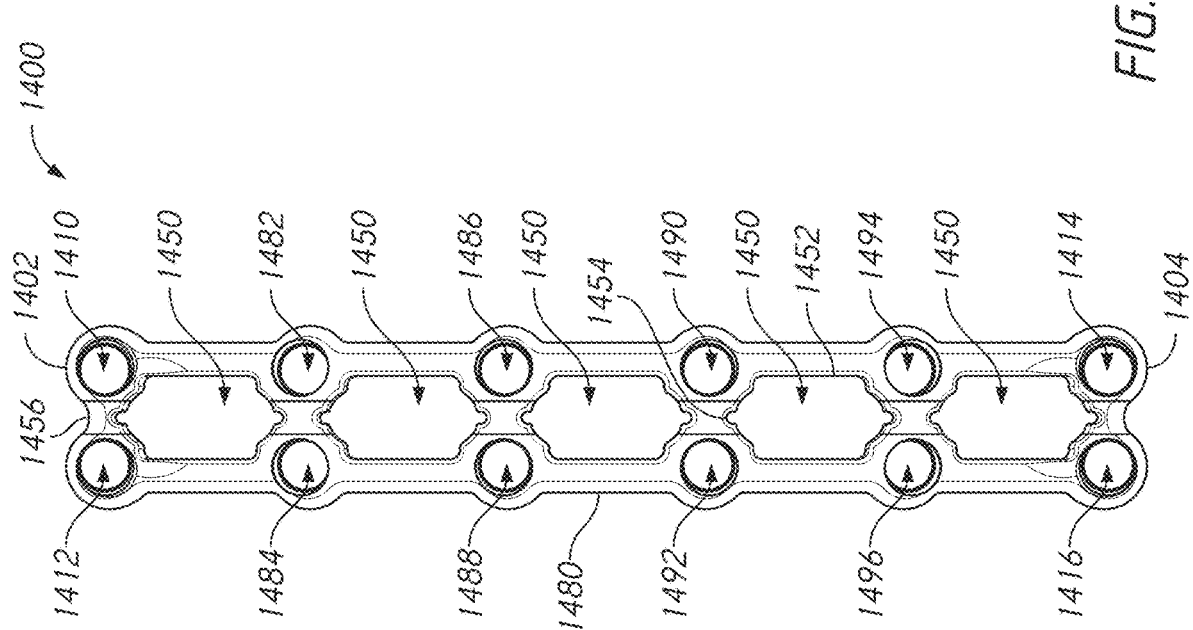
FIG. 84 is a top view of a five-level cervical plate.
Figure 85:
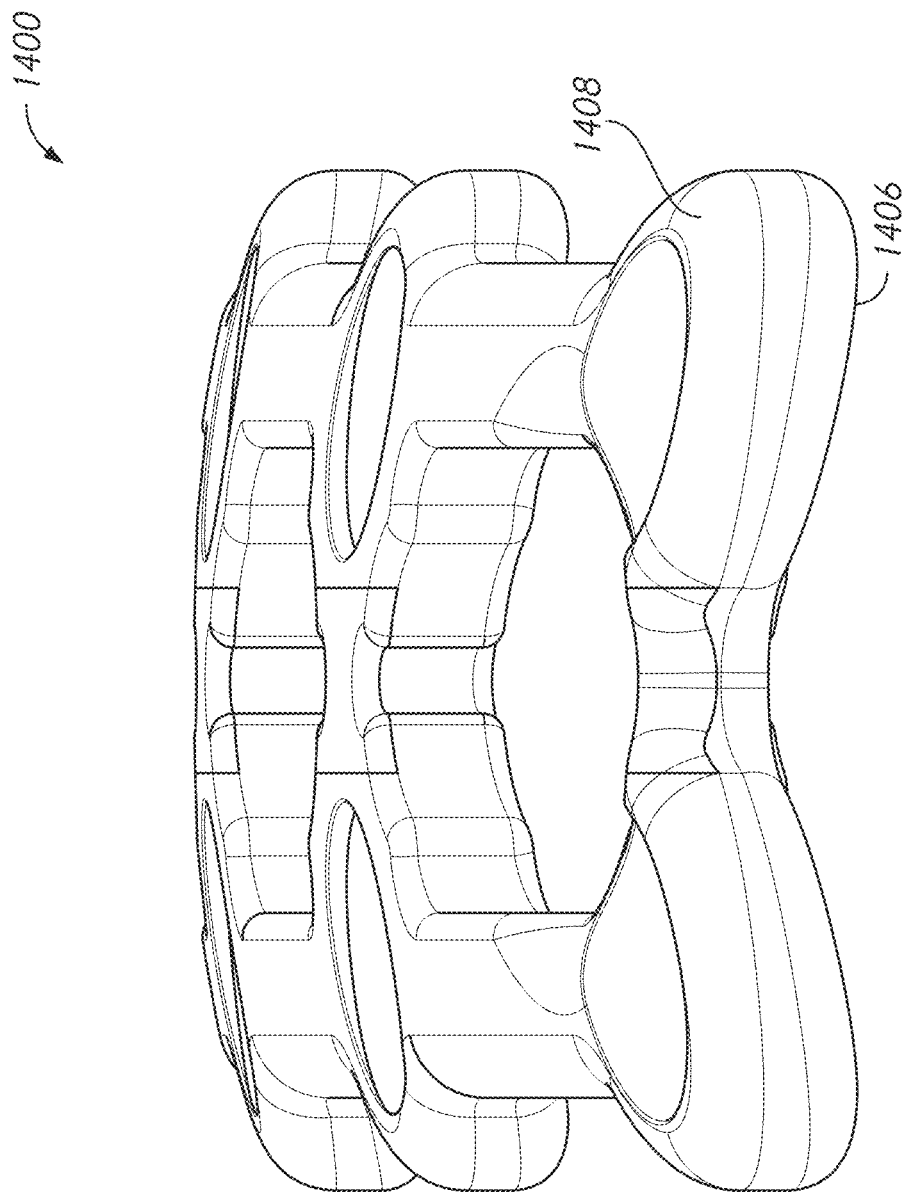
FIG. 85 is a side view of the five-level cervical plate of FIG. 84.
Figure 86:
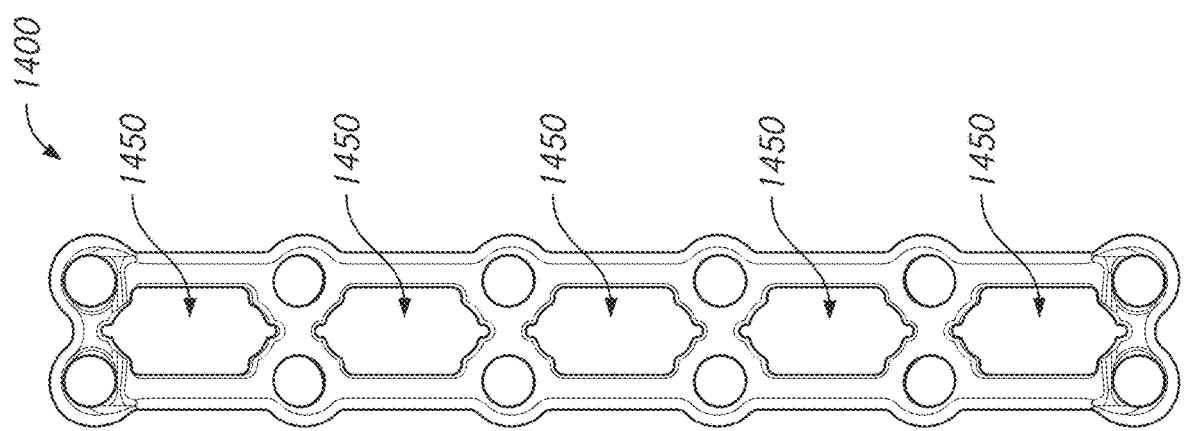
FIG. 86 is a bottom view of the five-level cervical plate of FIG. 84.
Figure 87:
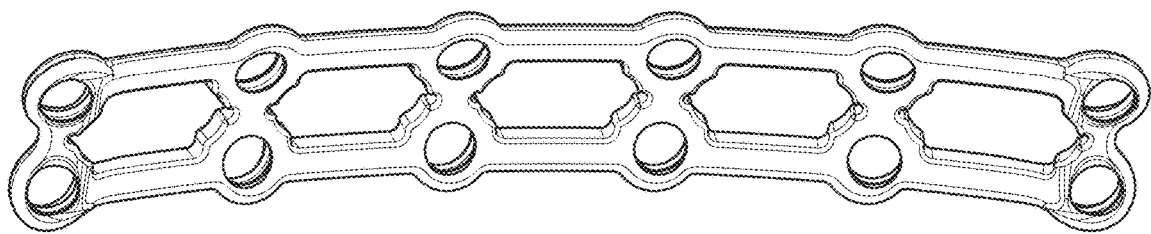
FIG. 87 is a perspective bottom view of the five-level cervical plate of FIG. 84.

FIG. 68 is a top view of a cervical plate 1000. FIG. 69 is a side view of the cervical plate 1000. FIG. 70 is a bottom view of the cervical plate 1000. FIG. 71 is a perspective bottom view of the cervical plate 1000. FIG. 72 is a top view of a two-level cervical plate 1100. FIG. 73 is a side view of the two-level cervical plate 1100. FIG. 74 is a bottom view of the cervical plate 1100. FIG. 75 is a perspective bottom view of the two-level cervical plate 1100. FIG. 76 is a top view of a three-level cervical plate 1200. FIG. 77 is a side view of the three-level cervical plate 1200. FIG. 78 is a bottom view of the three-level cervical plate 1200. FIG. 79 is a perspective bottom view of the three-level cervical plate 1200. FIG. 80 is a top view of a four-level cervical plate 1300. FIG. 81 is a side view of the four-level cervical plate 1300. FIG. 82 is a bottom view of the four-level cervical plate 1300. FIG. 83 is a perspective bottom view of the four-level cervical plate 1300. FIG. 84 is a top view of a five-level cervical plate 1400. FIG. 85 is a side view of the five-level cervical plate 1400. FIG. 86 is a bottom view of the five-level cervical plate 1400. FIG. 87 is a perspective bottom view of the five-level cervical plate 1400. The cervical plates 1000, 1100, 1200, 1300, 1400 can have any features described herein.

In some embodiments, the cervical plate 1000 can be utilized with one interbody spacer 200. In some embodiments, the two-level cervical plate 1100 can be utilized with two interbody spacers 200. In some embodiments, the three-level cervical plate 1200 can be utilized with three interbody spacers 200. In some embodiments, the four-level cervical plate 1300 can be utilized with four interbody spacers 200. In some embodiments, the five-level cervical plate 1400 can be utilized with five interbody spacers 200. Other methods of use are contemplated. In some embodiments, any of cervical plate 1000, 1100, 1200, 1300, 1400 can be utilized with one or more interbody spacers 200 at adjacent or non-adjacent levels. The cervical plates described herein can include a marking. The cervical plates described herein can include a marking to indicate orientation of the cervical plate. The cervical plates described herein can include a marking to indicate cephalad/caudal orientation. In some embodiments, the cervical plates described herein can include a stripe which indicates the cephalad/caudal orientation of the cervical plate.

The cervical plates described herein can include a superior portion and an inferior portion. The cervical plates described herein can include a bone facing surface and an access surface. The cervical plates described herein can include one or more holes oriented between the bone facing surface and the access surface. The cervical plates described herein can be designed to allow high angle anchor insertion. The cervical plates described herein can be designed to be at least partially inserted within a disc space as described herein. The cervical plates described herein can couple to the interbody spacer 200. The cervical plates described herein can include a concavity to accept the interbody spacer 200 at least partially therewithin. In some methods of use, the cervical plates described herein are configured to be placed adjacent to cervical vertebrae as described herein. The cervical plates described herein can be designed to facilitate insertion of one or more anchors 400 into the edge or corner of the vertebra.

The cervical plates described herein can include an engagement portion 1050, 1150, 1250, 1350, 1450. The engagement portion 1050, 1150, 1250, 1350, 1450 can be configured to engage the outer shaft 902 of the interbody implant inserter 900. The engagement portion 1050, 1150, 1250, 1350, 1450 can include a lumen. The engagement portion 1050, 1150, 1250, 1350, 1450 can include a shaped lumen. The engagement portion 1050, 1150, 1250, 1350, 1450 can include a diamond shaped lumen. The engagement portion 1050, 1150, 1250, 1350, 1450 can include a complementary retention feature 1052, 1152, 1252, 1352, 1452. The engagement portion 1050, 1150, 1250, 1350, 1450 can include a complementary anti-rotation feature 1054, 1154, 1254, 1354, 1454.

The complementary retention feature 1052, 1152, 1252, 1352, 1452 can be a keyed groove. The complementary retention feature 1052, 1152, 1252, 1352, 1452 can include one or more grooves. The complementary retention feature 1052, 1152, 1252, 1352, 1452 can be a solid, shaped surface. The complementary retention feature 1052, 1152, 1252, 1352, 1452 can provide a frictional fit. The complementary retention feature 1052, 1152, 1252, 1352, 1452 can provide an interference fit. The complementary retention feature 1052, 1152, 1252, 1352, 1452 can include two or more diametrically opposed structures. The complementary retention feature 1052, 1152, 1252, 1352, 1452 can include two or more structures equally spaced around the engagement feature. In the illustrated embodiment, the complementary retention feature 1052, 1152, 1252, 1352, 1452 includes two structures. Other configurations are contemplated, e.g. one structure, three structures, four structures, etc. In the illustrated embodiment, the complementary retention feature 1052, 1152, 1252, 1352, 1452 includes two grooves or recesses. The complementary retention feature 1052, 1152, 1252, 1352, 1452 can be disposed along a midline of the cervical plate 1050, 1150, 1250, 1350, 1450.

The cervical plates described herein can include the complementary anti-rotation feature 1054, 1154, 1254, 1354, 1454 configured to couple with the interbody implant inserter 900, as described herein. The complementary anti-rotation feature 1054, 1154, 1254, 1354, 1454 can be a keyed groove. The complementary anti-rotation feature 1054, 1154, 1254, 1354, 1454 can extend through the cervical plate. The complementary anti-rotation feature 1054, 1154, 1254, 1354, 1454 can include one or more grooves. The complementary anti-rotation feature 1054, 1154, 1254, 1354, 1454 can be a solid, shaped surface. The complementary anti-rotation feature 1054, 1154, 1254, 1354, 1454 can prevent or limit rotation of the cervical plate. The complementary anti-rotation feature 1054, 1154, 1254, 1354, 1454 can include two or more diametrically opposed structures. The complementary anti-rotation feature 1054, 1154, 1254, 1354, 1454 can include two or more structures equally spaced around the engagement portion 1050, 1150, 1250, 1350, 1450. In the illustrated embodiment, the complementary anti-rotation feature 1054, 1154, 1254, 1354, 1454 includes two structures. Other configurations are contemplated, e.g. one structure, three structures, four structures, etc.

The complementary retention feature 1052, 1152, 1252, 1352, 1452 and the complementary anti-rotation feature 1054, 1154, 1254, 1354, 1454 can alternate around an axis from the access surface to the bone facing surface. Additional details of the cervical plates are described herein.

15. Cervical Plate

FIGS. 68-71 depict views of an embodiment of the cervical plate 1000. The cervical plate 1000 can be designed to allow high angle anchor insertion. The anchor 400 can be inserted at any range of angles described herein. The cervical plate 1000 can have any features of any plate described herein.

The cervical plate 1000 can include a superior portion 1002 and an inferior portion 1004. The cervical plate 1000 can include a bone facing surface 1006 and an access surface 1008. The superior portion 1002 can include one or more holes 1010, 1012 oriented between the bone facing surface 1006 and the access surface 1008. The inferior portion 1004 can include one or more holes 1014, 1016 oriented between the bone facing surface 1006 and the access surface 1008. The holes 1010, 1012, 1014, 1016 are configured to accept anchors 400 and/or other attachment devices for anchoring the cervical plate 1000 to the vertebral bone.

The cervical plate 1000 can include the engagement portion 1050. The engagement portion 1050 can be configured to engage the outer shaft 902 of the interbody implant inserter 900. The engagement portion 1050 can include a lumen. The engagement portion 1050 can include a shaped lumen. The engagement portion 1050 can include the complementary retention feature 1052. The complementary retention feature 1052 can be a keyed groove. The complementary retention feature 1052 can extend through the cervical plate 1000. The complementary retention feature 1052 can include one or more grooves. The engagement portion 1050 can have any feature of the engagement portions described herein.

The cervical plate 1000 can include the complementary anti-rotation feature 1054 configured to couple with the interbody implant inserter 900, as described herein. The complementary anti-rotation feature 1054 can have any features of the complementary anti-rotation features described herein. The complementary anti-rotation feature 1054 can be a keyed groove. The complementary anti-rotation feature 1054 can extend through the cervical plate 1000. The complementary anti-rotation feature 1054 can include one or more grooves.

The complementary anti-rotation feature 1054 can limit or prevent rotation of the cervical plate 1000 relative to the outer shaft 902 of the interbody implant inserter 900. The complementary anti-rotation feature 1054 can prevent or limit rotation of the cervical plate 1000 during translation of the cervical plate 1000.

The complementary retention feature 1052 and the complementary anti-rotation feature 1054 can alternate around the engagement portion 1050. The complementary retention feature 1052 and the complementary anti-rotation feature 1054 can be the same or similar. The complementary retention feature 1052 and the complementary anti-rotation feature 1054 can be different. The complementary retention feature 1052 and the complementary anti-rotation feature 1054 can have different widths. The complementary retention feature 1052 and the complementary anti-rotation feature 1054 can have different shapes.

The outer shaft 902 can couple to the engagement portion 1050 of the cervical plate 1000. In some embodiments, the one or more features 922, 924 can couple with corresponding, complementary features 1052, 1054 of the cervical plate 1000. The engagement portion 1050 can have a corresponding shape as the features 922, 924 of the outer shaft 902. The features 922, 924 of the outer shaft 902 can be shaped to fit within the recessed engagement portion 1050.

The cervical plate 1000 can include a marking 1056. The marking 1056 can indicate orientation of the cervical plate 1000. The marking 1056 can indicate cephalad/caudal orientation. In some embodiments, the marking 1056 can facilitate alignment of the cervical plate 1000 in the cephalad/caudal direction.

The cervical plate 1000 can include an engagement feature 1058. The engagement feature 1058 can be a shaped surface. The engagement feature 1058 can be a flattened portion. The engagement feature 1058 can be one or more surfaces. The engagement feature 1058 can be a pair of diametrically opposed surfaces. In some embodiments, the engagement feature 1058 can facilitate the grip of the first retention feature 920. The first retention feature 920 is configured to couple with the engagement feature 1058 of the cervical plate 1000. The engagement feature 1058 can have a shape complementary to the first retention feature 920. In some embodiments, the first retention feature 920 includes a projection and the engagement feature 1058 includes a groove. In some embodiments, the first retention feature 920 includes a groove and the engagement feature 1058 includes a projection. The cervical plate 1000 can include a width. The width can be measured between the pair of diametrically opposed surfaces of the engagement feature 1058. The width can be the same as the width of one or more cervical plates described herein. The width can be the same to allow the first retention feature 920 of the interbody implant inserter 900 to grip one or more cervical plates.

16. Two-Level Cervical Plate

FIGS. 72-75 depict views of an embodiment of the two-level cervical plate 1100. The two-level cervical plate 1100 can be designed to allow high angle anchor insertion for at least some of the anchors inserted through the two-level cervical plate 1100. The two-level cervical plate 1100 can be utilized with any interbody implant inserter described herein. The two-level cervical plate 1100 can be utilized with the interbody implant inserter 900 described above. The two-level cervical plate 1100 can be utilized with the interbody implant inserter 1500 described below.

The two-level cervical plate 1100 can include a superior portion 1102 and an inferior portion 1104. The two-level cervical plate 1100 can include a bone facing surface 1106 and an access surface 1108. The superior portion 1102 can include one or more holes 1110, 1112 oriented between the bone facing surface 1106 and the access surface 1108. The inferior portion 1104 can include one or more holes 1114, 1116 oriented between the bone facing surface 1106 and the access surface 1108. In some embodiments, the holes 1110, 1112, 1114, 1116 are designed for high angle insertion. In some embodiments, the holes of the superior portion 1102 allow for high angle insertion of anchors to secure the two-level cervical plate 1100 to a superior vertebral body. In some embodiments, the holes of the inferior portion 1104 allow for high angle insertion of anchors to secure the two-level cervical plate 1100 to an inferior vertebral body.

The two-level cervical plate 1100 can include a middle portion 1180. The middle portion 1180 can be disposed between the superior portion 1102 and the inferior portion 1104. The middle portion 1180 can include one or more holes 1182, 1184 oriented between the bone facing surface 1106 and the access surface 1108. The middle portion 1180 can include two holes 1182, 1184 disposed between the superior portion 1102 and the inferior portion 1104.

The holes 1110, 1112, 1114, 1116, 1182, 1184 are configured to accept anchors 400 and/or other attachment devices for anchoring the two-level cervical plate 1100 to the vertebral bone. In some embodiments, the trajectories through the holes 1110, 1112 are the same or similar. In some embodiments, the trajectories through the holes 1114, 1116 are the same or similar. In some embodiments, the trajectories through the holes 1182, 1184 are the same or similar. In some embodiments, the trajectories through the holes 1110, 1114 are mirrored. In some embodiments, the trajectories through the holes 1112, 1116 are mirrored. In some embodiments, the trajectories through the holes 1182, 1184 are perpendicular or substantially perpendicular to the two-level cervical plate 1100.

The two-level cervical plate 1100 can include one or more engagement portions 1150. Each engagement portion 1150 can be recessed. Each engagement portion 1150 can be configured to engage the outer shaft 902, 1502 of the interbody implant inserter 900, 1500. Each engagement portion 1150 can include a lumen. Each engagement portion 1150 can include a shaped lumen. Each engagement portion 1150 can include the complementary retention feature 1152. In some embodiments, each engagement portion 1150 can function as a graft window. The engagement portion 1150 can have any feature of the engagement portions described herein.

The two-level cervical plate 1100 can include the complementary retention feature 1152 configured to couple with the interbody implant inserter 900, 1500. The complementary retention feature 1152 can be a keyed groove. The complementary retention feature 1152 can extend through the two-level cervical plate 1100. The complementary retention feature 1152 can include one or more grooves. The complementary retention feature 1152 can be shaped to allow the two-level cervical plate 1100 to slide relative to the interbody implant inserter 900, 1500.

The two-level cervical plate 1100 can include the complementary anti-rotation feature 1154 configured to couple with the interbody implant inserter 900, 1500. The complementary anti-rotation feature 1154 can have any features of the complementary anti-rotation features described herein. The complementary anti-rotation feature 1154 can be a keyed groove. The complementary anti-rotation feature 1154 can extend through the two-level cervical plate 1100. The complementary anti-rotation feature 1154 can include one or more grooves. The complementary anti-rotation feature 1154 is configured to engage the anti-rotation feature 924, 1524 of the outer shaft 902, 1502. The complementary anti-rotation feature 1154 can include two grooves to accept the two ridges of the anti-rotation feature 924, 1524 of the outer shaft 902, 1502. The complementary anti-rotation feature 1154 can be shaped to allow the two-level cervical plate 1100 to slide relative to the interbody implant inserter 900, 1500.

The complementary anti-rotation feature 1154 can limit or prevent rotation of the two-level cervical plate 1100 relative to the outer shaft 902, 1502 of the interbody implant inserter 900, 1500. The complementary anti-rotation feature 1154 can prevent or limit rotation of the two-level cervical plate 1100 during translation of the two-level cervical plate 1100.

The complementary retention feature 1152 and the complementary anti-rotation feature 1154 can alternate around the engagement portion 1150. The complementary retention feature 1152 and the complementary anti-rotation feature 1154 can be the same or similar. The complementary retention feature 1152 and the complementary anti-rotation feature 1154 can be different. The complementary retention feature 1152 and the complementary anti-rotation feature 1154 can have different shaped grooves.

The outer shaft 902, 1502 can couple to the engagement portion 1150 of the two-level cervical plate 1100. In some embodiments, the one or more features 922, 924, 1522, 1524 can couple with corresponding, complementary features 1152, 1154 in the two-level cervical plate 1100. The engagement portion 1150 can have a corresponding shape as the features 922, 924, 1522, 1524 of the outer shaft 902, 1502. The features 922, 924, 1522, 1524 of the outer shaft 902, 1502 can be shaped to fit within the recessed engagement portion 1150.

In the illustrated embodiment, each engagement portion 1150 can include a lumen comprising the complementary features 1152, 1154. One engagement portion 1150 can be disposed between the superior portion 1102 and the middle portion 1180. One engagement portion 1150 can be disposed between the middle portion 1180 and the inferior portion 1114. Other configurations are contemplated depending on the number and configuration of interbody implants 200.

The two-level cervical plate 1100 can include a marking 1156. The marking 1156 can indicate orientation of the two-level cervical plate 1100. The marking 1156 can indicate the cephalad/caudal orientation of the two-level cervical plate 1100. In some embodiments, the marking 1156 can facilitate alignment of the cervical plate 1000 relative to the interbody implant inserter 900, 1500.

17. Three-Level Cervical Plate

FIGS. 76-79 depict views of an embodiment of the three-level cervical plate 1200. The three-level cervical plate 1200 can be designed to allow high angle anchor insertion for at least some of the anchors inserted through the cervical plate. The three-level cervical plate 1200 can be utilized with any interbody implant inserter described herein.

The three-level cervical plate 1200 can include a superior portion 1202 and an inferior portion 1204. The three-level cervical plate 1200 can include a bone facing surface 1206 and an access surface 1208. The superior portion 1202 can include one or more holes 1210, 1212 oriented between the bone facing surface 1206 and the access surface 1208. The inferior portion 1204 can include one or more holes 1214, 1216 oriented between the bone facing surface 1206 and the access surface 1208. In some embodiments, the holes 1210, 1212, 1214, 1216 are designed for high angle insertion. In some embodiments, the holes of the superior portion 1202 allow for high angle insertion of anchors into harder cortical bone of a corner or edge of a superior vertebral body. In some embodiments, the holes of the inferior portion 1204 allow for high angle insertion of anchors into harder cortical bone of a corner or edge of an inferior vertebral body.

The three-level cervical plate 1200 can include a middle portion 1280. The middle portion 1280 can be disposed between the superior portion 1202 and the inferior portion 1204. The middle portion 1280 can include one or more holes 1282, 1284, 1286, 1288 oriented between the bone facing surface 1206 and the access surface 1208. The middle portion 1280 can include four holes 1282, 1284, 1286, 1288 disposed between the superior portion 1202 and the inferior portion 1204. The middle portion 1280 can include four holes 1282, 1284, 1286, 128 disposed between the one or more holes 1210, 1212 of the superior portion 1202 and the one or more holes 1214, 1216 of the inferior portion 1204.

The holes 1210, 1212, 1214, 1216, 1282, 1284, 1286, 1288 are configured to accept anchors 400 and/or other attachment devices for anchoring the three-level cervical plate 1200 to the vertebral bone. In some embodiments, the trajectories through the holes 1210, 1212 allow anchors 400 to engage the same vertebrae. In some embodiments, the trajectories through the holes 1214, 1216 allow anchors 400 to engage the same vertebrae. In some embodiments, the trajectories through the holes 1282, 1284 allow anchors 400 to engage the same vertebrae. In some embodiments, the trajectories through the holes 1286, 1288 allow anchors 400 to engage the same vertebrae. In some embodiments, the trajectories through the holes 1282, 1284, 1286, 1288 are perpendicular or substantially perpendicular to the three-level cervical plate 1200. In some embodiments, the trajectories through the holes 1210, 1212, 1214, 1216 are skewed relative to the three-level cervical plate 1200 to allow high angle anchor insertion.

The three-level cervical plate 1200 can include one or more engagement portions 1250. The three-level cervical plate 1200 can include three engagement portions 1250. The three engagement portions 1250 can be the same or similar. The three engagement portions 1250 can be different. Each engagement portion 1250 can be recessed. Each engagement portion 1250 can be configured to slide relative to the outer shaft 902, 1502 of the interbody implant inserter 900, 1500. Each engagement portion 1250 can be a through lumen. Each engagement portion 1250 can include a shaped through lumen. In some embodiments, the engagement portion 1250 can be packed with graft after removal of the interbody implant inserter 900, 1500. The engagement portion 1250 can have any feature of the engagement portions described herein.

The three-level cervical plate 1200 can include the complementary retention feature 1252 configured to engage with the interbody implant inserter 900, 1500. The complementary retention feature 1252 can be a keyed groove. The complementary retention feature 1252 can extend through the three-level cervical plate 1200. The complementary retention feature 1252 can include one or more grooves. The complementary retention feature 1252 can be shaped to allow the three-level cervical plate 1200 to slide relative to the interbody implant inserter 900, 1500.

The three-level cervical plate 1200 can include the complementary anti-rotation feature 1254 configured to engage with the interbody implant inserter 900, 1500. The complementary anti-rotation feature 1254 can have any features of the complementary anti-rotation features described herein. The complementary anti-rotation feature 1254 can be a keyed groove. The complementary anti-rotation feature 1254 can extend through the three-level cervical plate 1200. The complementary anti-rotation feature 1254 can include one or more grooves. The complementary anti-rotation feature 1254 can engage the anti-rotation feature 924, 1524 of the outer shaft 902, 1502. The complementary anti-rotation feature 1254 can include two grooves to accept the two ridges of the anti-rotation feature 924, 1524 of the outer shaft 902, 1502. The complementary anti-rotation feature 1254 can be shaped to allow the three-level cervical plate 1200 to slide relative to the interbody implant inserter 900, 1500.

The complementary anti-rotation feature 1254 can limit or prevent rotation of the three-level cervical plate 1200 relative to the outer shaft 902, 1502 of the interbody implant inserter 900, 1500. The complementary anti-rotation feature 1254 can maintain the orientation of the three-level cervical plate 1200 during translation of the three-level cervical plate 1200.

The complementary retention feature 1252 and the complementary anti-rotation feature 1254 can alternate to form the engagement portion 1250. The complementary retention feature 1252 and the complementary anti-rotation feature 1254 can each include a pair of shaped surfaces. The complementary retention feature 1252 and the complementary anti-rotation feature 1254 can be different shapes. The complementary retention feature 1252 and the complementary anti-rotation feature 1254 can each have diametrically opposed shaped surfaces The outer shaft 902, 1502 can be disposed within the engagement portion 1250 of the three-level cervical plate 1200. In some embodiments, the one or more features 922, 924, 1522, 1524 can contact corresponding, complementary features 1252, 1254 of the three-level cervical plate 1200. The engagement portion 1250 can have a corresponding shape as the features 922, 924, 1522, 1524 of the outer shaft 902, 1502. The features 922, 924, 1522, 1524 of the outer shaft 902, 1502 can be shaped to fit within the recessed engagement portion 1250.

In the illustrated embodiment, each engagement portion 1250 can include a lumen comprising the complementary features 1252, 1254. One engagement portion 1250 can be disposed toward the superior portion 1202. One engagement portion 1250 can be disposed toward the middle of the three-level cervical plate 1200. One engagement portion 1250 can be disposed toward the inferior portion 1214. Other configurations are contemplated depending on the number and configuration of interbody implants 200.

The three-level cervical plate 1200 can include a marking 1256. The marking 1256 can indicate the cephalad/caudal orientation of the three-level cervical plate 1200. The marking 1256 can extend from the superior portion 1202 to the inferior portion 1204.

18. Four-Level Cervical Plate

FIGS. 80-83 depict views of an embodiment of the four-level cervical plate 1300. The four-level cervical plate 1300 can be designed to allow high angle anchor insertion for at least some of the anchors inserted through the four-level cervical plate 1300. The four-level cervical plate 1300 can be utilized with any interbody implant inserter described herein.

The four-level cervical plate 1300 can include a superior portion 1302 and an inferior portion 1304. The four-level cervical plate 1300 can include a bone facing surface 1306 and an access surface 1308. The superior portion 1302 can include one or more holes 1310, 1312 oriented between the bone facing surface 1306 and the access surface 1308. The inferior portion 1304 can include one or more holes 1314, 1316 oriented between the bone facing surface 1306 and the access surface 1308. In some embodiments, the holes 1310, 1312, 1314, 1316 are designed for high angle insertion. In some embodiments, the holes on the superior portion 1302 allow for high angle insertion. In some embodiments, the holes on the inferior portion 1304 allow for high angle insertion.

The four-level cervical plate 1300 can include a middle portion 1380. The middle portion 1380 can be disposed between the superior portion 1302 and the inferior portion 1304. The middle portion 1380 can include one or more holes 1382, 1384, 1386, 1388, 1390, 1392 oriented between the bone facing surface 1306 and the access surface 1308. The middle portion 1380 can include six holes 1382, 1384, 1386, 1388, 1390, 1392 disposed between the superior portion 1302 and the inferior portion 1304. The middle portion 1380 can include six holes 1382, 1384, 1386, 1388, 1390, 1392 disposed between the one or more holes 1310, 1312 of the superior portion 1302 and the one or more holes 1314, 1316 of the inferior portion 1304. The holes 1382, 1384 can be parallel or substantially parallel. The holes 1386, 1388 can be parallel or substantially parallel. The holes 1390, 1392 can be parallel or substantially parallel.

The holes 1310, 1312, 1314, 1316, 1382, 1384, 1386, 1388, 1390, 1392 are configured to accept anchors 400 and/or other attachment devices for anchoring the four-level cervical plate 1300 to vertebral bodies. In some embodiments, the trajectories through the holes 1310, 1312 allow the same or similar angle of insertion. In some embodiments, the trajectories through the holes 1314, 1316 allow the same or similar angle of insertion. In some embodiments, the trajectories through the holes 1382, 1384 allow the same or similar angle of insertion. In some embodiments, the trajectories through the holes 1386, 1388 allow the same or similar angle of insertion. In some embodiments, the trajectories through the holes 1390, 1392 allow the same or similar angle of insertion. In some embodiments, the trajectories through the holes 1382, 1384, 1386, 1388, 1390, 1392 are straight through or relatively straight through the four-level cervical plate 1300.

The four-level cervical plate 1300 can include one or more engagement portions 1350. The four-level cervical plate 1300 can include four engagement portions 1350. The four engagement portions 1350 can have the same or similar shape. The four engagement portions 1350 can be different. Each engagement portion 1350 can be configured to engage the outer shaft 902, 1502 of the interbody implant inserter 900, 1500. The engagement portion 1250 can have any feature of the engagement portions described herein.

The four-level cervical plate 1300 can include the complementary retention feature 1352. The complementary retention feature 1352 can engage with the interbody implant inserter 900, 1500. The complementary retention feature 1352 can engage with the second retention feature 922, 1522 of the outer shaft 902, 1502. The complementary retention feature 1352 can be shaped to allow the four-level cervical plate 1300 to slide relative to the interbody implant inserter 900, 1500.

The four-level cervical plate 1300 can include the complementary anti-rotation feature 1354. The complementary anti-rotation feature 1354 can engage with the interbody implant inserter 900, 1500. The complementary anti-rotation feature 1354 can engage with the anti-rotation feature 924, 1524 of the outer shaft 902, 1502. The complementary anti-rotation feature 1254 can be shaped to allow the four-level cervical plate 1300 to slide relative to the interbody implant inserter 900, 1500. The complementary anti-rotation feature 1354 can limit or prevent rotation of the four-level cervical plate 1300 relative to the outer shaft 902, 1502 of the interbody implant inserter 900, 1500.

Each engagement portion 1350 can include an opening in the four-level cervical plate 1300 comprising the complementary features 1352, 1354. One engagement portion 1350 can be disposed toward the superior portion 1302. Two engagement portions 1350 can be disposed in the middle portion 1380 of the four-level cervical plate 1300. One engagement portion 1350 can be disposed toward the inferior portion 1314. Other configurations are contemplated. The cervical plates described herein can include any number of engagement portions.

The four-level cervical plate 1300 can include a marking 1356. The marking 1356 can indicate the cephalad/caudal orientation of the four-level cervical plate 1300. The marking 1356 can extend along the length of the four-level cervical plate 1300.

19. Five-Level Cervical Plate

FIGS. 84-87 depict views of an embodiment of the five-level cervical plate 1400. The five-level cervical plate 1400 can be designed to allow high angle anchor insertion for at least a portion of the anchors inserted through the five-level cervical plate 1400. The five-level cervical plate 1400 can be utilized with any interbody implant inserter described herein.

The five-level cervical plate 1400 can include a superior portion 1402 and an inferior portion 1404. The five-level cervical plate 1400 can include a bone facing surface 1406 and an access surface 1408. The superior portion 1402 can include one or more holes 1410, 1412 oriented between the bone facing surface 1406 and the access surface 1408. The inferior portion 1404 can include one or more holes 1414, 1416 oriented between the bone facing surface 1406 and the access surface 1408. In some embodiments, the holes 1410, 1412, 1414, 1416 are designed for high angle insertion. In some embodiments, the holes on the superior portion 1402 allow for angled insertion of the anchor into a superior vertebral body. In some embodiments, the holes on the inferior portion 1404 allow for angled insertion of the anchor into an inferior vertebral body.

The five-level cervical plate 1400 can include a middle portion 1480. The middle portion 1480 can be disposed between the superior portion 1402 and the inferior portion 1404. The middle portion 1480 can include one or more holes 1482, 1484, 1486, 1488, 1490, 1492, 1494, 1496 oriented between the bone facing surface 1406 and the access surface 1408. The middle portion 1480 can include eight holes 1482, 1484, 1486, 1488, 1490, 1492, 1494, 1496 disposed between the superior portion 1402 and the inferior portion 1404. The middle portion 1480 can include eight holes 1482, 1484, 1486, 1488, 1490, 1492, 1494, 1496 disposed between the one or more holes 1410, 1412 of the superior portion 1402 and the one or more holes 1414, 1416 of the inferior portion 1404.

The holes 1410, 1412, 1414, 1416, 1482, 1484, 1486, 1488, 1490, 1492, 1494, 1496 are configured to accept anchors 400 and/or other attachment devices for anchoring the five-level cervical plate 1400 to the vertebral bone. In some embodiments, the trajectories through the holes 1410, 1412 are skewed relative to the five-level cervical plate 1400. In some embodiments, the trajectories through the holes 1214, 1216 are skewed relative to the five-level cervical plate 1400. In some embodiments, the trajectories through the holes 1482, 1484, 1486, 1488, 1490, 1492, 1494, 1496 can be the same or similar.

The five-level cervical plate 1400 can include one or more engagement portions 1450. The five-level cervical plate 1400 can include five engagement portions 1450. Two or more of the engagement portions 1450 can have the same or similar shape. Two or more of the engagement portions 1450 can have different shapes. One or more of the engagement portions 1450 can be configured to engage the outer shaft 902, 1502 of the interbody implant inserter 900, 1500. The engagement portion 1450 can have any feature of the engagement portions described herein.

The five-level cervical plate 1400 can include the complementary retention feature 1452. The complementary retention feature 1452 can engage with the interbody implant inserter 900, 1500. The complementary retention feature 1452 can be shaped to allow the five-level cervical plate 1400 to slide relative to the interbody implant inserter 900, 1500 toward the interbody implant 200.

The five-level cervical plate 1400 can include the complementary anti-rotation feature 1454. The complementary anti-rotation feature 1454 can engage with the interbody implant inserter 900, 1500. The complementary anti-rotation feature 1454 can be shaped to allow the five-level cervical plate 1400 to slide relative to the interbody implant inserter 900, 1500 toward the interbody implant 200. The complementary anti-rotation feature 1454 can limit or prevent rotation of the five-level cervical plate 1400 relative to the outer shaft 902, 1502 of the interbody implant inserter 900, 1500 during the sliding movement.

One engagement portion 1450 can be disposed toward the superior portion 1402. Three engagement portions 1450 can be disposed in the middle of the five-level cervical plate 1400. One engagement portion 1450 can be disposed toward the inferior portion 1414. Other configurations are contemplated.

The five-level cervical plate 1400 can include a marking 1456. The marking 1456 can indicate the cephalad/caudal orientation of the five-level cervical plate 1400. The marking 1356 can extend along a longitudinal direction of the five-level cervical plate 1400. The cervical plates can include any markings. The cervical plates can include any markings to indicate orientation. The cervical plates can include any markings to provide information to the user.

20. Interbody Implant Inserter

Figure 88:
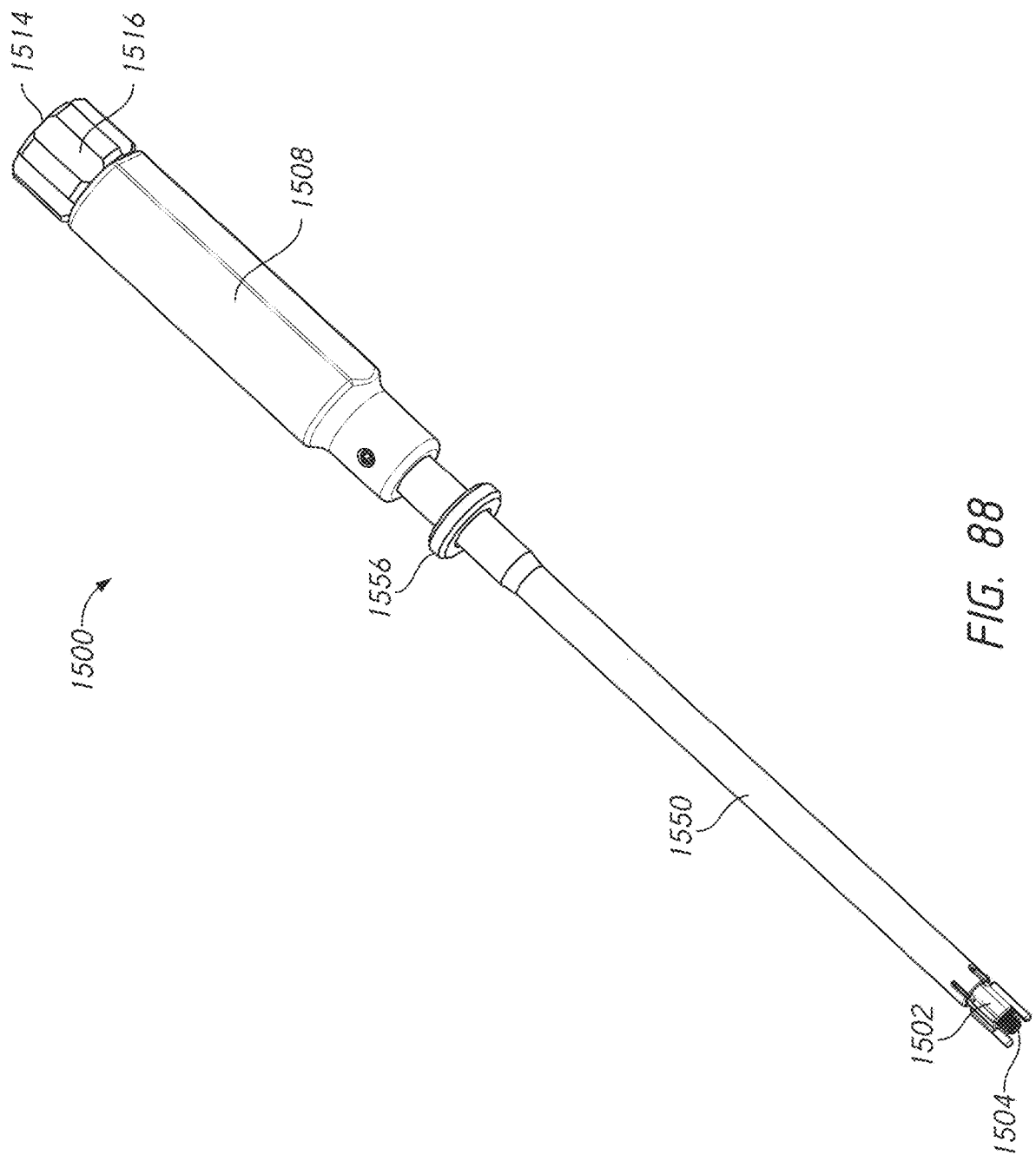
FIG. 88 is a perspective view of an embodiment of an interbody implant inserter.
Figure 89:
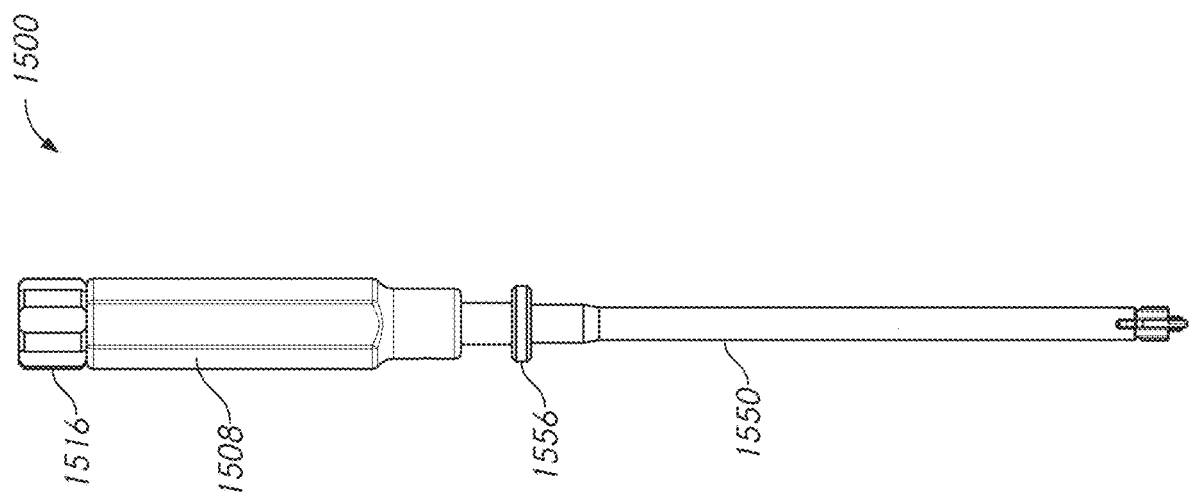
FIG. 89 is a front view of the interbody implant inserter of FIG. 88.
Figure 90:
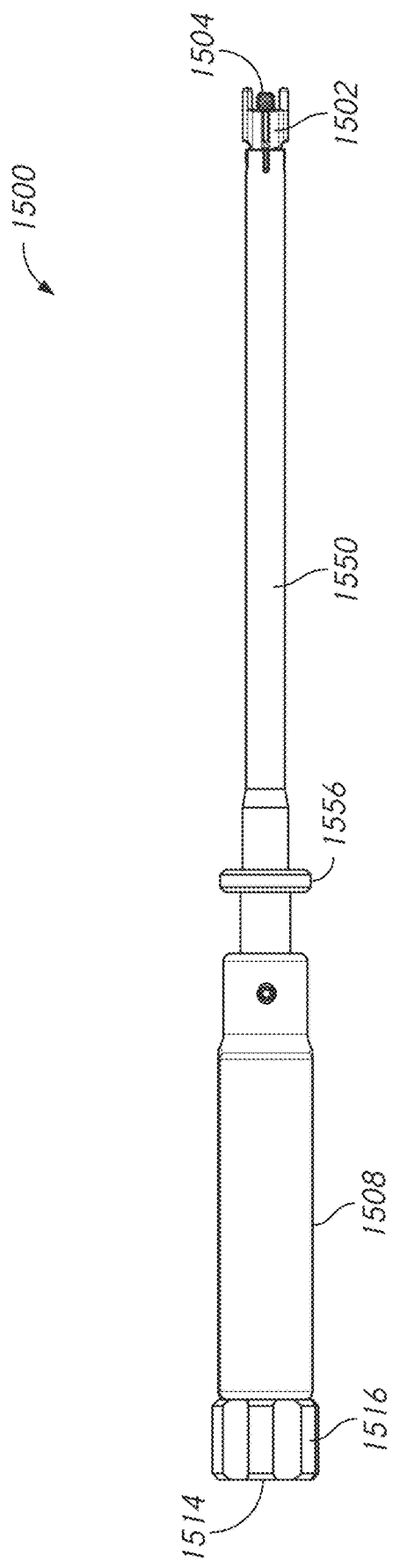
FIG. 90 is a side view of the interbody implant inserter of FIG. 88.
Figure 91:
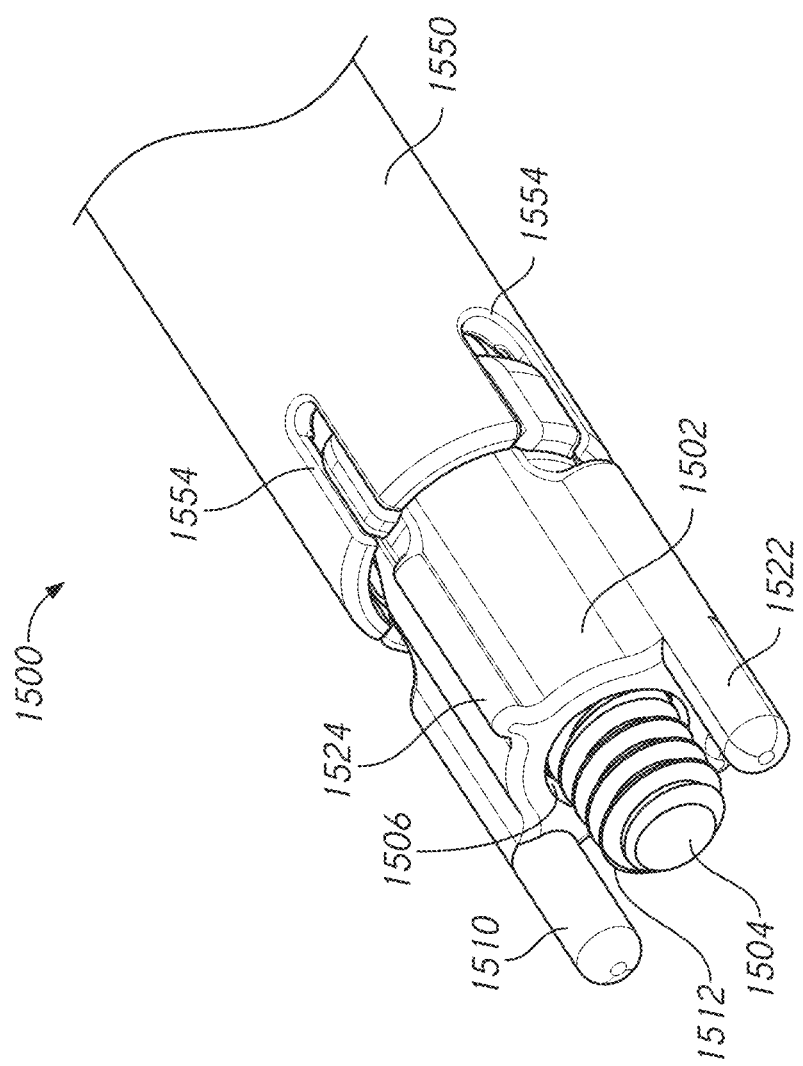
FIG. 91 is a bottom perspective view of the distal end of the interbody implant inserter of FIG. 88.
Figure 92:
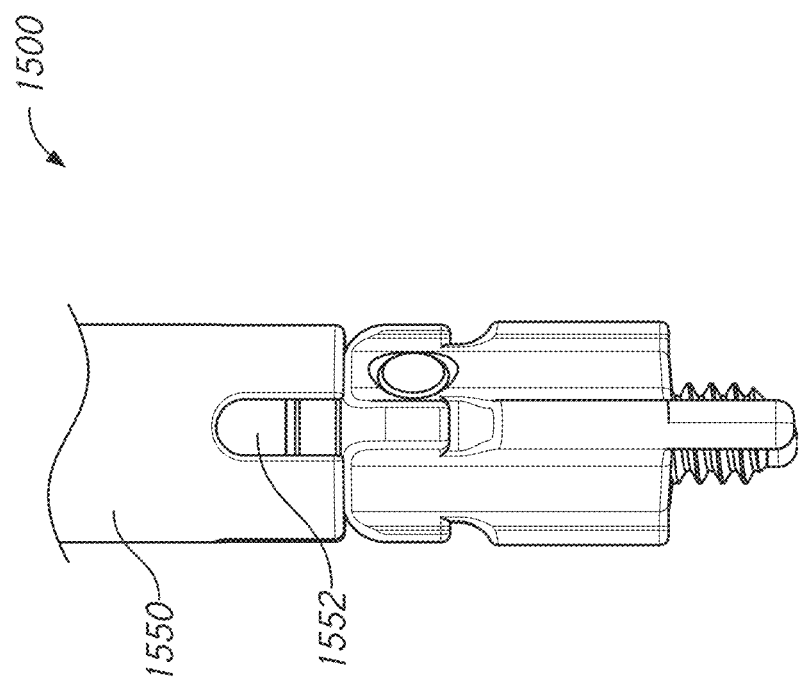
FIG. 92 is another side view of the interbody implant inserter of FIG. 88.
Figure 93:
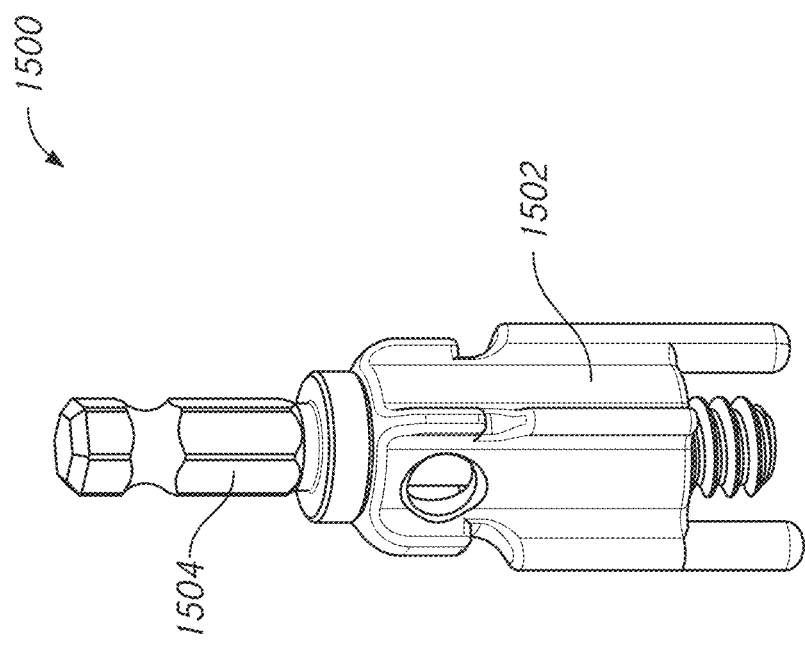
FIG. 93 is a view of the outer shaft and the internal shaft of the interbody implant inserter of FIG. 88.
Figure 94:
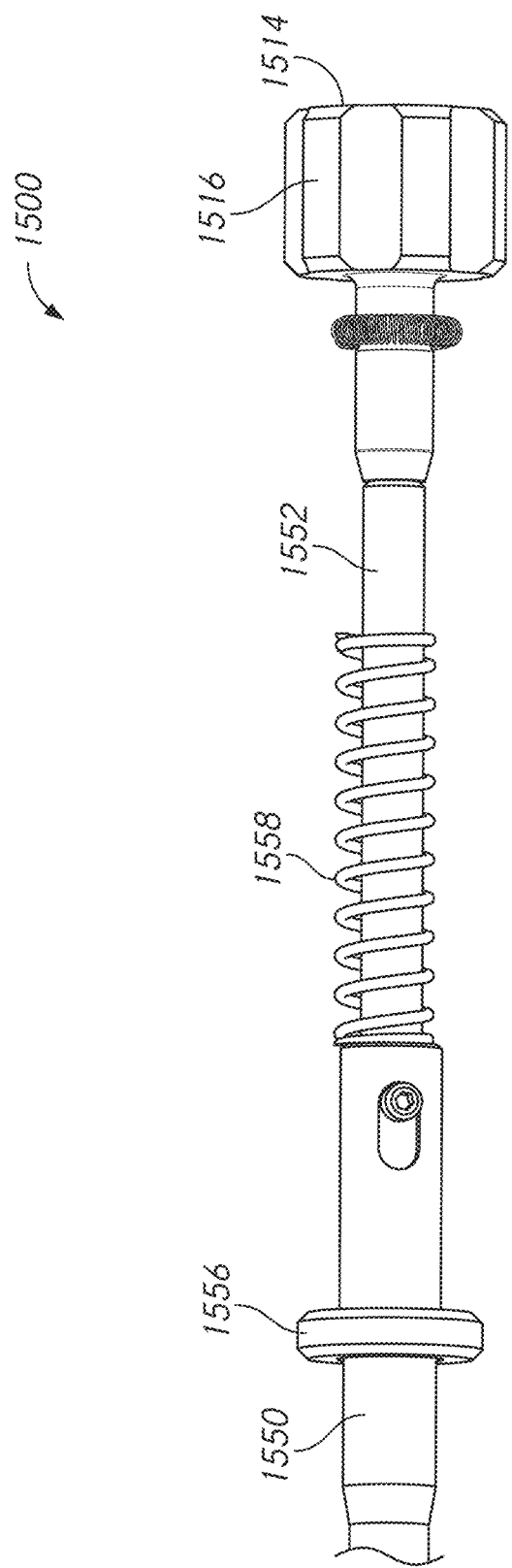
FIG. 94 is an internal view of the handle assembly of the interbody implant inserter of FIG. 88.

FIGS. 88-94 depict views of an embodiment of an interbody implant inserter 1500. FIG. 88 illustrates a perspective view. FIG. 89 illustrates a front view. FIG. 90 illustrates a side view. FIG. 91 illustrates a bottom view. FIG. 92 illustrates another bottom view. FIG. 93 is a view of the outer shaft and the internal shaft. FIG. 94 illustrates an internal view. The systems and methods described herein can include one or more of these components. The interbody implant inserter 1500 can be used in combination with any cervical plate described herein. The interbody implant inserter 1500 can be used in combination with the interbody implant 200. The interbody implant inserter 1500 can be used in combination with one or more anchors 400. The interbody implant inserter 1500 can include any features described herein. The interbody implant inserter 1500, the interbody spacer 200, and any cervical plate described herein can form an assembly.

The interbody implant inserter 1500 can comprise the outer shaft 1502 and the internal shaft 1504. The outer shaft 1502 can include a lumen 1506. The lumen 1506 can be sized to accommodate the internal shaft 1504. The internal shaft 1504 can be configured to rotate relative to the outer shaft 1502 when the internal shaft 1504 is disposed within the outer shaft 1502. While the internal shaft 1504 is illustrated as an elongate cylindrical shape, other configurations are contemplated. The outer shaft 1502 and the internal shaft 1504 can be shorter than in other embodiments. The outer shaft 1502 and the internal shaft 1504 can form a quick connect as described herein.

The interbody implant inserter 1500 can include additional shafts. The interbody implant inserter 1500 can include an external coupling shaft 1550. The external coupling shaft 1550 can slide relative to the outer shaft 1502. The interbody implant inserter 1500 can include an internal coupling shaft 1550. The external coupling shaft 1550 can slide relative to the internal coupling shaft 1552.

The external coupling shaft 1550 and the internal coupling shaft 1552 can include a ball and detent configuration. The ball and detent configuration can allow the external coupling shaft 1550 and the internal coupling shaft 1552 to releasably couple. When the ball and detent configuration is not engaged, the external coupling shaft 1550 and the internal coupling shaft 1552 can slide relative to each other. When the ball and detent configuration is engaged, the external coupling shaft 1550 and the internal coupling shaft 1552 cannot slide relative to each other. When the ball and detent configuration is engaged, the external coupling shaft 1550 and the internal coupling shaft 1552 are locked together. In some embodiments, the internal coupling shaft 1552 can rotate relative to the external coupling shaft 1550 when the ball and detent configuration is engaged. In some embodiments, the internal coupling shaft 1552 can rotate relative to the external coupling shaft 1550 when the ball and detent configuration is not engaged.

The internal coupling shaft 1552 can include a keyed socket. The internal shaft 1504 can include a keyed projection. Rotation of the internal coupling shaft 1552 can cause corresponding rotation of the internal shaft 1504. Other configurations to rotationally couple the internal coupling shaft 1552 and the internal shaft 1504 are contemplated.

The interbody implant inserter 1500 can include a handle 1508. In the illustrated embodiment, the handle 1508 comprises a cylindrical portion. The handle 1508 can be separately formed from the external coupling shaft 1550. The external coupling shaft 1550 and the internal coupling shaft 1552 can be received in the handle 1508. The handle 1508 can be located along a proximal portion of the outer shaft 1502. The external coupling shaft 1550 can slide relative to the handle 1508. The external coupling shaft 1550 can slide relative to the internal coupling shaft 1552.

The outer shaft 1502 can include a projection 1510. In the illustrated embodiment, the outer shaft 1502 can include two projections 1510. The two projections 1510 can be diametrically opposed on the body of the outer shaft 1502. The two projections 1510 can be diametrically opposed relative to the lumen 1506. The projection 1510 can be an extended point. The projection 1510 can have a circular cross-sectional shape. The projection 1510 can have a non-circular cross-sectional shape. The projection 1510 can be any interface configured to couple with the interbody implant 200.

The internal shaft 1504 can function to couple to the interbody implant 200, as described herein. The distal end of the internal shaft 1504 can include a second threaded portion 1512. The second threaded portion 1512 can couple with a corresponding threaded lumen in the interbody spacer 200. The second threaded portion 1512 can be near or at the distal end of the internal shaft 1504.

The interbody implant inserter 1500 can comprise an impact cap 1514. The impact cap 1514 can allow the user to apply a force to position the interbody implant 200 between adjacent vertebrae. The impact cap 1514 can have a flat proximal end to allow a force to be applied. While the impact cap 1514 is illustrated as an elongate cylindrical shape, other configurations are contemplated. The internal shaft 1504 can couple to the internal coupling shaft 1552. The internal coupling shaft 1552 can couple to the impact cap 1514.

The impact cap 1514 can include a thumbscrew 1516. The thumbscrew 1516 can be manipulated by the user to rotate the internal shaft 1504. In some embodiments, rotational movement of the thumbscrew 1516 by the user can cause rotational movement of the internal shaft 1504 relative to the outer shaft 1502. The thumbscrew 1516 can extend proximally from the handle 1508 when the internal coupling shaft 1552 is disposed within the external coupling shaft 1550 and the external coupling shaft 1550 is disposed within the handle 1508.

The interbody implant inserter 1500 has the ability to be impacted. The internal shaft 1504 can include an impact cap 1514 configured to allow the interbody implant inserter 1500 to be impacted. The impact cap 1514, the handle 1508, the outer shaft 1502, the internal shaft 1504, and the interbody implant 200 can translate together as a unit. The internal shaft 1504 and the interbody implant 200 can be rigidly coupled via threaded portions.

The outer shaft 1502 can include a second retention feature 1522 configured to couple with a corresponding feature of the cervical plate 700, as described herein. The second retention feature 1522 can be a keyed projection. The second retention feature 1522 can include one or more ridges. The second retention feature 1522 can be a solid, shaped surface. The second retention feature 1522 can provide a frictional fit. The second retention feature 1522 can provide an interference fit. The second retention feature 1522 can include two or more diametrically opposed structures. The second retention feature 1522 can include two or more structures equally spaced around the outer shaft 1502. In the illustrated embodiment, the second retention feature 1522 includes two structures. Other configurations are contemplated, e.g. one structure, three structures, four structures, etc. The second retention feature 1522 can include any features of the retention features described herein.

The outer shaft 1502 can include an anti-rotation feature 1524 configured to couple with a corresponding feature of the cervical plate, as described herein. The anti-rotation feature 1524 can be a keyed projection. The anti-rotation feature 1524 can be distal to the handle 1508. The anti-rotation feature 1524 can extend longitudinally. The anti-rotation feature 1524 can be near or at the proximal end of the outer shaft 1502. The anti-rotation feature 1524 can be along the length of the outer shaft 1502. The anti-rotation feature 1524 can be along a portion of the length of the outer shaft 1502 about which the cervical plate translates. The anti-rotation feature 1524 can include any features of the anti-rotation features described herein.

The external coupling shaft 1550 can slide relative to the outer shaft 1502. The external coupling shaft 1550 can have a release feature 1554. The release feature 1554 can have a corresponding shape as the second retention feature 1522 of the outer shaft 1502. The release feature 1554 can have a corresponding shape as the anti-rotation feature 1524 of the outer shaft 1502. The release feature 1554 can be one or more grooves. The release feature 1554 can be a groove extending to the distal end of the external coupling shaft 1550.

The external coupling shaft 1550 can include a collar 1556. The collar 1556 can be a protrusion. The collar 1556 can be knob. The external coupling shaft 1550 and the collar 1556 can be integrally formed. The user can grip the collar 1556 to slide the collar 1556 toward the handle 1508. The movement of the collar 1556 causes the release feature 1554 of the external coupling shaft 1550 to slide relative to the outer shaft 1502. The external coupling shaft 1550 disengages from the outer shaft 1502 when the collar 1556 is slid toward the handle 1508. The interbody implant inserter 1500 can include a spring 1558. The movement of the collar 1556 can depress the spring 1558. The spring 1558 can bias the external coupling shaft 1550 distally. The spring 1558 can bias the external coupling shaft 1550 such that the ball and detent configuration is not engaged. The spring 1558 can bias the external coupling shaft 1550 downward such that the release feature 1554 and the second retention feature 1522 interlock. The spring 1558 can bias the external coupling shaft 1550 downward such that the release feature 1554 and the anti-rotation feature 1524 interlock.

The force applied by the user to slide the collar 1556 can position a ball within a detent of the external coupling shaft 1550. The ball and detent can couple the external coupling shaft 1550 and the internal coupling shaft 1552. The external coupling shaft 1550, the internal coupling shaft 1552, the handle 1508, and the impact cap 1514 can be removed as a unit. The external coupling shaft 1550, the internal coupling shaft 1552, the handle 1508, and the impact cap 1514 can slide relative to the outer shaft 1502 and the internal shaft 1504. The outer shaft 1502 and the internal shaft 1504 can remain coupled to the interbody implant 200.

21. Methods of Use

In some methods of use, the interbody implant inserter 1500 is utilized. The interbody implant inserter 1500 can be used in combination with a multi-level cervical plate. The interbody implant inserter 1500 can be used with a single level cervical plate.

In some methods of use, the anterior face of the interbody implant 200 is mounted onto the interbody implant inserter 1500 using the projections 1510. The projections 1510 can be two distal pins for the alignment. In some methods of use, while maintaining the interbody implant 200 in place, a user can turn clockwise the thumbscrew 1516 until the second threaded portion 1512 of the internal shaft 1504 is fully engaged with the interbody implant 200. In some embodiments, the thumbscrew 1516 rotates the internal coupling shaft 1552 which in turn rotates the internal shaft 1504. In some methods of use, the internal coupling shaft 1552 rotates relative to the external coupling shaft 1550. In some methods of use, once the interbody implant 200 is secured, then the interbody implant 200 is placed into the intervertebral space using a slight impaction.

In some methods of use, the steps are repeated for the second level. In some methods of use, the interbody implant inserter 1500 is detached from the interbody implant 200 to position a second interbody implant 200. In some methods of use, another interbody implant inserter 1500 is utilized. In some methods of use, the anterior face of the second interbody implant 200 is mounted onto the second interbody implant inserter 1500 using the projections 1510. In some methods of use, while maintaining the second interbody implant 200 in place, a user can turn clockwise the thumbscrew 1516 of the second interbody implant inserter 1500 until the second threaded portion 1512 of the internal shaft 1504 is fully engaged with the second interbody implant 200. In some embodiments, the thumbscrew 1516 rotates the internal coupling shaft 1552 which in turn rotates the internal shaft 1504 of the second interbody implant inserter 1500. In some methods of use, the internal coupling shaft 1552 rotates relative to the external coupling shaft 1550 of the second interbody implant inserter 1500. In some methods of use, once the second interbody implant 200 is secured, then the second interbody implant 200 is placed into the intervertebral space using a slight impaction. In some methods of use, a user can repeat the steps for any additional level.

In some methods of use, the interbody implant inserter 1500 is detached from the interbody implant 200. In some methods of use, the interbody implant inserter 1500 is detached by pulling on the collar 1556. In some methods of use, pulling the collar 1556 disengages the external coupling shaft 1550 from the outer shaft 1502. In some methods of use, the interbody implant inserter 1500 is detached leaving the outer shaft 1502 and the internal shaft 1502 coupled to the interbody implant 200. The outer shaft 1502 and the internal shaft 1502 can be a temporary alignment fixation pin. This temporary alignment fixation pin will permit aligning the cervical plate with the interbody implant 200.

In some methods of use, the screw holes are prepared. In some methods of use, a template drill is utilized. In some methods of use, a template is inserted over the temporary alignment fixation pin to create a trajectory for the screws prior the cervical plate insertion. In some methods of use, a combo drill/awl is used to create a hole by breaking through the cortex of the vertebral body or by advancing into bone. In some methods of use, the user selects the screw length consistent with the drill size. In some methods of use, prior to creating a hole, the tip of the combo drill/awl is seated inside the template. In some methods of use, the user verifies that the combo drill guide is placed in the angle to the desired location. In some methods of use, the user verifies that the angles does not exceed (27°) range of motion or ROM. In some methods of use, a variable or fixed drill guide is be used to create the screw hole preparation. In some methods of use, the drill guide is seated into the template. In some methods of use, the drill is advanced through the variable or the fixed drill guide sleeve until reaching the stop collar located on the drill shaft. In some methods of use, tapping is utilized. In some methods of use, the tap is connected to the quick handle and the desired length is tapped.

In some methods of use, the user selects the appropriate cervical plate using preplanning fluoroscopy to determine the plate size and anticipated screw trajectories. In some methods of use, plate length is measured center hole to center hole. In some methods of use, a silver stripe indicates the cranial/caudal orientation which facilitates the correct cervical plate insertion. In some methods of use, the size of the cervical plate is measured using a caliper. In some methods of use, once the cervical plate size is determined, a user can attach a plate holder to the selected cervical plate and position the cervical plate into the operative site over the temporary alignment fixation pin. In some methods of use, the cervical plate is positioned over two temporary alignment fixation pins. In some embodiments, each temporary alignment fixation pin is coupled to an interbody implant. In some embodiments, the temporary alignment fixation pins are coupled to the most cranial interbody implant and the most caudal interbody implant. In some embodiments, temporary alignment fixation pins are not coupled to the intermediate interbody implants. In some embodiments, temporary alignment fixation pins are coupled to the intermediate interbody implants. In some methods of use, the cervical plate is positioned over two or more temporary alignment fixation pins.

In some methods of use, the screw is inserted. In some methods of use, the screwdriver is assembled to a modular handle. In some methods of use, the desired screw is loaded onto the screwdriver. In some methods of use, the screw is secured to the screwdriver and inserted into the plate until the head is fully seated. In some methods of use, screws may be loaded, inserted, and driven with straight, flexible screwdrivers depending on patient anatomy. In some methods of use, the same sequence is repeated until all the screws are fully inserted. In some methods of use, the screw is locked. In some methods of use, the breakaway driver is inserted into the head of the internal locking screw and turned clockwise until a click is reached. In some methods of use, the locking torque is 2 in-lbs.

In some methods of use, prior to final locking, the user confirms screw placement and angulation with x-ray or other imaging techniques. In some methods of use, the user can check the final position of the cervical plate and screws both visually and radiographically. In some methods of use, the user detaches the outer shaft 1502 and the internal shaft 1504 from the interbody implant 200 by turning the internal shaft 1504 counterclockwise. In some methods of use, the user detaches the outer shaft 1502 by sliding the outer shaft 1502 and the internal shaft 904 away from the interbody implant 200. The temporary alignment fixation pin can be removed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. An inserter assembly, comprising:
    an interbody implant inserter comprising a first retention feature and an anti-rotation feature, the interbody implant inserter comprising a proximal position along a length of the interbody implant inserter and a distal position along the length of the interbody implant inserter; and
    a cervical plate comprising an engagement portion, wherein the engagement portion comprises a complementary retention feature and a complementary anti-rotation feature; and
    an interbody spacer, wherein the interbody implant inserter is configured to couple with the interbody spacer, wherein the cervical plate is disposed at the proximal position and is configured to translate along the length of the interbody implant inserter toward the distal position.

2. The inserter assembly of claim 1, wherein the first retention feature comprises a leaf spring.

3. The inserter assembly of claim 1, wherein the first retention feature comprises a flexible region.

4. The inserter assembly of claim 1, wherein the complementary retention feature comprises a groove.

5. The inserter assembly of claim 1, wherein the anti-rotation feature comprises a ridge.

6. The inserter assembly of claim 1, wherein the interbody implant inserter comprises a second retention feature.

7. The inserter assembly of claim 6, wherein the cervical plate is retained at the distal position by the second retention feature.

8. The inserter assembly of claim 6, wherein the second retention feature is a ridge.

9. The inserter assembly of claim 1, wherein the interbody implant inserter comprises an internal shaft and an outer shaft, wherein the first retention feature and the anti-rotation feature are disposed on the outer shaft.

10. The inserter assembly of claim 1, wherein the cervical plate is a two-level cervical plate.

11. The inserter assembly of claim 1, wherein the cervical plate is a three-level cervical plate.

12. The inserter assembly of claim 1, wherein the cervical plate is a four-level cervical plate.

13. The inserter assembly of claim 1, wherein the cervical plate is a five-level cervical plate.

14. The inserter assembly of claim 1, wherein the first retention feature comprises a lever.

15. The inserter assembly of claim 1, wherein the first retention feature comprises a projection.

16. The inserter assembly of claim 1, wherein the first retention feature comprises a spring.

17. The inserter assembly of claim 1, wherein the interbody implant inserter comprises a second retention feature comprising a ridge.

18. The inserter assembly of claim 17, wherein the complementary retention feature comprises a groove.

19. The inserter assembly of claim 1, wherein the anti-rotation feature comprises a ridge and the complementary anti-rotation feature comprises a groove.

20. The inserter assembly of claim 1, wherein the first retention feature and the anti-rotation feature are located on a first temporary alignment fixation pin.

21. The inserter assembly of claim 20, wherein the first temporary alignment fixation pin is configured to remain coupled to the interbody spacer when a portion of the interbody implant inserter is removed.

22. The inserter assembly of claim 20, wherein a portion of the interbody implant inserter is configured to be removed from the first temporary alignment fixation pin before positioning the cervical plate.

23. The inserter assembly of claim 20, further comprising a second interbody implant inserter; and a second interbody spacer, wherein the second interbody implant inserter is configured to couple with the second interbody spacer.

24. The inserter assembly of claim 23, wherein the second interbody implant inserter comprises a second temporary alignment fixation pin.

25. The inserter assembly of claim 24, wherein the second temporary alignment fixation pin is configured to remain coupled to the second interbody spacer when a portion of the second interbody implant inserter is removed.

26. The inserter assembly of claim 24, wherein a portion of the second interbody implant inserter is configured to be removed from the second temporary alignment fixation pin before positioning the cervical plate.

* * * * *